United States Patent
Asselin et al.

(10) Patent No.: US 7,671,056 B2
(45) Date of Patent: Mar. 2, 2010

(54) PIPERAZINE-PIPERIDINE ANTAGONISTS AND AGONISTS OF THE 5-HT$_{1A}$ RECEPTOR

(75) Inventors: Magda Asselin, Mahwah, NJ (US); George Theodore Grosu, Pearl River, NY (US); Annmarie Louise Sabb, Pennington, NJ (US); Wayne Everett Childers, New Hope, PA (US); Lisa Marie Havran, Florence, NJ (US); Zhongqi Shen, Plainsboro, NJ (US); James Jacob Bicksler, Titusville, NJ (US); Dan Chaekoo Chong, Plainsboro, NJ (US)

(73) Assignee: Wyeth LLC, Madison, NJ (US)

( * ) Notice: Subject to any disclaimer, the term of this patent is extended or adjusted under 35 U.S.C. 154(b) by 280 days.

(21) Appl. No.: 11/450,942

(22) Filed: Jun. 9, 2006

(65) Prior Publication Data

US 2007/0027160 A1    Feb. 1, 2007

Related U.S. Application Data

(60) Provisional application No. 60/689,469, filed on Jun. 10, 2005.

(51) Int. Cl.
*A61K 31/496* (2006.01)
*C07D 401/14* (2006.01)
*C07D 405/14* (2006.01)
*C07D 409/14* (2006.01)
*C07D 413/14* (2006.01)

(52) U.S. Cl. .............. 514/253.06; 514/253.07; 514/253.08; 514/253.09; 514/253.1; 514/253.11; 544/363; 544/360; 544/364

(58) Field of Classification Search ............... None
See application file for complete search history.

(56) References Cited

U.S. PATENT DOCUMENTS

| | | | |
|---|---|---|---|
| 4,465,482 A | 8/1984 | Tittel et al. |
| 4,624,954 A | 11/1986 | Jirkovsky et al. |
| 4,665,183 A | 5/1987 | Jirkovsky et al. |
| 4,904,658 A | 2/1990 | Tseng et al. |
| 5,219,857 A | 6/1993 | Tseng et al. |
| 5,260,331 A | 11/1993 | White et al. |
| 5,288,748 A | 2/1994 | Wikstrom et al. |
| 5,422,355 A | 6/1995 | White et al. |
| 5,538,956 A | 7/1996 | Minchin et al. |
| 6,084,130 A | 7/2000 | Romero et al. |
| 6,127,357 A | 10/2000 | Cliffe et al. |
| 6,465,482 B2 | 10/2002 | Mewshaw et al. |
| 6,469,007 B2 | 10/2002 | Childers et al. |
| 6,586,436 B2 | 7/2003 | Childers et al. |
| 6,620,808 B2 | 9/2003 | Van Der Klish et al. |
| 6,635,270 B2 | 10/2003 | Hong et al. |
| 6,821,985 B2 | 11/2004 | Chenard et al. |
| 6,825,212 B2 | 11/2004 | Bernotas et al. |
| 6,878,742 B2 | 4/2005 | Kreft et al. |
| 6,995,176 B2 | 2/2006 | Bernotas et al. |
| 7,041,695 B2 | 5/2006 | Cole |
| 2003/0060513 A1 | 3/2003 | Arneric et al. |
| 2003/0220348 A1 | 11/2003 | Xie et al. |
| 2004/0014972 A1 | 1/2004 | Gottschlich et al. |
| 2005/0032873 A1 | 2/2005 | Hatzenbuhler et al. |
| 2005/0182049 A1 | 8/2005 | Howard |
| 2005/0197356 A1 | 9/2005 | Graziani et al. |
| 2005/0197379 A1 | 9/2005 | Summers et al. |
| 2005/0215561 A1 | 9/2005 | Ghosh et al. |
| 2005/0256103 A1 | 11/2005 | Suzuki et al. |
| 2005/0282825 A1 | 12/2005 | Malamas et al. |
| 2005/0282826 A1 | 12/2005 | Malamas et al. |
| 2006/0182805 A1 | 8/2006 | Pfeiffer et al. |
| 2006/0287335 A1 | 12/2006 | Sukoff et al. |
| 2007/0027160 A1 | 2/2007 | Asselin et al. |
| 2007/0146072 A1 | 6/2007 | Ohta et al. |
| 2007/0299083 A1 | 12/2007 | Schmid et al. |

(Continued)

FOREIGN PATENT DOCUMENTS

EP    1203584    5/2002

(Continued)

OTHER PUBLICATIONS

Araneda, et al., "5-Hydroxytryptamine$_2$ and 5-Hydroxytryptamine$_{1A}$ Receptors Mediate Opposing Responses on Membrane Excitability in Rat Association Cortex", Neuroscience, 40(2):399-412 (1991).

(Continued)

*Primary Examiner*—Emily Bernhardt
(74) *Attorney, Agent, or Firm*—Rebecca R. Barrett

(57) ABSTRACT

The present invention relates to novel piperazine-piperidine compounds. The compounds are useful as 5-HT1A binding agents, particularly as 5-HT1A receptor antagonists and agonists. These compounds are useful in treating central nervous system disorders, such as cognition disorders, anxiety disorders, depression and sexual dysfunction. The invention relates to compounds and pharmaceutically acceptable salts of formula (I'):

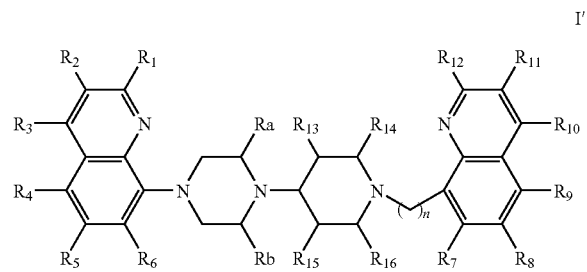

wherein $R_1$-$R_{16}$, $R_a$, $R_b$, and n are set forth in the specification. The invention also relates to pharmaceutical compositions comprising compounds and pharmaceutically acceptable salts of formula (I').

67 Claims, No Drawings

U.S. PATENT DOCUMENTS

| | | |
|---|---|---|
| 2008/0045510 A1 | 2/2008 | Liang et al. |
| 2008/0058523 A1 | 3/2008 | Liu et al. |

FOREIGN PATENT DOCUMENTS

| | | |
|---|---|---|
| EP | 1541197 | 6/2005 |
| WO | WO-94/02475 | 2/1994 |
| WO | WO-94/13643 | 6/1994 |
| WO | WO-94/13644 | 6/1994 |
| WO | WO-94/13661 | 6/1994 |
| WO | WO-94/13676 | 6/1994 |
| WO | WO-94/13677 | 6/1994 |
| WO | WO-95/33743 | 12/1995 |
| WO | WO-96/38414 | 12/1996 |
| WO | WO-97/03982 | 2/1997 |
| WO | WO-97/36907 | 10/1997 |
| WO | WO-98/15275 | 4/1998 |
| WO | WO-99/42456 | 8/1999 |
| WO | WO-99/51240 | 10/1999 |
| WO | WO-00/32187 | 6/2000 |
| WO | WO-00/40554 | 7/2000 |
| WO | WO-01/77100 | 10/2001 |
| WO | WO-02/20491 | 3/2002 |
| WO | WO-02/088132 | 11/2002 |
| WO | WO-02/088145 | 11/2002 |
| WO | WO-03/010169 | 2/2003 |
| WO | WO 03/087086 | 10/2003 |
| WO | WO-2004/016256 | 2/2004 |
| WO | WO-2004/024731 | 3/2004 |
| WO | WO-2004/045509 | 6/2004 |
| WO | WO-2004/045718 | 6/2004 |
| WO | WO-2004/099191 | 11/2004 |
| WO | WO-2004/099214 | 11/2004 |
| WO | WO-2005/056560 | 6/2005 |
| WO | WO-2006/042249 | 4/2006 |
| WO | WO-2006/135839 | 12/2006 |
| WO | WO-2007/146072 | 12/2007 |
| WO | WO-2007/146073 | 12/2007 |
| WO | WO-2007/146115 | 12/2007 |
| WO | WO-2007/146202 | 12/2007 |
| WO | WO-2008/067399 | 6/2008 |

OTHER PUBLICATIONS

Artigas, et al., "Acceleration of the Effect of Selected Antidepressant Drugs in Major Depression by 5-$HT_{1A}$ Antagonists", Trends Neurosci., 19(9):378-383 (1996).

Balducci, et al., "Reversal of Visual Attention Dysfunction after AMPA Lesions of the Nucleus Basalis Maqnocellularis (NBM) by the Cholinesterase Inhibitor Donepezil and by a 5-$HT_{1A}$ Receptor Antagonist WAY 100635", Psychopharmacology, 167:28-36 (2003).

Blier, et al., "Effectiveness of Pindolol with Selected Antidepressant Drugs in the Treatment of Major Depression", J. Clin. Psychopharmacol., 15(3):217-222 (1995).

Blier, et al., "Modifications of the Serotonin System by Antidepressant Treatments: Implications for the Therapeutic Response in Major Depression", Journal of Clinical Psychopharmacology, 7(6 Suppl):24S-35S (1987).

Boast, et al., "5HT Antagonists Attenuate MK801-Impaired Radial Arm Maze Performance in Rats", Neurobiology of Learning and Memory, 71:259-271 (1999).

Bowen, et al., "Neurotransmission—the Link Integrating Alzheimer Research?", Trends in Neurosciences, 17(4):149-150 (1994).

Carli, et al., "WAY 100635, a 5-$HT_{1A}$ Receptor Antagonist, Prevents the Impairment of Spatial Learning Caused by Blockade of Hippocampal NMDA Receptors", Neuropharmacology, 38:1165-1173 (1999).

Carli, et al., "WAY 100635, a 5-$HT_{1A}$ Receptor Antagonist, Prevents the Impairment of Spatial Learning Caused by Intrahippocampal Administration of Scopolamine or 7-Chloro-Kynurenic Acid", Brain Research, 774:167-174 (1997).

Carli, et al., "(S)-WAY 100135, a 5-$HT_{1A}$ Receptor Antagonist, Prevents the Impairment of Spatial Learning Caused by Intrahippocampal Scopolamine", European Journal of Pharmacology, 283:133-139 (1995).

Childers, et al., "Synthesis and Biological Evaluation of Benzodioxanylpiperazine Derivatives as Potent Serotonin 5-$HT_{1A}$ Antagonists: The Discovery of Lecozotan", J. Med. Chem., 48:3467-3470 (2005).

Dijk, et al., "NMDA-Induced Glutamate and Aspartate Release from Rat Cortical Pyramidal Neurones: Evidence for Modulation By a 5-$HT_{1A}$ Antagonist", British Journal of Pharmacology, 115:1169-1174 (1995).

Dimitriou, "Buspirone Augmentation of Antidepressant Therapy", J. Clinical Psychopharmacol., 18(6):465-469 (1998).

Driver, et al., "A Second-Generation Catalyst for Aryl Halide Amination: Mixed Secondary Amines from Aryl Halides and Primary Amines Catalyzed by $(DPPF)PdCI_2$,", J. Am. Chem. Soc., 118:7217-7218 (1996).

Dunlop, et al., "Characterization of 5-$HT_{1A}$ Receptor Functional Coupling in Cells Expressing the Human 5-$HT_{1A}$ Receptor as Assesed with the Cytosensor Microphysiometer", Journal of Pharmacological and Toxicological Methods, 40:47-55 (1998).

Feiger, "A Double-Blind Comparison of Gepirone Extended Release, Imipramine, and Placebo in the Treatment of Outpatient Major Depression", Psychopharmacol. Bull., 32(4):659-665 (1996).

Grof, et al., "An Open Study of Oral Flesinoxan, a 5-$HT_{1A}$ Receptor Agonist, in Treatment-Resistant Depression", International Clinical Psychopharmacology, 8:167-172 (1993).

Harder, et al., "The 5-$HT_{1A}$ Antagonist, WAY 100 635, Alleviates Cognitive Impairments Induced by Dizocilpine (MK-801) in Monkeys", Neuropharmacology, 39:547-552 (2000).

Harder, et al., "The 5-$HT_{1A}$ Antagonist, WAY 100635, Ameliorates the Cognitive Impairment Induced by Fornix Transection in the Marmoset", Psychopharmacology, 127:245-254 (1996).

Hume, et al., "Evaluation of [O-methyl-$^3$H]WAY-100635 as an in vivo Radioligand for 5-$HT_{1A}$ Receptors in Rat Brain", European Journal of Pharmacology, 271:515-523 (1994).

Jones. "Synthesis of the Quinoline Ring System". Heterocyclic Compounds: vol. 32 (Quinolines), Chapter 2, Interscience, New York, pp. 93-318 (1977).

Matsuyama, et al., "Regulation of Glutamate Release via NMDA and 5-$HT_{1A}$ Receptors in Guinea Pig Dentate Gyrus", Brain Research, 728:175-180 (1996).

Mcloughlin, et al., "Central Serotonergic Hyperresponsivity in Late-Onset Alzheimer's Disease", American Journal of Psychiatry, 151(11):1701-1703 (1994).

Perez, et al., "Randomised, Double-Blind, Placebo-Controlled Trial in Pindolol in Combination with Fluoxetine Antidepressant Treatment", The Lancet, 349:1594-1597 (1997).

Rabiner, et al., "5-Hydroxytryptamine$_{1A}$ Receptor Occupancy by Novel Full Antagonist 2-[4-[4-(7-Chloro-2,3-dihydro-1,4-benzdioxyn-5-yl)-1-piperazinyl]butyl]-1,2-benzisothiazol-3-(2H)-one-1,1-dioxide: A[$^{11}$C][O-methyl-3H]-N-(2-(4-(2-methoxyphenyl)-1-piperazinyl)ethyl)-N-(2-pyridinyl)cyclohexanecarboxamide Trihydrochloride (WAY-100635) Positron Emission Tomography Study in Humans", Journal of Pharmacology and Experimental Therapeutics, 301(3):1144-1150 (2002).

Sakai, et al., "Inhibitory Modulation of Long-Term Potentiation via the 5-$HT_{1A}$ Receptor in Slices of the Rat Hippocampal Dentate Gyrus", Brain Research, 613:326-330 (1993).

Schechter, et al., "Lecozotan (SRA-333): A Selective Serotonin 1A Receptor Antagonist That Enhances the Stimulated Release of Glutamate and Acetylcholine in the Hippocampus and Possesses Cognitive-Enhancing Properties", Journal of Pharmacology and Experimental Therapeutics, 314(3):1274-1289 (2005).

Tome, et al., "Serotonergic Autoreceptor Blockade in the Reduction of Antidepressant Latency: Personality Variables and Response to Paroxetine and Pindolol", J. Affect Disord., 44:101-109 (1997).

Wilcox, et al., "A Double-Blind Trial of Low- and High-Dose Ranges of Gepirone-ER Compared with Placebo in the Treatment of Depressed Outpatients", Psychopharmacol. Bull., 32(3):335-342 (1996).

Wolfe, et al., "An Improved Catalyst System for Aromatic Carbon—Nitrogen Bond Formation: The Possible Involvement of Bis(Phosphine) Palladium Complexes as Key Intermediates", J. Am Chem. Soc., 118:7215-7216 (1996).

Yasuno, et al., "Inhibitory Effect of Hippocampal 5-$HT_{1A}$ Receptors on Human Explicit Memory", American Journal of Psychiatry, 160(2):334-340 (2003).

Yuen, et al., "Serotonin 5-$HT_{1A}$ Receptors Regulate NMDA Receptor Channels through a Microtubule-Dependent Mechanism", Journal of Neuroscience, 25(23):5488-5501 (2005).

Yoo, et al., "Synthesis of Heteroarylpiperazines and Heteroarylbipiperidines with a Restricted Side Chain and Their Affinities for 5-$HT_{1A}$ Receptor", Arch. Pharm. Pharm. Med. Chem., 336:208-215 (2003).

Invitation to Pay Additional Fees with Partial Search Report, issued for International Application No. PCT/US2006/022719, dated Apr. 20, 2007.

Artigas, et al., "Pindolol Induces a Rapid Improvement of Depressed Patients Treated with Serotonin Reuptake Inhibitors." Archives of General Psychiatry., vol. 51, No. 3, Mar. 1, 1994. pages 248-251.

Blackman, *Operant Conditioning: An Experimental Analysis of Behavior*, Methuen (1974) (3 pages).

Bourin, Michel et al. "Evidence for the Activity of Lamotrigine at 5-HT1A Receptors in the Mouse Forced Swimming Test." Journal of Psychiatry & Neuroscience. vol. 30, No. 4, Jul. 2005. pages 275-282. XP002502356.

Buchwald, et al., "An Improved Catalyst System for Aromatic Carbon-Nitrogen Bond Formation: The Possible Involvement of Bis(Phosphine) Palladium Complexes as Key Intermediates", J. Am. Chem. Soc., 118:7215-7216 (1996).

Buchwald, et al., "Long-Term, Continuous Intravenous Heparin Administration by an Implantable Infusion Pump in Ambulatory Patients with Recurrent Venous Thrombosis", Surgery, 88:507 (1980).

Caliendo, et al., "Derivatives as 5$HT_{1A}$ Receptor Ligands - Past and Present", Current Medicinal Chemistry, 12:1721-1753 (2005).

Chanda, et al., "Identification of Residues Important for Ligand Binding to the Human 5-Hydroxytryptamine 1A Serotonin Receptor", Mol. Pharmacol, 43:516-520 (1993).

Cheeta, Survjit et al. "The Role of 5-HT1A Receptors in Mediating the Anxiogenic Effects of Nicotine Following Lateral Septal Administration." European Journal of Neuroscience, Oxford University Press., vol. 12, No. 10, Oct. 1, 2000, pp. 3797-3802. XP009106393.

Comery, et al., "Acute γ-Secretase Inhibition Improves Contextual Fear Conditioning in the Tg2576 Mouse Model of Alzheimer's Disease", Journal of Neuroscience, 25(39):8898-8902 (2005).

Controlled Drug Bioavailability, Drug Product Design and Performance, Smolen and Ball, Eds. (1984) (3 pages).

Day, et al., "Post-Training N-Methyl-D-Aspartate Receptor Blockade Offers Protection from Retrograde Interference but does not Affect Consolidation of Weak or Strong Memory Traces in the Water Maze", Neuroscience, 137:19-28 (2006).

During, et al., "Controlled Release of Dopamine from a Polymeric Brain Implant: In Vivo Characterization", Ann. Neural., 25:351 (1989).

Elsinga, P H et al. "Positron Emission Tomography Studies on Binding of Central Nervous System Drugs and P-glycoprotein Function in the Rodent Brain." Molecular Imaging and Biology 200501 US, vol. 7, No. 1, Jan. 2005, pp. 37-44. XP002502358.

Emilien, et al., "Prospects for Pharmacological Intervention in Alzheimer Disease", Arch. Neurol., 57:454-459 (2000).

Foley, et al., "The 5-$HT_6$ Receptor Antagonist SB-271046 Reverses Scopolamine-Disrupted Consolidation of a Passive Avoidance Task and Ameliorates Spatial Task Deficits in Aged Rats", Neuropsychopharmacology, 29:93-100 (2004).

Gartside, S E et al. "Interaction Between a Selective 5-HT1A Receptor Antoganist and an SSRI in Vivo: Effects on 5-Ht Cell Firing and Extracellular 5-Ht." British Journal of Clinical Pharmacology. Blackwell Scientific Publ. Jan. 1, 1995, pp. 1064-1070. XP000604130.

Goodson, "Chapter 6: Dental Applications" *Medical Applications of Controlled Release*, vol. 2, pp. 115-138 (1984).

Hartwig, et al., "A Second-Generation Catalyst for Aryl Halide Amination: Mixed Secondary Amines from ARyl Halides and Primary Amines Catalyzed by (DPPF)$PdCL_2$ ", J. Am. Chem. Soc., 118:7217-7218 (1996).

Howard, et al., "Intracerebral Drug Delivery in Rats with Lesion-Induced Memory Deficits", J. Neurosurg., 71:105-112 (1989).

International Search Report and Written Opinion issued for PCT/US2007/013433, dated Apr. 17, 2008 (20 pages).

International Search Report and Written Opinion issued for PCT/US2007/085777, dated Oct. 29, 2008 (22 pages).

International Search Report and Written Opinion issued for PCT/US2008/054044, dated Aug. 1, 2008 (15 pages).

International Search Report for International Application No. PCT/US2007/085790 mailed Aug. 1, 2008 (2 pages).

International Search Report for International Patent Application No. PCT/US2007/013434 mailed Dec. 10, 2008 (54 pages).

Kenny, Paul J et al. "Anxiogenic Effects of Nicotine in the Dorsal Hippocampus are Mediated by 5-HT1A and Not by Muscarinic M1 Receptors." Neuropharmacology, vol. 39, No. 2, Jan. 4, 2000, pp. 300-307.

Kung, et al., "Radiopharmaceuticals for CNS Receptor Imaging with Spect", Nucl. Med. Biol., 17(1):85-92 (1990).

Langer, "New Methods of Drug Delivery", Science, 249:1527-1533 (1990).

Langer, et al., "Chemical and Physical Structure of Polymers as Carriers for Controlled Release of Bioactive Agents: A Review", J. Macrol. Sci. Rev. Marcol. Chem., 2:61-126 (1983).

Levy, et al., "Inhibition of Calcification of Bioprosthetic Heart Valves by Local Controlled-Release Diphosphonate", Science, 228:190-192 (1935).

Lopez-Berestein, et al., *Liposomes in the Therapy of Infectious Diseases and Cancer*, pp. 317-327 and 353-365 (1989).

Madjid, Nather et al. "5-Hydroxytryptamine 1A Receptor Blockade Facilities Aversive Learning in Mice: Interactions with Cholinergic and Glutamatergic Mechanisms." Journal of Pharmacology and Experimental Therapeutics, vol. 316, No. 2, Feb. 2006, pp. 581-591.

Manske, "The Chemistry of Quinolines", Chemical Reviews, 30(1):113-144 (1942).

Medical Applications of Controlled Release, Langer and Wise, Eds. (1974) (27 pages).

Mitchell, P J et al. "Potentiation of the Time-Dependent, Antidepressant-induced Changes in the Agnostic Behaviour of Resident Rats by the 5-HT1A Receptor Antagonist, Way-1000365." Behavioral Pharmacology, Rapid Science Publishers. vol. 8, No. 6-7. Jan. 1, 1997. pp. 585-606.

Redrobe, J P et al. "Evidence of the Activity of Lithium on 5-HT1B Receptors in the Mouse Forced Simming Test: Comparison with Carbamazepine and Sodium Valprote." Psychopharmacology. vol. 141, No. 4, Feb. 1999. pp. 370-377.

Robbins, "The 5-Choice Serial Reaction Time Task: Behavioural Pharmacology and Functional Neurochemistry", Psychopharmacology, 163:362-380 (2002).

Romero, Luz et al. "The 5-HT-1A Antagonist Way-100365 Selectively Potentiates the Presynaptic Effects of Serotonergic Antidepressants in Rat Brain." Neuroscience Letters. vol. 219, No. 2, 1996, pp. 123-126.

Salvadori, "Radiopharmaceuticals, Drug Development and Pharmaceutical Regulations in Europe", Current Radiopharmaceuticals, 1:7-11 (2008).

Saudek, et al., "A Preliminary Trial of the Programmable Implantable Medication System for Insulin Delivery", New Engl. J. Med., 321:574-579 (1989).

Schiapparelli, et al. "Opposing Effects of AMPA and 5-HT1A Receptor Blockade on Passive Avoidance and Object Recognition Performance: Correlation with AMPA Receptor Subunit Expression in Rat Hippocampus." Neuropharmacology, Pergmon Press, Oxford. vol. 50, No. 7, Jun. 1, 2006, pp. 897-907.

Sefton, "Implantable Pumps", CRC Crit. Ref. Biomed. Eng., 14(3):201-240 (1987).

Sharp, T. et al. "Effects of Co-Administration of a Monoamine Oxidase Inhibitor and a 5-ht1a Receptor Antagonist on 5-Hydroxytryptamine Cell Firing and Release." *European Journal of Pharmacology.* Amsterdam, NL. vol. 320, 1997, pp. 15-19.

Skraup, "Eine Syntheses Des Chinolins.", Monatsh., 1, pp. 316-318 (1880).

Thompson, et al., "7-Chloro-3methyl-3,4-dihydro-2H-1,2,4-benzothiadiazine S,S-dioxide (IDRA 21), a Congener of Aniracetam, Potently Abates Pharmacologically Induced Cognitive Impairments in Patas Monkeys", Proc. Natl. Acad. Sci. USA, 92:7667-7671 (1995).

Trillant, Anne-Cecile et al. " Synergistic Neurochemical and Behavioural Effects of Fluoxetine and 5-HT1A Receptor Antagonists." European Journal of Pharmacology. vol. 357, No. 2-3, Sep. 18, 1998, pp. 179-183.

Winter, J C et al. "The Discrminative Stimulus Effects of KA 672, a Putative Cognitive Enhancer: Evidence for a 5-ht1a Component." *Pharmacology Biochemistry and Behavoior*. Elsevier, US. vol. 60, No. 3, 1998, pp. 703-707.

Yamada, et al., "Benzothiadiazides Inhibit Rapid Glutamate Receptor Desensitization and Enhance Glutamatergic Synaptic Currents", J. Neurosc., 13:3904-3915 (1993).

Zivkovic, et al., "7-Chloro-3-Methyl-3-4-Dihydro-2H-1,2,4 Benzothiadiazine S,S-Dioxide (IDRA21): A Benzothiadiazine Derivative that Enhances Cognition by Attenuating DL-$\alpha$-Amino-2,3-Dihydro-5-Methyl-3-Oxo-4-IsoxazolepropanoicAcid (AMPA) Receptor Desensitization", J. Pharmacol. Exp. Therap., 272:300-309 (1995).

PIPERAZINE-PIPERIDINE ANTAGONISTS AND AGONISTS OF THE 5-HT$_{1A}$ RECEPTOR

Throughout this application, various publications are referenced. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure, as it appears in the U.S. Patent and Trademark Office patent file or records, but otherwise reserves any and all copyright rights whatsoever.

FIELD OF THE INVENTION

The present invention relates to novel piperazine-piperidine compounds. The compounds are useful as 5-HT$_{1A}$ binding agents, particularly as 5-HT$_{1A}$ receptor antagonists and agonists. These compounds are useful in treating central nervous system disorders, such as cognition disorders, anxiety disorders, and depression.

BACKGROUND OF THE INVENTION

Certain N-aryl-piperazine derivatives possess pharmaceutical activity. In particular, certain N-aryl piperazine derivatives act on the central nervous system (CNS) by binding to 5-HT receptors. In pharmacological testing, it has been shown that the certain N-aryl-piperazine derivatives bind to receptors of the 5-HT$_{1A}$ type. Many of the N-aryl piperazine derivatives exhibit activity as 5-HT$_{1A}$ antagonists. See, for example, W. C. Childers, et al., *J. Med. Chem.*, 48: 3467-3470 (2005), U.S. Pat. Nos. 6,465,482, 6,127,357, 6,469,007, and 6,586,436, and PCT Publication No. WO 97/03982, the disclosures of which are incorporated herein by reference.

Pharmaceutical compounds that interact with the 5-HT$_{1A}$ receptor are useful to treat a wide variety of central nervous system disorders, such as cognition disorders, anxiety disorders, and depression. The present invention is directed to novel 5-HT$_{1A}$ antagonists and agonists, which would be useful for these and other uses.

SUMMARY OF THE INVENTION

In one aspect, the invention provides compounds of the Formula (I):

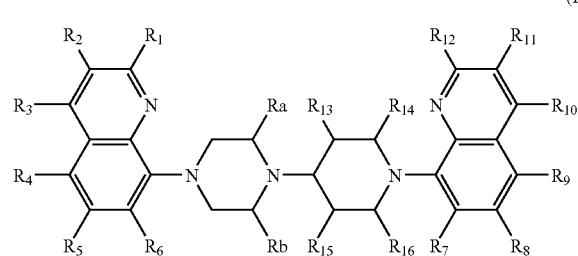

(I)

and pharmaceutically acceptable salts thereof, wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$, are each independently —H, $(C_1-C_6)$-alkyl, $(C_1-C_6)$-haloalkyl, $(C_2-C_6)$-alkenyl, or $(C_2-C_6)$-alkynyl, halogen, —CF$_3$, —NO$_2$, —CN, —OR$_{25}$, —OSO$_2$R$_{25}$, —SR$_{25}$, —SO$_2$R$_{25}$, —SO$_2$N(R$_{25}$)$_2$, —N(R$_{25}$)$_2$, C(O), —COR$_{25}$, —CO$_2$R$_{25}$, —NR$_{25}$CO$_2$R$_{25}$, —NR$_{25}$COR$_{25}$, —NR$_{25}$CON(R$_{25}$)$_2$, or —CON(R$_{25}$)$_2$;

$R_a$ and $R_b$ are each independently —H or —CH$_3$; and $R_{25}$ is —H, linear or branched $(C_1-C_6)$-alkyl, $(C_1-C_6)$-haloalkyl, $(C_2-C_6)$-alkenyl, or $(C_2-C_6)$-alkynyl.

In another aspect, the invention provides compounds of the Formula (I'):

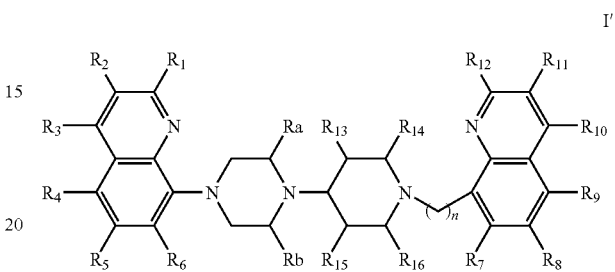

I' and pharmaceutically acceptable salts thereof, wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$, are each independently —H, $(C_1-C_6)$-alkyl, $(C_1-C_6)$-haloalkyl, $(C_2-C_6)$-alkenyl, or $(C_2-C_6)$-alkynyl, halogen, —CF$_3$, —NO$_2$, —CN, —OR$_{25}$, —OSO$_2$R$_{25}$, —SR$_{25}$, —SO$_2$R$_{25}$, —SO$_2$N(R$_{25}$)$_2$, —N(R$_{25}$)$_2$, C(O), —COR$_{25}$, —CO$_2$R$_{25}$, —NR$_{25}$CO$_2$R$_{25}$, —NR$_{25}$COR$_{25}$, —NR$_{25}$CON(R$_{25}$)$_2$, or —CON(R$_{25}$)$_2$;

$R_a$ and $R_b$ are each independently —H or —CH$_3$; and $R_{25}$ is —H, linear or branched $(C_1-C_6)$-alkyl, $(C_1-C_6)$-haloalkyl, $(C_2-C_6)$-alkenyl, or $(C_2-C_6)$-alkynyl; and where n is an integer from 1 to 2.

In another aspect, the invention provides compounds of the Formula (I"):

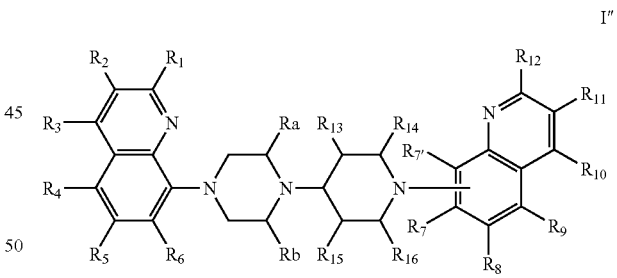

I"

and pharmaceutically acceptable salts thereof, wherein $R_1$, $R_2$, $R_3$, $R_4$, $R_5$, $R_6$, $R_7$, $R_{7'}$, $R_8$, $R_9$, $R_{10}$, $R_{11}$, $R_{12}$, $R_{13}$, $R_{14}$, $R_{15}$, and $R_{16}$, are each independently —H, $(C_1-C_6)$-alkyl, $(C_1-C_6)$-haloalkyl, $(C_2-C_6)$-alkenyl, or $(C_2-C_6)$-alkynyl, halogen, —CF$_3$, —NO$_2$, —CN, —OR$_{25}$, —OSO$_2$R$_{25}$, —SR$_{25}$, —SO$_2$R$_{25}$, —SO$_2$N(R$_{25}$)$_2$, —N(R$_{25}$)$_2$, C(O), —COR$_{25}$, —CO$_2$R$_{25}$, —NR$_{25}$CO$_2$R$_{25}$, —NR$_{25}$COR$_{25}$, NR$_{25}$CON(R$_{25}$)$_2$, or —CON(R$_{25}$)$_2$;

$R_a$ and $R_b$ are each independently —H or —CH$_3$;

$R_{25}$ is —H; or linear or branched $(C_1-C_6)$-alkyl, $(C_1-C_6)$-haloalkyl, $(C_2-C_6)$-alkenyl, or $(C_2-C_6)$-alkynyl and where the piperidine group can be attached to the nonhetero atom containing ring of the quinoline through positions $R_7$, $R_{7'}$, $R_8$, or $R_9$.

In another aspect, the invention provides compounds of the Formula (I″a):

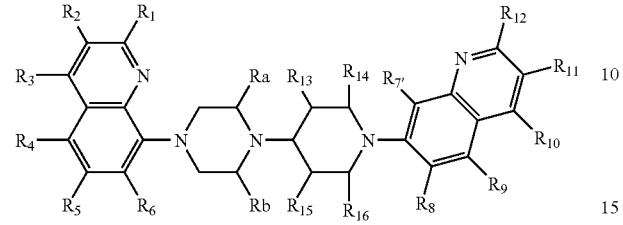

(I″a)

and pharmaceutically acceptable salts thereof,
wherein $R_1$, $R_2$, $R_3$, $R_4$, $R_5$, $R_6$, $R_{7'}$, $R_8$, $R_9$, $R_{10}$, $R_{11}$, $R_{12}$, $R_{13}$, $R_{14}$, $R_{15}$, and $R_{16}$, are each independently —H, $(C_1-C_6)$-alkyl, $(C_1-C_6)$-haloalkyl, $(C_2-C_6)$-alkenyl, or $(C_2-C_6)$-alkynyl, halogen, —$CF_3$, —$NO_2$, —CN, —$OR_{25}$, —$OSO_2R_{25}$, —$SR_{25}$, —$SO_2R_{25}$, —$SO_2N(R_{25})_2$, —$N(R_{25})_2$, —C(O), —$COR_{25}$, —$CO_2R_{25}$, —$NR_{25}CO_2R_{25}$, —$NR_{25}COR_{25}$, —$NR_{25}CON(R_{25})$, or —$CON(R_{25})_2$;

$R_a$ and $R_b$ are each independently —H or —$CH_3$; and $R_{25}$ is —H; or linear or branched $(C_1-C_6)$-alkyl, $(C_1-C_6)$-haloalkyl, $(C_2-C_6)$-alkenyl, or $(C_2-C_6)$-alkynyl.

In another aspect, the invention provides compounds of the Formula (II):

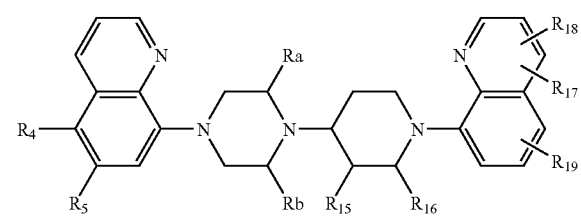

(II)

and pharmaceutically acceptable salts thereof,
wherein $R_4$, $R_5$, $R_{15}$, $R_{16}$, $R_{17}$, $R_{18}$ and $R_{19}$ are each independently —H, $(C_1-C_6)$-alkyl, $(C_1-C_6)$-haloalkyl, $(C_2-C_6)$-alkenyl, or $(C_2-C_6)$-alkynyl, halogen, —$CF_3$, —$NO_2$, —CN, —$OR_{25}$, —$OSO_2R_{25}$, —$SR_{25}$, —$SO_2R_{25}$, —$SO_2N(R_{25})_2$, —$N(R_{25})_2$, C(O), —$COR_{25}$, —$CO_2R_{25}$, —$NR_{25}CO_2R_{25}$, —$NR_{25}COR_{25}$, —$NR_{25}CON(R_{25})_2$, or —$CON(R_{25})_2$;

$R_a$ and P are each independently —H or —$CH_3$;

$R_{25}$ is —H; or linear or branched $(C_1-C_6)$-alkyl, $(C_1-C_6)$-haloalkyl, $(C_2-C_6)$-alkenyl, or $(C_2-C_6)$-alkynyl; and $R_4$ and $R_5$ cannot both be hydrogen.

In a further aspect, the invention provides compounds of the Formula (III):

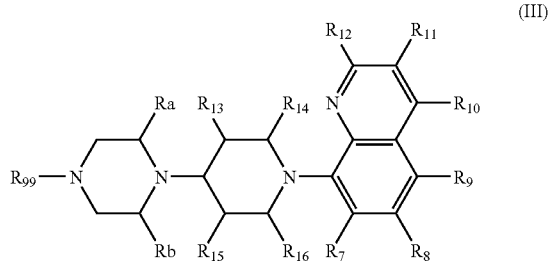

(III)

and pharmaceutically acceptable salts thereof,
wherein $R_{99}$ is selected from:

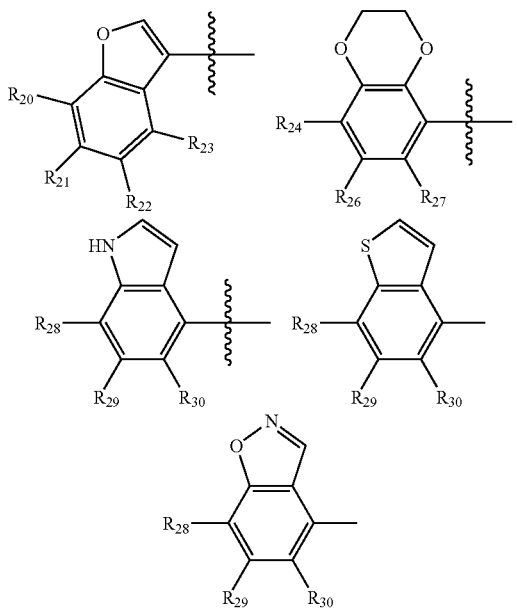

and wherein
$R_7$, $R_8$, $R_9$, $R_{10}$, $R_{11}$, $R_{12}$, $R_{13}$, $R_{14}$, $R_{15}$, $R_{16}$, $R_{20}$, $R_{21}$, $R_{22}$, $R_{23}$, $R_{24}$, $R_{26}$, $R_{27}$, $R_{28}$, $R_{29}$, and $R_{30}$ are each independently —H, $(C_1-C_6)$-alkyl, $(C_1-C_6)$-haloalkyl, $(C_2-C_6)$-alkenyl, or $(C_2-C_6)$ alkynyl, halogen, —$CF_3$, —$NO_2$, —CN, —$OR_{25}$, —$OSO_2R_{25}$, —$SR_{25}$, —$SO_2R_{25}$, —$SO_2N(R_{25})_2$, —$N(R_{25})_2$, C(O), —$COR_{25}$, —$CO_2R_{25}$, —$NR_{25}CO_2R_{25}$, —$NR_{25}COR_{25}$, —$NR_{25}CON(R_{25})_2$, or —$CON(R_{25})_2$;

$R_a$ and $R_b$ are each independently —H or —$CH_3$;

$R_{25}$ is —H; or linear or branched $(C_1-C_6)$-alkyl, $(C_1-C_6)$-haloalkyl, $(C_2-C_6)$-alkenyl, or $(C_2-C_6)$-alkynyl.

In yet another aspect, the invention provides compounds of the Formula (IV):

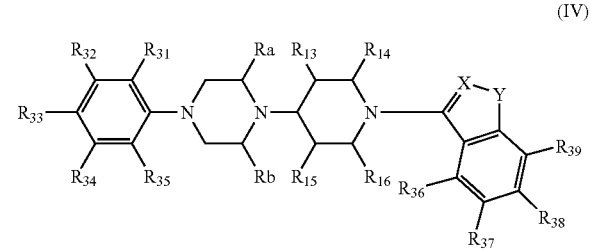

(IV)

and pharmaceutically acceptable salts thereof,
wherein X is $CR_{25}$, N, O or S; Y is $CR_{25}$, $NR_{25}$, O or S; with the proviso that when X is $CR_{25}$, Y is not N;

$R_{13}$, $R_{14}$, $R_{15}$, $R_{16}$, $R_{31}$, $R_{32}$, $R_{33}$, $R_{34}$, $R_{35}$, $R_{36}$, $R_{37}$, $R_{38}$ and $R_{39}$ are each independently —H, $(C_1\text{-}C_6)$-alkyl, $(C_1\text{-}C_6)$-haloalkyl, $(C_2\text{-}C_6)$-alkenyl, or $(C_2\text{-}C_6)$alkynyl, halogen, —$CF_3$, —$NO_2$, —CN, —$OR_{25}$, —$OSO_2R_{25}$, —$SR_{25}$, —$SO_2R_{25}$, —$SO_2N(R_{25})_2$, —$N(R_{25})_2$, C(O), —$COR_{25}$, —$CO_2R_{25}$, —$NR_{25}CO_2R_{25}$, —$NR_{25}COR_{25}$, —$NR_{25}CON(R_{25})_2$, or —$CON(R_{25})_2$;

$R_a$ and $R_b$ are each independently —H or —$CH_3$; and $R_{25}$ is —H; or linear or branched $(C_1\text{-}C_6)$-alkyl, $(C_1\text{-}C_6)$-haloalkyl, $(C_2\text{-}C_6)$-alkenyl, or $(C_2\text{-}C_6)$-alkynyl.

In another aspect, the compounds and pharmaceutically acceptable salts of the compounds of Formulas (I), (I'), (I"), (I"a), (II), (III), and (IV) are also useful when formulated as pharmaceutical compositions. These pharmaceutical compositions comprise compounds and pharmaceutically acceptable salts of the compounds of Formulas (I), (I'), (I"), (II), (III), or (IV) and a pharmaceutically acceptable carrier.

In another aspect, the compounds and pharmaceutically acceptable salts of the compounds of Formulas (I), (II), (I"), (I"a), (II), (III), and (IV) are useful as 5-$HT_{1A}$ receptor agonists and antagonists.

In another aspect, the pharmaceutical compositions comprising one or more compounds and pharmaceutically acceptable salts of the compounds of Formulas (I), (I'), (I"), (I"a), (II), (III), or (IV) are useful as 5-$HT_{1A}$ receptor agonists and antagonists.

In one aspect, the invention provides methods for treating a 5-$HT_{1A}$-related disorder, comprising administering to a patient in need thereof one or more of the compounds or pharmaceutically acceptable salts of compounds of Formulas (I), (I'), (I"), (I"a), (II), (III), and (IV) in a therapeutically effective amount to treat a 5-$HT_{1A}$-related disorder.

In one aspect, the invention provides methods for treating a 5-$HT_{1A}$-related disorder, comprising administering to a patient in need thereof a pharmaceutical formulation comprising one or more of the compounds or pharmaceutically acceptable salts of compounds of Formulas (I), (I'), (I"), (I"a), (II), (III), and (IV) in a therapeutically effective amount to treat a 5-$HT_{1A}$-related disorder.

In one aspect, the invention provides methods for treating a cognition-related disorder, comprising administering to a patient in need thereof one or more of the compounds or pharmaceutically acceptable salts of compounds of Formulas (I), (I'), (I"), (I"a), (II), (III), and (IV) in a therapeutically effective amount to treat a cognition-related disorder.

In one aspect, the invention provides methods for treating a cognition-related disorder, comprising administering to a patient in need thereof a pharmaceutical formulation comprising one or more of the compounds or pharmaceutically acceptable salts of compounds of Formulas (I), (I'), (I"), (I"a), (II), (III), and (IV) in an amount effective to treat a cognition-related disorder.

In another aspect, the invention provides methods for treating an anxiety-related disorder, comprising administering to a patient in need thereof one or more of the compounds or pharmaceutically acceptable salts of compound of Formulas (I), (I'), (I"), (I"a), (II), (III), and (IV) in an amount effective to treat an anxiety-related disorder.

In another aspect, the invention provides methods for treating an anxiety-related disorder, comprising administering to a patient in need thereof a pharmaceutical formulation comprising one or more of the compounds or pharmaceutically acceptable salts of compound of Formulas (I), (I'), (I"), (I"a), (II), (III), and (IV) in an amount effective to treat an anxiety-related disorder.

In one aspect, the invention provides methods for treating Alzheimer's disease to a patient in need thereof. The method includes administering to the patient an effective amount of a compound or a pharmaceutically acceptable salt of a compound of Formula (I), Formula (I'), Formula (I"), Formula (I"a), Formula (II), Formula (III), or Formula (IV). In one embodiment, the method includes administering to the patient a pharmaceutical composition comprising one or more of the compounds or pharmaceutically acceptable salts of compounds of Formulas (I), (I'), (I"), (I"a), (II), (III), and (IV) in an amount effective to treat Alzheimer's disease.

In one aspect, the invention provides methods for treating mild cognitive impairment (MCI) to a patient in need thereof. The method includes administering to the patient an effective amount of a compound or a pharmaceutically acceptable salt of a compound of Formula (I), Formula (I'), Formula (I"), Formula (I"a), Formula (II), Formula (III), or Formula (IV). In one embodiment, the method includes administering to the patient a pharmaceutical composition comprising one or more of the compounds or pharmaceutically acceptable salts of compounds of Formulas (I), (I'), (I"), (I"a), (II), (III), and (IV) in an amount effective to treat mild cognitive impairment.

In one aspect, the invention provides methods for treating depression to a patient in need thereof. The method includes administering to the patient an effective amount of a compound or a pharmaceutically acceptable salt of a compound of Formula (I), Formula (I'), Formula (I"), Formula (I"a), Formula (II), Formula (III), or Formula (IV). In one embodiment, the method includes administering to the patient a pharmaceutical composition comprising one or more of the compounds or pharmaceutically acceptable salts of compounds of Formulas (I), (I'), (I"), (I"a), (II), (III), and (IV) in an amount effective to treat depression.

In one aspect, the treatment methods of the invention include administering a second therapeutic agent.

In one aspect, the invention provides methods for treating sexual dysfunction associated with drug treatment in a patient in need thereof. The method includes administering to the patient an effective amount of a compound or a pharmaceutically acceptable salt of a compound of Formula (I), Formula (I'), Formula (I"), Formula (I"a), Formula (II), Formula (III), or Formula (IV). In one embodiment, the method includes administering to the patient a pharmaceutical composition comprising one or more of the compounds or pharmaceutically acceptable salts of compounds of Formulas (I), (I'), (I"), (I"a), (II), (III), and (IV) in an amount effective to treat sexual dysfunction.

In one aspect, the invention provides methods of improving sexual function in a patient in need thereof, the method comprising administering to the patient a pharmaceutically effective amount of a compound or a pharmaceutically acceptable salt of a compound of Formula (I), Formula (I'), Formula (I"), Formula (I"a), Formula (II), Formula (III), or Formula (IV). In one embodiment, the method includes administering to the patient a pharmaceutical composition comprising one or more of the compounds or pharmaceutically acceptable salts of compounds of Formulas (I), (I'), (I"), (I"a), (II), (III), and (IV) in an amount effective to improve sexual function.

In one aspect, the invention provides methods of synthesizing the compounds and pharmaceutically acceptable salts of compounds of Formulas (I), (I'), (I"), (I"a), (II), (III), and (IV).

In another aspect, the invention provides compounds and pharmaceutically acceptable salts of compounds of Formulas (I), (I'), (I"), (I"a), (II), (III), and (IV) made by particular processes.

DETAILED DESCRIPTION OF THE INVENTION

Definitions

The term "$(C_1-C_6)$-alkyl" as used herein refers to a linear or branched, saturated hydrocarbon having from 1 to 6 carbon atoms. Representative $(C_1-C_6)$-alkyl groups include, but are not limited to, methyl, ethyl, propyl, isopropyl, butyl, sec-butyl, tert-butyl, pentyl, isopentyl, neopentyl, hexyl, isohexyl, and neohexyl. In one embodiment, the $(C_1-C_6)$-alkyl group is optionally substituted with one or more of the following groups: halogen, —$N_3$, —$NO_2$, —CN, —OR', —SR', —$SO_2R'$, —$SO_2N(R')_2$, —$N(R')_2$, —COR', —$CO_2R'$, —NR'$CO_2R'$, —NR'COR', —NR'CONR', or —CON(R')$_2$, wherein each R' is independently hydrogen or unsubstituted $(C_1-C_6)$-alkyl.

The term "$(C_2-C_6)$-alkenyl" as used herein refers to a linear or branched hydrocarbon having from 2 to 6 carbon atoms and having at least one carbon-carbon double bond. In one embodiment, the $(C_2-C_6)$-alkenyl has one or two double bonds. The $(C_2-C_6)$-alkenyl moiety may exist in the E or Z conformation and the compounds of the present invention include both conformations. In one embodiment, the $(C_2-C_6)$-alkenyl group is optionally substituted with one or more of the following groups: halogen, —$N_3$, —$NO_2$, —CN, —OR', —SR', —$SO_2R'$, —$SO_2N(R')_2$, —$N(R')_2$, —COR', —$CO_2R'$, —NR'$CO_2R'$, —NR'COR', —NR'CONR', or —CON(R')$_2$, wherein each R' is independently hydrogen or unsubstituted $(C_1-C_6)$-alkyl.

The term "$(C_2-C_6)$-alkynyl" as used herein refers to a linear or branched hydrocarbon having from 2 to 6 carbon atoms and having at least one carbon-carbon triple bond. In one embodiment, the $(C_2-C_6)$-alkenyl group is optionally substituted with one or more of the following groups: halogen, —$N_3$, —$NO_2$, —CN, —OR', —SR', —$SO_2R'$, —$SO_2N(R')_2$, —$N(R')_2$, —COR', —$CO_2R'$, —NR'$CO_2R'$, —NR'COR', —NR'CONR', or —CON(R')$_2$, wherein each R' is independently hydrogen or unsubstituted $(C_1-C_6)$-alkyl.

"$(C_1-C_6)$-haloalkyl" refers to a $C_1-C_6$ alkyl group, as defined above, wherein one or more of the $C_1-C_6$ alkyl group's hydrogen atoms has been replaced with —F, —Cl, —Br or —I. Representative examples of an alkylhalo group include, but are not limited to, —$CH_2F$, —$CCl_3$, —$CF_3$, —$CH_2Cl$, —$CH_2CH_2Br$, —$CH_2CH_2I$, —$CH_2CH_2CH_2F$, —$CH_2CH_2CH_2Cl$, —$CH_2CH_2CH_2CH_2Br$, —$CH_2CH_2CH_2CH_2I$, —$CH_2CH_2CH_2CH_2CH_2Br$, —$CH_2CH_2CH_2CH_2CH_2I$, —$CH_2CH(Br)CH_3$, —$CH_2CH(Cl)CH_2CH_3$, —$CH(F)CH_2CH_3$, —$C(CH_3)_2(CH_2Cl)$, —$CH_2CH_2CH_2CH_2CH_2CH_2Br$, and —$CH_2CH_2CH_2CH_2CH_2CH_2I$.

The term "administer", "administering", or "administration", as used herein refers to either directly administering a compound or pharmaceutically acceptable salt of the compound or a composition to an animal, or administering a prodrug derivative or analog of the compound or pharmaceutically acceptable salt of the compound or composition to the animal, which can form an equivalent amount of active compound within the animal's body.

The term "animal" as used herein includes, without limitation, a human, mouse, rat, guinea pig, dog, cat, horse, cow, pig, monkey, chimpanzee, baboon, or rhesus. In one embodiment, the animal is a mammal. In another embodiment, the animal is a human.

The term "aryl" as used herein refers to an aromatic species containing 1 to 3 aromatic rings, either fused or linked. In one embodiment, the aryl group is optionally substituted with one or more of the following groups: —V-halogen, —V—$N_3$, —V—$NO_2$, —V—CN, —V—OR', —V—SR', —V—$SO_2R'$, —V—$SO_2N(R')_2$, —V—$N(R')_2$, —V—COR', —V—$CO_2R'$, —V—NR'$CO_2R'$, —V—NR'COR', —V—NR'CONR', or —V—CON(R')$_2$, wherein each R' is independently hydrogen or unsubstituted $(C_1-C_6)$-alkyl; and wherein each V is independently a bond or $(C_1-C_6)$-alkyl.

The term "conditions effective to" as used herein refers to synthetic reaction conditions which will be apparent to those skilled in the art of synthetic organic chemistry.

The term "cyclic group" as used herein includes a cycloalkyl group and a heterocyclic group. Any suitable ring position of the cyclic group may be covalently linked to the defined chemical structure. In one embodiment, the cyclic group is optionally substituted with one or more of the following groups: —V-halogen, —V—$N_3$, —V—$NO_2$, —V—CN, —V—OR', —V—SR', —V—$SO_2R'$, —V—$SO_2N(R')_2$, —V—$N(R')_2$, —V—COR', —V—$CO_2R'$, —V—NR'$CO_2R'$, —V—NR'COR', —V—NR'CONR', or —V—CON(R')$_2$, wherein each R' is independently hydrogen or unsubstituted $(C_1-C_6)$-alkyl; and wherein each V is independently a bond or $(C_1-C_6)$-alkyl.

The term "cycloalkyl group" as used herein refers to a three- to seven-membered saturated or partially unsaturated carbon ring. Any suitable ring position of the cycloalkyl group may be covalently linked to the defined chemical structure. Exemplary cycloalkyl groups include cyclopropyl, cyclobutyl, cyclopentyl, cyclohexyl, and cycloheptyl. In one embodiment, the cycloalkyl group is optionally substituted with one or more of the following groups: —V-halogen, —V—$N_3$, —V—$NO_2$, —V—CN, —V—OR', —V—SR', —V—$SO_2R'$, —V—$SO_2N(R')_2$, —V—$N(R')_2$, —V—COR', —V—$CO_2R'$, —V—NR'$CO_2R'$, —V—NR'COR', —V—NR'CONR', or —V—CON(R')$_2$, wherein each R' is independently hydrogen or unsubstituted $(C_1-C_6)$-alkyl; and wherein each V is independently a bond or $(C_1-C_6)$-alkyl.

The term "effective amount" as used herein refers to an amount of a compound or pharmaceutically acceptable salt of a compound that, when administered to an animal, is effective to prevent, to at least partially ameliorate, or to cure, a condition from which the animal suffers or is suspected to suffer.

The term "halogen" as used herein refers to fluorine, chlorine, bromine, and iodine.

The term "heterocyclic group" as used herein refers to a three- to seven-membered saturated, partially saturated, or unsaturated cycloalkyl group in which one to four of the ring carbon atoms have been independently replaced with a N, O, or S atom. Any suitable ring position of the heterocyclic group may be covalently linked to the defined chemical structure. Exemplary heterocyclic groups include, but are not limited to, azepanyl, azetidinyl, aziridinyl, furanyl, furazanyl, homopiperazinyl, imidazolidinyl, imidazolinyl, isothiazolyl, isoxazolyl, morpholinyl, oxadiazolyl, oxazolidinyl, oxazolyl, oxazolidinyl, pyrimidinyl, phenanthridinyl, phenanthrolinyl, piperazinyl, piperidinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyrimidinyl, pyrrolidinyl, pyrrolinyl, quinuclidinyl, tetrahydrofuranyl, thiadiazinyl, thiadiazolyl, thienyl, thienothiazolyl, thienooxazolyl, thienoimidazolyl, thiomorpholinyl, thiophenyl, triazinyl, and triazolyl. In one embodiment, the heterocyclic group is optionally substituted with one or more of the following groups: —V-halogen, —V—$N_3$, —V—$NO_2$, —V—CN, —V—OR', —V—SR', —V—$SO_2R'$, —V—$SO_2N(R')_2$, —V—N(R')$_2$, —V—COR', —V—CO$_2$R', —V—NR'CO$_2$R', —V—NR'COR', —V—NR'CONR', or —V—CON(R')$_2$, wherein each R' is independently hydrogen or unsubstituted (C$_1$-C$_6$)-alkyl; and wherein each V is independently a bond or (C$_1$-C$_6$)-alkyl.

The term "isolated and purified" as used herein refers to separate from other components of a reaction mixture or a natural source. In certain embodiments, the isolate contains at least about 50%, at least about 55%, at least about 60%, at least about 65%, at least about 70%, at least about 75%, at least about 80%, at least about 85%, at least about 90%, at least about 95%, or at least about 98% of the compound or pharmaceutically acceptable salt of the compound by weight of the isolate.

The term "pharmaceutically acceptable salt", as used herein, refers to salts derived from organic and inorganic acids of a compound of the present invention. Exemplary salts include, but are not limited to, sulfate, citrate, acetate, oxalate, chloride, hydrochloride, bromide, hydrobromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, succinate, fumarate, maleate, malonate, mandelate, malate, phthalate, and pamoate. The term "pharmaceutically acceptable salt" as used herein also refers to a salt of a compound of the present invention having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—(C$_1$-C$_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like. The term "pharmaceutically acceptable salt" also includes hydrates of a compound of the present invention.

The term "phenyl" as used herein refers to a substituted or unsubstituted phenyl group. In one embodiment, the phenyl group is optionally substituted with one or more of the following groups: —V-halogen, —V—N$_3$, —V—NO$_2$, —V—CN, —V—OR', —V—SR', —V—SO$_2$R', —V—SO$_2$N(R')$_2$, —V—N(R')$_2$, —V—COR', —V—CO$_2$R', —V—NR'CO$_2$R', —V—NR'COR', —V—NR'CONR', or —V—CON(R')$_2$, wherein each R' is independently hydrogen or unsubstituted (C$_1$-C$_6$)-alkyl; and wherein each V is independently a bond or (C$_1$-C$_6$)-alkyl.

The term "substantially free of its corresponding opposite enantiomer" as used herein means that the compound contains no more than about 10% by weight of its corresponding opposite enantiomer. In other embodiments, the compound that is substantially free of its corresponding opposite enantiomer contains no more than about 5%, no more than about 1%, no more than about 0.5%, or no more than about 0.1% by weight of its corresponding opposite enantiomer. An enantiomer that is substantially free of its corresponding opposite enantiomer includes a compound that has been isolated and purified or has been prepared substantially free of its corresponding opposite enantiomer.

The term "5-HT$_{1A}$-related disorder" as used herein refers to a condition which is mediated through the 5-HT$_{1A}$ receptor. In some embodiments, a 5-HT$_{1A}$-related disorder is a condition for which it would be beneficial to prevent activation of the 5-HT$_{1A}$ receptor. In other embodiments, a 5-HT$_{1A}$-related disorder is a condition for which it would be beneficial to activate the 5-HT$_{1A}$ receptor. In one embodiment, a 5-HT$_{1A}$-related disorder affects the central nervous system (i.e., a CNS-related disorder). Exemplary 5-HT$_{1A}$-related disorders include, without limitation, depression, single episodic or recurrent major depressive disorders, dysthymic disorders, depressive neurosis and neurotic depression, melancholic depression including anorexia, weight loss, insomnia, early morning waking or psychomotor retardation; atypical depression (or reactive depression) including increased appetite, hypersomnia, psychomotor agitation or irritability, seasonal affective disorder, pediatric depression, child abuse induced depression and postpartum depression; bipolar disorders or manic depression, for example, bipolar I disorder, bipolar II disorder and cyclothymic disorder; conduct disorder; disruptive behavior disorder; disorders of attention and learning such as attention deficit hyperactivity disorder (ADHD) and dyslexia; behavioral disturbances associated with mental retardation, autistic disorder, pervasive development disorder and conduct disorder; anxiety disorders such as panic disorder with or without agoraphobia, agoraphobia without history of panic disorder, specific phobias, for example, specific animal phobias, social anxiety, social phobia, obsessive-compulsive disorder, stress disorders including post-traumatic stress disorder and acute stress disorder, and generalized anxiety disorders; borderline personality disorder; schizophrenia and other psychotic disorders, for example, schizophreniform disorders, schizoaffective disorders, delusional disorders, brief psychotic disorders, shared psychotic disorders, psychotic disorders with delusions or hallucinations, psychotic episodes of anxiety, anxiety associated with psychosis, psychotic mood disorders such as severe major depressive disorder; mood disorders associated with psychotic disorders such as acute mania and depression associated with bipolar disorder; mood disorders associated with schizophrenia, substance-induced psychotic disorder, shared psychotic disorder, and psychotic disorder due to a general medical condition; delirium, dementia, and amnestic and other cognitive or neurodegenerative disorders, such as Parkinson's disease (PD), Huntington's disease (HD), Alzheimer's disease, senile dementia, dementia of the Alzheimer's type, mild cognitive impairment (MCI), memory disorders, loss of executive function, vascular dementia, and other dementias, for example, due to HIV disease, head trauma, Parkinson's disease, Huntington's disease, Pick's disease, Creutzfeldt-Jakob disease, or due to multiple etiologies; cognitive deficits associated with neurological conditions including, for example, Parkinson's disease (PD), Huntington's disease (HD), Alzheimer's disease; movement disorders such as akinesias, dyskinesias, including familial paroxysmal dyskinesias, spasticities, Tourette's syndrome, Scott syndrome, PALSYS and akinetic-rigid syndrome; extra-pyramidal movement disorders such as medication-induced movement disorders, for example, neuroleptic-induced Parkinsonism, neuroleptic malignant syndrome, neuroleptic-induced acute dystonia, neuroleptic-induced acute akathisia, neuroleptic-induced tardive dyskinesia and medication-induced postural tremor; chemical dependencies and addictions (e.g., dependencies on, or addictions to, alcohol, heroin, cocaine, benzodiazepines, nicotine, or phenobarbitol); behavioral addictions such as an addiction to gambling; and ocular disorders such as glaucoma and ischemic retinopathy; sexual dysfunction associated with drug treatment (e.g., sexual dysfunction associated with SSRI's).

One nonlimiting example of a 5-HT$_{1A}$-related disorder is a cognition-related disorder (e.g., cognitive dysfunction). Exemplary cognition-related disorders include, without limitation, mild cognitive impairment (MCI), dementia, delirium, amnestic disorder, Alzheimer's disease, Parkinson's disease, Huntington's disease, memory disorders including memory deficits associated with depression, senile dementia, dementia of Alzheimer's disease, cognitive deficits or cognitive dysfunction associated with neurological conditions including, for example, Parkinson's disease (PD), Huntington's disease (HD), Alzheimer's disease, depression and schizophrenia (and other psychotic disorders such as paranoia and mano-depressive illness); cognitive dysfunction in schizophrenia, disorders of attention and learning such as attention deficit disorders (e.g., attention deficit hyperactivity disorder (ADHD)) and dyslexia, cognitive dysfunction associated with developmental disorders such as Down's syndrome and Fragile X syndrome, loss of executive function, loss of learned information, vascular dementia, schizophrenia, cognitive decline, neurodegenerative disorder, and other dementias, for example, due to HIV disease, head trauma, Parkinson's disease, Huntington's disease, Pick's disease, Creutzfeldt-Jakob disease, or due to multiple etiologies. Cognition-related disorders also include, without limitation, cognitive dysfunction associated with MCI and dementias such as Lewy Body, vascular, and post stroke dementias. Cognitive dysfunction associated with surgical procedures, traumatic brain injury or stroke may also be treated in accordance with the present invention.

Another nonlimiting example of a 5-HT$_{1A}$-related disorder is an anxiety-related disorder. Exemplary anxiety-related disorders include, without limitation, generalized anxiety disorder, attention deficit disorder, attention deficit hyperactivity disorder, obsessive compulsive disorder, substance addiction, withdrawal from drug, alcohol or nicotine addiction, panic disorder, panic attacks, post-traumatic stress disorder, premenstrual dysphoric disorder, social anxiety disorder, eating disorders such as anorexia nervosa and bulimia nervosa, vasomotor flushing, and phobias, including social phobia, agoraphobia, and specific phobias. Substance addition includes, without limitation, drug, alcohol or nicotine addiction.

Compounds of the Invention

In one embodiment, the present invention is directed to compounds of the Formula (I):

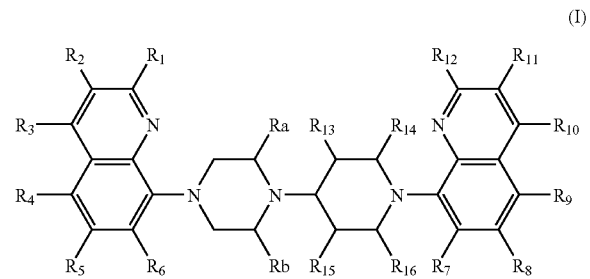

(I)

and pharmaceutically acceptable salts thereof, wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$, are each independently —H, $(C_1-C_6)$-alkyl, $(C_1-C_6)$-haloalkyl, $(C_2-C_6)$-alkenyl, or $(C_2-C_6)$-alkynyl, halogen, —CF$_3$, —NO$_2$, —CN, —OR$_{25}$, —OSO$_2$R$_{25}$, —SR$_{25}$, —SO$_2$R$_{25}$, —SO$_2$N(R$_{25}$)$_2$, —N(R$_{25}$)$_2$, —C(O), —COR$_{25}$, —CO$_2$R$_{25}$, —NR$_{25}$CO$_2$R$_{25}$, —NR$_{25}$COR$_{25}$, —NR$_{25}$CON(R$_{25}$)$_2$, or —CON(R$_{25}$)$_2$;

$R_a$ and $R_b$ are each independently —H or —CH$_3$; and $R_{25}$ is —H; or linear or branched $(C_1-C_6)$-alkyl, $(C_1-C_6)$-haloalkyl, $(C_2-C_6)$-alkenyl, or $(C_2-C_6)$-alkynyl.

In one embodiment, $R_1$ is —H, $(C_1-C_6)$-alkyl, —OR$_{25}$, halogen, or —CF$_3$. In another embodiment, $R_1$ is —H, $(C_1-C_6)$-alkyl, —OR$_{25}$, halogen, or —CF$_3$ and one of $R_{13}$, $R_{14}$, $R_{15}$, and $R_{16}$ is —H, $(C_1-C_6)$-alkyl, —OR$_{25}$, or halogen. In a further embodiment, $R_1$ is —H, $(C_1-C_6)$-alkyl, —OR$_{25}$, halogen, or —CF$_3$; one of $R_{13}$, $R_{14}$, $R_{15}$, and $R_{16}$ is —H, $(C_1-C_6)$-alkyl, —OR$_{25}$, or halogen, and $R_7$, $R_8$, $R_9$, $R_{10}$, $R_{11}$, and $R_{12}$ are each hydrogen. In yet another embodiment, $R_1$ is —H, $(C_1-C_6)$-alkyl, —OR$_{25}$, halogen, or —CF$_3$; one of $R_{13}$, $R_{14}$, $R_{15}$, and $R_{16}$ is —H, $(C_1-C_6)$-alkyl, —OR$_{25}$, or halogen, and $R_2$, $R_3$, $R_4$, $R_5$, $R_6$, $R_7$, $R_8$, $R_9$, $R_{10}$, $R_{11}$, and $R_{12}$ are each hydrogen. In one embodiment, $R_1$ is —H, $(C_1-C_6)$-alkyl, —OR$_{25}$, halogen or —CF$_3$ and $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ are each hydrogen.

In one embodiment, $R_4$ is —H, $(C_1-C_6)$-alkyl, —OR$_{25}$, halogen, or —CF$_3$. In another embodiment, $R_4$ is —H, $(C_1-C_6)$-alkyl, —OR$_{25}$, halogen, or —CF$_3$ and one of $R_{13}$, $R_{14}$, $R_{15}$, and $R_{16}$ is —H, $(C_1-C_6)$-alkyl, —OR$_{25}$, or halogen. In a further embodiment, $R_4$ is —H, $(C_1-C_6)$-alkyl, —OR$_{25}$, halogen, or —CF$_3$; one of $R_{13}$, $R_{14}$, $R_{15}$, and $R_{16}$ is —H, $(C_1-C_6)$-alkyl, —OR$_{25}$, or halogen, and $R_7$, $R_8$, $R_9$, $R_{10}$, $R_{11}$, and $R_{12}$ are each hydrogen. In yet another embodiment, $R_4$ is —H, $(C_1-C_6)$-alkyl, —OR$_{25}$, halogen, or —CF$_3$; one of $R_{13}$, $R_{14}$, $R_{15}$, and $R_{16}$ is —H, $(C_1-C_6)$-alkyl, —OR$_{25}$, or halogen, and $R_1$, $R_2$, $R_3$, $R_5$, $R_6$, $R_7$, $R_8$, $R_9$, $R_{10}$, $R_{11}$, and $R_{12}$ are each hydrogen. In one embodiment, $R_4$ is —H, $(C_1-C_6)$-alkyl, —OR$_{25}$, halogen or —CF$_3$ and $R_1$, $R_2$, $R_3$, $R_5$, $R_6$, $R_7$, $R_8$, $R_9$, $R_{10}$, $R_{11}$, $R_{12}$, $R_{13}$, $R_{14}$, $R_{15}$, and $R_{16}$ are each hydrogen.

In one embodiment, $R_5$ is —H, $(C_1-C_6)$-alkyl, —OR$_{25}$, halogen, or —CF$_3$. In another embodiment, $R_5$ is —H, $(C_1-C_6)$-alkyl, —OR$_{25}$, halogen, or —CF$_3$ and one of $R_{13}$, $R_{14}$, $R_{15}$, and $R_{16}$ is —H, $(C_1-C_6)$-alkyl, —OR$_{25}$, or halogen. In a further embodiment, $R_5$ is —H, $(C_1-C_6)$-alkyl, —OR$_{25}$, halogen, or —CF$_3$; one of $R_{13}$, $R_{14}$, $R_{15}$, and $R_{16}$ is —H, $(C_1-C_6)$-alkyl, —OR$_{25}$, or halogen, and $R_7$, $R_8$, $R_9$, $R_{10}$, $R_{11}$, and $R_{12}$ are each hydrogen. In yet another embodiment, $R_5$ is —H, $(C_1-C_6)$-alkyl, —OR$_{25}$, halogen, or —CF$_3$; one of $R_{13}$, $R_{14}$, $R_{15}$, and $R_{16}$ is —H, $(C_1-C_6)$-alkyl, —OR$_{25}$, or halogen; and $R_1$, $R_2$, $R_3$, $R_4$, $R_6$, $R_7$, $R_8$, $R_9$, $R_{10}$, $R_{11}$, and $R_{12}$ are each hydrogen. In one embodiment, $R_5$ is —H, $(C_1-C_6)$-alkyl, —OR$_{25}$, halogen or —CF$_3$ and $R_1$, $R_2$, $R_3$, $R_4$, $R_6$, $R_7$, $R_8$, $R_9$, $R_{10}$, $R_{11}$, $R_{12}$, $R_{13}$, $R_{14}$, $R_{15}$, and $R_{16}$ are each hydrogen. In a further embodiment, one of $R_{13}$, $R_{14}$, $R_{15}$, and $R_{16}$ is —H, $(C_1-C_6)$-alkyl, halogen, —CF$_3$, or —OR$_{25}$; $R_5$ is —H, $(C_1-C_6)$-alkyl, —OR$_{25}$, halogen, or —CF$_3$; and the remaining R groups are each hydrogen.

In one embodiment, $R_8$ is —H, $(C_1-C_6)$-alkyl, —OR$_{25}$, halogen, —CF$_3$, —NO$_2$ or —CN. In another embodiment, $R_8$ is —H, $(C_1-C_6)$-alkyl, —OR$_{25}$, halogen, —CF$_3$, —NO$_2$ or —CN; one of $R_1$, $R_2$, $R_3$, $R_4$, $R_5$ and $R_6$ is —H, $(C_1-C_6)$-alkyl, —OR$_{25}$, halogen, or —CF$_3$; $R_a$ and $R_b$ are each independently —H or —CH$_3$; and each remaining R group is hydrogen. In a further embodiment, $R_8$ is —H, $(C_1-C_6)$-alkyl, —OR$_{25}$, halogen, —CF$_3$, —NO$_2$ or —CN; one of $R_1$, $R_2$, $R_3$, $R_4$, $R_5$ and $R_6$ is —H, $(C_1-C_6)$-alkyl, —OR$_{25}$, halogen, or —CF$_3$; one of $R_{13}$, $R_{14}$, $R_{15}$, and $R_{16}$ is —H, $(C_1-C_6)$-alkyl, —OR$_{25}$, or halogen, and each remaining R group is hydrogen. In one embodiment, $R_8$ is —H, $(C_1-C_6)$-alkyl, —OR$_{25}$, halogen, —CF$_3$, —NO$_2$ or —CN and one of $R_4$ or $R_5$ is —H, $(C_1-C_6)$-alkyl, —OR$_{25}$, halogen, or —CF$_3$, and each remaining R group is hydrogen. In one embodiment $R_8$ is —H, $(C_1$-$C_6)$-alkyl, —$OR_{25}$, halogen, —$CF_3$, —$NO_2$ or —CN; and all other R groups are each hydrogen. In one embodiment, $R_8$ is —H, $(C_1$-$C_6)$-alkyl, —$OR_{25}$, halogen, —$CF_3$, —$NO_2$ or —CN; one of $R_{13}$, $R_{14}$, $R_{15}$, and $R_{16}$ is —H, $(C_1$-$C_6)$-alkyl, —$OR_{25}$, or halogen, and each remaining R group is hydrogen.

In one embodiment, $R_9$ is —H, $(C_1$-$C_6)$-alkyl, —$OR_{25}$, halogen, —$CF_3$, —$NO_2$ or —CN. In another embodiment, $R_9$ is —H, $(C_1$-$C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1$-$C_6)$-alkyl, —$OR_{25}$, halogen, or —$CF_3$; and $R_a$ and $R_b$ are each independently —H or —$CH_3$; and each remaining R group is hydrogen. In a further embodiment, $R_9$ is —H, $(C_1$-$C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1$-$C_6)$-alkyl, —$OR_{25}$, halogen, or —$CF_3$; one of $R_{13}$, $R_{14}$, $R_{15}$, and $R_{16}$ is —H, $(C_1$-$C_6)$-alkyl, —$OR_{25}$, or halogen, and each remaining R group is hydrogen. In one embodiment, $R_9$ is —H, $(C_1$-$C_6)$-alkyl, —$OR_{25}$, halogen, —$CF_3$, —$NO_2$ or —CN and one of $R_4$ or $R_5$ is —H, $(C_1$-$C_6)$-alkyl, —$OR_{25}$, halogen, or —$CF_3$, and each remaining R group is hydrogen. In one embodiment $R_9$ is —H, $(C_1$-$C_6)$-alkyl, —$OR_{25}$, halogen, —$CF_3$, —$NO_2$ or —CN; and all other R groups are each hydrogen. In one embodiment, $R_9$ is —H, $(C_1$-$C_6)$-alkyl, —$OR_{25}$, halogen, —$CF_3$, —$NO_2$ or —CN; one of $R_{13}$, $R_{14}$, $R_{15}$, and $R_{16}$ is —H, $(C_1$-$C_6)$-alkyl, —$OR_{25}$, or halogen, and each remaining R group is hydrogen.

In one embodiment, $R_7$ is —H, $(C_1$-$C_6)$-alkyl, —$OR_{25}$, halogen, —$CF_3$, —$NO_2$ or —CN. In one embodiment, $R_7$ is —H, $(C_1$-$C_6)$-alkyl or halogen. In one embodiment, $R_7$ is $(C_1$-$C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1$-$C_6)$-alkyl, —$OR_{25}$, halogen, or —$CF_3$; and $R_a$ and $R_b$ are each independently —H or —$CH_3$; and each remaining R group is hydrogen. In one embodiment, $R_7$ is —H, $(C_1$-$C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1$-$C_6)$-alkyl, —$OR_{25}$, halogen, or —$CF_3$; and each remaining R group is hydrogen.

In one embodiment, $R_{10}$ is —H, $(C_1$-$C_6)$-alkyl, —$OR_{25}$, halogen, —$CF_3$, —$NO_2$ or —CN. In one embodiment, $R_{10}$ is —H, $(C_1$-$C_6)$-alkyl, —$OR_{25}$, halogen, or —$CF_3$. In one embodiment, $R_{10}$ is —H, —$CH_3$, —$OCH_3$, —F or —$CF_3$. In one embodiment, $R_{10}$ is —H, $(C_1$-$C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1$-$C_6)$-alkyl, —$OR_{25}$, halogen, or —$CF_3$; and $R_a$ and $R_b$ are each independently —H or —$CH_3$; and each remaining R group is hydrogen. In one embodiment, $R_{10}$ is —H, $(C_1$-$C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1$-$C_6)$-alkyl, —$OR_{25}$, halogen, or —$CF_3$; and each remaining R group is hydrogen.

In one embodiment, $R_{11}$ is —H, $(C_1$-$C_6)$-alkyl, —$OR_{25}$, halogen, —$CF_3$, —$NO_2$ or —CN. In one embodiment, $R_{11}$ is —H, $(C_1$-$C_6)$-alkyl, halogen, or —$CF_3$. In one embodiment, $R_{11}$ is —$CH_3$, —F or —$CF_3$. In one embodiment, $R_{11}$ is —H, $(C_1$-$C_6)$-alkyl, —$OR_{25}$, halogen, —$CF_3$, or —$NO_2$. In one embodiment, $R_1$ is —H, $(C_1$-$C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1$-$C_6)$-alkyl, —$OR_{25}$, halogen, or —$CF_3$; and $R_a$ and $R_b$ are each independently —H or —$CH_3$; and each remaining R group is hydrogen. In one embodiment, $R_{11}$ is —H, $(C_1$-$C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1$-$C_6)$-alkyl, —$OR_{25}$, halogen, or —$CF_3$; and each remaining R group is hydrogen.

In one embodiment, $R_{12}$ is —H, $(C_1$-$C_6)$-alkyl, —$OR_{25}$, halogen, —$CF_3$, —$NO_2$ or —CN. In one embodiment, $R_{12}$ is —H, $(C_1$-$C_6)$-alkyl, halogen, or —$CF_3$. In one embodiment, $R_{12}$ is —$CH_3$, —F or —$CF_3$. In one embodiment, $R_{12}$ is —H, $(C_1$-$C_6)$-alkyl, —$OR_{25}$, halogen, —$CF_3$, or —$NO_2$. In one embodiment, $R_{12}$ is —H, $(C_1$-$C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1$-$C_6)$-alkyl, —$OR_{25}$, halogen, or —$CF_3$; and $R_a$ and $R_b$ are each independently —H or —$CH_3$; and each remaining R group is hydrogen. In one embodiment, $R_{12}$ is —H, $(C_1$-$C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1$-$C_6)$-alkyl, —$OR_{25}$, halogen, or —$CF_3$; and each remaining R group is hydrogen.

In one embodiment, $R_5$ is —H, $(C_1$-$C_6)$-alkyl, —$OR_{25}$, halogen, or —$CF_3$ and one of $R_7$, $R_8$, $R_9$, $R_{10}$, $R_{11}$ and $R_{12}$ is —H, $(C_1$-$C_6)$-alkyl, —$OR_{25}$, halogen, —$CF_3$, —$NO_2$ or —CN. In another embodiment, $R_5$ is —H, $(C_1$-$C_6)$-alkyl, —$OR_{25}$, halogen, or —$CF_3$ and one of $R_7$, $R_8$, $R_9$, $R_{10}$, $R_{11}$, $R_{12}$ is —H, $(C_1$-$C_6)$-alkyl, —$OR_{25}$, halogen, —$CF_3$, —$NO_2$ or —CN; and each remaining R group is hydrogen. In some embodiments, $R_5$ is —H, $(C_1$-$C_6)$-alkyl, —$OR_{25}$, halogen, or —$CF_3$ and $R_9$ is —H, $(C_1$-$C_6)$-alkyl, —$OR_{25}$, halogen, —$CF_3$, —$NO_2$ or —CN; and each remaining R group is hydrogen. In one embodiment, $R_5$ is —$OR_{25}$ and one of $R_7$, $R_8$, $R_9$, $R_{10}$, $R_{11}$ and $R_{12}$ is —H, $(C_1$-$C_6)$-alkyl, —$OR_{25}$, halogen, —$CF_3$, —$NO_2$ or —CN. In one embodiment, $R_5$ is —$OR_{25}$ and $R_9$ is halogen. In one embodiment, $R_5$ is —$OR_{25}$ and $R_9$ is halogen and each remaining R group is hydrogen.

In a further embodiment, $R_5$ is —H, $(C_1$-$C_6)$-alkyl, —$OR_{25}$, halogen, or —$CF_3$; one of $R_7$, $R_8$, $R_9$, $R_{10}$, $R_{11}$, and $R_{12}$ is —H, $(C_1$-$C_6)$-alkyl, —$OR_{25}$, halogen, —$CF_3$, —$NO_2$ or —CN; one of $R_{13}$, $R_{14}$, $R_{15}$, and $R_{16}$ is —H, $(C_1$-$C_6)$-alkyl, —$OR_{25}$, or halogen, and each remaining R group is hydrogen.

In a further embodiment, $R_5$ is —H, $(C_1$-$C_6)$-alkyl, —$OR_{25}$, halogen, or —$CF_3$; two of $R_7$, $R_8$, $R_9$, $R_{10}$, $R_{11}$, and $R_{12}$ are each independently —H, $(C_1$-$C_6)$-alkyl, —$OR_{25}$, halogen, —$CF_3$, —$NO_2$ or —CN; one of $R_{13}$, $R_{14}$, $R_{15}$, and $R_{16}$ is —H, $(C_1$-$C_6)$-alkyl, —$OR_{25}$, or halogen, and each remaining R group is hydrogen.

In a further embodiment, $R_5$ is —H, $(C_1$-$C_6)$-alkyl, —$OR_{25}$, halogen, or —$CF_3$; three of $R_7$, $R_8$, $R_9$, $R_{10}$, $R_{11}$, and $R_{12}$ are each independently —H, $(C_1$-$C_6)$-alkyl, —$OR_{25}$, halogen, —$CF_3$, —$NO_2$ or —CN; one of $R_{13}$, $R_{14}$, $R_{15}$, and $R_{16}$ is —H, $(C_1$-$C_6)$-alkyl, —$OR_{25}$, or halogen, and each remaining R group is hydrogen.

In one embodiment, $R_5$ is —H, $(C_1$-$C_6)$-alkyl, —$OR_{25}$, halogen, or —$CF_3$; $R_9$ is —H, $(C_1$-$C_6)$-alkyl, —$OR_{25}$, halogen, —$CF_3$, —$NO_2$ or —CN; and two of $R_{10}$, $R_{11}$ and $R_{12}$ are each independently —H, $(C_1$-$C_6)$-alkyl, —$OR_{25}$, halogen, —$CF_3$, —$NO_2$ or —CN. In another embodiment, $R_5$ is —H, $(C_1$-$C_6)$-alkyl, —$OR_{25}$, halogen, or —$CF_3$; $R_9$ is —H, $(C_1$-$C_6)$-alkyl, —$OR_{25}$, halogen, —$CF_3$, —$NO_2$ or —CN; two of $R_{10}$, $R_{11}$, $R_{12}$ are each independently —H, $(C_1$-$C_6)$-alkyl, —$OR_{25}$, halogen, —$CF_3$, —$NO_2$ or —CN; and each remaining R group is hydrogen. In some embodiments, $R_5$ is —$OR_{25}$; $R_9$ is halogen; two of $R_{10}$, $R_{11}$, $R_{12}$ are each independently —H, $(C_1$-$C_6)$-alkyl, —$OR_{25}$, halogen, —$CF_3$, —$NO_2$ or —CN; and each remaining R group is hydrogen. In some embodiments, $R_5$ is —$OCH_3$; $R_9$ is halogen; two of $R_{10}$, $R_{11}$, $R_{12}$ are each independently —H, $(C_1$-$C_6)$-alkyl, —$OR_{25}$, halogen, —$CF_3$, —$NO_2$ or —CN; and each remaining R group is hydrogen.

In some embodiments, $R_5$ is —H, $(C_1$-$C_6)$-alkyl, —$OR_{25}$, halogen, or —$CF_3$; $R_9$ is —H, $(C_1$-$C_6)$-alkyl, —$OR_{25}$, halogen, —$CF_3$, —$NO_2$ or —CN; $R_{10}$ and $R_{12}$ are each independently —H, $(C_1-C_6)$-alkyl, —OR$_{25}$, halogen, —CF$_3$, —NO$_2$ or —CN; and each remaining R group is hydrogen. In some embodiments, R$_5$ is —H, $(C_1-C_6)$-alkyl, —OR$_{25}$, halogen, or —CF$_3$; R$_9$ is —H, $(C_1-C_6)$-alkyl, —OR$_{25}$, halogen, —CF$_3$, —NO$_2$ or —CN; R$_{10}$ and R$_1$ are each independently —H, $(C_1-C_6)$-alkyl, —OR$_{25}$, halogen, —CF$_3$, —NO$_2$ or —CN; and each remaining R group is hydrogen. In some embodiments, R$_5$ is —H, $(C_1-C_6)$-alkyl, —OR$_{25}$, halogen, or —CF$_3$; R$_9$ is —H, $(C_1-C_6)$-alkyl, —OR$_{25}$, halogen, —CF$_3$, —NO$_2$ or —CN; R$_{11}$ and R$_{12}$ are each independently —H, $(C_1-C_6)$-alkyl, —OR$_{25}$, halogen, —CF$_3$, —NO$_2$ or —CN; and each remaining R group is hydrogen.

In some embodiments, R$_5$ is —H or —OR$_{25}$, R$_9$ is —H or halogen, R$_{10}$ and R$_{12}$ are each independently, —H, halogen, or —CF$_3$; and each remaining R group is hydrogen.

In one embodiment, R$_4$ is —H, $(C_1-C_6)$-alkyl, —OR$_{25}$, halogen, or —CF$_3$ and one of R$_7$, R$_8$, R$_9$, R$_{10}$, R$_{11}$ and R$_{12}$ is —H, $(C_1-C_6)$-alkyl, —OR$_{25}$, halogen, —CF$_3$, —NO$_2$ or —CN. In another embodiment, R$_4$ is —H, $(C_1-C_6)$-alkyl, —OR$_{25}$, halogen, or —CF$_3$; one of R$_7$, R$_8$, R$_9$, R$_{10}$, R$_{11}$, and R$_{12}$ is —H, $(C_1-C_6)$-alkyl, —OR$_{25}$, halogen, —CF$_3$, —NO$_2$ or —CN; and each remaining R group is hydrogen. In a further embodiment, R$_4$ is —H, $(C_1-C_6)$-alkyl, —OR$_{25}$, halogen, or —CF$_3$; one of R$_7$, R$_8$, R$_9$, R$_{10}$, R$_{11}$; R$_{12}$ is —H, $(C_1-C_6)$-alkyl, —OR$_{25}$, halogen, —CF$_3$, —NO$_2$ or —CN; one of R$_{13}$, R$_{14}$, R$_{15}$, and R$_{16}$ is —H, $(C_1-C_6)$-alkyl, —OR$_{25}$, or halogen, and each remaining R group is hydrogen.

In one embodiment, one of R$_{13}$, R$_{14}$, R$_{15}$, and R$_{16}$ is —H, $(C_1-C_6)$-alkyl, halogen, —CF$_3$, or —OR$_{25}$.

In one embodiment, R$_1$, R$_2$, R$_3$, R$_6$, R$_7$, R$_8$, R$_9$, R$_{10}$, R$_{11}$, R$_{12}$, R$_{13}$, R$_{14}$, R$_{15}$, and R$_{16}$ are each hydrogen.

In one embodiment, R$_1$, R$_2$, R$_3$, R$_4$, R$_7$, R$_9$, R$_{10}$, R$_{11}$, and R$_{12}$ are each hydrogen.

In one embodiment, R$_1$, R$_2$, R$_3$, R$_4$, R$_7$, R$_8$, R$_{10}$, R$_{11}$, and R$_{12}$ are each hydrogen.

In one embodiment, R$_1$, R$_2$, R$_3$, R$_4$, R$_7$, R$_8$, R$_9$, R$_{11}$, and R$_{12}$ are each hydrogen.

In one embodiment, R$_1$, R$_2$, R$_3$, R$_4$, R$_7$, R$_8$, R$_9$, R$_{10}$, and R$_{12}$ are each hydrogen.

In one embodiment, R$_1$, R$_2$, R$_3$, R$_4$, R$_7$, R$_8$, R$_9$, R$_{10}$, and R$_{11}$ are each hydrogen.

In one embodiment, R$_1$, R$_2$, R$_3$, R$_4$, R$_7$, R$_8$, and R$_1$ are each hydrogen.

In one embodiment, R$_1$, R$_2$, R$_3$, R$_4$, R$_7$, R$_8$, R$_9$ and R$_1$ are each hydrogen.

In one embodiment, R$_1$, R$_2$, R$_3$, R$_4$, R$_5$, R$_6$, R$_7$, R$_8$, R$_9$, and R$_{12}$ are each hydrogen.

In another embodiment, R$_{13}$, R$_{14}$, R$_{15}$, and R$_{16}$ are each hydrogen.

In one embodiment, R$_3$, R$_6$, R$_7$, R$_8$, R$_9$, R$_{12}$, R$_{13}$, R$_{14}$, R$_{15}$, and R$_{16}$ are each hydrogen.

In one embodiment, R$_1$, R$_2$, R$_3$, R$_4$, R$_6$, R$_7$, R$_8$, and R$_{11}$ are each hydrogen.

In one embodiment, R$_1$, R$_2$, R$_3$, R$_4$, R$_6$, R$_7$, R$_8$, R$_{11}$, R$_{13}$, R$_{14}$, R$_{15}$, and R$_{16}$ are each hydrogen.

In one embodiment, R$_1$, R$_2$, R$_3$, R$_4$, R$_6$, R$_7$, R$_8$, R$_{10}$, R$_{11}$, R$_{12}$, R$_{13}$, R$_{14}$, R$_{15}$, and R$_{16}$ are each hydrogen.

In one embodiment, R$_1$, R$_2$, R$_3$, R$_4$, R$_6$, R$_7$, R$_8$, R$_9$, R$_{10}$, R$_{11}$ and R$_{12}$ are each hydrogen.

In one embodiment, R$_1$, R$_2$, R$_3$, R$_4$, R$_6$, R$_7$, R$_8$, R$_9$, R$_{10}$, R$_{11}$, R$_{12}$ R$_{13}$, R$_{14}$, R$_{15}$, and R$_{16}$ are each hydrogen.

In one embodiment, R$_1$ is —H, —CF$_3$ or $(C_1-C_6)$-alkyl; R$_4$ and R$_5$ are each —H, halogen, —OR$_{25}$, or —CF$_3$; R$_7$, R$_8$, R$_9$, R$_{10}$, R$_{11}$, and R$_{12}$ are each —H, halogen, -alkyl, —OR$_{25}$, —CF$_3$, or —NO$_2$; and R$_{16}$ is —H or —CH$_3$.

In one embodiment, any one of R$_1$, R$_2$, R$_3$, R$_4$, R$_5$, and R$_6$ is —H, $(C_1-C_6)$-alkyl, —OR$_{25}$, halogen or —CF$_3$; and any one of R$_7$, R$_8$, R$_9$, R$_{10}$, R$_{11}$, and R$_{12}$ is —H, $(C_1-C_6)$-alkyl, —OR$_{25}$, halogen, or —CF$_3$, —NO$_2$, or —CN.

In one embodiment, any one of R$_1$, R$_2$, R$_3$, R$_4$, R$_5$, and R$_6$ is —H, $(C_1-C_6)$-alkyl, —OR$_{25}$, halogen, —CF$_3$, —NO$_2$, or —CN; and any two of R$_7$, R$_8$, R$_9$, R$_{10}$, R$_{11}$, and R$_{12}$ are each independently —H, $(C_1-C_6)$-alkyl, —OR$_{25}$, halogen, —CF$_3$.

In one embodiment, any one of R$_1$, R$_2$, R$_3$, R$_4$, R$_5$, and R$_6$ is —H, $(C_1-C_6)$-alkyl, —OR$_{25}$, halogen, —CF$_3$, —NO$_2$, or —CN; and any three of R$_7$, R$_8$, R$_9$, R$_{10}$, R$_{11}$, and R$_{12}$ are each independently —H, $(C_1-C_6)$-alkyl, —OR$_{25}$, halogen, —CF$_3$.

In one embodiment, any one of R$_1$, R$_2$, R$_3$, R$_4$, R$_5$, and R$_6$ is —H, $(C_1-C_6)$-alkyl, —OR$_{25}$, halogen or —CF$_3$; and any one of R$_{13}$, R$_{14}$, R$_{15}$, and R$_{16}$ is —H, $(C_1-C_6)$-alkyl, —OR$_{25}$, halogen or —CF$_3$.

In one embodiment, any one of R$_7$, R$_8$, R$_9$, R$_{10}$, R$_{11}$, and R$_{12}$ is —H, $C_1-C_6$-alkyl, —OR$_{25}$, halogen, —CF$_3$, —NO$_2$, or —CN; and any one of R$_{13}$, R$_{14}$, R$_{15}$, and R$_{16}$ is —H, $(C_1-C_6)$-alkyl, —OR$_{25}$, halogen, —CF$_3$.

In one embodiment, R$_4$ is —H, $(C_1-C_6)$-alkyl, —OR$_{25}$, halogen, or —CF$_3$ and any one of R$_{13}$, R$_{14}$, R$_{15}$, and R$_{16}$ is —H, $(C_1-C_6)$-alkyl, —OR$_{25}$, halogen or —CF$_3$; and any one of R$_7$, R$_8$, R$_9$, R$_{10}$, R$_{11}$, and R$_{12}$ is —H, $(C_1-C_6)$-alkyl, —OR$_{25}$, halogen, or —CF$_3$, —NO$_2$, or —CN In one embodiment, R$_4$ is —H, $(C_1-C_6)$-alkyl, —OR$_{25}$, halogen, or —CF$_3$ and any one of R$_{13}$, R$_{14}$, R$_{15}$, and R$_{16}$ is —H, $(C_1-C_6)$-alkyl, —OR$_{25}$, halogen or —CF$_3$; and any two of R$_7$, R$_8$, R$_9$, R$_{10}$, R$_{11}$, and R$_{12}$ are each independently —H, $(C_1-C_6)$-alkyl, —OR$_{25}$, halogen, or —CF$_3$, —NO$_2$, or —CN; wherein the any two of R$_7$, R$_8$, R$_9$, R$_{10}$, R$_{11}$, and R$_{12}$ can be either on the same ring of the quinoline or on different rings.

In one embodiment, R$_5$ is —H, $(C_1-C_6)$-alkyl, halogen, or —CF$_3$ and any one of R$_{13}$, R$_{14}$, R$_{15}$, and R$_{16}$ is —H, $(C_1-C_6)$-alkyl, —OR$_{25}$, halogen or —CF$_3$; and any one of R$_7$, R$_8$, R$_9$, R$_{10}$, R$_{11}$, and R$_{12}$ is —H, $(C_1-C_6)$-alkyl, —OR$_{25}$, halogen, or —CF$_3$, —NO$_2$, or —CN. In one embodiment, R$_5$ is —OR$_{25}$; any one of R$_{13}$, R$_{14}$, R$_{15}$, and R$_{16}$ is —H, $(C_1-C_6)$-alkyl, —OR$_{25}$, halogen or —CF$_3$; and any one of R$_7$, R$_8$, R$_9$, R$_{10}$, R$_{11}$, and R$_{12}$ is —H, $(C_1-C_6)$-alkyl, —OR$_{25}$, halogen, or —CF$_3$, —NO$_2$, or —CN In one embodiment, R$_5$ is —H, $(C_1-C_6)$-alkyl, —OR$_{25}$, halogen, or —CF$_3$ and any one of R$_{13}$, R$_{14}$, R$_{15}$, and R$_{16}$ is —H, $(C_1-C_6)$-alkyl, —OR$_{25}$, halogen or —CF$_3$; and any two of R$_7$, R$_8$, R$_9$, R$_{10}$, R$_{11}$, and R$_{12}$ are each independently —H, $(C_1-C_6)$-alkyl, —OR$_{25}$, halogen, or —CF$_3$, —NO$_2$, or —CN; wherein the any two of R$_7$, R$_8$, R$_9$, R$_{10}$, R$_{11}$, and R$_{12}$ can be either on the same ring of the quinoline or on different rings.

In one embodiment, R$_5$ is —OR$_{25}$; R$_9$ is halogen; any one of R$_{13}$, R$_{14}$, R$_{15}$, and R$_{16}$ is —H, $(C_1-C_6)$-alkyl, —OR$_{25}$, halogen or —CF$_3$; and any two of R$_7$, R$_8$, R$_{10}$, R$_{11}$, and R$_{12}$ are each independently —OR$_{25}$, halogen, or —CF$_3$; wherein the any two of R$_7$, R$_8$, R$_9$, R$_{10}$, R$_{11}$, and R$_{12}$ can be either on the same ring of the quinoline or on different rings.

In one embodiment, R$_1$ is —H or $(C_1-C_6)$-alkyl; R$_2$, R$_8$, and R$_9$ are each —H or halogen; R$_4$ is —H, halogen, —OR$_{25}$, or —CF$_3$; R$_5$ is —H, halogen, or —OR$_{25}$; and R$_3$, R$_6$, R$_7$, R$_{12}$, R$_{13}$, R$_{14}$, R$_{15}$, R$_{16}$, R$_a$ and R$_b$ are each hydrogen.

In one embodiment, R$_1$ is —H or —CH$_3$; R$_2$, R$_8$, and R$_9$ are each —H or F; R$_4$ is —H, F, —OCH$_3$, or —CF$_3$; R$_5$ is —H, F, or —OCH$_3$; and R$_3$, R$_6$, R$_7$, R$_{10}$, R$_{11}$, R$_{12}$, R$_{13}$, R$_{14}$, R$_{15}$, R$_{16}$, R$_a$ and R$_b$ are each hydrogen.

In one embodiment, R$_{25}$ is $(C_1-C_6)$-haloalkyl.

In another embodiment, R$_{25}$ is $(C_1-C_6)$-fluoroalkyl.

In one embodiment, R$_{25}$ is $(C_1-C_6)$-alkyl. In one embodiment, R$_{25}$ is —CH$_3$.

In one embodiment, the compounds of Formula (I) are antagonists of the 5-$HT_{1A}$ receptor. In another embodiment, the compounds of Formula (I) are agonists of the 5-$HT_{1A}$ receptor.

In another aspect, the invention provides compounds of the Formula (I'):

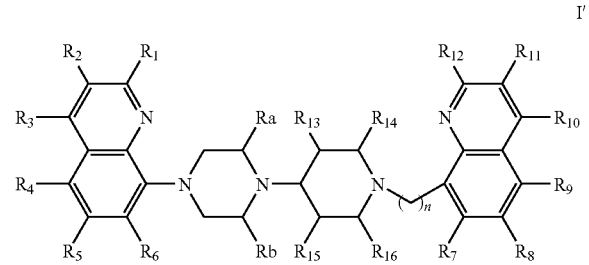

and pharmaceutically acceptable salts thereof, wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$, are each independently —H, $(C_1-C_6)$-alkyl, $(C_1-C_6)$-haloalkyl, $(C_2-C_6)$-alkenyl, or $(C_2-C_6)$-alkynyl, halogen, —$CF_3$, —$NO_2$, —CN, —$OR_{25}$, —$OSO_2R_{25}$, —$SR_{25}$, —$SO_2R_{25}$, —$SO_2N(R_{25})_2$, —$N(R_{25})_2$, —C(O), —$COR_{25}$, —$CO_2R_{25}$, —$NR_{25}CO_2R_{25}$, —$NR_{25}COR_{25}$, —$NR_{25}CON(R_{25})_2$, or —$CON(R_{25})_2$;

$R_a$ and $R_b$ are each independently —H or —$CH_3$;

$R_{25}$ is —H; or linear or branched $(C_1-C_6)$-alkyl, $(C_1-C_6)$-haloalkyl, $(C_2-C_6)$-alkenyl, or $(C_2-C_6)$-alkynyl; and n is 0, 1, or 2.

In one embodiment, $R_1$ is —H, $(C_1-C_6)$-alkyl, —$OR_{25}$, halogen, or —$CF_3$. In another embodiment, $R_1$ is —H, $(C_1-C_6)$-alkyl, —$OR_{25}$, halogen, or —$CF_3$ and one of $R_{13}$, $R_{14}$, $R_{15}$, and $R_{16}$ is —H, $(C_1-C_6)$-alkyl, —$OR_{25}$, or halogen. In a further embodiment, $R_1$ is —H, $(C_1-C_6)$-alkyl, —$OR_{25}$, halogen, or —$CF_3$; one of $R_{13}$, $R_{14}$, $R_{15}$, and $R_{16}$ is —H, $(C_1-C_6)$-alkyl, —$OR_{25}$, or halogen, and $R_7$, $R_8$, $R_9$, $R_{10}$, $R_{11}$, and $R_{12}$ are each hydrogen. In yet another embodiment, $R_1$ is —H, $(C_1-C_6)$-alkyl, —$OR_{25}$, halogen, or —$CF_3$; one of $R_{13}$, $R_{14}$, $R_{15}$, and $R_{16}$ is —H, $(C_1-C_6)$-alkyl, —$OR_{25}$, or halogen, and $R_2$, $R_3$, $R_4$, $R_5$, $R_6$, $R_7$, $R_8$, $R_9$, $R_{10}$, $R_{11}$, and $R_{12}$ are each hydrogen. In one embodiment, $R_1$ is —H, $(C_1-C_6)$-alkyl, —$OR_{25}$, halogen or —$CF_3$ and $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ are each hydrogen.

In one embodiment, $R_4$ is —H, $(C_1-C_6)$-alkyl, —$OR_{25}$, halogen, or —$CF_3$. In another embodiment, $R_4$ is —H, $(C_1-C_6)$-alkyl, —$OR_{25}$, halogen, or —$CF_3$ and one of $R_{13}$, $R_{14}$, $R_{15}$, and $R_{16}$ is —H, $(C_1-C_6)$-alkyl, —$OR_{25}$, or halogen. In a further embodiment, $R_4$ is —H, $(C_1-C_6)$-alkyl, —$OR_{25}$, halogen, or —$CF_3$; one of $R_{13}$, $R_{14}$, $R_{15}$, and $R_{16}$ is —H, $(C_1-C_6)$-alkyl, —$OR_{25}$, or halogen, and $R_7$, $R_8$, $R_9$, $R_{10}$, $R_{11}$, and $R_{12}$ are each hydrogen. In yet another embodiment, $R_4$ is —H, $(C_1-C_6)$-alkyl, —$OR_{25}$, halogen, or —$CF_3$; one of $R_{13}$, $R_{14}$, $R_{15}$, and $R_{16}$ is —H, $(C_1-C_6)$-alkyl, —$OR_{25}$, or halogen, and $R_1$, $R_2$, $R_3$, $R_5$, $R_6$, $R_7$, $R_8$, $R_9$, $R_{10}$, $R_{11}$, and $R_{12}$ are each hydrogen. In one embodiment, $R_4$ is —H, $(C_1-C_6)$-alkyl, —$OR_{25}$, halogen or —$CF_3$ and $R_1$, $R_2$, $R_3$, $R_5$, $R_6$, $R_7$, $R_8$, $R_9$, $R_{10}$, $R_{11}$, $R_{12}$, $R_{13}$, $R_{14}$, $R_{15}$, and $R_{16}$ are each hydrogen.

In one embodiment, $R_5$ is —H, $(C_1-C_6)$-alkyl, —$OR_{25}$, halogen, or —$CF_3$. In another embodiment, $R_5$ is —H, $(C_1-C_6)$-alkyl, —$OR_{25}$, halogen, or —$CF_3$ and one of $R_{13}$, $R_{14}$, $R_{15}$, and $R_{16}$ is —H, $(C_1-C_6)$-alkyl, —$OR_{25}$, or halogen. In a further embodiment, $R_5$ is —H, $(C_1-C_6)$-alkyl, —$OR_{25}$, or halogen, one of $R_{13}$, $R_{14}$, $R_{15}$, and $R_{16}$ is —H, $(C_1-C_6)$-alkyl, —$OR_{25}$, halogen or —$CF_3$, and $R_7$, $R_8$, $R_9$, $R_{10}$, $R_{11}$, and $R_{12}$ are each hydrogen. In yet another embodiment, $R_5$ is —H, $(C_1-C_6)$-alkyl, —$OR_{25}$, halogen, or —$CF_3$; one of $R_{13}$, $R_{14}$, $R_{15}$, and $R_{16}$ is —H, $(C_1-C_6)$-alkyl, —$OR_{25}$, or halogen; and $R_1$, $R_2$, $R_3$, $R_4$, $R_6$, $R_7$, $R_8$, $R_9$, $R_{10}$, $R_{11}$, and $R_{12}$ are each hydrogen. In one embodiment, $R_5$ is —H, $(C_1-C_6)$-alkyl, —$OR_{25}$, halogen or —$CF_3$ and $R_1$, $R_2$, $R_3$, $R_4$, $R_6$, $R_7$, $R_8$, $R_9$, $R_{10}$, $R_{11}$, $R_{12}$, $R_{13}$, $R_{14}$, $R_{15}$, and $R_{16}$ are each hydrogen. In a further embodiment, one of $R_{13}$, $R_{14}$, $R_{15}$, and $R_{16}$ is —H, $(C_1-C_6)$-alkyl, halogen, —$CF_3$, or —$OR_{25}$; $R_5$ is —H, $(C_1-C_6)$-alkyl, —$OR_{25}$, halogen, or —$CF_3$; and each remaining R group is hydrogen.

In one embodiment, $R_5$ is —H, $(C_1-C_6)$-alkyl, —$OR_{25}$, halogen or —$CF_3$; $R_1$, $R_2$, $R_3$, $R_4$, $R_6$, $R_7$, $R_8$, $R_9$, $R_{10}$, $R_{11}$, $R_{12}$, $R_{13}$, $R_{14}$, $R_{15}$, and $R_{16}$ are each hydrogen; and n is 1. In one embodiment, $R_5$ is —H or —$OR_{25}$; $R_1$, $R_2$, $R_3$, $R_4$, $R_6$, $R_7$, $R_8$, $R_9$, $R_{10}$, $R_{11}$, $R_{12}$, $R_{13}$, $R_{14}$, $R_{15}$, and $R_{16}$ are each hydrogen; and n is 1. In one embodiment, $R_5$ is —H, $(C_1-C_6)$-alkyl, —$OR_{25}$, halogen or —$CF_3$; $R_1$, $R_2$, $R_3$, $R_4$, $R_6$, $R_7$, $R_8$, $R_9$, $R_{10}$, $R_{11}$, $R_{12}$, $R_{13}$, $R_{14}$, $R_{15}$, and $R_{16}$ are each hydrogen; and n is 2. In one embodiment, $R_5$ is —H or —$OR_{25}$; $R_1$, $R_2$, $R_3$, $R_4$, $R_6$, $R_7$, $R_8$, $R_9$, $R_{10}$, $R_{11}$, $R_{12}$, $R_{13}$, $R_{14}$, $R_{15}$, and $R_{16}$ are each hydrogen; and n is 2.

In one embodiment, $R_8$ is —H, $(C_1-C_6)$-alkyl, —$OR_{25}$, halogen, —$CF_3$, —$NO_2$ or —CN. In another embodiment, $R_8$ is —H, $(C_1-C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1-C_6)$-alkyl, —$OR_{25}$, halogen, or —$CF_3$; $R_a$ and $R_b$ are each independently —H or —$CH_3$; and each remaining R group is hydrogen. In a further embodiment, $R_8$ is —H, $(C_1-C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1-C_6)$-alkyl, —$OR_{25}$, halogen, or —$CF_3$; one of $R_{13}$, $R_{14}$, $R_{15}$, and $R_{16}$ is —H, $(C_1-C_6)$-alkyl, —$OR_{25}$, or halogen, and each remaining R group is hydrogen. In one embodiment, $R_8$ is —H, $(C_1-C_6)$-alkyl, —$OR_{25}$, halogen, —$CF_3$, —$NO_2$ or —CN and one of $R_4$ or $R_5$ is —H, $(C_1-C_6)$-alkyl, —$OR_{25}$, halogen, or —$CF_3$, and each remaining R group is hydrogen. In one embodiment $R_8$ is —H, $(C_1-C_6)$-alkyl, —$OR_{25}$, halogen, —$CF_3$, —$NO_2$ or —CN; and all other R groups are each hydrogen. In one embodiment, $R_8$ is —H, $(C_1-C_6)$-alkyl, —$OR_{25}$, halogen, —$CF_3$, —$NO_2$ or —CN; one of $R_{13}$, $R_{14}$, $R_{15}$, and $R_{16}$ is —H, $(C_1-C_6)$-alkyl, —$OR_{25}$, or halogen, and each remaining R group is hydrogen.

In one embodiment, $R_9$ is —H, $(C_1-C_6)$-alkyl, —$OR_{25}$, halogen, —$CF_3$, —$NO_2$ or —CN. In another embodiment, $R_9$ is —H, $(C_1-C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1-C_6)$-alkyl, —$OR_{25}$, halogen, or —$CF_3$; and $R_a$ and $R_b$ are each independently —H or —$CH_3$; and each remaining R group is hydrogen. In a further embodiment, $R_9$ is —H, $(C_1-C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1-C_6)$-alkyl, —$OR_{25}$, halogen, or —$CF_3$; one of $R_{13}$, $R_{14}$, $R_{15}$, and $R_{16}$ is —H, $(C_1-C_6)$-alkyl, —$OR_{25}$, or halogen, and each remaining R group is hydrogen. In one embodiment, $R_9$ is —H, $(C_1-C_6)$-alkyl, —$OR_{25}$, halogen, —$CF_3$, —$NO_2$ or —CN and one of $R_4$ or $R_5$ is —H, $(C_1-C_6)$-alkyl, —$OR_{25}$, halogen, or —$CF_3$, and each remaining R group is hydrogen. In one embodiment $R_9$ is —H, $(C_1-C_6)$-alkyl, —$OR_{25}$, halogen, —$CF_3$, —$NO_2$ or —CN; and all other R groups are each hydrogen. In one embodiment, $R_9$ is —H, $(C_1-C_6)$-alkyl, —$OR_{25}$, halogen, —$CF_3$, —$NO_2$ or —CN; one of $R_{13}$, $R_{14}$, $R_{15}$, and $R_{16}$ is —H, $(C_1-C_6)$-alkyl, —$OR_{25}$, or halogen, and each remaining R group is hydrogen.

In one embodiment, $R_7$ is —H, $(C_1-C_6)$-alkyl, —$OR_{25}$, halogen, —$CF_3$, —$NO_2$ or —CN. In one embodiment, $R_7$ is —H, $(C_1-C_6)$-alkyl or halogen. In one embodiment, $R_7$ is —H, $(C_1-C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1-C_6)$-alkyl, —$OR_{25}$, halogen, or —$CF_3$; and $R_a$ and $R_b$ are each independently —H or —$CH_3$; and each remaining R group is hydrogen. In one embodiment, $R_7$ is —H, $(C_1-C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1-C_6)$-alkyl, —$OR_{25}$, halogen, or —$CF_3$; and each remaining R group is hydrogen.

In one embodiment, $R_{10}$ is —H, $(C_1-C_6)$-alkyl, —$OR_{25}$, halogen, —$CF_3$, —$NO_2$ or —CN. In one embodiment, $R_{10}$ is —H, $(C_1-C_6)$-alkyl, —$OR_{25}$, halogen, or —$CF_3$. In one embodiment, $R_{10}$ is —H, —$CH_3$, —$OCH_3$, —F or —$CF_3$. In one embodiment, $R_{10}$ is —H, $(C_1-C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1-C_6)$-alkyl, —$OR_{25}$, halogen, or —$CF_3$; $R_a$ and $R_b$ are each independently —H or —$CH_3$; and each remaining R group is hydrogen. In one embodiment, $R_{10}$ is —H, $(C_1-C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1-C_6)$-alkyl, —$OR_{25}$, halogen, or —$CF_3$; and each remaining R group is hydrogen.

In one embodiment, $R_{11}$ is —H, $(C_1-C_6)$-alkyl, —$OR_{25}$, halogen, —$CF_3$, —$NO_2$ or —CN. In one embodiment, $R_{11}$ is —H, $(C_1-C_6)$-alkyl, halogen, or —$CF_3$. In one embodiment, $R_{11}$ is —H, —$CH_3$, —F or —$CF_3$. In one embodiment, $R_{11}$ is —H, $(C_1-C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1-C_6)$-alkyl, —$OR_{25}$, halogen, or —$CF_3$; $R_a$ and $R_b$ are each independently —H or —$CH_3$; and each remaining R group is hydrogen. In one embodiment, $R_{11}$ is —H, $(C_1-C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1-C_6)$-alkyl, —$OR_{25}$, halogen, or —$CF_3$; and each remaining R group is hydrogen.

In one embodiment, $R_{12}$ is —H, $(C_1-C_6)$-alkyl, —$OR_{25}$, halogen, —$CF_3$, —$NO_2$ or —CN. In one embodiment, $R_{12}$ is —H, $(C_1-C_6)$-alkyl, halogen, or —$CF_3$. In one embodiment, $R_{12}$ is —H, —$CH_3$, —F or —$CF_3$. In one embodiment, $R_{12}$ is —H, $(C_1-C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1-C_6)$-alkyl, —$OR_{25}$, halogen, or —$CF_3$; and $R_a$ and $R_b$ are each independently —H or —$CH_3$; and each remaining R group is hydrogen. In one embodiment, $R_{12}$ is —H, $(C_1-C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1-C_6)$-alkyl, —$OR_{25}$, halogen, or —$CF_3$; and each remaining R group is hydrogen.

In one embodiment, $R_5$ is —H, $(C_1-C_6)$-alkyl, —$OR_{25}$, halogen, or —$CF_3$ and one of $R_7$, $R_8$, $R_9$, $R_{10}$, $R_{11}$, and $R_{12}$ is —H, $(C_1-C_6)$-alkyl, —$OR_{25}$, halogen, —$CF_3$, —$NO_2$ or —CN. In another embodiment, $R_5$ is —H, $(C_1-C_6)$-alkyl, —$OR_{25}$, halogen, or —$CF_3$ and one of $R_7$, $R_8$, $R_9$, $R_{10}$, $R_{11}$, $R_{12}$ is —H, $(C_1-C_6)$-alkyl, —$OR_{25}$, halogen, —$CF_3$, —$NO_2$ or —CN; and each remaining R group is hydrogen. In some embodiments, $R_5$ is —H, $(C_1-C_6)$-alkyl, —$OR_{25}$, halogen, or —$CF_3$ and $R_9$ is $(C_1-C_6)$-alkyl, —$OR_{25}$, halogen, —$CF_3$, —$NO_2$ or —CN; and each remaining R group is hydrogen.

In a further embodiment, $R_5$ is —H, $(C_1-C_6)$-alkyl, —$OR_{25}$, halogen, or —$CF_3$; one of $R_7$, $R_8$, $R_9$, $R_{10}$, $R_{11}$, and $R_{12}$ is —H, $(C_1-C_6)$-alkyl, —$OR_{25}$, halogen, —$CF_3$, —$NO_2$ or —CN; one of $R_{13}$, $R_{14}$, $R_{15}$, and $R_{16}$ is —H, $(C_1-C_6)$-alkyl, —$OR_{25}$, or halogen, and each remaining R group is hydrogen.

In a further embodiment, $R_5$ is —H, $(C_1-C_6)$-alkyl, —$OR_{25}$, halogen, or —$CF_3$; two of $R_7$, $R_8$, $R_9$, $R_{10}$, $R_{11}$, and $R_{12}$ are each independently —H, $(C_1-C_6)$-alkyl, —$OR_{25}$, halogen, —$CF_3$, —$NO_2$ or —CN; one of $R_{13}$, $R_{14}$, $R_{15}$, and $R_{16}$ is —H, $(C_1-C_6)$-alkyl, —$OR_{25}$, or halogen, and each remaining R group is hydrogen.

In a further embodiment, $R_5$ is —H, $(C_1-C_6)$-alkyl, —$OR_{25}$, halogen, or —$CF_3$; three of $R_7$, $R_8$, $R_9$, $R_{10}$, $R_{11}$, and $R_{12}$ are each independently —H, $(C_1-C_6)$-alkyl, —$OR_{25}$, halogen, —$CF_3$, —$NO_2$ or —CN; one of $R_{13}$, $R_{14}$, $R_{15}$, and $R_{16}$ is —H, $(C_1-C_6)$-alkyl, —$OR_{25}$, or halogen, and each remaining R group is hydrogen.

In one embodiment, $R_5$ is —H, $(C_1-C_6)$-alkyl, —$OR_{25}$, halogen, or —$CF_3$; $R_9$ is —H, $(C_1-C_6)$-alkyl, —$OR_{25}$, halogen, —$CF_3$, —$NO_2$ or —CN; and two of $R_{10}$, $R_{11}$, and $R_{12}$ are each independently —H, $(C_1-C_6)$-alkyl, —$OR_{25}$, halogen, —$CF_3$, —$NO_2$ or —CN. In another embodiment, $R_5$ is —H, $(C_1-C_6)$-alkyl, —$OR_{25}$, halogen, or —$CF_3$; $R_9$ is —H, $(C_1-C_6)$-alkyl, —$OR_{25}$, halogen, —$CF_3$, —$NO_2$ or —CN; two of $R_{10}$, $R_{11}$, $R_{12}$ are each independently —H, $(C_1-C_6)$-alkyl, —$OR_{25}$, halogen, —$CF_3$, —$NO_2$ or —CN; and each remaining R group is hydrogen. In some embodiments, $R_5$ is —H or —$OR_{25}$; $R_9$ is —H or halogen; two of $R_{10}$, $R_{11}$, $R_{12}$ are each independently —H, $(C_1-C_6)$-alkyl, —$OR_{25}$, halogen, —$CF_3$, —$NO_2$ or —CN; and each remaining R group is hydrogen. In some embodiments, $R_5$ is —H, or —$OCH_3$; $R_9$ is —H or halogen; two of $R_{10}$, $R_{11}$, $R_{12}$ are each independently —H, $(C_1-C_6)$-alkyl, —$OR_{25}$, halogen, —$CF_3$, —$NO_2$ or —CN; and each remaining R group is hydrogen. In some embodiments, $R_5$ is —H, $(C_1-C_6)$-alkyl, —$OR_{25}$, halogen, or —$CF_3$; $R_9$ is —H, $(C_1-C_6)$-alkyl, —$OR_{25}$, halogen, —$CF_3$, —$NO_2$ or —CN; $R_{10}$ and $R_{12}$ are each independently —H, $(C_1-C_6)$-alkyl, —$OR_{25}$, halogen, —$CF_3$, —$NO_2$ or —CN; and each remaining R group is hydrogen. In some embodiments, $R_5$ is —H, $(C_1-C_6)$-alkyl, —$OR_{25}$, halogen, or —$CF_3$; $R_9$ is —H, $(C_1-C_6)$-alkyl, —$OR_{25}$, halogen, —$CF_3$, —$NO_2$ or —CN; $R_{10}$ and $R_1$, are each independently —H, $(C_1-C_6)$-alkyl, —$OR_{25}$, halogen, —$CF_3$, —$NO_2$ or —CN; and each remaining R group is hydrogen. In some embodiments, $R_5$ is —H, $(C_1-C_6)$-alkyl, —$OR_{25}$, halogen, or —$CF_3$; $R_9$ is —H, $(C_1-C_6)$-alkyl, —$OR_{25}$, halogen, —$CF_3$, —$NO_2$ or —CN; $R_{11}$ and $R_{12}$ are each independently —H, $(C_1-C_6)$-alkyl, —$OR_{25}$, halogen, —$CF_3$, —$NO_2$ or —CN; and each remaining R group is hydrogen.

In some embodiments, $R_5$ is —H or —$OR_{25}$; $R_9$ is —H or halogen; and each remaining R group is hydrogen. In some embodiments, $R_5$ is —H or —$OR_{25}$, $R_9$ is —H or halogen; $R_{10}$ and $R_{12}$ are each independently —H, halogen, or —$CF_3$; and each remaining R group is hydrogen.

In one embodiment, $R_4$ is —H, $(C_1-C_6)$-alkyl, —$OR_{25}$, halogen, or —$CF_3$ and one of $R_7$, $R_8$, $R_9$, $R_{10}$, $R_{11}$, and $R_{12}$ is —H, $(C_1-C_6)$-alkyl, —$OR_{25}$, halogen, —$CF_3$, —$NO_2$ or —CN. In another embodiment, $R_4$ is —H, $(C_1-C_6)$-alkyl, —$OR_{25}$, halogen, or —$CF_3$; one of $R_7$, $R_8$, $R_9$, $R_{10}$, $R_{11}$, and $R_{12}$ is —H, $(C_1-C_6)$-alkyl, —$OR_{25}$, halogen, —$CF_3$, —$NO_2$ or —CN; and each remaining R group is hydrogen. In a further embodiment, $R_4$ is —H, $(C_1-C_6)$-alkyl, —$OR_{25}$, halogen, or —$CF_3$; one of $R_7$, $R_8$, $R_9$, $R_{10}$, $R_{11}$; $R_{12}$ is —H, $(C_1-C_6)$-alkyl, —$OR_{25}$, halogen, —$CF_3$, —$NO_2$ or —CN; one of $R_{13}$, $R_{14}$, $R_{15}$, and $R_{16}$ is —H, $(C_1-C_6)$-alkyl, —$OR_{25}$, or halogen, and each remaining R group is hydrogen.

In one embodiment, one of $R_{13}$, $R_{14}$, $R_{15}$, and $R_{16}$ is —H, $(C_1-C_6)$-alkyl, halogen, —$CF_3$, or —$OR_{25}$.

In one embodiment, $R_1$, $R_2$, $R_3$, $R_6$, $R_7$, $R_8$, $R_9$, $R_{10}$, $R_{11}$, $R_{12}$, $R_{13}$, $R_{14}$, $R_{15}$, and $R_{16}$ are each hydrogen.

In one embodiment, $R_1$, $R_2$, $R_3$, $R_4$, $R_7$, $R_9$, $R_{10}$, $R_{11}$, and $R_{12}$ are each hydrogen.

In one embodiment, $R_1$, $R_2$, $R_3$, $R_4$, $R_7$, $R_8$, $R_{10}$, $R_{11}$, and $R_{12}$ are each hydrogen.

In one embodiment, $R_1$, $R_2$, $R_3$, $R_4$, $R_7$, $R_8$, $R_9$, $R_1$, and $R_{12}$ are each hydrogen.

In one embodiment, $R_1$, $R_2$, $R_3$, $R_4$, $R_7$, $R_8$, $R_9$, $R_{10}$, and $R_{12}$ are each hydrogen.

In one embodiment, $R_1$, $R_2$, $R_3$, $R_4$, $R_7$, $R_8$, $R_9$, $R_{10}$, and $R_1$ are each hydrogen.

In one embodiment, $R_1$, $R_2$, $R_3$, $R_4$, $R_7$, $R_8$, and $R_1$ are each hydrogen.

In one embodiment, $R_1$, $R_2$, $R_3$, $R_4$, $R_7$, $R_8$, $R_9$ and $R_{11}$ are each hydrogen.

In one embodiment, $R_1$, $R_2$, $R_3$, $R_4$, $R_5$, $R_6$, $R_7$, $R_8$, $R_9$, and $R_{12}$ are each hydrogen.

In another embodiment, $R_{13}$, $R_{14}$, $R_{15}$, and $R_{16}$ are each hydrogen.

In one embodiment, $R_3$, $R_6$, $R_7$, $R_8$, $R_9$, $R_{12}$, $R_{13}$, $R_{14}$, $R_{15}$, and $R_{16}$ are each hydrogen.

In one embodiment, $R_1$, $R_2$, $R_3$, $R_4$, $R_6$, $R_7$, $R_8$, $R_9$, $R_1$, $R_{13}$, $R_{14}$, $R_{15}$, and $R_{16}$ are each hydrogen.

In one embodiment, $R_1$, $R_2$, $R_3$, $R_4$, $R_6$, $R_7$, $R_8$, $R_9$, $R_{10}$, $R_{11}$, $R_{12}$, $R_{13}$, $R_{14}$, $R_{15}$, and $R_{16}$ are each hydrogen.

In one embodiment, $R_1$, $R_2$, $R_3$, $R_4$, $R_6$, $R_7$, $R_8$, $R_{10}$, $R_{11}$, $R_{12}$, $R_{13}$, $R_{14}$, $R_{15}$, and $R_{16}$ are each hydrogen.

In one embodiment, any one of $R_1$, $R_2$, $R_3$, $R_4$, $R_5$, and $R_6$ is —H, $(C_1$-$C_6)$-alkyl, —$OR_{25}$, halogen or —$CF_3$; and any one of $R_7$, $R_8$, $R_9$, $R_{10}$, $R_{11}$, and $R_{12}$ is —H, $(C_1$-$C_6)$-alkyl, —$OR_{25}$, halogen, or —$CF_3$, —$NO_2$, or —CN.

In one embodiment, any one of $R_1$, $R_2$, $R_3$, $R_4$, $R_5$, and $R_6$ is —H, $(C_1$-$C_6)$-alkyl, —$OR_{25}$, halogen, —$CF_3$, —$NO_2$, or —CN; and any two of $R_7$, $R_8$, $R_9$, $R_{10}$, $R_{11}$, and $R_{12}$ are each independently —H, $(C_1$-$C_6)$-alkyl, —$OR_{25}$, halogen, —$CF_3$.

In one embodiment, any one of $R_1$, $R_2$, $R_3$, $R_4$, $R_5$, and $R_6$ is —H, $(C_1$-$C_6)$-alkyl, —$OR_{25}$, halogen, —$CF_3$, —$NO_2$, or —CN; and any three of $R_7$, $R_8$, $R_9$, $R_{10}$, $R_{11}$, and $R_{12}$ are each independently —H, $(C_1$-$C_6)$-alkyl, —$OR_{25}$, halogen, —$CF_3$.

In one embodiment, any one of $R_1$, $R_2$, $R_3$, $R_4$, $R_5$, and $R_6$ is —H, $(C_1$-$C_6)$-alkyl, —$OR_{25}$, halogen or —$CF_3$; and any one of $R_{13}$, $R_{14}$, $R_{15}$, and $R_{16}$ is —H, $(C_1$-$C_6)$-alkyl, —$OR_{25}$, halogen or —$CF_3$.

In one embodiment, any one of $R_7$, $R_8$, $R_9$, $R_{10}$, $R_{11}$, and $R_{12}$ is —H, $(C_1$-$C_6)$-alkyl, —$OR_{25}$, halogen, —$CF_3$, —$NO_2$, or —CN; and any one of $R_{13}$, $R_{14}$, $R_{15}$, and $R_{16}$ is —H, $(C_1$-$C_6)$-alkyl, —$OR_{25}$, halogen, —$CF_3$.

In one embodiment, $R_4$ is —H, $(C_1$-$C_6)$-alkyl, —$OR_{25}$, halogen, or —$CF_3$ and any one of $R_{13}$, $R_{14}$, $R_{15}$, and $R_{16}$ is —H, $(C_1$-$C_6)$-alkyl, —$OR_{25}$, halogen or —$CF_3$; and any one of $R_7$, $R_8$, $R_9$, $R_{10}$, $R_{11}$, and $R_{12}$ is —H, $(C_1$-$C_6)$-alkyl, —$OR_{25}$, halogen, or —$CF_3$, —$NO_2$, or —CN In one embodiment, $R_4$ is —H, $(C_1$-$C_6)$-alkyl, —$OR_{25}$, halogen, or —$CF_3$ and any one of $R_{13}$, $R_{14}$, $R_{15}$, and $R_{16}$ is —H, $(C_1$-$C_6)$-alkyl, —$OR_{25}$, halogen or —$CF_3$; and any two of $R_7$, $R_8$, $R_9$, $R_{10}$, $R_{11}$, and $R_{12}$ are each independently —H, $(C_1$-$C_6)$-alkyl, —$OR_{25}$, halogen, or —$CF_3$, —$NO_2$, or —CN; wherein the any two of $R_7$, $R_8$, $R_9$, $R_{10}$, $R_{11}$, and $R_{12}$ can be either on the same ring of the quinoline or on different rings.

In one embodiment, $R_5$ is —H, $(C_1$-$C_6)$-alkyl, —$OR_{25}$, halogen, or —$CF_3$ and any one of $R_{13}$, $R_{14}$, $R_{15}$, and $R_{16}$ is —H, $(C_1$-$C_6)$-alkyl, —$OR_{25}$, halogen or —$CF_3$; and any one of $R_7$, $R_8$, $R_9$, $R_{10}$, $R_{11}$, and $R_{12}$ is —H, $(C_1$-$C_6)$-alkyl, —$OR_{25}$, halogen, or —$CF_3$, —$NO_2$, or —CN In one embodiment, $R_5$ is —H, $(C_1$-$C_6)$-alkyl, —$OR_{25}$, halogen, or —$CF_3$ and any one of $R_{13}$, $R_{14}$, $R_{15}$, and $R_{16}$ is —H, $(C_1$-$C_6)$-alkyl, —$OR_{25}$, halogen or —$CF_3$; and any two of $R_7$, $R_8$, $R_9$, $R_{10}$, $R_{11}$, and $R_{12}$ are each independently —H, $(C_1$-$C_6)$-alkyl, —$OR_{25}$, halogen, or —$CF_3$, —$NO_2$, or —CN; wherein the any two of $R_7$, $R_8$, $R_9$, $R_{10}$, $R_{11}$, and $R_{12}$ can be either on the same ring of the quinoline or on different rings.

In one embodiment, $R_1$ is —H or $(C_1$-$C_6)$-alkyl; $R_2$, $R_8$, and $R_9$ are each —H or halogen; $R_4$ is —H, halogen, —$OR_{25}$, or —$CF_3$; $R_5$ is —H, halogen, or —$OR_{25}$; and $R_3$, $R_6$, $R_7$, $R_{12}$, $R_{13}$, $R_{14}$, $R_{15}$, $R_{16}$, $R_a$ and $R_b$ are each hydrogen.

In one embodiment, $R_1$ is —H or —$CH_3$; $R_2$, $R_8$, and $R_9$ are each —H or F; $R_4$ is —H, F, —$OCH_3$, or —$CF_3$; $R_5$ is —H, F, —$OCH_3$; and $R_3$, $R_6$, $R_7$, $R_{10}$, $R_{11}$, $R_{12}$, $R_{13}$, $R_{14}$, $R_{15}$, $R_{16}$, $R_a$ and $R_b$ are each hydrogen.

In one embodiment, $R_1$ is —H, —$CF_3$ or $(C_1$-$C_6)$-alkyl; $R_4$ and $R_5$ are each —H, halogen, —$OR_{25}$, or —$CF_3$; $R_7$, $R_8$, $R_9$, $R_{10}$, $R_{11}$, and $R_{12}$ are each —H, halogen, -alkyl, —$OR_{25}$, —$CF_3$, or —$NO_2$; $R_{16}$ is —H or —$CH_3$ In one embodiment, $R_{25}$ is $(C_1$-$C_6)$-haloalkyl.

In another embodiment, $R_{25}$ is $(C_1$-$C_6)$-fluoroalkyl.

In one embodiment, $R_{25}$ is $(C_1$-$C_6)$-alkyl. In one embodiment, $R_{25}$ is —$CH_3$.

In one embodiment, the compounds of Formula (I) are antagonists of the 5-$HT_{1A}$ receptor. In another embodiment, the compounds of Formula (I) are agonists of the 5-$HT_{1A}$ receptor.

In another aspect, the invention provides compounds of the Formula (I"):

I"

and pharmaceutically acceptable salts thereof, wherein $R_1$, $R_2$, $R_3$, $R_4$, $R_5$, $R_6$, $R_7$, $R_{7'}$, $R_8$, $R_9$, $R_{10}$, $R_{11}$, $R_{12}$, $R_{13}$, $R_{14}$, $R_{15}$, and $R_{16}$, are each independently —H, $(C_1$-$C_6)$-alkyl, $(C_1$-$C_6)$-haloalkyl, $(C_2$-$C_6)$-alkenyl, or $(C_2$-$C_6)$-alkynyl, halogen, —$CF_3$, —$NO_2$, —CN, —$OR_{25}$, —$OSO_2R_{25}$, —$SR_{25}$, —$SO_2R_{25}$, —$SO_2N(R_{25})_2$, —$N(R_{25})_2$, —C(O), —$COR_{25}$, —$CO_2R_{25}$, —$NR_{25}CO_2R_{25}$, —$NR_{25}COR_{25}$, —$NR_{25}CON(R_{25})_2$, or —$CON(R_{25})_2$ except for the R groups through which the piperidine is connected;

$R_a$ and $R_b$ are each independently —H or —$CH_3$; and $R_{25}$ is —H; or linear or branched $(C_1$-$C_6)$-alkyl, $(C_1$-$C_6)$-haloalkyl, $(C_2$-$C_6)$-alkenyl, or $(C_2$-$C_6)$-alkynyl; and where the piperidine group can be attached to the non-hetero atom containing ring of the quinoline through positions $R_7$, $R_{7'}$, $R_8$, or $R_9$.

In one embodiment, $R_4$ is —H, $(C_1$-$C_6)$-alkyl, —$OR_{25}$, halogen, or —$CF_3$. In another embodiment, $R_4$ is —H, $(C_1$-$C_6)$-alkyl, —$OR_{25}$, halogen, or —$CF_3$ and one of $R_{13}$, $R_{14}$, $R_{15}$, and $R_{16}$ is —H, $(C_1$-$C_6)$-alkyl, —$OR_{25}$, or halogen. In a further embodiment, $R_4$ is —H, $(C_1$-$C_6)$-alkyl, —$OR_{25}$, halogen, or —$CF_3$; one of $R_{13}$, $R_{14}$, $R_{15}$, and $R_{16}$ is —H, $(C_1$-$C_6)$-alkyl, —$OR_{25}$, or halogen or —$CF_3$; the piperidine is connected through one of $R_7$, $R_{7'}$, $R_8$, or $R_9$; and the remainder of the R groups of the quinoline attached to the piperidine are each hydrogen. In yet another embodiment, $R_4$ is —H, $(C_1$-$C_6)$-alkyl, —$OR_{25}$, halogen, or —$CF_3$; one of $R_{13}$, $R_{14}$, $R_{15}$, and $R_{16}$ is —H, $(C_1$-$C_6)$-alkyl, —$OR_{25}$, or halogen; the piperidine is connected through $R_{7'}$; and each remaining R group is hydrogen. In yet another embodiment, $R_4$ is —H, $(C_1$-$C_6)$-alkyl, —$OR_{25}$, halogen, or —$CF_3$; one of $R_{13}$, $R_{14}$, $R_{15}$, and $R_{16}$ is —H, $(C_1$-$C_6)$-alkyl, —$OR_{25}$, or halogen; the piperidine is connected through $R_7$; and each remaining R group is hydrogen. In yet another embodiment, $R_4$ is —H, $(C_1$-$C_6)$-alkyl, —$OR_{25}$, halogen, or —$CF_3$; one of $R_{13}$, $R_{14}$, $R_{15}$, and $R_{16}$ is —H, $(C_1$-$C_6)$-alkyl, —$OR_{25}$, or halogen; the piperidine is connected through $R_8$; and each remaining R group is hydrogen. In yet another embodiment, $R_4$ is —H, $(C_1$-$C_6)$-alkyl, —$OR_{25}$, halogen, or —$CF_3$; one of $R_{13}$, $R_{14}$, $R_{15}$, and $R_{16}$ is —H, $(C_1$-$C_6)$-alkyl, —$OR_{25}$, or halogen; the piperidine is connected through $R_9$; and each remaining R group is hydrogen. In one embodiment, $R_4$ is —H, $(C_1$-$C_6)$-alkyl, —$OR_{25}$, halogen or —$CF_3$, the piperidine is connected through $R_{7'}$, and each remaining R group is hydrogen. In one embodiment, $R_4$ is —H, $(C_1$-$C_6)$-alkyl, —$OR_{25}$, halogen or —$CF_3$, the piperidine is connected through $R_7$, and each remaining R group is hydrogen. In one embodiment, $R_4$ is —H, $(C_1$-$C_6)$-alkyl, —$OR_{25}$, halogen or —$CF_3$, the piperidine is connected through $R_8$, and each remaining R group is hydrogen. In one embodiment, $R_4$ is —H, $(C_1$-$C_6)$-alkyl, —$OR_{25}$, halogen or —$CF_3$, the piperidine is connected through $R_9$, and each remaining R group is hydrogen.

In one embodiment, $R_5$ is —H, $(C_1$-$C_6)$-alkyl, —$OR_{25}$, halogen, or —$CF_3$. In another embodiment, $R_5$ is —H, $(C_1$-$C_6)$-alkyl, —$OR_{25}$, halogen, or —$CF_3$ and one of $R_{13}$, $R_{14}$, $R_{15}$, and $R_{16}$ is —H, $(C_1$-$C_6)$-alkyl, —$OR_{25}$, or halogen. In a further embodiment, $R_5$ is —H, $(C_1$-$C_6)$-alkyl, —$OR_{25}$, halogen, or —$CF_3$; one of $R_{13}$, $R_{14}$, $R_{15}$, and $R_{16}$ is —H, $(C_1$-$C_6)$-alkyl, —$OR_{25}$, or halogen; the piperidine is connected through one of $R_7$, $R_{7'}$, $R_8$, or $R_9$; and the remainder of the R groups of the quinoline attached to the piperidine are each hydrogen. In yet another embodiment, $R_5$ is —H, $(C_1$-$C_6)$-alkyl, —$OR_{25}$, halogen, or —$CF_3$; one of $R_{13}$, $R_{14}$, $R_{15}$, and $R_{16}$ is —H, $(C_1$-$C_6)$-alkyl, —$OR_{25}$, or halogen; the piperidine is connected through $R_{7'}$; and each remaining R group is hydrogen. In yet another embodiment, $R_5$ is —H, $(C_1$-$C_6)$-alkyl, —$OR_{25}$, halogen, or —$CF_3$; one of $R_{13}$, $R_{14}$, $R_{15}$, and $R_{16}$ is —H, $(C_1$-$C_6)$-alkyl, —$OR_{25}$, or halogen; the piperidine is connected through $R_7$; and each remaining R group is hydrogen. In yet another embodiment, $R_5$ is —H, $(C_1$-$C_6)$-alkyl, —$OR_{25}$, halogen, or —$CF_3$; one of $R_{13}$, $R_{14}$, $R_{15}$, and $R_{16}$ is —H, $(C_1$-$C_6)$-alkyl, —$OR_{25}$, or halogen; the piperidine is connected through $R_8$; and each remaining R group is hydrogen. In yet another embodiment, $R_5$ is —H, $(C_1$-$C_6)$-alkyl, —$OR_{25}$, halogen, or —$CF_3$; one of $R_{13}$, $R_{14}$, $R_{15}$, and $R_{16}$ is —H, $(C_1$-$C_6)$-alkyl, —$OR_{25}$, or halogen; the piperidine is connected through $R_9$; and each remaining R group is hydrogen. In one embodiment, $R_5$ is —H, $(C_1$-$C_6)$-alkyl, —$OR_{25}$, halogen or —$CF_3$, the piperidine is connected through $R_{7'}$, and each remaining R group is hydrogen. In one embodiment, $R_5$ is —H, $(C_1$-$C_6)$-alkyl, —$OR_{25}$, halogen or —$CF_3$, the piperidine is connected through $R_7$, and each remaining R group is hydrogen. In one embodiment, $R_5$ is —H, $(C_1$-$C_6)$-alkyl, —$OR_{25}$, halogen or —$CF_3$, the piperidine is connected through $R_8$, and each remaining R group is hydrogen. In one embodiment, $R_5$ is —H, $(C_1$-$C_6)$-alkyl, —$OR_{25}$, halogen or —$CF_3$, the piperidine is connected through $R_9$, and each remaining R group is hydrogen. In a further embodiment, one of $R_{13}$, $R_{14}$, $R_{15}$, and $R_{16}$ is —H, $(C_1$-$C_6)$-alkyl, halogen, —$CF_3$, or —$OR_{25}$; $R_5$ is —H, $(C_1$-$C_6)$-alkyl, —$OR_{25}$, halogen, or —$CF_3$; and each remaining R group is hydrogen.

In one embodiment, $R_5$ is —H, $(C_1$-$C_6)$-alkyl, —$OR_{25}$, halogen, or —$CF_3$ and one of $R_7$, $R_{7'}$, $R_8$, $R_9$, $R_{10}$, $R_{11}$, and $R_{12}$ is —H, $(C_1$-$C_6)$-alkyl, —$OR_{25}$, halogen, —$CF_3$, —$NO_2$ or —CN except for the R group through which the piperidine is connected. In another embodiment, $R_5$ is —H, $(C_1$-$C_6)$-alkyl, —$OR_{25}$, halogen, or —$CF_3$ and one of $R_7$, $R_{7'}$, $R_8$, $R_9$, $R_{10}$, $R_{11}$, or $R_{12}$ is —H, $(C_1$-$C_6)$-alkyl, —$OR_{25}$, halogen, —$CF_3$, —$NO_2$ or —CN except for the R group through which the piperidine is connected; and each remaining R group is hydrogen except for the R group through which the piperidine is connected. In some embodiments, $R_5$ is —H or —$OR_{25}$ and $R_9$ is —H, $(C_1$-$C_6)$-alkyl, —$OR_{25}$, halogen, —$CF_3$, —$NO_2$ or —CN; and each remaining R group is hydrogen except for the R group through which the piperidine is connected. In some embodiments, $R_5$ is —H, $(C_1$-$C_6)$-alkyl, —$OR_{25}$, halogen, or —$CF_3$, $R_9$ is —H or halogen and each remaining R group is —H or hydrogen except for the R group through which the piperidine is connected.

In a further embodiment, $R_5$ is —H, $(C_1$-$C_6)$-alkyl, —$OR_{25}$, halogen, or —$CF_3$; one of $R_7$, $R_{7'}$, $R_8$, $R_9$, $R_{10}$, $R_{11}$; $R_{12}$ is —H, $(C_1$-$C_6)$-alkyl, —$OR_{25}$, halogen, —$CF_3$, —$NO_2$ or —CN except for the R group through which the piperidine is connected; one of $R_{13}$, $R_{14}$, $R_{15}$, and $R_{16}$ is —H, $(C_1$-$C_6)$-alkyl, —$OR_{25}$, or halogen, and each remaining R group is hydrogen except for the R group through which the piperidine is connected.

In a further embodiment, $R_5$ is —H, $(C_1$-$C_6)$-alkyl, —$OR_{25}$, halogen, or —$CF_3$; and $R_7$ is —H, $(C_1$-$C_6)$-alkyl, —$OR_{25}$, halogen, —$CF_3$, —$NO_2$ or —CN, and each remaining R group is hydrogen except for the R group through which the piperidine is connected. In one embodiment, the piperidine is connected through $R_7$; $R_5$ is —H, $(C_1$-$C_6)$-alkyl, —$OR_{25}$, halogen, or —$CF_3$; and $R_7$ is —H, $(C_1$-$C_6)$-alkyl, —$OR_{25}$, halogen, —$CF_3$, —$NO_2$ or —CN. In one embodiment, the piperidine is connected through $R_7$; $R_5$ is —H or —$OR_{25}$; and $R_7$ is —H or halogen.

In one embodiment, $R_5$ is —H, $(C_1$-$C_6)$-alkyl, —$OR_{25}$, halogen, or —$CF_3$; two of $R_7$, $R_{7'}$, $R_8$, $R_9$, $R_{10}$, $R_{11}$; $R_{12}$ are each independently —H, $(C_1$-$C_6)$-alkyl, —$OR_{25}$, halogen, —$CF_3$, —$NO_2$ or —CN except for the R group through which the piperidine is connected; and each remaining R group is hydrogen except for the R group through which the piperidine is connected.

In one embodiment, $R_5$ is —H, $(C_1$-$C_6)$-alkyl, —$OR_{25}$, halogen, or —$CF_3$; two of $R_7$, $R_{7'}$, $R_8$, $R_9$, $R_{10}$, $R_{11}$; $R_{12}$ are each independently —H, $(C_1$-$C_6)$-alkyl, —$OR_{25}$, halogen, —$CF_3$, —$NO_2$ or —CN except for the R group through which the piperidine is connected; one of $R_{13}$, $R_{14}$, $R_{15}$, and $R_{16}$ is —H, $(C_1$-$C_6)$-alkyl, —$OR_{25}$, or halogen, and each remaining R group is hydrogen except for the R group through which the piperidine is connected.

In one embodiment, $R_5$ is —H, $(C_1$-$C_6)$-alkyl, —$OR_{25}$, halogen, or —$CF_3$; three of $R_7$, $R_{7'}$, $R_8$, $R_9$, $R_{10}$, $R_1$; $R_{12}$ are each independently —H, $(C_1$-$C_6)$-alkyl, —$OR_{25}$, halogen, —$CF_3$, —$NO_2$ or —CN except for the R group through which the piperidine is connected; one of $R_{13}$, $R_{14}$, $R_{15}$, and $R_{16}$ is —H, $(C_1$-$C_6)$-alkyl, —$OR_{25}$, or halogen, and each remaining R group is hydrogen except for the R group through which the piperidine is connected.

In one embodiment, $R_5$ is —H, $(C_1$-$C_6)$-alkyl, —$OR_{25}$, halogen, or —$CF_3$; $R_9$ is —H, $(C_1$-$C_6)$-alkyl, —$OR_{25}$, halogen, —$CF_3$, —$NO_2$ or —CN; and two of $R_{10}$, $R_{11}$, and $R_{12}$ are each independently —H, $(C_1$-$C_6)$-alkyl, —$OR_{25}$, halogen, —$CF_3$, —$NO_2$ or —CN. In another embodiment, $R_5$ is —H, $(C_1$-$C_6)$-alkyl, —$OR_{25}$, halogen, or —$CF_3$; $R_9$ is —H, $(C_1$-$C_6)$-alkyl, —$OR_{25}$, halogen, —$CF_3$, —$NO_2$ or —CN; two of $R_{10}$, $R_{11}$, $R_{12}$ are each independently —H, $(C_1$-$C_6)$-alkyl, —$OR_{25}$, halogen, —$CF_3$, —$NO_2$ or —CN; and each remaining R group is hydrogen except for the R group through which the piperidine is connected. In some embodiments, $R_5$ is —H or —$OR_{25}$; $R_9$ is —H or halogen; two of $R_{10}$, $R_{11}$, $R_{12}$ are each independently —H, $(C_1$-$C_6)$-alkyl, —$OR_{25}$, halogen, —$CF_3$, —$NO_2$ or —CN; and each remaining R group is hydrogen except for the R group through which the piperidine is connected. In some embodiments, $R_5$ is —H or —$OCH_3$; $R_9$ is —H or halogen; two of $R_{10}$, $R_{11}$, $R_{12}$ are each independently —H, $(C_1$-$C_6)$-alkyl, —$OR_{25}$, halogen, —$CF_3$, —$NO_2$ or —CN; and each remaining R group is hydrogen except for the R group through which the piperidine is connected.

In some embodiments, $R_5$ is —H, —($C_1$-$C_6$)-alkyl, —$OR_{25}$, halogen, or —$CF_3$; $R_9$ is —H, ($C_1$-$C_6$)-alkyl, —$OR_{25}$, halogen, —$CF_3$, —$NO_2$ or —CN; $R_7$, $R_{10}$ and $R_{12}$ are each independently —H, ($C_1$-$C_6$)-alkyl, —$OR_{25}$, halogen, —$CF_3$, —$NO_2$ or —CN; and each remaining R group is hydrogen except for the R group through which the piperidine is connected. In some embodiments, $R_5$ is —H, —($C_1$-$C_6$)-alkyl, —$OR_{25}$, halogen, or —$CF_3$; $R_9$ is —H, ($C_1$-$C_6$)-alkyl, —$OR_{25}$, halogen, —$CF_3$, —$NO_2$ or —CN; $R_{10}$ and $R_{11}$ are each independently —H, ($C_1$-$C_6$)-alkyl, —$OR_{25}$, halogen, —$CF_3$, —$NO_2$ or —CN; and each remaining R group is hydrogen except for the R group through which the piperidine is connected. In some embodiments, In some embodiments, $R_5$ is —H, —($C_1$-$C_6$)-alkyl, —$OR_{25}$, halogen, or —$CF_3$; $R_9$ is —H, ($C_1$-$C_6$)-alkyl, —$OR_{25}$, halogen, —$CF_3$, —$NO_2$ or —CN; $R_1$, and $R_{12}$ are each independently —H, ($C_1$-$C_6$)-alkyl, —$OR_{25}$, halogen, —$CF_3$, —$NO_2$ or —CN; and each remaining R group is hydrogen except for the R group through which the piperidine is connected.

In one embodiment, $R_4$ is —H, ($C_1$-$C_6$)-alkyl, —$OR_{25}$, halogen, or —$CF_3$ and one of $R_7$, $R_7$, $R_b$, $R_9$, $R_{10}$, $R_{11}$, and $R_{12}$ is —H, ($C_1$-$C_6$)-alkyl, —$OR_{25}$, halogen, —$CF_3$, —$NO_2$ or —CN. In another embodiment, $R_4$ is —H, ($C_1$-$C_6$)-alkyl, —$OR_{25}$, halogen, or —$CF_3$; one of $R_7$, $R_7$, $R_9$, $R_9$, $R_{10}$, $R_{11}$, and $R_{12}$ is —H, ($C_1$-$C_6$)-alkyl, —$OR_{25}$, halogen, —$CF_3$, —$NO_2$ or —CN; and each remaining R group is hydrogen except for the R group through which the piperidine is connected. In a further embodiment, $R_4$ is —H, ($C_1$-$C_6$)-alkyl, —$OR_{25}$, halogen, or —$CF_3$; one of $R_7$, $R_7$, $R_9$, $R_9$, $R_{10}$, $R_{11}$, $R_{12}$ is —H, ($C_1$-$C_6$)-alkyl, —$OR_{25}$, halogen, —$CF_3$, —$NO_2$ or —CN; one of $R_{13}$, $R_{14}$, $R_{15}$, and $R_{16}$ is —H, ($C_1$-$C_6$)-alkyl, —$OR_{25}$, or halogen, and each remaining R group is hydrogen except for the R group through which the piperidine is connected.

In one embodiment, one of $R_{13}$, $R_{14}$, $R_{15}$, and $R_{16}$ is —H, ($C_1$-$C_6$)-alkyl, halogen, —$CF_3$, or —$OR_{25}$.

In one embodiment, $R_8$ is —H, ($C_1$-$C_6$)-alkyl, —$OR_{25}$, halogen, —$CF_3$, —$NO_2$ or —CN. In another embodiment, $R_8$ is —H, ($C_1$-$C_6$)-alkyl, —$OR_{25}$, halogen, —$CF_3$, —$NO_2$ or —CN; one of $R_1$, $R_2$, $R_3$, $R_4$, and $R_6$ is —H, ($C_1$-$C_6$)-alkyl, —$OR_{25}$, halogen, or —$CF_3$; $R_a$ and $R_b$ are each independently —H or —$CH_3$; and each remaining R group is hydrogen except for the R group through which the piperidine is connected. In a further embodiment, $R_8$ is —H, ($C_1$-$C_6$)-alkyl, —$OR_{25}$, halogen, —$CF_3$, —$NO_2$ or —CN; one of $R_1$, $R_2$, $R_3$, $R_4$, $R_5$, and $R_6$ is —H, ($C_1$-$C_6$)-alkyl, —$OR_{25}$, halogen, or —$CF_3$; one of $R_{13}$, $R_{14}$, $R_{15}$, and $R_{16}$ is —H, ($C_1$-$C_6$)-alkyl, —$OR_{25}$, or halogen, $R_a$ and $R_b$ are each independently —H or —$CH_3$; and each remaining R group is hydrogen except for the R group through which the piperidine is connected. In one embodiment, $R_5$ is —H, ($C_1$-$C_6$)-alkyl, —$OR_{25}$, halogen, —$CF_3$, —$NO_2$ or —CN and one of $R_4$ or $R_5$ is —H, ($C_1$-$C_6$)-alkyl, —$OR_{25}$, halogen, or —$CF_3$ and each remaining R group is hydrogen except for the R group through which the piperidine is connected. In one embodiment $R_8$ is —H, ($C_1$-$C_6$)-alkyl, —$OR_{25}$, halogen, —$CF_3$, —$NO_2$ or —CN; and all other R groups are each hydrogen except for the R group through which the piperidine is connected. In one embodiment, $R_8$ is —H, ($C_1$-$C_6$)-alkyl, —$OR_{25}$, halogen, —$CF_3$, —$NO_2$ or —CN; one of $R_{13}$, $R_{14}$, $R_{15}$, and $R_{16}$ is —H, ($C_1$-$C_6$)-alkyl, —$OR_{25}$, or halogen, $R_a$ and $R_b$ are each independently —H or —$CH_3$; and each remaining R group is hydrogen except for the R group through which the piperidine is connected.

In one embodiment, $R_9$ is —H, ($C_1$-$C_6$)-alkyl, —$OR_{25}$, halogen, —$CF_3$, —$NO_2$ or —CN. In another embodiment, $R_9$ is —H, ($C_1$-$C_6$)-alkyl, —$OR_{25}$, halogen, —$CF_3$, —$NO_2$ or —CN; one of $R_1$, $R_2$, $R_3$, $R_4$, $R_5$ and $R_6$, is —H, ($C_1$-$C_6$)-alkyl, —$OR_{25}$, halogen, or —$CF_3$; $R_a$ and $R_b$ are each independently —H or —$CH_3$; and each remaining R group is hydrogen except for the R group through which the piperidine is connected. In a further embodiment, $R_9$ is —H, ($C_1$-$C_6$)-alkyl, —$OR_{25}$, halogen, —$CF_3$, —$NO_2$ or —CN; one of $R_1$, $R_2$, $R_3$, $R_4$, $R_5$ and $R_6$ is —H, ($C_1$-$C_6$)-alkyl, —$OR_{25}$, halogen, or —$CF_3$; one of $R_{13}$, $R_{14}$, $R_{15}$, and $R_{16}$ is —H, ($C_1$-$C_6$)-alkyl, —$OR_{25}$, or halogen; $R_a$ and $R_b$ are each independently —H or —$CH_3$; and each remaining R group is hydrogen except for the R group through which the piperidine is connected. In one embodiment, $R_9$ is —H, ($C_1$-$C_6$)-alkyl, —$OR_{25}$, halogen, —$CF_3$, —$NO_2$ or —CN and one of $R_4$ or $R_5$ is —H, ($C_1$-$C_6$)-alkyl, —$OR_{25}$, halogen, or —$CF_3$. In one embodiment $R_9$ is —H, ($C_1$-$C_6$)-alkyl, —$OR_{25}$, halogen, —$CF_3$, —$NO_2$ or —CN; and all other R groups are each hydrogen except for the R group through which the piperidine is connected. In one embodiment, $R_9$ is —H, ($C_1$-$C_6$)-alkyl, —$OR_{25}$, halogen, —$CF_3$, —$NO_2$ or —CN; one of $R_{13}$, $R_{14}$, $R_{15}$, and $R_{16}$ is —H, ($C_1$-$C_6$)-alkyl, —$OR_{25}$, or halogen, and each remaining R group is hydrogen except for the R group through which the piperidine is connected.

In one embodiment, $R_7$ is —H, ($C_1$-$C_6$)-alkyl, —$OR_{25}$, halogen, —$CF_3$, —$NO_2$ or —CN. In one embodiment, $R_7$ is —H, ($C_1$-$C_6$)-alkyl or halogen. In one embodiment, $R_7$ is —H, ($C_1$-$C_6$)-alkyl, —$OR_{25}$, halogen, —$CF_3$, —$NO_2$ or —CN; one of $R_1$, $R_2$, $R_3$, $R_4$, $R_5$ and $R_6$ is —H, ($C_1$-$C_6$)-alkyl, —$OR_{25}$, halogen, or —$CF_3$; and $R_a$ and $R_b$ are each independently —H or —$CH_3$; and each remaining R group is hydrogen, except for the R group through which the piperidine is connected. In one embodiment, $R_7$ is —H, ($C_1$-$C_6$)-alkyl, —$OR_{25}$, halogen, —$CF_3$, —$NO_2$ or —N; one of $R_1$, $R_2$, $R_3$, $R_4$, $R_5$ and $R_6$ is —H, ($C_1$-$C_6$)-alkyl, —$OR_{25}$, halogen, or —$CF_3$; and each remaining R group is hydrogen, except for the R group through which the piperidine is connected.

In one embodiment, $R_{10}$ is —H, ($C_1$-$C_6$)-alkyl, —$OR_{25}$, halogen, —$CF_3$, —$NO_2$ or —CN. In one embodiment, $R_{10}$ is —H, ($C_1$-$C_6$)-alkyl, —$OR_{25}$, halogen, or —$CF_3$. In one embodiment, $R_{10}$ is —H, $CH_3$, —$OCH_3$, —F or —$CF_3$. In one embodiment, $R_{10}$ is —H, ($C_1$-$C_6$)-alkyl, —$OR_{25}$, halogen, —$CF_3$, —$NO_2$ or —CN; one of $R_1$, $R_2$, $R_3$, $R_4$, $R_5$ and $R_6$ is —H, ($C_1$-$C_6$)-alkyl, —$OR_{25}$, halogen, or —$CF_3$; and $R_a$ and $R_b$ are each independently —H or —$CH_3$; and each remaining R group is hydrogen, except for the R group through which the piperidine is connected. In one embodiment, $R_{10}$ is —H, ($C_1$-$C_6$)-alkyl, —$OR_{25}$, halogen, —$CF_3$, —$NO_2$ or —CN; one of $R_1$, $R_2$, $R_3$, $R_4$, $R_5$ and $R_6$ is —H, ($C_1$-$C_6$)-alkyl, —$OR_{25}$, halogen, or —$CF_3$; and each remaining R group is hydrogen, except for the R group through which the piperidine is connected.

In one embodiment, $R_{11}$ is —H, ($C_1$-$C_6$)-alkyl, —$OR_{25}$, halogen, —$CF_3$, —$NO_2$ or —CN. In one embodiment, $R_{11}$ is —H, ($C_1$-$C_6$)-alkyl, halogen, or —$CF_3$. In one embodiment, $R_{11}$ is —H, —$CH_3$, —F or —$CF_3$. In one embodiment, $R_{11}$ is —H, ($C_1$-$C_6$)-alkyl, —$OR_{25}$, halogen, —$CF_3$, —$NO_2$ or —CN; one of $R_1$, $R_2$, $R_3$, $R_4$, $R_5$ and $R_6$ is —H, ($C_1$-$C_6$)-alkyl, —$OR_{25}$, halogen, or —$CF_3$; and $R_a$ and $R_b$ are each independently —H or —$CH_3$; and each remaining R group is hydrogen, except for the R group through which the piperidine is connected. In one embodiment, $R_{11}$ is —H, ($C_1$-$C_6$)-alkyl, —$OR_{25}$, halogen, —$CF_3$, —$NO_2$ or —N; one of $R_1$, $R_2$, $R_3$, $R_4$, $R_5$ and $R_6$ is —H, ($C_1$-$C_6$)-alkyl, —$OR_{25}$, halogen, or —$CF_3$; and each remaining R group is hydrogen, except for the R group through which the piperidine is connected.

In one embodiment, $R_{12}$ is —H, $(C_1-C_6)$-alkyl, —$OR_{25}$, halogen, —$CF_3$, —$NO_2$ or —CN. In one embodiment, $R_{12}$ is —H, $(C_1-C_6)$-alkyl, halogen, or —$CF_3$. In one embodiment, $R_{12}$ is —H, —$CH_3$, —F or —$CF_3$. In one embodiment, $R_{12}$ is —H, $(C_1-C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1-C_6)$-alkyl, —$OR_{25}$, halogen, or —$CF_3$; and $R_a$ and $R_b$ are each independently —H or —$CH_3$; and each remaining R group is hydrogen, except for the R group through which the piperidine is connected. In one embodiment, $R_{12}$ is —H, $(C_1-C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1-C_6)$-alkyl, —$OR_{25}$, halogen, or —$CF_3$; and each remaining R group is hydrogen, except for the R group through which the piperidine is connected.

In one embodiment, $R_1$, $R_2$, $R_3$, $R_4$, $R_7$, $R_{7'}$, $R_9$, $R_{10}$, $R_{11}$, and $R_{12}$, are each hydrogen except for the R group through which the piperidine is connected.

In one embodiment, $R_1$, $R_2$, $R_3$, $R_4$, $R_7$, $R_{7'}$, $R_8$, $R_{10}$, $R_{11}$, and $R_{12}$, are each hydrogen except for the R group through which the piperidine is connected.

In one embodiment, $R_1$, $R_2$, $R_3$, $R_4$, $R_7$, $R_{7'}$, $R_8$, $R_9$, $R_1$, and $R_{12}$, are each hydrogen except for the R group through which the piperidine is connected.

In one embodiment, $R_1$, $R_2$, $R_3$, $R_4$, $R_7$, $R_{7'}$, $R_8$, $R_9$, $R_{10}$, and $R_{11}$, are each hydrogen except for the R group through which the piperidine is connected.

In one embodiment, $R_1$, $R_2$, $R_3$, $R_4$, $R_7$, $R_{7'}$, $R_8$, and $R_{11}$, are each hydrogen except for the R group through which the piperidine is connected.

In one embodiment, $R_1$, $R_2$, $R_3$, $R_4$, $R_7$, $R_{7'}$, $R_8$, $R_9$, and $R_{11}$, are each hydrogen except for the R group through which the piperidine is connected.

In one embodiment, $R_1$, $R_2$, $R_3$, $R_4$, $R_7$, $R_{7'}$, $R_8$, $R_9$, $R_{10}$, $R_{11}$, and $R_{12}$, are each hydrogen except for the R group through which the piperidine is connected.

In one embodiment, $R_1$, $R_2$, $R_3$, $R_6$, $R_{7'}$, $R_7$, $R_8$, $R_9$, $R_{10}$, $R_{11}$, $R_{12}$, $R_{13}$, $R_{14}$, $R_{15}$, and $R_{16}$ are each hydrogen except for the R group through which the piperidine is connected.

In one embodiment, $R_1$, $R_2$, $R_3$, $R_6$, $R_{7'}$, $R_7$, $R_8$, $R_9$, $R_{10}$, $R_{11}$, and $R_{12}$ are each hydrogen except for the R group through which the piperidine is connected.

In one embodiment, $R_1$, $R_2$, $R_3$, $R_4$, $R_5$, $R_6$, $R_{7'}$, $R_7$, $R_{10}$, $R_{11}$, $R_{12}$, $R_{13}$, $R_{14}$, $R_{15}$, and $R_{16}$ are each hydrogen except for the R group through which the piperidine is connected.

In one embodiment, $R_1$, $R_2$, $R_3$, $R_4$, $R_5$, $R_6$, $R_7$—, $R_7$, $R_{10}$, $R_{11}$, and $R_{12}$ are each hydrogen.

In another embodiment, $R_{13}$, $R_{14}$, $R_{15}$, and $R_{16}$ are each hydrogen.

In one embodiment, $R_3$, $R_6$, $R_{7'}$, $R_7$, $R_{10}$, $R_{11}$, $R_{12}$, $R_{13}$, $R_{14}$, $R_{15}$, and $R_{16}$ are each hydrogen except for the R group through which the piperidine is connected.

In one embodiment, $R_1$, $R_2$, $R_3$, $R_4$, $R_6$, $R_7$, $R_8$, $R_{10}$, $R_{11}$, $R_{12}$, $R_{13}$, $R_{14}$, $R_{15}$, and $R_{16}$ are each hydrogen except for the R group through which the piperidine is connected.

In one embodiment, $R_1$, $R_2$, $R_3$, $R_4$, $R_6$, $R_7$, $R_8$, $R_9$, $R_{10}$, $R_{11}$, $R_{12}$, $R_{13}$, $R_{14}$, $R_{15}$, and $R_{16}$ are each hydrogen except for the R group through which the piperidine is connected.

In one embodiment, $R_1$ is —H or $(C_1-C_6)$-alkyl; $R_4$ and $R_5$ are each independently —H, halogen, —$OR_{25}$, or —$CF_3$; $R_7$, $R_{7'}$, $R_8$, $R_9$, $R_{10}$, $R_{11}$, and $R_{12}$ are each independently —H, halogen, $(C_1-C_6)$-alkyl, —$OR_{25}$, —$CF_3$, $NO_2$ or CN except for the R group through which the piperidine is connected.

In one embodiment, $R_5$ is —H, halogen, or —$OR_{25}$; and $R_3$, $R_6$, $R_{7'}$, $R_7$, $R_8$, $R_9$, $R_{12}$, $R_{13}$, $R_{14}$, $R_{15}$, and $R_{16}$ are each hydrogen except for the R group through which the piperidine is connected.

In one embodiment, $R_1$ is —H or $(C_1-C_6)$-alkyl; $R_2$, $R_8$, and $R_9$ are each —H or halogen; $R_4$ is —H, halogen, —$OR_{25}$, or —$CF_3$; $R_5$ is —H, halogen, or —$OR_{25}$; and $R_3$, $R_6$, $R_7$, $R_{7'}$, $R_8$, $R_9$, $R_{12}$, $R_{13}$, $R_{14}$, $R_{15}$, and $R_{16}$ are each hydrogen except for the R group through which the piperidine is connected. In one embodiment, $R_1$ is —H or $(C_1-C_6)$-alkyl; $R_2$, $R_8$, and $R_9$ are each —H or F; $R_4$ is H, F, —$OR_{25}$, or —$CF_3$; $R_5$ is —H, F, or —$OR_{25}$; and $R_3$, $R_6$, $R_7$, $R_{7'}$, $R_8$, $R_9$, $R_{12}$, $R_{13}$, $R_{14}$, $R_{15}$, and $R_{16}$ are each hydrogen except for the R group through which the piperidine is connected.

In one embodiment, any one of $R_1$, $R_2$, $R_3$, $R_4$, $R_5$, and $R_6$ is —H, $(C_1-C_6)$-alkyl, —$OR_{25}$, halogen; and any one of $R_{7'}$, $R_7$, $R_8$, $R_9$, $R_{10}$, $R_{11}$, and $R_{12}$ is —H, $(C_1-C_6)$-alkyl, —$OR_{25}$, halogen, or —$CF_3$, —$NO_2$, or —CN except for the R group through which the piperidine is connected.

In one embodiment, $R_5$ is —H, $(C_1-C_6)$-alkyl, —$OR_{25}$, halogen or —$CF_3$; and any one of $R_7$, $R_{7'}$, $R_8$, $R_9$, $R_{10}$, $R_{11}$, and $R_{12}$ is —H, $(C_1-C_6)$-alkyl, —$OR_{25}$, halogen, or —$CF_3$, —$NO_2$, or —CN, except for the R group through which the piperidine is connected.

In one embodiment, $R_5$ is —H, $(C_1-C_6)$-alkyl, —$OR_{25}$, halogen or —$CF_3$; and any two of $R_7$, $R_{7'}$, $R_8$, $R_9$, $R_{10}$, $R_{11}$, and $R_{12}$ are each independently —H, $(C_1-C_6)$-alkyl, —$OR_{25}$, halogen, or —$CF_3$, —$NO_2$, or —CN, except for the R group through which the piperidine is connected.

In one embodiment, $R_5$ is —H, $(C_1-C_6)$-alkyl, —$OR_{25}$, halogen or —$CF_3$; and any three of $R_7$, $R_{7'}$, $R_8$, $R_9$, $R_{10}$, $R_{11}$, and $R_{12}$ are each independently —H, $(C_1-C_6)$-alkyl, —$OR_{25}$, halogen, or —$CF_3$, —$NO_2$, or —CN, except for the R group through which the piperidine is connected.

In one embodiment, any one of $R_1$, $R_2$, $R_3$, $R_4$, $R_5$, and $R_6$ is —H, $(C_1-C_6)$-alkyl, —$OR_{25}$, halogen; and any one of $R_{13}$, $R_{14}$, $R_{15}$, and $R_{16}$ is —H, $(C_1-C_6)$-alkyl, —$OR_{25}$, or halogen.

In one embodiment, any one of $R_7$, $R_{7'}$, $R_8$, $R_9$, $R_{10}$, $R_{11}$, and $R_{12}$ is —H, $(C_1-C_6)$-alkyl, —$OR_{25}$, halogen, or —$CF_3$, —$NO_2$, or —CN except for the R group through which the piperidine is connected; and any one of $R_{13}$, $R_{14}$, $R_{15}$, and $R_{16}$ is —H, $(C_1-C_6)$-alkyl, —$OR_{25}$, halogen or —$CF_3$.

In one embodiment, $R_4$ is —H, $(C_1-C_6)$-alkyl, —$OR_{25}$, halogen, or —$CF_3$ and any one of $R_{13}$, $R_{14}$, $R_{15}$, and $R_{16}$ is —H, $(C_1-C_6)$-alkyl, —$OR_{25}$, or halogen; and any one of $R_{7'}$, $R_7$, $R_8$, $R_9$, $R_{10}$, $R_{11}$, and $R_{12}$ is —H, $(C_1-C_6)$-alkyl, —$OR_{25}$, halogen, or —$CF_3$, —$NO_2$, or —CN except for the R group through which the piperidine is connected.

In one embodiment, $R_4$ is —H, $(C_1-C_6)$-alkyl, —$OR_{25}$, halogen, or —$CF_3$ and any one of $R_{13}$, $R_{14}$, $R_{15}$, and $R_{16}$ is —H, $(C_1-C_6)$-alkyl, —$OR_{25}$, or halogen; and any two of $R_{7'}$, $R_7$, $R_8$, $R_9$, $R_{10}$, $R_{11}$, and $R_{12}$ are each independently —H, $(C_1-C_6)$-alkyl, —$OR_{25}$, halogen, or —$CF_3$, —$NO_2$, or —CN except for the R group through which the piperidine is connected; wherein the any two of $R_{7'}$, $R_7$, $R_8$, $R_9$, $R_{10}$, $R_{11}$, and $R_{12}$ can be either on the same ring of the quinoline or on different rings.

In one embodiment, $R_5$ is —H, $(C_1-C_6)$-alkyl, —$OR_{25}$, halogen, or —$CF_3$ and any one of $R_{13}$, $R_{14}$, $R_{15}$, and $R_{16}$ is —H, $(C_1-C_6)$-alkyl, —$OR_{25}$, or halogen; and any one of $R_{7'}$, $R_7$, $R_8$, $R_9$, $R_{10}$, $R_{11}$, and $R_{12}$ is —H, $(C_1-C_6)$-alkyl, —$OR_{25}$, halogen, or —$CF_3$, —$NO_2$, or —CN except for the R group through which the piperidine is connected In one embodiment, $R_5$ is —H, $(C_1-C_6)$-alkyl, —$OR_{25}$, halogen, or —$CF_3$ and any one of $R_{13}$, $R_{14}$, $R_{15}$, and $R_{16}$ is —H, $(C_1-C_6)$-alkyl, —$OR_{25}$, or halogen; and any two of $R_{7'}$, $R_7$, $R_8$, $R_9$, $R_{10}$, $R_1$, and $R_{12}$ are each independently —H, $(C_1-C_6)$-alkyl, —$OR_{25}$, halogen, or —$CF_3$, —$NO_2$, or —CN except for the R group through which the piperidine is connected; wherein the any two of $R_{7'}$, $R_7$, $R_8$, $R_9$, $R_{10}$, $R_{11}$, and $R_{12}$ can be either on the same ring of the quinoline or on different rings.

In one embodiment, the piperidine N is connected through the $R_7$ of the quinoline. In another embodiment, the piperidine N is connected through the $R_{7'}$ of the quinoline. In yet another embodiment, the piperidine N is connected through the $R_8$ of the quinoline. In still another embodiment, the piperidine N is connected through the $R_9$ of the quinoline.

In one embodiment, $R_{25}$ is $(C_1-C_6)$-haloalkyl.

In another embodiment, $R_{25}$ is $(C_1-C_6)$-fluoroalkyl.

In one embodiment, $R_{25}$ is $(C_1-C_6)$-alkyl. In one embodiment, $R_{25}$ is —$CH_3$.

In one embodiment, the compounds of Formula (I") are antagonists of the 5-$HT_{1A}$ receptor. In another embodiment, the compounds of Formula (I") are agonists of the 5-$HT_{1A}$ receptor.

In another embodiment, the compounds of Formula (I") have the Formula (I")a:

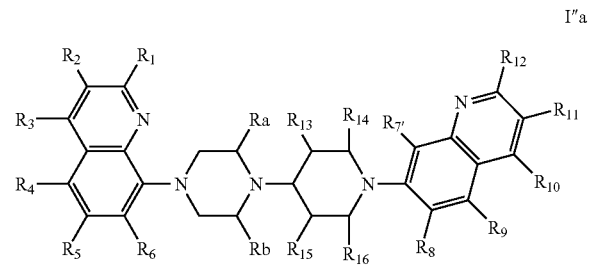

I"a and pharmaceutically acceptable salts thereof, wherein $R_a$, $R_b$, $R_1$, $R_2$, $R_3$, $R_4$, $R_5$, $R_6$, $R_{7'}$, $R_8$, $R_9$, $R_{10}$, $R_{11}$, $R_{12}$, $R_{13}$, $R_{14}$, $R_{15}$, $R_{16}$, and $R_{25}$ are defined as above for Formula (I")

In one embodiment, $R_1$ is —H, $(C_1-C_6)$-alkyl, —$OR_{25}$, halogen, or —$CF_3$. In another embodiment, $R_1$ is —H, $(C_1-C_6)$-alkyl, —$OR_{25}$, halogen, or —$CF_3$ and one of $R_{13}$, $R_{14}$, $R_{15}$, and $R_{16}$ is —H, $(C_1-C_6)$-alkyl, —$OR_{25}$, or halogen. In a further embodiment, $R_1$ is —H, $(C_1-C_6)$-alkyl, —$OR_{25}$, halogen, or —$CF_3$; one of $R_{13}$, $R_{14}$, $R_{15}$, and $R_{16}$ is —H, $(C_1-C_6)$-alkyl, —$OR_{25}$, or halogen, and $R_{7'}$, $R_8$, $R_9$, $R_{10}$, $R_{11}$, and $R_{12}$ are each hydrogen. In yet another embodiment, $R_1$ is —H, $(C_1-C_6)$-alkyl, —$OR_{25}$, halogen, or —$CF_3$; one of $R_{13}$, $R_{14}$, $R_{15}$, and $R_{16}$ is —H, $(C_1-C_6)$-alkyl, —$OR_{25}$, or halogen, and $R_2$, $R_3$, $R_4$ $R_5$, $R_6$, $R_{7'}$, $R_8$, $R_9$, $R_{10}$, $R_{11}$, and $R_{12}$ are each hydrogen. In one embodiment, $R_1$ is —H, $(C_1-C_6)$-alkyl, —$OR_{25}$, halogen or —$CF_3$ and $R_2$, $R_3$, $R_4$, $R_5$, $R_6$, $R_{7'}$, $R_8$, $R_9$, $R_{10}$, $R_{11}$, $R_{12}$, $R_{13}$, $R_{14}$, $R_{15}$, and $R_{16}$ are each hydrogen.

In one embodiment, $R_4$ is —H, $(C_1-C_6)$-alkyl, —$OR_{25}$, halogen, or —$CF_3$. In another embodiment, $R_4$ is —H, $(C_1-C_6)$-alkyl, —$OR_{25}$, halogen, or —$CF_3$ and one of $R_{13}$, $R_{14}$, $R_{15}$, and $R_{16}$ is —H, $(C_1-C_6)$-alkyl, —$OR_{25}$, or halogen. In a further embodiment, $R_4$ is —H, $(C_1-C_6)$-alkyl, —$OR_{25}$, halogen, or —$CF_3$; one of $R_{13}$, $R_{14}$, $R_{15}$, and $R_{16}$ is —H, $(C_1-C_6)$-alkyl, —$OR_{25}$, or halogen, and $R_{7'}$, $R_8$, $R_9$, $R_{10}$, $R_{11}$, and $R_{12}$ are each hydrogen. In yet another embodiment, $R_4$ is —H, $(C_1-C_6)$-alkyl, —$OR_{25}$, halogen, or —$CF_3$; one of $R_{13}$, $R_{14}$, $R_{15}$, and $R_{16}$ is —H, $(C_1-C_6)$-alkyl, —$OR_{25}$, or halogen, and $R_1$, $R_2$, $R_3$, $R_5$, $R_6$, $R_{7'}$, $R_8$, $R_9$, $R_{10}$, $R_{11}$, and $R_{12}$ are each hydrogen. In one embodiment, $R_4$ is —H, $(C_1-C_6)$-alkyl, —$OR_{25}$, halogen or —$CF_3$ and $R_1$, $R_2$, $R_3$, $R_5$, $R_6$, $R_{7'}$, $R_8$, $R_9$, $R_{10}$, $R_{11}$, $R_{12}$, $R_{13}$, $R_{14}$, $R_{15}$, and $R_{16}$ are each hydrogen.

In one embodiment, $R_5$ is —H, $(C_1-C_6)$-alkyl, —$OR_{25}$, halogen, or —$CF_3$. In another embodiment, $R_5$ is —H, $(C_1-C_6)$-alkyl, —$OR_{25}$, halogen, or —$CF_3$ and one of $R_{13}$, $R_{14}$, $R_{15}$, and $R_{16}$ is —H, $(C_1-C_6)$-alkyl, —$OR_{25}$, or halogen. In a further embodiment, $R_5$ is —H, $(C_1-C_6)$-alkyl, —$OR_{25}$, halogen, or —$CF_3$; one of $R_{13}$, $R_{14}$, $R_{15}$, and $R_{16}$ is —H, $(C_1-C_6)$-alkyl, —$OR_{25}$, or halogen, and $R_{7'}$, $R_8$, $R_9$, $R_{10}$, $R_{11}$, and $R_{12}$ are each hydrogen. In yet another embodiment, $R_5$ is —H, $(C_1-C_6)$-alkyl, —$OR_{25}$, halogen, or —$CF_3$; one of $R_{13}$, $R_{14}$, $R_{15}$, and $R_{16}$ is —H, $(C_1-C_6)$-alkyl, —$OR_{25}$, or halogen; and $R_1$, $R_2$, $R_3$, $R_4$, $R_6$, $R_{7'}$, $R_8$, $R_9$, $R_{10}$, $R_{11}$, and $R_{12}$ are each hydrogen. In one embodiment, $R_5$ is —H, $(C_1-C_6)$-alkyl, —$OR_{25}$, halogen or —$CF_3$ and $R_1$, $R_2$, $R_3$, $R_4$, $R_6$, $R_{7'}$, $R_8$, $R_9$, $R_{10}$, $R_{11}$, $R_{12}$, $R_{13}$, $R_{14}$, $R_{15}$, and $R_{16}$ are each hydrogen. In a further embodiment, one of $R_{13}$, $R_{14}$, $R_{15}$, and $R_{16}$ is —H, $(C_1-C_6)$-alkyl, halogen, —$CF_3$, or —$OR_{25}$; $R_5$ is —H, $(C_1-C_6)$-alkyl, —$OR_{25}$, halogen, or —$CF_3$; and each remaining R group is hydrogen.

In one embodiment, $R_7$ is —H, $(C_1-C_6)$-alkyl, —$OR_{25}$, halogen, —$CF_3$, —$NO_2$ or —CN. In one embodiment, $R_7$ is —H, $(C_1-C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1-C_6)$-alkyl, —$OR_{25}$, halogen, or —$CF_3$; and $R_a$ and $R_b$ are each independently —H or —$CH_3$; and each remaining R group is hydrogen. In one embodiment, $R_7$ is —H, $(C_1-C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1-C_6)$-alkyl, —$OR_{25}$, halogen, or —$CF_3$; and each remaining R group is hydrogen. In one embodiment, $R_7$ is —H, $(C_1-C_6)$-alkyl, —$OR_{25}$, halogen, —$CF_3$, —$NO_2$ or —CN; and each remaining R group is hydrogen.

In one embodiment, $R_8$ is —H, $(C_1-C_6)$-alkyl, —$OR_{25}$, halogen, —$CF_3$, —$NO_2$ or —CN. In another embodiment, $R_8$ is —H, $(C_1-C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1-C_6)$-alkyl, —$OR_{25}$, halogen, or —$CF_3$; $R_a$ and $R_b$ are each independently —H or —$CH_3$; and each remaining R group is hydrogen. In a further embodiment, $R_8$ is —H, $(C_1-C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1-C_6)$-alkyl, —$OR_{25}$, halogen, or —$CF_3$; one of $R_{13}$, $R_{14}$, $R_{15}$, and $R_{16}$ is —H, $(C_1-C_6)$-alkyl, —$OR_{25}$, or halogen, $R_a$ and $R_b$ are each independently —H or —$CH_3$, and each remaining R group is hydrogen. In one embodiment, $R_8$ is —H, $(C_1-C_6)$-alkyl, —$OR_{25}$, halogen, —$CF_3$, —$NO_2$ or —CN; one of $R_4$ or $R_5$ is —H, $(C_1-C_6)$-alkyl, —$OR_{25}$, halogen, or —$CF_3$, $R_a$ and $R_b$ are each independently —H or —$CH_3$, and each remaining R group is hydrogen. In one embodiment, $R_8$ is —H, $(C_1-C_6)$-alkyl, —$OR_{25}$, halogen, —$CF_3$, —$NO_2$ or —CN; and all other R groups are each hydrogen. In one embodiment, $R_8$ is —H, $(C_1-C_6)$-alkyl, —$OR_{25}$, halogen, —$CF_3$, —$NO_2$ or —CN; one of $R_{13}$, $R_{14}$, $R_{15}$, and $R_{16}$ is —H, $(C_1-C_6)$-alkyl, —$OR_{25}$, or halogen, $R_a$ and $R_b$ are each independently —H or —$CH_3$, and each remaining R group is hydrogen.

In one embodiment, $R_9$ is —H, $(C_1-C_6)$-alkyl, —$OR_{25}$, halogen, —$CF_3$, —$NO_2$ or —CN. In another embodiment, $R_9$ is —H, $(C_1-C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1-C_6)$-alkyl, —$OR_{25}$, halogen, or —$CF_3$; $R_a$ and $R_b$ are each independently —H or —$CH_3$; and each remaining R group is hydrogen. In a further embodiment, $R_9$ is —H, $(C_1-C_6)$-alkyl, —$OR_{25}$, halogen, —$CF_3$, —$NO_2$ or —CN; one of $R_1$, $R_2$, $R_3$, $R_4$, $R_5$ and $R_b$ is —H, $(C_1-C_6)$-alkyl, —$OR_{25}$, halogen, or —$CF_3$; one of $R_{13}$, $R_{14}$, $R_{15}$, and $R_{16}$ is —H, $(C_1-C_6)$-alkyl, —$OR_{25}$, or halogen, and each remaining R group is hydrogen. In one embodiment, $R_9$ is —H, $(C_1-C_6)$-alkyl, —$OR_{25}$, halogen, —$CF_3$, —$NO_2$ or —CN; one of $R_4$ or $R_5$ is —H, $(C_1-C_6)$-alkyl, —$OR_{25}$, halogen, or —$CF_3$, and each remaining R group is hydrogen. In one embodiment $R_9$ is —H, $(C_1-C_6)$-alkyl, —$OR_{25}$, halogen, —$CF_3$, —$NO_2$ or —CN;

and all other R groups are each hydrogen. In one embodiment, $R_9$ is —H, $(C_1$-$C_6)$-alkyl, —$OR_{25}$, halogen, —$CF_3$, —$NO_2$ or —CN; one of $R_{13}$, $R_{14}$, $R_{15}$, and $R_{16}$ is —H, $(C_1$-$C_6)$-alkyl, —$OR_{25}$, or halogen; and each remaining R group is hydrogen.

In one embodiment, $R_{10}$ is —H, $(C_1$-$C_6)$-alkyl, —$OR_{25}$, halogen, —$CF_3$, —$NO_2$ or —CN. In one embodiment, $R_{10}$ is —H, $(C_1$-$C_6)$-alkyl, —$OR_{25}$, halogen, or —$CF_3$. In one embodiment, $R_{10}$ is —H, —$CH_3$, —$OCH_3$, —F or —$CF_3$. In one embodiment, $R_{10}$ is —H, $(C_1$-$C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1$-$C_6)$-alkyl, —$OR_{25}$, halogen, or —$CF_3$; $R_a$ and $R_b$ are each independently —H or —$CH_3$; and each remaining R group is hydrogen. In one embodiment, $R_{10}$ is —H, $(C_1$-$C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1$-$C_6)$-alkyl, —$OR_{25}$, halogen, or —$CF_3$; and each remaining R group is hydrogen.

In one embodiment, $R_{11}$ is —H, $(C_1$-$C_6)$-alkyl, —$OR_{25}$, halogen, —$CF_3$, —$NO_2$ or —CN. In one embodiment, $R_{11}$ is —H, $(C_1$-$C_6)$-alkyl, halogen, or —$CF_3$. In one embodiment, $R_{11}$ is —H, —$CH_3$, —F or —$CF_3$. In one embodiment, $R_{11}$ is —H, $(C_1$-$C_6)$-alkyl, —$OR_{25}$, halogen, —$CF_3$, or —$NO_2$. In one embodiment, $R_{11}$ is —H, $(C_1$-$C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1$-$C_6)$-alkyl, —$OR_{25}$, halogen, or —$CF_3$; and $R_a$ and $R_b$ are each independently —H or —$CH_3$; and each remaining R group is hydrogen. In one embodiment, $R_{11}$ is —H, $(C_1$-$C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1$-$C_6)$-alkyl, —$OR_{25}$, halogen, or —$CF_3$; and each remaining R group is hydrogen.

In one embodiment, $R_{12}$ is —H, $(C_1$-$C_6)$-alkyl, —$OR_{25}$, halogen, —$CF_3$, —$NO_2$ or —CN. In one embodiment, $R_{12}$ is —H, $(C_1$-$C_6)$-alkyl, halogen, or —$CF_3$. In one embodiment, $R_{12}$ is —H, —$CH_3$, —F or —$CF_3$. In one embodiment, $R_{12}$ is —H, $(C_1$-$C_6)$-alkyl, —$OR_{25}$, halogen, —$CF_3$, or —$NO_2$. In one embodiment, $R_{12}$ is —H, $(C_1$-$C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1$-$C_6)$-alkyl, —$OR_{25}$, halogen, or —$CF_3$; $R_a$ and $R_b$ are each independently —H or —$CH_3$; and each remaining R group is hydrogen. In one embodiment, $R_{12}$ is —H, $(C_1$-$C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1$-$C_6)$-alkyl, —$OR_{25}$, halogen, or —$CF_3$; and each remaining R group is hydrogen.

In one embodiment, $R_5$ is —H, $(C_1$-$C_6)$-alkyl, —$OR_{25}$, halogen, or —$CF_3$ and one of $R_7$, $R_8$, $R_9$, $R_{10}$, $R_{11}$, and $R_{12}$ is —H, $(C_1$-$C_6)$-alkyl, —$OR_{25}$, halogen, —$CF_3$, —$NO_2$ or —CN. In another embodiment, $R_5$ is —H, $(C_1$-$C_6)$-alkyl, —$OR_{25}$, halogen, or —$CF_3$ and one of $R_7$, $R_8$, $R_9$, $R_{10}$, $R_{11}$, $R_{12}$ is —H, $(C_1$-$C_6)$-alkyl, —$OR_{25}$, halogen, —$CF_3$, —$NO_2$ or —CN; and each remaining R group is hydrogen. In some embodiments, $R_5$ is —H, $(C_1$-$C_6)$-alkyl, —$OR_{25}$, halogen, or —$CF_3$ and $R_9$ is —H, $(C_1$-$C_6)$-alkyl, —$OR_{25}$, halogen, —$CF_3$, —$NO_2$ or —CN; and each remaining R group is hydrogen. In some embodiments, $R_5$ is —H, $(C_1$-$C_6)$-alkyl, —$OR_{25}$, halogen, or —$CF_3$ and $R_7$ is —H, $(C_1$-$C_6)$-alkyl, —$OR_{25}$, halogen, —$CF_3$, —$NO_2$ or —CN; and each remaining R group is hydrogen. In some embodiments, $R_5$ is —H or —$OR_{25}$ and $R_7$ is —H or halogen; and each remaining R group is hydrogen.

In a further embodiment, $R_5$ is —H, $(C_1$-$C_6)$-alkyl, —$OR_{25}$, halogen, or —$CF_3$; one of $R_7$, $R_8$, $R_9$, $R_{10}$, $R_{11}$, and $R_{12}$ is —H, $(C_1$-$C_6)$-alkyl, —$OR_{25}$, halogen, —$CF_3$, —$NO_2$ or —CN; one of $R_{13}$, $R_{14}$, $R_{15}$, and $R_{16}$ is —H, $(C_1$-$C_6)$-alkyl, —$OR_{25}$, or halogen, and each remaining R group is hydrogen.

In a further embodiment, $R_5$ is —H, $(C_1$-$C_6)$-alkyl, —$OR_{25}$, halogen, or —$CF_3$; two of $R_7$, $R_8$, $R_9$, $R_{10}$, $R_{11}$, and $R_{12}$ are each independently —H, $(C_1$-$C_6)$-alkyl, —$OR_{25}$, halogen, —$CF_3$, —$NO_2$ or —CN; one of $R_{13}$, $R_{14}$, $R_{15}$, and $R_{16}$ is —H, $(C_1$-$C_6)$-alkyl, —$OR_{25}$, or halogen, and each remaining R group is hydrogen.

In a further embodiment, $R_5$ is —H, $(C_1$-$C_6)$-alkyl, —$OR_{25}$, halogen, or —$CF_3$; three of $R_7$, $R_8$, $R_9$, $R_{10}$, $R_{11}$, and $R_{12}$ are each independently —H, $(C_1$-$C_6)$-alkyl, —$OR_{25}$, halogen, —$CF_3$, —$NO_2$ or —CN; one of $R_{13}$, $R_{14}$, $R_{15}$, and $R_{16}$ is —H, $(C_1$-$C_6)$-alkyl, —$OR_{25}$, or halogen, and each remaining R group is hydrogen.

In one embodiment, $R_5$ is —H, $(C_1$-$C_6)$-alkyl, —$OR_{25}$, halogen, or —$CF_3$; $R_9$ is —H, $(C_1$-$C_6)$-alkyl, —$OR_{25}$, halogen, —$CF_3$, —$NO_2$ or —CN; and two of $R_{10}$, $R_{11}$ and $R_{12}$ are each independently —H, $(C_1$-$C_6)$-alkyl, —$OR_{25}$, halogen, —$CF_3$, —$NO_2$ or —CN. In another embodiment, $R_5$ is —H, $(C_1$-$C_6)$-alkyl, —$OR_{25}$, halogen, or —$CF_3$; $R_9$ is —H, $(C_1$-$C_6)$-alkyl, —$OR_{25}$, halogen, —$CF_3$, —$NO_2$ or —CN; two of $R_{10}$, $R_{11}$, $R_{12}$ are each independently —H, $(C_1$-$C_6)$-alkyl, —$OR_{25}$, halogen, —$CF_3$, —$NO_2$ or —CN; and each remaining R group is hydrogen. In some embodiments, $R_5$ is —H or —$OR_{25}$; $R_9$ is —H or halogen; two of $R_{10}$, $R_{11}$, $R_{12}$ are each independently —H, $(C_1$-$C_6)$-alkyl, —$OR_{25}$, halogen, —$CF_3$, —$NO_2$ or —CN; and each remaining R group is hydrogen. In some embodiments, $R_5$ is —H or —$OCH_3$; $R_9$ is —H or halogen; two of $R_{10}$, $R_{11}$, $R_{12}$ are each independently —H, $(C_1$-$C_6)$-alkyl, —$OR_{25}$, halogen, —$CF_3$, —$NO_2$ or —CN; and each remaining R group is hydrogen. In some embodiments, $R_5$ is —H, $(C_1$-$C_6)$-alkyl, —$OR_{25}$, halogen, or —$CF_3$; $R_9$ is —H, $(C_1$-$C_6)$-alkyl, —$OR_{25}$, halogen, —$CF_3$, —$NO_2$ or —CN; $R_{10}$ and $R_{12}$ are each independently —H, $(C_1$-$C_6)$-alkyl, —$OR_{25}$, halogen, —$CF_3$, —$NO_2$ or —CN; and each remaining R group is hydrogen. In some embodiments, $R_5$ is —H, $(C_1$-$C_6)$-alkyl, —$OR_{25}$, halogen, or —$CF_3$; $R_9$ is —H, $(C_1$-$C_6)$-alkyl, —$OR_{25}$, halogen, —$CF_3$, —$NO_2$ or —CN; $R_{10}$ and $R_1$, are each independently —H, $(C_1$-$C_6)$-alkyl, —$OR_{25}$, halogen, —$CF_3$, —$NO_2$ or —CN; and each remaining R group is hydrogen. In some embodiments, $R_5$ is —H, $(C_1$-$C_6)$-alkyl, —$OR_{25}$, halogen, or —$CF_3$; $R_5$ is —H, $(C_1$-$C_6)$-alkyl, —$OR_{25}$, halogen, —$CF_3$, —$NO_2$ or —CN; $R_1$, and $R_{12}$ are each independently —H, $(C_1$-$C_6)$-alkyl, —$OR_{25}$, halogen, —$CF_3$, —$NO_2$ or —CN; and each remaining R group is hydrogen.

In one embodiment, $R_4$ is —H, $(C_1$-$C_6)$-alkyl, —$OR_{25}$, halogen, or —$CF_3$ and one of $R_7$, $R_8$, $R_9$, $R_{10}$, $R_{11}$ and $R_{12}$ is —H, $(C_1$-$C_6)$-alkyl, —$OR_{25}$, halogen, —$CF_3$, —$NO_2$ or —CN. In another embodiment, $R_4$ is —H, $(C_1$-$C_6)$-alkyl, —$OR_{25}$, halogen, or —$CF_3$; one of $R_7$, $R_8$, $R_9$, $R_{10}$, $R_{11}$, and $R_{12}$ is —H, $(C_1$-$C_6)$-alkyl, —$OR_{25}$, halogen, —$CF_3$, —$NO_2$ or —CN; and each remaining R group is hydrogen. In a further embodiment, $R_4$ is —H, $(C_1$-$C_6)$-alkyl, —$OR_{25}$, halogen, or —$CF_3$; one of $R_7$, $R_8$, $R_9$, $R_{10}$, $R_1$; $R_{12}$ is —H, $(C_1$-$C_6)$-alkyl, —$OR_{25}$, halogen, —$CF_3$, —$NO_2$ or —CN; one of $R_{13}$, $R_{14}$, $R_{15}$, and $R_{16}$ is —H, $(C_1$-$C_6)$-alkyl, —$OR_{25}$, or halogen, and each remaining R group is hydrogen.

In one embodiment, one of $R_{13}$, $R_{14}$, $R_{15}$, and $R_{16}$ is —H, $(C_1$-$C_6)$-alkyl, halogen, —$CF_3$, or —$OR_{25}$.

In one embodiment, $R_1$, $R_2$, $R_3$, $R_6$, $R_7$, $R_8$, $R_9$, $R_{10}$, $R_{11}$, $R_{12}$, $R_{13}$, $R_{14}$, $R_{15}$, and $R_{16}$ are each hydrogen.

In one embodiment, $R_1$, $R_2$, $R_3$, $R_4$, $R_7$, $R_9$, $R_{10}$, $R_{11}$, and $R_{12}$ are each hydrogen.

In one embodiment, $R_1$, $R_2$, $R_3$, $R_4$, $R_7$, $R_8$, $R_{10}$, $R_{11}$, and $R_{12}$ are each hydrogen.

In one embodiment, $R_1$, $R_2$, $R_3$, $R_4$, $R_7$, $R_9$, $R_9$, $R_{11}$, and $R_{12}$ are each hydrogen.

In one embodiment, $R_1$, $R_2$, $R_3$, $R_4$, $R_{7'}$, $R_8$, $R_9$, $R_{10}$, and $R_{12}$ are each hydrogen.

In one embodiment, $R_1$, $R_2$, $R_3$, $R_4$, $R_{7'}$, $R_8$, $R_9$, $R_{10}$, and $R_1$, are each hydrogen.

In one embodiment, $R_1$, $R_2$, $R_3$, $R_4$, $R_{7'}$, $R_9$, and $R_{11}$ are each hydrogen.

In one embodiment, $R_1$, $R_2$, $R_3$, $R_4$, $R_{7'}$, $R_9$, $R_9$ and $R_{11}$ are each hydrogen.

In one embodiment, $R_1$, $R_2$, $R_3$, $R_4$, $R_5$, $R_6$, $R_{7'}$, $R_8$, $R_9$, and $R_{12}$ are each hydrogen.

In another embodiment, $R_{13}$, $R_{14}$, $R_{15}$, and $R_{16}$ are each hydrogen.

In one embodiment, $R_3$, $R_6$, $R_{7'}$—, $R_9$, $R_9$, $R_{12}$, $R_{13}$, $R_{14}$, $R_{15}$, and $R_{16}$ are each hydrogen.

In one embodiment, $R_1$, $R_2$, $R_3$, $R_4$, $R_6$, $R_8$, $R_9$, $R_{10}$, $R_{11}$, $R_{12}$, $R_{13}$, $R_{14}$, $R_{15}$, and $R_{16}$ are each hydrogen.

In one embodiment, $R_1$, $R_2$, $R_3$, $R_4$, $R_6$, $R_9$, $R_{10}$, $R_{11}$, $R_{12}$, $R_{13}$, $R_{14}$, $R_{15}$, and $R_{16}$ are each hydrogen.

In one embodiment, any one of $R_{7'}$, $R_8$, $R_9$, $R_{10}$, $R_{11}$, and $R_{12}$ is —H, $(C_1$-$C_6)$-alkyl, —$OR_{25}$, halogen, —$CF_3$, —$NO_2$, or —CN; and any one of $R_{13}$, $R_{14}$, $R_{15}$, and $R_{16}$ is —H, $(C_1$-$C_6)$-alkyl, —$OR_{25}$, halogen, —$CF_3$.

In one embodiment, any one of $R_1$, $R_2$, $R_3$, $R_4$, $R_5$, and $R_6$ is —H, $(C_1$-$C_6)$-alkyl, —$OR_{25}$, halogen or —$CF_3$; and any one of $R_{7'}$, $R_8$, $R_9$, $R_{10}$, $R_{11}$, and $R_{12}$ is —H, $(C_1$-$C_6)$-alkyl, —$OR_{25}$, halogen, or —$CF_3$, —$NO_2$, or —CN.

In one embodiment, any one of $R_1$, $R_2$, $R_3$, $R_4$, $R_5$, and $R_6$ is —H, $(C_1$-$C_6)$-alkyl, —$OR_{25}$, halogen or —$CF_3$; and any one of $R_{13}$, $R_{14}$, $R_{15}$, and $R_{16}$ is —H, $(C_1$-$C_6)$-alkyl, —$OR_{25}$, halogen or —$CF_3$.

In one embodiment, $R_4$ is —H, $(C_1$-$C_6)$-alkyl, —$OR_{25}$, halogen, or —$CF_3$ and any one of $R_{13}$, $R_{14}$, $R_{15}$, and $R_{16}$ is —H, $(C_1$-$C_6)$-alkyl, —$OR_{25}$, halogen or —$CF_3$; and any one of $R_{7'}$, $R_8$, $R_9$, $R_{10}$, $R_{11}$, and $R_{12}$ is —H, $(C_1$-$C_6)$-alkyl, —$OR_{25}$, halogen, or —$CF_3$, —$NO_2$, or —CN.

In one embodiment, $R_4$ is —H, $(C_1$-$C_6)$-alkyl, —$OR_{25}$, halogen, or —$CF_3$ and any one of $R_{13}$, $R_{14}$, $R_{15}$, and $R_{16}$ is —H, $(C_1$-$C_6)$-alkyl, —$OR_{25}$, halogen or —$CF_3$; and any two of $R_{7'}$, $R_8$, $R_9$, $R_{10}$, $R_{11}$, and $R_{12}$ are each independently —H, $(C_1$-$C_6)$-alkyl, —$OR_{25}$, halogen, or —$CF_3$, —$NO_2$, or —CN; wherein the any two of $R_{7'}$, $R_8$, $R_9$, $R_{10}$, $R_{11}$, and $R_{12}$ can be either on the same ring of the quinoline or on different rings.

In one embodiment, $R_5$ is —H, $(C_1$-$C_6)$-alkyl, —$OR_{25}$, halogen, or —$CF_3$ and any one of $R_{13}$, $R_{14}$, $R_{15}$, and $R_{16}$ is —H, $(C_1$-$C_6)$-alkyl, —$OR_{25}$, halogen or —$CF_3$; and any one of $R_{7'}$, $R_8$, $R_9$, $R_{10}$, $R_{11}$, and $R_{12}$ is —H, $(C_1$-$C_6)$-alkyl, —$OR_{25}$, halogen, or —$CF_3$, —$NO_2$, or —CN.

In one embodiment, $R_5$ is —H, $(C_1$-$C_6)$-alkyl, —$OR_{25}$, halogen, or —$CF_3$ and any one of $R_{13}$, $R_{14}$, $R_{15}$, and $R_{16}$ is —H, $(C_1$-$C_6)$-alkyl, —$OR_{25}$, halogen or —$CF_3$; and any two of $R_{7'}$, $R_8$, $R_9$, $R_{10}$, $R_{11}$, and $R_{12}$ are each independently —H, $(C_1$-$C_6)$-alkyl, —$OR_{25}$, halogen, or —$CF_3$, —$NO_2$, or —CN; wherein the any two of $R_{7'}$, $R_8$, $R_9$, $R_{10}$, $R_{11}$, and $R_{12}$ can be either on the same ring of the quinoline or on different rings.

In one embodiment, $R_1$ is —H or $(C_1$-$C_6)$-alkyl; $R_2$, $R_8$, and $R_9$ are each independently —H or halogen; $R_4$ is —H, halogen, —$OR_{25}$, or —$CF_3$; $R_5$ is —H, halogen, or —$OR_{25}$; and $R_3$, $R_6$, $R_7$, $R_{12}$, $R_{13}$, $R_{14}$, $R_{15}$, $R_{16}$, $R_a$ and $R_b$ are each hydrogen.

In one embodiment, $R_1$ is —H or —$CH_3$; $R_2$, $R_8$, and $R_9$ are each independently —H or F; $R_4$ is —H, F, —$OCH_3$, or —$CF_3$; $R_5$ is —H, F, —$OCH_3$; and $R_3$, $R_6$, $R_{7'}$, $R_{10}$, $R_{11}$, $R_{12}$, $R_{13}$, $R_{14}$, $R_{15}$, $R_{16}$, $R_a$ and $R_b$ are each hydrogen.

In one embodiment, $R_1$ is —H, —$CF_3$ or $(C_1$-$C_6)$-alkyl; $R_4$ and $R_5$ are each independently —H, halogen, —$OR_{25}$, or —$CF_3$; $R_{7'}$, $R_8$, $R_9$, $R_{10}$, $R_{11}$, and $R_{12}$ are each independently —H, halogen, $(C_1$-$C_6)$-alkyl, —$OR_{25}$, —$CF_3$, or —$NO_2$; $R_{16}$ is —H or —$CH_3$.

In one embodiment, $R_{25}$ is $(C_1$-$C_6)$-haloalkyl.

In another embodiment, $R_{25}$ is $(C_1$-$C_6)$-fluoroalkyl.

In one embodiment, $R_{25}$ is $(C_1$-$C_6)$-alkyl. In one embodiment, $R_{25}$ is —$CH_3$.

In another aspect, the invention provides compounds of the Formula (II):

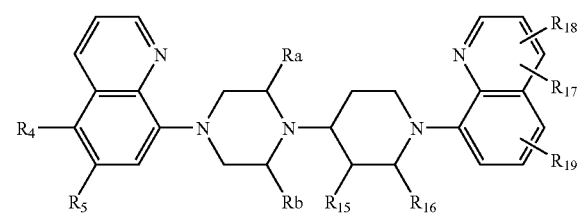

(II)

and pharmaceutically acceptable salts thereof, wherein $R_a$, $R_b$, $R_4$, $R_5$, $R_{15}$, $R_{16}$, and $R_{25}$ are defined as above for Formula (I);

$R_{17}$, $R_{19}$, and $R_{19}$ are each independently —H, $(C_1$-$C_6)$-alkyl, $(C_1$-$C_6)$-haloalkyl, $(C_2$-$C_6)$-alkenyl, or $(C_2$-$C_6)$-alkynyl, halogen, —$CF_3$, —$NO_2$, —CN, —$OR_{25}$, —$OSO_2R_{25}$, —$SR_{25}$, —$SO_2R_{25}$, —$SO_2N(R_{25})_2$, —$N(R_{25})_2$, —$C(O)$, —$COR_{25}$, —$CO_2R_{25}$, —$NR_{25}CO_2R_{25}$, —$NR_{25}COR_{25}$, —$NR_{25}CON(R_{25})_2$, or —$CON(R_{25})_2$; and $R_4$ and $R_5$ cannot both be hydrogen.

In one embodiment, $R_4$ and $R_5$ are each independently —H, —$OR_{25}$, halogen, or $(C_1$-$C_6)$-alkyl; $R_{15}$ and $R_{16}$ are each independently —H or —$CH_3$; and $R_{17}$, $R_{18}$, and $R_{19}$ are each independently —H, —$OR_{25}$, halogen, $(C_1$-$C_6)$-alkyl, —$CF_3$, —$NO_2$, —CN. In one embodiment, $R_4$ and $R_5$ are each independently —H, —$OCH_3$, F, or —$CH_3$; $R_{15}$ and $R_{16}$ are each independently —H or —$CH_3$; and $R_{17}$, $R_{18}$, and $R_{19}$ are each independently —H, —$OCH_3$, —F, —$CH_3$, —$CF_3$, —$NO_2$, —CN, or —Br.

In one embodiment, $R_4$ and $R_5$ are each independently —H, or —$OR_{25}$; $R_{15}$ and $R_{16}$ are each independently —H or —$CH_3$; and $R_{17}$, $R_{18}$, and $R_{19}$ are each independently —H, —$OR_{25}$, halogen, $(C_1$-$C_6)$-alkyl, or —$CF_3$. In one embodiment, $R_4$ and $R_5$ are each independently —H, or —$OR_{25}$; $R_a$, $R_b$, $R_{15}$ and $R_{16}$ are hydrogen; and $R_{17}$, $R_{18}$, and $R_{19}$ are each independently —H, —$OR_{25}$, halogen, $(C_1$-$C_6)$-alkyl, or —$CF_3$.

In another embodiment, $R_{19}$ is in the para position relative to the nitrogen of the piperidine.

In one embodiment, $R_{17}$ and $R_{18}$ are located at positions 2 and 4 of the quinoline ring (i.e., at the ortho and para positions relative to the nitrogen of the quinoline ring).

In one embodiment, $R_5$ is —H, $(C_1$-$C_6)$-alkyl, —$OR_{25}$, halogen, or —$CF_3$.

In another embodiment, $R_5$ is —H, $(C_1$-$C_6)$-alkyl, —$OR_{25}$, halogen, or —$CF_3$ and one of $R_{15}$ and $R_{16}$ is —H, $(C_1$-$C_6)$-alkyl, —$OR_{25}$, or halogen.

In yet another embodiment, $R_5$ is —H, $(C_1$-$C_6)$-alkyl, —$OR_{25}$, halogen, or —$CF_3$; $R_{15}$ is —H, $(C_1$-$C_6)$-alkyl, —$OR_{25}$, or halogen, and $R_4$ and $R_{16}$ are each hydrogen.

In one embodiment, $R_5$ is —H, $(C_1$-$C_6)$-alkyl, —$OR_{25}$, halogen, or —$CF_3$; $R_{16}$ is —H, $(C_1$-$C_6)$-alkyl, —$OR_{25}$, or halogen, and $R_4$ and $R_{15}$ are each hydrogen.

In one embodiment, $R_5$ is —H, $(C_1-C_6)$-alkyl, —$OR_{25}$, halogen or —$CF_3$ and $R_4$, $R_{15}$, $R_{16}$, $R_{17}$, $R_{18}$ and $R_{19}$ are each hydrogen.

In one embodiment, $R_5$ is —H, $(C_1-C_6)$-alkyl, —$OR_{25}$, halogen, or —$CF_3$ and one of $R_{17}$, $R_{18}$ and $R_{19}$ is —H, $(C_1-C_6)$-alkyl, —$OR_{25}$, halogen, or —$CF_3$. In another embodiment, $R_5$ is —H, $(C_1-C_6)$-alkyl, —$OR_{25}$, halogen, or —$CF_3$; one of $R_{17}$, $R_{18}$ and $R_{19}$ is —H, $(C_1-C_6)$-alkyl, —$OR_{25}$, halogen, or —$CF_3$; and each remaining R group is hydrogen.

In one embodiment, $R_5$, $R_{17}$, $R_{18}$, and $R_{19}$ are each independently —H, $(C_1-C_6)$-alkyl, —$OR_{25}$, halogen or —$CF_3$ and $R_4$, $R_{15}$, and $R_{16}$ are each hydrogen. In one embodiment, $R_5$ is —H, —$OR_{25}$ or halogen; $R_{17}$ and $R_{18}$ are each independently —H, $(C_1-C_6)$-alkyl, —$OR_{25}$, halogen or —$CF_3$; $R_{19}$ is —H or halogen; and $R_a$, $R_b$, $R_4$, $R_{15}$, and $R_{16}$ are each hydrogen.

In one embodiment, $R_4$ is —H, $(C_1-C_6)$-alkyl, —$OR_{25}$, halogen, or —$CF_3$.

In another embodiment, $R_4$ is —H, $(C_1-C_6)$-alkyl, —$OR_{25}$, halogen, or —$CF_3$ and one of $R_{15}$, and $R_{16}$ is —H, $(C_1-C_6)$-alkyl, —$OR_{25}$, or halogen.

In a further embodiment, $R_4$ is —H, $(C_1-C_6)$-alkyl, —$OR_{25}$, halogen, or —$CF_3$; one of $R_{15}$ and $R_{16}$ is —H, $(C_1-C_6)$-alkyl, —$OR_{25}$, or halogen; and $R_{17}$, $R_{18}$ and $R_{19}$ are each hydrogen.

In yet another embodiment, $R_4$ is —H, $(C_1-C_6)$-alkyl, —$OR_{25}$, halogen, or —$CF_3$; $R_{15}$ is —H, $(C_1-C_6)$-alkyl, —$OR_{25}$, or halogen, and $R_5$ and $R_{16}$ are each hydrogen.

In one embodiment, $R_4$ is —H, $(C_1-C_6)$-alkyl, —$OR_{25}$, halogen, or —$CF_3$; $R_{16}$ is —H, $(C_1-C_6)$-alkyl, —$OR_{25}$, or halogen, and $R_5$ and $R_{15}$ are each hydrogen.

In one embodiment, $R_4$ is —H, $(C_1-C_6)$-alkyl, —$OR_{25}$, halogen or —$CF_3$ and $R_5$, $R_{15}$, $R_{16}$, $R_{17}$, $R_{18}$ and $R_{19}$ are each hydrogen.

In one embodiment, $R_5$ is —H, $(C_1-C_6)$-alkyl, —$OR_{25}$, halogen, or —$CF_3$ and one of $R_{17}$, $R_{18}$ and $R_{19}$ is —H, $(C_1-C_6)$-alkyl, —$OR_{25}$, halogen, or —$CF_3$.

In one embodiment, $R_5$ is —H, $(C_1-C_6)$-alkyl, —$OR_{25}$, halogen, or —$CF_3$ and two of $R_{17}$, $R_{18}$ and $R_{19}$ are each independently —H, $(C_1-C_6)$-alkyl, —$OR_{25}$, halogen, or —$CF_3$.

In one embodiment, $R_5$, $R_{17}$, $R_{18}$ and $R_{19}$ are each independently —H, $(C_1-C_6)$-alkyl, —$OR_{25}$, halogen, or —$CF_3$.

In another embodiment, $R_5$ is —H, $(C_1-C_6)$-alkyl, halogen, or —$CF_3$ and one of $R_{17}$, $R_{18}$ and $R_{19}$ is —H, $(C_1-C_6)$-alkyl, —$OR_{25}$, halogen, or —$CF_3$; and each remaining R group is hydrogen.

In another embodiment, $R_5$ is —H, $(C_1-C_6)$-alkyl, —$OR_{25}$, halogen, or —$CF_3$ and two of $R_{17}$, $R_{18}$ and $R_{19}$ are each independently —H, $(C_1-C_6)$-alkyl, —$OR_{25}$, halogen, or —$CF_3$; and each remaining R group is hydrogen.

In one embodiment, $R_5$, $R_{17}$, $R_{18}$ and $R_{19}$ are each independently —H, $(C_1-C_6)$-alkyl, —$OR_{25}$, halogen, or —$CF_3$ and each remaining R group is hydrogen.

In a further embodiment, $R_5$ is —H, $(C_1-C_6)$-alkyl, —$OR_{25}$, halogen, or —$CF_3$; one of $R_{17}$, $R_{18}$ and $R_{19}$ is —H, $(C_1-C_6)$-alkyl, —$OR_{25}$, halogen, or —$CF_3$; one of $R_{15}$ and $R_{16}$ is —H, $(C_1-C_6)$-alkyl, —$OR_{25}$, or halogen; and each remaining R group is hydrogen.

In one embodiment, $R_5$ is —H, $(C_1-C_6)$-alkyl, —$OR_{25}$, halogen, or —$CF_3$; and any two of $R_{17}$, $R_{18}$ and $R_{19}$ are each independently —H, $(C_1-C_6)$-alkyl, —$OR_{25}$, halogen, or —$CF_3$; and one of $R_{15}$, and $R_{16}$ is —H, $(C_1-C_6)$-alkyl, —$OR_{25}$, halogen, or —$CF_3$.

In one embodiment, $R_5$ is —H, $(C_1-C_6)$-alkyl, —$OR_{25}$, halogen, or —$CF_3$; $R_{17}$, $R_{18}$ and $R_{19}$ are each independently —H, $(C_1-C_6)$-alkyl, —$OR_{25}$, halogen, or —$CF_3$; and one of $R_{15}$, and $R_{16}$ is —H, $(C_1-C_6)$-alkyl, —$OR_{25}$, halogen, or —$CF_3$.

In one embodiment, $R_4$ is —H, $(C_1-C_6)$-alkyl, —$OR_{25}$, halogen, or —$CF_3$ and one of $R_{17}$, $R_{18}$ and $R_{19}$ is —H, $(C_1-C_6)$-alkyl, —$OR_{25}$, halogen, or —$CF_3$.

In another embodiment, $R_4$ is —H, $(C_1-C_6)$-alkyl, —$OR_{25}$, halogen, or —$CF_3$ and one of $R_{17}$, $R_{18}$ and $R_{19}$ is —H, $(C_1-C_6)$-alkyl, —$OR_{25}$, halogen, or —$CF_3$; and each remaining R group is hydrogen.

In a further embodiment, $R_4$ is —H, $(C_1-C_6)$-alkyl, —$OR_{25}$, halogen, or —$CF_3$; one of $R_{17}$, $R_{18}$ and $R_{19}$ is —H, $(C_1-C_6)$-alkyl, —$OR_{25}$, halogen, or —$CF_3$; one of $R_{15}$ and $R_{16}$ is —H, $(C_1-C_6)$-alkyl, —$OR_{25}$, or halogen; and each remaining R group is hydrogen.

In a further embodiment, $R_4$ is —H, $(C_1-C_6)$-alkyl, —$OR_{25}$, halogen, or —$CF_3$; and any two of $R_{17}$, $R_{18}$ and $R_{19}$ are each independently —H, $(C_1-C_6)$-alkyl, —$OR_{25}$, halogen, or —$CF_3$. In one embodiment, $R_4$, $R_{17}$, $R_{18}$ and $R_{19}$ are each independently —H, $(C_1-C_6)$-alkyl, —$OR_{25}$, halogen, or —$CF_3$ and each remaining R group is hydrogen.

In one embodiment, one of $R_{15}$ and $R_{16}$ is —H, $(C_1-C_6)$-alkyl, halogen, —$CF_3$, or —$OR_{25}$. In a further embodiment, one of $R_{15}$ and $R_{16}$ is —H, $(C_1-C_6)$-alkyl, halogen, —$CF_3$, or —$OR_{25}$; $R_5$ is —H, $(C_1-C_6)$-alkyl, —$OR_{25}$, halogen, or —$CF_3$; and each remaining R group is hydrogen.

In a further embodiment, one of $R_{15}$ and $R_{16}$ is —H, $(C_1-C_6)$-alkyl, halogen, —$CF_3$, or —$OR_{25}$; $R_4$ is —H, $(C_1-C_6)$-alkyl, —$OR_{25}$, halogen, or —$CF_3$; and each remaining R group is hydrogen.

In one embodiment, $R_4$, $R_{15}$, $R_{16}$, $R_{17}$, $R_{18}$ and $R_{19}$ are each hydrogen.

In one embodiment, $R_4$, $R_{15}$, $R_{16}$, $R_{17}$, and $R_{18}$ are each hydrogen.

In one embodiment, $R_4$, $R_{15}$, and $R_{16}$ are each hydrogen.

In one embodiment, $R_5$, $R_{15}$, $R_{16}$, $R_{17}$, $R_{18}$ and $R_{19}$ are each hydrogen.

In one embodiment, $R_5$, $R_{15}$, $R_{16}$, $R_{17}$, and $R_{18}$ are each hydrogen.

In one embodiment, $R_4$, $R_{15}$, $R_{16}$, and $R_{19}$ are each hydrogen.

In one embodiment, $R_5$, $R_{15}$, and $R_{16}$ are each hydrogen.

In one embodiment, $R_5$ is —H, —$OR_{25}$ or halogen; $R_4$, $R_{15}$, $R_{16}$, $R_{17}$, and $R_{18}$ are each hydrogen; and $R_{19}$ is —H or halogen.

In one embodiment, $R_5$ is —H, —$OCH_3$ or F; $R_4$, $R_{15}$, $R_{16}$, $R_{17}$, and $R_{18}$ are each hydrogen; and $R_{19}$ is —H or F.

In one embodiment, $R_5$ is —H, —$OCH_3$ or F; $R_4$, $R_{15}$, and $R_{16}$ are each hydrogen; and one of $R_{18}$ or $R_{19}$ is —H or F. In one embodiment, $R_5$ is —H, —$OCH_3$ or F; $R_4$, $R_{15}$, $R_{16}$ and $R_{17}$ are each hydrogen; and $R_{18}$ and $R_{19}$ are each independently —H, —$CH_3$ or halogen.

In one embodiment, $R_4$ is hydrogen, $R_5$ is —H, —$OR_{25}$; and $R_{17}$, $R_{18}$, and $R_{19}$ are each independently —H, —$OR_{25}$, halogen, $(C_1-C_6)$-alkyl, or —$CF_3$. In one embodiment, $R_4$ is hydrogen, $R_5$ is —$OR_2$; $R_{17}$, and $R_{18}$ are each independently —H, —$OR_{25}$, halogen, $(C_1-C_6)$-alkyl, or —$CF_3$; and $R_{19}$ is —H or halogen.

In one embodiment, $R_5$ is —H, —$OR_{25}$ or halogen; $R_{17}$ and $R_{18}$ are each independently —H, $(C_1-C_6)$-alkyl, —$OR_{25}$, halogen or —$CF_3$; $R_{19}$ is H or halogen; and $R_a$, $R_b$, $R_4$, $R_{15}$, and $R_{16}$ are each hydrogen.

In one embodiment, $R_5$ is —H, —$OCH_3$ or F; $R_{17}$ is —H, —$OCH_3$; $R_{18}$ is —H, —$CF_3$; $R_{19}$ is —H, F; and $R_a$, $R_b$, $R_4$, $R_{15}$, and $R_{16}$ are each hydrogen.

In one embodiment, $R_4$ is —H, —$OR_{25}$ or halogen; $R_5$, $R_{15}$, $R_{16}$, $R_{17}$ and $R_{18}$ are each hydrogen; and $R_{19}$ is —H or halogen. In one embodiment, $R_5$ is —H, —OCH$_3$ or F; $R_4$, $R_{15}$, $R_{16}$ and $R_{19}$ are each hydrogen; and $R_{17}$ and $R_{18}$ are each —H, —CH$_3$ or halogen.

In one embodiment, $R_4$ is —H, —OCH$_3$ or F; $R_5$, $R_{15}$, $R_{16}$, $R_{17}$ and $R_{18}$ are each hydrogen; and $R_{19}$ is —H or F.

In one embodiment, $R_4$ is —H, —OCH$_3$ or F; $R_5$, $R_{15}$, and $R_{16}$ are each hydrogen; and one of $R_{18}$ or $R_{19}$ is —H or F. In one embodiment, $R_4$ is —H, —OCH$_3$ or F; $R_5$, $R_{15}$, $R_{16}$ and $R_{17}$ are each hydrogen; and $R_{18}$ and $R_{19}$ are each —H, —CH$_3$ or halogen. In one embodiment, $R_4$ is —H, —OCH$_3$ or F; $R_4$, $R_5$, $R_{16}$ and $R_{19}$ are each hydrogen; and $R_{17}$ and $R_{18}$ are each —H, —CH$_3$ or halogen.

In one embodiment, the compounds of Formula (II) are antagonists of the 5-HT$_{1A}$ receptor.

In another embodiment, the compounds of Formula (II) are agonists of the 5-HT$_{1A}$ receptor.

Illustrative examples of compounds of Formula (I), Formula (I'), Formula (I''), or Formula (1''a) and Formula (II) are set forth below and include, without limitation:

6-methoxy-8-[4-(1-quinolin-8-yl-piperidin-4-yl)-piperazin-1-yl]-quinoline;
6-fluoro-8-[4-(1-quinolin-8-yl-piperidin-4-yl)-piperazin-1-yl]-quinoline;
5-fluoro-8-[4-(1-quinolin-8-yl-piperidin-4-yl)-piperazin-1-yl]-quinoline;
7-fluoro-8-(4-(4-(6-methoxyquinolin-8-yl)piperazin-1-yl)piperidin-1-yl)quinoline;
6-fluoro-8-{4-[1-(8-fluoroquinolin-7-yl)piperidin-4-yl]piperazin-1-yl}quinoline;
3-trifluoromethyl-8-(4-(4-(6-methoxyquinolin-8-yl)piperazin-1-yl)piperidin-1-yl)quinoline;
6-methoxy-8-(4-(1-(quinolin-8-ylmethyl)piperidin-4-yl)piperazin-1-yl)quinoline;
5-fluoro-4-methoxy-8-(4-(4-(6-methoxyquinolin-8-yl)piperazin-1-yl)piperidin-1-yl)-2-(trifluoromethyl)quinoline;
5-fluoro-8-(4-(4-(6-methoxyquinolin-8-yl)piperazin-1-yl)piperidin-1-yl)quinoline;
8-[4-(1-quinolin-8-yl-piperidinyl)-piperazin-1-yl]-quinoline;
6-chloro-8-[4-(4-(6-chloro)-quinolin-8-yl-piperidin-1-yl)-piperazin-1-yl]-quinoline;
6-fluoro-8-[4-(4-(6-chloro)-quinolin-8-yl-piperidin-1-yl)-piperazin-1-yl]-quinoline;
5-chloro-8-[4-(1-quinolin-8-yl-piperidin-4-yl)-piperazin-1-yl]-quinoline;
2-methyl-8-[4-(1-quinolin-8-yl-piperidin-4-yl)-piperazin-1-yl]-quinoline;
6-chloro-8-[4-(1-quinolin-8-yl-piperidin-4-yl)-piperazin-1-yl]-quinoline;
8-[4-(1-quinolin-8-yl-piperidin-4-yl)-piperazin-1-yl]-5-trifluoromethyl-quinoline;
5-methoxy-8-[4-(1-quinolin-8-yl-piperidin-4-yl)-piperazin-1-yl]-quinoline;
5-fluoro-8-[4-(4-quinolin-8-yl-piperazin-1-yl)-piperidin-1-yl]-quinoline;
6-methoxy-8-[4-(2-methylquinolin-8-yl-piperidin-4-yl)-piperazin-1-yl]-quinoline;
6-fluoro-8-(4-(1-(2-methylquinolin-8-yl)piperidin-4-yl)piperazin-1-yl)quinoline;
6-methoxy-8-[4-(3-methylquinolin-8-yl-piperidin-4-yl)-piperazin-1-yl]-quinoline;
6-methoxy-8-(4-(1-(4-methylquinolin-8-yl)piperidin-4-yl)piperazin-1-yl)quinoline;
6-methoxy-8-(4-(1-(2,4-dimethylquinolin-8-yl)piperidin-4-yl)piperazin-1-yl)quinoline;
6-methoxy-8-(4-(1-(2,4-dimethyl-5-fluoroquinolin-8-yl)piperidin-4-yl)piperazin-1-yl)quinoline;
6-methoxy-8-(4-(1-(2-(trifluoromethyl)quinolin-8-yl)piperidin-4-yl)piperazin-1-yl)quinoline;
6-fluoro-8-(4-(1-(5-fluoroquinolin-8-yl)piperidin-4-yl)piperazin-1-yl)quinoline;
6-methoxy-8-(4-(1-(6-bromoquinolin-8-yl)piperidin-4-yl)piperazin-1-yl)quinoline;
6-methoxy-8-(4-(1-(6-fluoroquinolin-8-yl)piperidin-4-yl)piperazin-1-yl)quinoline;
6-fluoro-8-(4-(1-(7-fluoroquinolin-8-yl)piperidin-4-yl)piperazin-1-yl)quinoline;
6-methoxy-8-{4-[1-(8-fluoroquinolin-7-yl)piperidin-4-yl]piperazin-1-yl}quinoline;
6-methoxy-8-{4-[1-(2-trifluoromethyl-4-methoxyquinolin-7-yl)piperidin-4-yl]piperazin-1-yl}quinoline;
6-methoxy-8-(4-(1-(2-trifluoromethyl-4-methoxyquinolin-8-yl)piperidin-4-yl)piperazin-1-yl)quinoline;
5-fluoro-8-(4-(4-(6-methoxyquinolin-8-yl)piperazin-1-yl)piperidin-1-yl)-2-trifluoromethylquinoline;
5-fluoro-8-(4-(4-(6-methoxyquinolin-8-yl)piperazin-1-yl)piperidin-1-yl)-3-trifluoromethylquinoline;
5-fluoro-8-(4-(4-(6-methoxyquinolin-8-yl)piperazin-1-yl)piperidin-1-yl)-4-trifluoromethylquinoline;
2,5-difluoro-8-(4-(4-(6-methoxyquinolin-8-yl)piperazin-1-yl)piperidin-1-yl)quinoline;
3,5-difluoro-8-(4-(4-(6-methoxyquinolin-8-yl)piperazin-1-yl)piperidin-1-yl)quinoline;
4,5-difluoro-8-(4-(4-(6-methoxyquinolin-8-yl)piperazin-1-yl)piperidin-1-yl)quinoline;

and pharmaceutically acceptable salts thereof.

In a further aspect, the invention provides compounds of the Formula (III):

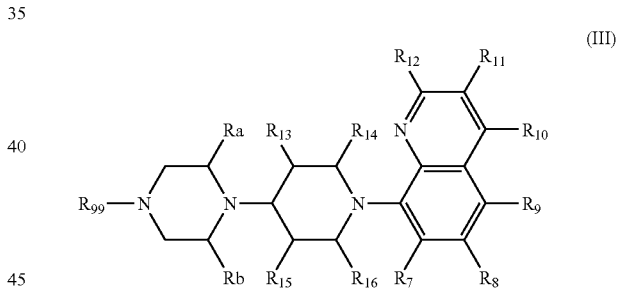

(III)

and pharmaceutically acceptable salts thereof
wherein $R_{99}$ is selected from:

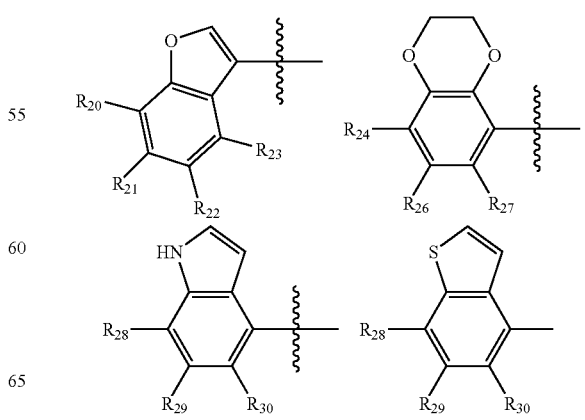

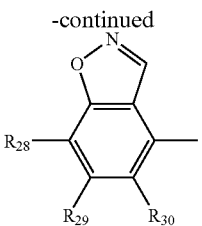

and $R_7$, $R_8$, $R_9$, $R_{10}$, $R_{11}$, $R_{12}$, $R_{13}$, $R_{14}$, $R_{15}$, $R_{16}$, $R_{20}$, $R_{21}$, $R_{22}$, $R_{23}$, $R_{24}$, $R_{26}$, $R_{27}$, $R_{28}$, $R_{29}$ and $R_{30}$ are each independently —H, $(C_1$-$C_6)$-alkyl, $(C_1$-$C_6)$-haloalkyl, $(C_2$-$C_6)$-alkenyl, or $(C_2$-$C_6)$-alkynyl, halogen, —$CF_3$, —$NO_2$, —CN, —$OR_{25}$, —$OSO_2R_{25}$, —$SR_{25}$, —$SO_2R_{25}$, —$SO_2N(R_{25})_2$, —$N(R_{25})_2$, —C(O), —$COR_{25}$, —$CO_2R_{25}$, —$NR_{25}CO_2R_{25}$, —$NR_{25}COR_{25}$, —$NR_{25}CON(R_{25})_2$, or —$CON(R_{25})_2$;

$R_a$ and $R_b$ are each independently —H or —$CH_3$; and $R_{25}$ is —H; or linear or branched $(C_1$-$C_6)$-alkyl, $(C_1$-$C_6)$-haloalkyl, $(C_2$-$C_6)$-alkenyl, or $(C_2$-$C_6)$-alkynyl.

In one embodiment, any of $R_7$, $R_8$, $R_9$, $R_{10}$, $R_{11}$, and $R_{12}$ are each independently —H, $(C_1$-$C_6)$-alkyl, halogen, —$CF_3$, —$OR_{25}$, —$NO_2$ or —CN; and the remaining $R_7$-$R_{12}$ are each hydrogen. In one embodiment, any of $R_7$, $R_8$, $R_9$, $R_{10}$, $R_{11}$, and $R_{12}$ are each independently —H, $(C_1$-$C_6)$-alkyl, halogen, —$CF_3$, —$OR_{25}$, —$NO_2$ or —CN; and the remaining $R_7$-$R_{16}$ are each hydrogen.

In one embodiment, any of $R_7$, $R_8$, $R_9$, $R_{10}$, $R_{11}$, and $R_{12}$ are each independently —H, halogen, or —$CF_3$; and the remaining $R_7$-$R_{12}$ are each hydrogen. In one embodiment, any of $R_7$, $R_8$, $R_9$, $R_{10}$, $R_{11}$, and $R_{12}$ are each independently —H, halogen, or —$CF_3$; and the remaining $R_7$-$R_{16}$ are each hydrogen.

In one embodiment, any two of $R_7$, $R_8$, $R_9$, $R_{10}$, $R_{11}$, and $R_{12}$ are each independently —H, $(C_1$-$C_6)$-alkyl, halogen, —$CF_3$, —$OR_{25}$, —$NO_2$ or —CN; and the remaining $R_7$-$R_{12}$ are each hydrogen. In one embodiment, any two of $R_7$, $R_8$, $R_9$, $R_{10}$, $R_{11}$, and $R_{12}$ are each independently —H, $(C_1$-$C_6)$-alkyl, halogen, —$CF_3$, —$OR_{25}$, —$NO_2$ or —CN; and the remaining $R_7$-$R_{16}$ are each hydrogen.

In one embodiment, any three of $R_7$, $R_8$, $R_9$, $R_{10}$, $R_{11}$, and $R_{12}$ are each independently —H, halogen, or —$CF_3$ and the remaining $R_7$-$R_{12}$ are each hydrogen. In one embodiment, any three of $R_7$, $R_8$, $R_9$, $R_{10}$, $R_{11}$, and $R_{12}$ are each independently —H, halogen, or —$CF_3$ and the remaining $R_7$-$R_{16}$ are each hydrogen.

In one embodiment, $R_7$ is —H, $(C_1$-$C_6)$-alkyl, —$OR_{25}$, halogen, —$CF_3$, —$NO_2$ or —CN. In one embodiment, $R_7$ is —H, $(C_1$-$C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1$-$C_6)$-alkyl, —$OR_{25}$, halogen, or —$CF_3$; and $R_a$ and $R_b$ are each independently —H or —$CH_3$; and each remaining R group is hydrogen. In one embodiment, $R_7$ is —H, $(C_1$-$C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1$-$C_6)$-alkyl, —$OR_{25}$, halogen, or —$CF_3$; and each remaining R group is hydrogen.

In one embodiment, $R_{10}$ is —H, $(C_1$-$C_6)$-alkyl, —$OR_{25}$, halogen, —$CF_3$, —$NO_2$ or —CN. In one embodiment, $R_{10}$ is —H, $(C_1$-$C_6)$-alkyl, —$OR_{25}$, halogen, or —$CF_3$. In one embodiment, $R_{10}$ is —H, —$CH_3$, —$OCH_3$, —F or —$CF_3$. In one embodiment, $R_{10}$ is —H, $(C_1$-$C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1$-$C_6)$-alkyl, —$OR_{25}$, halogen, or —$CF_3$; and $R_a$ and $R_b$ are each independently —H or —$CH_3$; and each remaining R group is hydrogen. In one embodiment, $R_{10}$ is —H, $(C_1$-$C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1$-$C_6)$-alkyl, —$OR_{25}$, halogen, or —$CF_3$; and each remaining R group is hydrogen.

In one embodiment, $R_{11}$ is —H, $(C_1$-$C_6)$-alkyl, —$OR_{25}$, halogen, —$CF_3$, —$NO_2$ or —CN. In one embodiment, $R_{10}$ is —H, $(C_1$-$C_6)$-alkyl, halogen, or —$CF_3$. In one embodiment, $R_{11}$ is —H, —$CH_3$, —F or —$CF_3$. In one embodiment, $R_{11}$ is —H, $(C_1$-$C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1$-$C_6)$-alkyl, —$OR_{25}$, halogen, or —$CF_3$; $R_a$ and $R_b$ are each independently —H or —$CH_3$; and each remaining R group is hydrogen. In one embodiment, $R_{11}$ is —H, $(C_1$-$C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1$-$C_6)$-alkyl, —$OR_{25}$, halogen, or —$CF_3$; and each remaining R group is hydrogen.

In one embodiment, $R_{12}$ is —H, $(C_1$-$C_6)$-alkyl, —$OR_{25}$, halogen, —$CF_3$, —$NO_2$ or —CN. In one embodiment, $R_{12}$ is —H, $(C_1$-$C_6)$-alkyl, halogen, or —$CF_3$. In one embodiment, $R_{12}$ is —H, —$CH_3$, —F or —$CF_3$. In one embodiment, $R_{12}$ is —H, $(C_1$-$C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1$-$C_6)$-alkyl, —$OR_{25}$, halogen, or —$CF_3$; $R_a$ and $R_b$ are each independently —H or —$CH_3$; and each remaining R group is hydrogen. In one embodiment, $R_{12}$ is —H, $(C_1$-$C_6)$-alkyl, —$OR_{25}$, halogen, —$CF_3$, —$NO_2$ or —CN; one of $R_1$, $R_2$, $R_3$, $R_4$, $R_5$ and $R_6$ is —H, $(C_1$-$C_6)$-alkyl, —$OR_{25}$, halogen, or —$CF_3$; and each remaining R group is hydrogen.

In one embodiment, $R_7$ is —H, $(C_1$-$C_6)$-alkyl, halogen, —$CF_3$, —$OR_{25}$, —$NO_2$ or —CN and $R_8$, $R_9$, $R_{10}$, $R_{11}$, and $R_{12}$ are each hydrogen. In one embodiment, $R_7$ is —H, $(C_1$-$C_6)$-alkyl, halogen, —$CF_3$, —$OR_{25}$, —$NO_2$ or —CN; $R_a$ and $R_b$ are each independently —H or —$CH_3$; and each remaining R group is hydrogen.

In one embodiment, $R_8$ is —H, $(C_1$-$C_6)$-alkyl, halogen, —$CF_3$, —$OR_{25}$, —$NO_2$ or —CN and $R_7$, $R_9$, $R_{10}$, $R_{11}$, and $R_{12}$ are each hydrogen. In one embodiment, $R_8$ is —H, $(C_1$-$C_6)$-alkyl, halogen, —$CF_3$, —$OR_{25}$, —$NO_2$ or —CN; $R_a$ and $R_b$ are each independently —H or —$CH_3$; and each remaining R group is hydrogen.

In one embodiment, $R_9$ is —H, $(C_1$-$C_6)$-alkyl, halogen, —$CF_3$, —$OR_{25}$, —$NO_2$ or —CN and $R_7$, $R_8$, $R_{10}$, $R_{11}$, and $R_{12}$ are each hydrogen. In one embodiment, $R_9$ is —H, $(C_1$-$C_6)$-alkyl, halogen, —$CF_3$, —$OR_{25}$, —$NO_2$ or —CN; $R_a$ and $R_b$ are each independently —H or —$CH_3$; and each remaining R group is hydrogen.

In one embodiment, $R_7$, $R_8$, $R_9$, $R_{10}$, $R_{11}$, $R_{12}$, $R_{13}$, $R_{14}$, $R_{15}$, $R_{16}$, $R_{20}$, $R_{21}$, $R_{22}$, $R_{23}$, $R_{24}$, $R_{26}$, $R_{27}$, $R_{28}$, $R_{29}$ and $R_{30}$ are each hydrogen.

In one embodiment, $R_{25}$ is $(C_1$-$C_6)$-alkyl.

In one embodiment, $R_{99}$ is

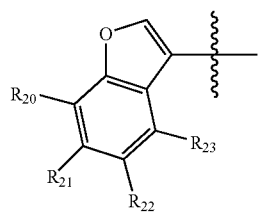

and $R_{20}$, $R_{21}$, $R_{22}$, and $R_{23}$ are each independently —H, —$OR_{25}$, —$CH_3$, halogen, —$CF_3$, —$NO_2$ or —CN.

In one embodiment, $R_{99}$ is the benzofuran above and $R_{20}$, $R_{21}$, $R_{22}$, and $R_{23}$ are each —H.

In one embodiment, $R_{99}$ is the benzofuran above; $R_7$, $R_8$, $R_9$, $R_{10}$, $R_{11}$, $R_{12}$, $R_{20}$, $R_{21}$, $R_{22}$ and $R_{23}$ are each independently —H, $(C_1-C_6)$-alkyl, halogen, —$CF_3$, —$OR_{25}$, —$NO_2$ or —CN.

In one embodiment, $R_{99}$ is the benzofuran above; $R_7$, $R_8$, $R_9$, $R_{10}$, $R_{11}$, and $R_{12}$, are each independently —H, $(C_1-C_6)$-alkyl, halogen, —$CF_3$, —$OR_{25}$, —$NO_2$ or —CN; and $R_{13}$, $R_{14}$, $R_{15}$, and $R_{15}$ are each hydrogen.

In one embodiment, $R_{99}$ is the benzofuran above; $R_8$ is —H, $(C_1-C_6)$-alkyl, halogen, —$CF_3$, —$OR_{25}$, —$NO_2$ or —CN; and $R_7$, $R_9$, $R_{10}$, $R_{11}$, and $R_{12}$ are each independently —H, $(C_1-C_6)$-alkyl, halogen, —$CF_3$, or —$OCH_3$.

In one embodiment, $R_{99}$ is the benzofuran above; $R_8$ is —H, $(C_1-C_6)$-alkyl, halogen, —$CF_3$, —$OR_{25}$, —$NO_2$ or —CN; $R_{15}$ and $R_{16}$ are each independently —H, $(C_1-C_6)$-alkyl, halogen, —$CF_3$, or —$OR_{25}$; and $R_7$, $R_9$, $R_{10}$, $R_{11}$, $R_{12}$, $R_{13}$ and $R_{14}$ are each hydrogen.

In one embodiment, $R_{99}$ is the benzofuran above; $R_8$ is —H, $(C_1-C_6)$-alkyl, halogen, —$CF_3$, —$OR_{25}$, —$NO_2$ or —CN; and $R_7$, $R_9$, $R_{10}$, $R_{11}$, $R_{12}$, $R_{13}$, $R_{14}$, $R_{15}$, and $R_{16}$ are each hydrogen.

In one embodiment, $R_{99}$ is the benzofuran above; $R_8$ is —H, $(C_1-C_6)$-alkyl, halogen, —$CF_3$, —$OR_{25}$, —$NO_2$ or —CN; and $R_7$, $R_9$, $R_{10}$, $R_{11}$, $R_{12}$, $R_{20}$, $R_{21}$, $R_{22}$ and $R_{23}$ are each hydrogen.

In one embodiment, $R_{99}$ is the benzofuran above; $R_8$ is —H or halogen and $R_7$, $R_9$, $R_{10}$, $R_{11}$, $R_{12}$, $R_{20}$, $R_{21}$, $R_{22}$ and $R_{23}$ are each hydrogen. In one embodiment, $R_{99}$ is the benzofuran above; $R_8$ is —H or halogen and $R_7$, $R_9$, $R_{10}$, $R_{11}$, $R_{12}$, $R_{13}$, $R_{14}$, $R_{15}$, $R_{16}$, $R_{20}$, $R_{21}$, $R_{22}$ and $R_{23}$ are each hydrogen.

In one embodiment, $R_{99}$ is the benzofuran above; and $R_8$ and $R_{22}$ are each —H or halogen. In one embodiment, $R_{99}$ is the benzofuran above; $R_8$ and $R_{22}$ are each —H or halogen; and each remaining R group is hydrogen.

In one embodiment, $R_{99}$ is the benzofuran above; and $R_8$ and $R_{22}$ are each independently —H, —Cl or —F.

In one embodiment, $R_{99}$ is the benzofuran above; $R_8$ and $R_{22}$ are each independently —H, —Cl or —F; and $R_7$, $R_9$, $R_{10}$, $R_{11}$, $R_{12}$, $R_{20}$, $R_{21}$, and $R_{23}$ are each hydrogen.

In one embodiment, $R_{99}$ is the benzofuran above; $R_8$ and $R_{22}$ are each independently —H, —Cl or —F; and $R_7$, $R_9$, $R_{10}$, $R_{11}$, $R_{12}$, $R_{13}$, $R_{14}$, $R_{15}$, $R_{16}$, $R_{20}$, $R_{21}$, and $R_{23}$ are each hydrogen.

In one embodiment, $R_{99}$ is the benzofuran above; $R_9$ is —H, $(C_1-C_6)$-alkyl, halogen, —$CF_3$, —$OR_{25}$, —$NO_2$ or —CN; $R_7$, $R_8$, $R_{10}$, and $R_{12}$ are each independently —H, $(C_1-C_6)$-alkyl, halogen, —$CF_3$, or —$OCH_3$; and $R_{13}$, $R_{14}$, $R_{15}$, and $R_{16}$ are each hydrogen.

In one embodiment, $R_{99}$ is the benzofuran above; $R_9$ is —H, $(C_1-C_6)$-alkyl, halogen, —$CF_3$, —$OR_{25}$, —$NO_2$ or —CN; $R_{15}$ and $R_{16}$ are each independently —H, $(C_1-C_6)$-alkyl, halogen, —$CF_3$, or —$OR_{25}$; and $R_7$, $R_8$, $R_{10}$, $R_{11}$, $R_{12}$, $R_{13}$ and $R_{14}$ are each hydrogen.

In one embodiment, $R_{99}$ is the benzofuran above; $R_9$ is —H, $(C_1-C_6)$-alkyl, halogen, —$CF_3$, —$OR_{25}$, —$NO_2$ or —CN; and $R_7$, $R_8$, $R_{10}$, $R_{11}$, $R_{12}$, $R_{13}$, $R_{14}$, $R_{15}$, and $R_{16}$ are each hydrogen.

In one embodiment, $R_{99}$ is the benzofuran above; $R_9$ is —H, $(C_1-C_6)$-alkyl, halogen, —$CF_3$, —$OR_{25}$, —$NO_2$ or —CN; and $R_7$, $R_8$, $R_{10}$, $R_{11}$, $R_{12}$, $R_{20}$, $R_{21}$, $R_{22}$ and $R_{23}$ are each hydrogen.

In one embodiment, $R_{99}$ is the benzofuran above; one of $R_7$, $R_8$, $R_9$, $R_{10}$, $R_{11}$, and $R_{12}$ is —H, $(C_1-C_6)$-alkyl, —$CF_3$, —$OR_{25}$, —$NO_2$ or —CN; and each remaining R group is H.

In one embodiment, $R_{99}$ is the benzofuran above; one of $R_{20}$, $R_{21}$, $R_{22}$, and $R_{23}$ is —H, $(C_1-C_6)$-alkyl, halogen, —$CF_3$, —$OR_{25}$, —$NO_2$ or —CN; and each remaining R group is H.

In one embodiment, $R_{99}$ is the benzofuran above; one of $R_7$, $R_8$, $R_9$, $R_{10}$, $R_{11}$, and $R_{12}$ is —H, $(C_1-C_6)$-alkyl, halogen, —$CF_3$, —$OR_{25}$, —$NO_2$ or —CN; one of $R_{13}$, $R_{14}$, $R_{15}$, and $R_{16}$ is —H, $(C_1-C_6)$-alkyl, halogen, —$CF_3$, —$OR_{25}$, —$NO_2$ or —CN; and each remaining R group is H.

In one embodiment, $R_{99}$ is the benzofuran above; one of $R_7$, $R_8$, $R_9$, $R_{10}$, $R_{11}$ and $R_{12}$ is —H, $(C_1-C_6)$-alkyl, halogen, —$CF_3$, —$OR_{25}$, —$NO_2$ or —CN; and one of $R_{20}$, $R_{21}$, $R_{22}$, and $R_{23}$ is —H, $(C_1-C_6)$-alkyl, halogen, —$CF_3$, —$OR_{25}$, —$NO_2$ or —CN.

In one embodiment, $R_{99}$ is the benzofuran above; one of $R_7$, $R_8$, $R_9$, $R_{10}$, $R_{11}$ and $R_{12}$ is —H, $(C_1-C_6)$-alkyl, halogen, —$CF_3$, —$OR_{25}$, —$NO_2$ or —CN; one of $R_{20}$, $R_{21}$, $R_{22}$, and $R_{23}$ is —H, $(C_1-C_6)$-alkyl, halogen, —$CF_3$, —$OR_{25}$, —$NO_2$ or —CN; and the remaining R groups are hydrogen.

In one embodiment, $R_{99}$ is the benzofuran above; two of $R_7$, $R_8$, $R_9$, $R_{10}$, $R_{11}$, and $R_{12}$ are each independently —H, $(C_1-C_6)$-alkyl, halogen, —$CF_3$, —$OR_{25}$, —$NO_2$ or —CN; and each remaining R group is hydrogen.

In one embodiment, $R_{99}$ is the benzofuran above; two of $R_7$, $R_8$, $R_9$, $R_{10}$, $R_{11}$, and $R_{12}$ are each independently —H, $(C_1-C_6)$-alkyl, halogen, —$CF_3$, —$OR_{25}$, —$NO_2$ or —CN; one of $R_{20}$, $R_{21}$, $R_{22}$, and $R_{23}$ is —H, $(C_1-C_6)$-alkyl, halogen, —$CF_3$, —$OR_{25}$, —$NO_2$ or —CN; and each remaining R group is hydrogen.

In one embodiment, $R_{99}$ is the benzofuran above; two of $R_7$, $R_8$, $R_9$, $R_{10}$, $R_{11}$, and $R_{12}$ are each independently —H, $(C_1-C_6)$-alkyl, halogen, —$CF_3$, —$OR_{25}$, —$NO_2$ or —CN; one of $R_{20}$, $R_{21}$, $R_{22}$, and $R_{23}$ is —H, $(C_1-C_6)$-alkyl, halogen, —$CF_3$, —$OR_{25}$, —$NO_2$ or —CN; one of $R_{13}$, $R_{14}$, $R_{15}$, and $R_{16}$ is —H, $(C_1-C_6)$-alkyl, halogen, —$CF_3$, —$OR_{25}$, —$NO_2$ or —CN; and each remaining R group is hydrogen.

In one embodiment, $R_{99}$ is the benzofuran above; $R_9$ and $R_{22}$ are each independently —H, $(C_1-C_6)$-alkyl, halogen, —$CF_3$, —$OR_{25}$, —$NO_2$ or —CN; and each remaining R group is hydrogen. In one embodiment, $R_{99}$ is the benzofuran above; $R_9$ and $R_{22}$ are each independently —H or halogen; and each remaining R group is hydrogen.

In another embodiment, $R_{99}$ is and $R_{24}$, $R_{26}$, and $R_{27}$ are each independently, —H, $(C_1-C_6)$-alkyl, halogen, —$CF_3$, —$OR_{25}$, —$NO_2$ or —CN. In one embodiment, $R_{99}$ is the benzo[1,4]dioxane above and $R_{24}$, $R_{26}$, and $R_{27}$ are each hydrogen.

In one embodiment, $R_{99}$ is the benzo[1,4]dioxane above and $R_7$, $R_8$, $R_9$, $R_{10}$, $R_{11}$, $R_{12}$, $R_{13}$, $R_{14}$, $R_{15}$, and $R_{16}$ are each independently —H, $(C_1-C_6)$-alkyl, halogen, —$CF_3$, —$OR_{25}$, —$NO_2$ or —CN.

In one embodiment, $R_{99}$ is the benzo[1,4]dioxane above; $R_7$, $R_8$, $R_9$, $R_{10}$, $R_{11}$, and $R_{12}$ are each independently —H, $(C_1-C_6)$-alkyl, halogen, —$CF_3$, —$OR_{25}$, —$NO_2$ or —CN; and $R_{13}$, $R_{14}$, $R_{15}$, and $R_{15}$ are each hydrogen.

In one embodiment, $R_{99}$ is the benzo[1,4]dioxane above and $R_7$, $R_8$, $R_9$, $R_{10}$, $R_{11}$, $R_{12}$, $R_{13}$, $R_{14}$, $R_{15}$, $R_{16}$, $R_{24}$, $R_{26}$, and $R_{27}$ are each hydrogen. In one embodiment, $R_{99}$ is the benzo[1,4]dioxane above and $R_7$, $R_8$, $R_9$, $R_{10}$, $R_{11}$, $R_{12}$, $R_{13}$, $R_{14}$, $R_{15}$, $R_{16}$, $R_{24}$, $R_{26}$, $R_{27}$, $R_a$ and $R_b$ are each hydrogen.

In one embodiment, $R_{99}$ is the benzo[1,4]dioxane above and $R_9$ is —H, $(C_1$-$C_6)$-alkyl, halogen, —$CF_3$, —$OR_{25}$, —$NO_2$ or —CN.

In one embodiment, $R_{99}$ is the benzo[1,4]dioxane above; $R_9$ is —H, $(C_1$-$C_6)$-alkyl, halogen, —$CF_3$, —$OR_{25}$, —$NO_2$ or —CN; $R_{15}$ and $R_{16}$ are each independently —H, $(C_1$-$C_6)$-alkyl, halogen, —$CF_3$, —$OR_{25}$, —$NO_2$ or —CN; and $R_7$, $R_8$, $R_{10}$, $R_{11}$, and $R_{12}$ are each hydrogen.

In one embodiment, $R_{99}$ is the benzo[1,4]dioxane above; $R_9$ is —H, $(C_1$-$C_6)$-alkyl, halogen, —$CF_3$, —$OR_{25}$, —$NO_2$ or —CN; and $R_7$, $R_8$, $R_{10}$, $R_{11}$, $R_{12}$, $R_{13}$, $R_{14}$, $R_{15}$, and $R_{16}$ are each hydrogen.

In one embodiment, $R_{99}$ is the benzo[1,4]dioxane above; $R_8$ is —H, $(C_1$-$C_6)$-alkyl, halogen, —$CF_3$, —$OR_{25}$, —$NO_2$ or —CN.

In one embodiment, $R_{99}$ is the benzo[1,4]dioxane above; $R_8$ is —H, $(C_1$-$C_6)$-alkyl, halogen, —$CF_3$, —$OR_{25}$, —$NO_2$ or —CN; $R_{15}$ and $R_{16}$ are each independently —H, $(C_1$-$C_6)$-alkyl, halogen, —$CF_3$, —$OR_{25}$, —$NO_2$ or —CN; and $R_7$, $R_9$, $R_{10}$, $R_{11}$, and $R_{12}$ are each hydrogen.

In one embodiment, $R_{99}$ is the benzo[1,4]dioxane above; $R_8$ is —H, $(C_1$-$C_6)$-alkyl, halogen, —$CF_3$, —$OR_{25}$, —$NO_2$ or —CN; and $R_7$, $R_9$, $R_{10}$, $R_{11}$, $R_{12}$, $R_{13}$, $R_{14}$, $R_{15}$, and $R_{16}$ are each hydrogen.

In one embodiment, $R_{99}$ is the benzo[1,4]dioxane above; one of $R_7$, $R_8$, $R_9$, $R_{10}$, $R_{11}$, and $R_{12}$ is —H, $(C_1$-$C_6)$-alkyl, halogen, —$CF_3$, —$OR_{25}$, —$NO_2$ or —CN; and each remaining R group is hydrogen.

In one embodiment, $R_{99}$ is the benzo[1,4]dioxane above; one of $R_7$, $R_8$, $R_9$, $R_{10}$, $R_{11}$, and $R_{12}$ is —H, $(C_1$-$C_6)$-alkyl, halogen, —$CF_3$, —$OR_{25}$, —$NO_2$ or —CN; one of $R_{24}$, $R_{26}$, and $R_{27}$ is —H, $(C_1$-$C_6)$-alkyl, halogen, —$CF_3$, —$OR_{25}$, —$NO_2$ or —CN; and each remaining R group is hydrogen.

In one embodiment, $R_{99}$ is the benzo[1,4]dioxane above; one of $R_7$, $R_8$, $R_9$, $R_{10}$, $R_1$, and $R_{12}$ is —H, $(C_1$-$C_6)$-alkyl, halogen, —$CF_3$, —$OR_{25}$, —$NO_2$ or —CN; one of $R_{24}$, $R_{26}$, and $R_{27}$ is —H, $(C_1$-$C_6)$-alkyl, halogen, —$CF_3$, —$OR_{25}$, —$NO_2$ or —CN; one of $R_{13}$, $R_{14}$, $R_{15}$, and $R_{16}$ is —H, $(C_1$-$C_6)$-alkyl, halogen, —$CF_3$, —$OR_{25}$, —$NO_2$ or —CN; and each remaining R group is hydrogen.

In one embodiment, $R_{99}$ is the benzo[1,4]dioxane above; two of $R_7$, $R_8$, $R_9$, $R_{10}$, $R_{11}$, and $R_{12}$ are each independently —H, $(C_1$-$C_6)$-alkyl, halogen, —$CF_3$, —$OR_{25}$, —$NO_2$ or —CN; and each remaining R group is hydrogen.

In one embodiment, $R_{99}$ is the benzo[1,4]dioxane above; two of $R_7$, $R_8$, $R_9$, $R_{10}$, $R_{11}$, and $R_{12}$ are each independently —H, $(C_1$-$C_6)$-alkyl, halogen, —$CF_3$, —$OR_{25}$, —$NO_2$ or —CN; one of $R_{24}$, $R_{26}$, and $R_{27}$ is —H, $(C_1$-$C_6)$-alkyl, halogen, —$CF_3$, —$OR_{25}$, —$NO_2$ or —CN; and each remaining R group is hydrogen.

In one embodiment, $R_{99}$ is the benzo[1,4]dioxane above; two of $R_7$, $R_8$, $R_9$, $R_{10}$, $R_{11}$, and $R_{12}$ are each independently —H, $(C_1$-$C_6)$-alkyl, halogen, —$CF_3$, —$OR_{25}$, —$NO_2$ or —CN; one of $R_{24}$, $R_{26}$, $R_{27}$ is —H, $(C_1$-$C_6)$-alkyl, halogen, —$CF_3$, —$OR_{25}$, —$NO_2$ or —CN; one of $R_{13}$, $R_{14}$, $R_{15}$, and $R_{16}$ is —H, $(C_1$-$C_6)$-alkyl, halogen, —$CF_3$, —$OR_{25}$, —$NO_2$ or —CN; and each remaining R group is hydrogen.

In a further embodiment, $R_{99}$ is

[Structure: indole ring with HN, and substituents $R_{28}$, $R_{29}$, $R_{30}$]

and $R_{28}$, $R_{29}$ and $R_{30}$ are each independently —H, $(C_1$-$C_6)$-alkyl, halogen, —$CF_3$, —$OR_{25}$, —$NO_2$ or —CN.

In one embodiment, $R_{99}$ is the indole above and $R_{28}$, $R_{29}$, and $R_{30}$ are each hydrogen.

In one embodiment, $R_{99}$ is the indole above and $R_7$, $R_8$, $R_9$, $R_{10}$, $R_{11}$, $R_{12}$, $R_{13}$, $R_{14}$, $R_{15}$, and $R_{16}$ are each independently —H, $(C_1$-$C_6)$-alkyl, halogen, —$CF_3$, —$OR_{25}$, —$NO_2$ or —CN.

In one embodiment, $R_{99}$ is the indole above; $R_7$, $R_8$, $R_9$, $R_{10}$, $R_{11}$, and $R_{12}$ are each independently —H, $(C_1$-$C_6)$-alkyl, halogen, —$CF_3$, —$OR_{25}$, —$NO_2$ or —CN; and $R_{13}$, $R_{14}$, $R_{15}$, and $R_{16}$ are each hydrogen.

In one embodiment, $R_{99}$ is the indole above; $R_8$ is —H, $(C_1$-$C_6)$-alkyl, halogen, —$CF_3$, —$OR_{25}$, —$NO_2$ or —CN.

In one embodiment, $R_{99}$ is the indole above; $R_8$ is —H, $(C_1$-$C_6)$-alkyl, halogen, —$CF_3$, —$OR_{25}$, —$NO_2$ or —CN; and $R_7$, $R_8$, $R_{10}$, $R_{11}$, $R_{12}$, $R_{28}$, $R_{29}$, and $R_{30}$ are each hydrogen. In one embodiment, $R_{99}$ is the indole above; $R_8$ is —H or halogen and $R_7$, $R_9$, $R_{10}$, $R_{11}$, $R_{12}$, $R_{28}$, $R_{29}$, and $R_{30}$ are each hydrogen. In one embodiment, $R_{99}$ is the indole above; $R_8$ is —H or halogen and $R_7$, $R_9$, $R_{10}$, $R_{11}$, $R_{12}$, $R_{13}$, $R_{14}$, $R_{15}$, $R_{16}$, $R_{28}$, $R_{29}$, and $R_{30}$ are each hydrogen. In one embodiment, $R_{99}$ is the indole above; $R_8$ is —H or halogen and $R_7$, $R_9$, $R_{10}$, $R_{11}$, $R_{12}$, $R_{13}$, $R_{14}$, $R_{15}$, $R_{16}$, $R_{28}$, $R_{29}$, $R_{30}$, $R_a$ and $R_b$ are each hydrogen.

In one embodiment, $R_{99}$ is the indole above; $R_8$ is —H, $(C_1$-$C_6)$-alkyl, halogen, —$CF_3$, —$OR_{25}$, —$NO_2$ or —CN; and $R_7$, $R_9$, $R_{10}$, $R_{11}$, $R_{12}$, $R_{13}$, $R_{14}$, $R_{15}$, and $R_{16}$ are each hydrogen.

In one embodiment, $R_{99}$ is the indole above; $R_8$ is —H, $(C_1$-$C_6)$-alkyl, halogen, —$CF_3$, —$OR_{25}$, —$NO_2$ or —CN; $R_{15}$ and $R_{16}$ are each —H, $(C_1$-$C_6)$-alkyl, halogen, —$CF_3$, —$OR_{25}$, —$NO_2$ or —CN; and $R_7$, $R_9$, $R_{10}$, $R_{11}$, and $R_{12}$ are each hydrogen.

In one embodiment, $R_{99}$ is the indole above; $R_9$ is —H, $(C_1$-$C_6)$-alkyl, halogen, —$CF_3$, —$OR_{25}$, —$NO_2$ or —CN.

In one embodiment, $R_{99}$ is the indole above; $R_9$ is —H, $(C_1$-$C_6)$-alkyl, halogen, —$CF_3$, —$OR_{25}$, —$NO_2$ or —CN; and $R_7$, $R_8$, $R_1$, $R_{11}$, $R_{12}$, $R_{28}$, $R_{29}$, and $R_{30}$ are each hydrogen.

In one embodiment, $R_{99}$ is the indole above; $R_9$ is —H, $(C_1$-$C_6)$-alkyl, halogen, —$CF_3$, —$OR_{25}$, —$NO_2$ or —CN; and $R_7$, $R_8$, $R_{10}$, $R_{11}$, $R_{12}$, $R_{13}$, $R_{14}$, $R_{15}$, and $R_{16}$ are each hydrogen.

In one embodiment, $R_{99}$ is the indole above; $R_9$ is —H, $(C_1$-$C_6)$-alkyl, halogen, —$CF_3$, —$OR_{25}$, —$NO_2$ or —CN; $R_{15}$ and $R_{16}$ are each —H, $(C_1$-$C_6)$-alkyl, halogen, —$CF_3$, —$OR_{25}$, —$NO_2$ or —CN; and $R_7$, $R_8$, $R_{10}$, $R_{11}$, and $R_{12}$ are each hydrogen.

In one embodiment, $R_{99}$ is the indole above; one of $R_7$, $R_8$, $R_9$, $R_{10}$, $R_{11}$, and $R_{12}$ is —H, $(C_1$-$C_6)$-alkyl, halogen, —$CF_3$, —$OR_{25}$, —$NO_2$ or —CN; and each remaining R group is H. In one embodiment, $R_{99}$ is the indole above; one of $R_7$, $R_8$, $R_9$, $R_{10}$, $R_{11}$, and $R_{12}$ is —H or halogen and each remaining R group is H.

In one embodiment, $R_{99}$ is the indole above; one of $R_7$, $R_8$, $R_9$, $R_{10}$, $R_{11}$, and $R_{12}$ is —H, $(C_1$-$C_6)$-alkyl, halogen, —$CF_3$, —$OR_{25}$, —$NO_2$ or —CN; one of $R_{28}$, $R_{29}$, and $R_{30}$ is —H, ($C_1$-$C_6$)-alkyl, halogen, —$CF_3$, —$OR_{25}$, —$NO_2$ or —CN; and each remaining R group is H.

In one embodiment, $R_{99}$ is the indole above; one of $R_7$, $R_8$, $R_9$, $R_{10}$, $R_{11}$, and $R_{12}$ is —H, ($C_1$-$C_6$)-alkyl, halogen, —$CF_3$, —$OR_{25}$, —$NO_2$ or —CN; one of $R_{28}$, $R_{29}$, and $R_{30}$ is —H, ($C_1$-$C_6$)-alkyl, halogen, —$CF_3$, —$OR_{25}$, —$NO_2$ or —CN; one of $R_{13}$, $R_{14}$, $R_{15}$, and $R_{16}$ is —H, ($C_1$-$C_6$)-alkyl, halogen, —$CF_3$, —$OR_{25}$, —$NO_2$ or —CN; and each remaining R group is hydrogen.

In one embodiment, $R_{99}$ is the indole above; two of $R_7$, $R_8$, $R_9$, $R_{10}$, $R_{11}$, and $R_{12}$ are each independently —H, ($C_1$-$C_6$)-alkyl, halogen, —$CF_3$, —$OR_{25}$, —$NO_2$ or —CN; and each remaining R group is hydrogen.

In one embodiment, $R_{99}$ is the indole above; two of $R_7$, $R_8$, $R_9$, $R_{10}$, $R_{11}$, and $R_{12}$ are each independently —H, ($C_1$-$C_6$)-alkyl, halogen, —$CF_3$, —$OR_{25}$, —$NO_2$ or —CN; one of $R_{28}$, $R_{29}$, and $R_{30}$ is —H, —$OR_{25}$, —$CH_3$, halogen, —$CF_3$, —$NO_2$ or —CN; and each remaining R group is hydrogen.

In one embodiment, $R_{99}$ is the indole above; two of $R_7$, $R_8$, $R_9$, $R_{10}$, $R_{11}$, and $R_{12}$ are each independently —H, ($C_1$-$C_6$)-alkyl, halogen, —$CF_3$, —$OR_{25}$, —$NO_2$ or —CN; one of $R_{28}$, $R_{29}$, and $R_{30}$ is —H, ($C_1$-$C_6$)-alkyl, halogen, —$CF_3$, —$OR_{25}$, —$NO_2$ or —CN; one of $R_{13}$, $R_{14}$, $R_{15}$, and $R_{16}$ is —H, ($C_1$-$C_6$)-alkyl, halogen, —$CF_3$, —$OR_{25}$, —$NO_2$ or —CN; and each remaining R group is hydrogen.

In yet another aspect, the invention provides compounds of the Formula (IV):

and pharmaceutically acceptable salts thereof, wherein X is $CR_{25}$, N, O or S; Y is $CR_{25}$, $NR_{25}$, O or S; with the proviso that when X is $CR_{25}$, Y is not $NR_{25}$; $R_{13}$, $R_{14}$, $R_{15}$, $R_{16}$, $R_{31}$, $R_{32}$, $R_{33}$, $R_{34}$, $R_{35}$, $R_{36}$, $R_{37}$, $R_{38}$ and $R_{39}$ are each independently —H, ($C_1$-$C_6$)-alkyl, ($C_1$-$C_6$)-haloalkyl, ($C_2$-$C_6$)-alkenyl, or ($C_2$-$C_6$)-alkynyl, halogen, —$CF_3$, —$NO_2$, —CN, —$OR_{25}$, —$OSO_2R_{25}$, —$SR_{25}$, —$SO_2R_{25}$, —$SO_2N(R_{25})_2$, —$N(R_{25})_2$, —C(O), —$COR_{25}$, —$CO_2R_{25}$, —$NR_{25}CO_2R_{25}$, —$NR_{25}COR_{25}$, —$NR_{25}CON(R_{25})_2$, or —$CON(R_{25})_2$; $R_a$ and $R_b$ are each independently —H or —$CH_3$; $R_{25}$ is —H; or linear or branched ($C_1$-$C_6$)-alkyl, ($C_1$-$C_6$)-haloalkyl, ($C_2$-$C_6$)-alkenyl, or ($C_2$-$C_6$-alkynyl).

In one embodiment, X is $CR_{25}$ or N; Y is O or S; one of $R_{31}$, $R_{32}$, $R_{33}$, $R_{34}$ and $R_{35}$ is —H, ($C_1$-$C_6$)-alkyl, —$OR_{25}$, halogen, or —$CF_3$; and each remaining R group is hydrogen.

In one embodiment, X is $CR_{25}$ or N; Y is O or S; one of $R_{31}$, $R_{32}$, $R_{33}$, $R_{34}$ and $R_{35}$ is —H, ($C_1$-$C_6$)-alkyl, —$OR_{25}$, halogen, or —$CF_3$; one of $R_{36}$, $R_{37}$, $R_{38}$ and $R_{39}$ is —H, ($C_1$-$C_6$)-alkyl, —$OR_{25}$, —$CH_3$, halogen, or —$CF_3$; and each remaining R group is hydrogen.

In one embodiment, X is $CR_{25}$ or N; Y is O or S; one of $R_{31}$, $R_{32}$, $R_{33}$, $R_{34}$ and $R_{35}$ is —H, ($C_1$-$C_6$)-alkyl, —$OR_{25}$, halogen, or —$CF_3$; one of $R_{13}$, $R_{14}$, $R_{15}$, and $R_{16}$ is —H, ($C_1$-$C_6$)-alkyl, —$OR_{25}$, —$CH_3$, halogen, or —$CF_3$; and each remaining R group is hydrogen.

In one embodiment, X is $CR_{25}$ or N; Y is O or S; one of $R_{31}$, $R_{32}$, $R_{33}$, $R_{34}$ and $R_{35}$ is —H, ($C_1$-$C_6$)-alkyl, —$OR_{25}$, halogen, or —$CF_3$; one of $R_{13}$, $R_{14}$, $R_{15}$, and $R_{16}$ is —H, ($C_1$-$C_6$)-alkyl, —$OR_{25}$, halogen, or —$CF_3$; one of $R_{36}$, $R_{37}$, $R_{38}$ and $R_{39}$ is —H, ($C_1$-$C_6$)-alkyl, —$OR_{25}$, halogen, or —$CF_3$; and each remaining R group is hydrogen.

In one embodiment, X is $CR_{25}$ or N; Y is O or S; $R_{13}$, $R_{14}$, $R_{15}$, $R_{16}$, $R_{31}$, $R_{32}$, $R_{33}$, $R_{34}$, $R_{35}$, $R_{36}$, $R_{37}$, $R_{38}$, and $R_{39}$ are each independently —H, ($C_1$-$C_6$)-alkyl, —$OR_{25}$, halogen, —$CF_3$, —$NO_2$, or —CN.

In one embodiment, X is $CR_{25}$ or N; Y is O or S; $R_{13}$, $R_{14}$, $R_{15}$, and $R_{15}$ are each independently —H, ($C_1$-$C_6$)-alkyl, —$OR_{25}$, halogen, or —$CF_3$; and $R_{31}$, $R_{32}$, $R_{33}$, $R_{34}$, $R_{35}$, $R_{36}$, $R_{37}$, $R_{38}$ and $R_{39}$ are each hydrogen.

In one embodiment, X is $CR_{25}$ or N; Y is O or S; $R_{31}$, $R_{32}$, $R_{33}$, $R_{34}$, $R_{35}$, $R_{36}$, $R_{37}$, $R_{38}$ and $R_{39}$ are each independently —H, ($C_1$-$C_6$)-alkyl, —$OR_{25}$, halogen, or —$CF_3$; and $R_{13}$, $R_{14}$, $R_{15}$, and $R_{15}$ are each hydrogen.

In one embodiment, X is $CR_{25}$ or N; Y is O or S; $R_{31}$ is —H, ($C_1$-$C_6$)-alkyl, —$OR_{25}$, halogen, or —$CF_3$. In one embodiment, X is $CR_{25}$ or N; Y is O or S; $R_{31}$ is —H or —$OR_{25}$.

In one embodiment, X is $CR_{25}$ or N; Y is O or S; $R_{31}$ is —H, ($C_1$-$C_6$)-alkyl, —$OR_{25}$, halogen, or —$CF_3$ and each remaining R group is hydrogen. In one embodiment, X is $CR_{25}$ or N; Y is O or S; $R_{31}$ is —H or —$OR_{25}$ and each remaining R group is hydrogen.

In one embodiment, X is $CR_{25}$ or N; Y is O or S; $R_{31}$ is —H, ($C_1$-$C_6$)-alkyl, —$OR_{25}$, halogen, or —$CF_3$; and $R_{13}$, $R_{14}$, $R_{15}$, $R_{16}$, $R_{32}$, $R_{33}$, $R_{34}$, $R_{35}$, $R_{36}$, $R_{37}$, $R_{38}$, and $R_{39}$ are each hydrogen.

In one embodiment, X is $CR_{25}$ or N; Y is O or S; $R_{31}$ is —H, ($C_1$-$C_6$)-alkyl, —$OR_{25}$, —$CH_3$, halogen, or —$CF_3$; $R_{16}$ is —H, ($C_1$-$C_6$)-alkyl, —$OR_{25}$, halogen, or —$CF_3$; and $R_{13}$, $R_{14}$, $R_{15}$, $R_{32}$, $R_{33}$, $R_{34}$, $R_{35}$, $R_{36}$, $R_{37}$, $R_{38}$, and $R_{39}$ are each hydrogen.

In one embodiment, X is $CR_{25}$ or N; Y is O or S; $R_{31}$ is —H, ($C_1$-$C_6$)-alkyl, —$OR_{25}$, or —$CF_3$; $R_{15}$ is —H, ($C_1$-$C_6$)-alkyl, —$OR_{25}$, halogen, or —$CF_3$; and $R_{13}$, $R_{14}$, $R_{16}$, $R_{32}$, $R_{33}$, $R_{34}$, $R_{35}$, $R_{36}$, $R_{37}$, $R_{38}$, and $R_{39}$ are each hydrogen.

In one embodiment, $R_{31}$ is —H, ($C_1$-$C_6$)-alkyl, halogen, —$CF_3$, or —$OR_{25}$; $R_{32}$, $R_{33}$, $R_{34}$, $R_{35}$, $R_{36}$, $R_{37}$, $R_{38}$ and $R_{39}$ are each independently —H, —$CH_3$, halogen, —$CF_3$, or —$OR_{25}$; and $R_{13}$, $R_{14}$, $R_{15}$, and $R_{16}$ are each hydrogen.

In one embodiment, $R_{31}$ is —H, ($C_1$-$C_6$)-alkyl, halogen, —$CF_3$, or —$OR_{25}$; $R_{15}$ and $R_{16}$ are each independently —H, —$CH_3$, halogen, —$CF_3$, or —$OR_{25}$; and $R_{32}$, $R_{33}$, $R_{34}$, $R_{35}$, $R_{36}$, $R_{37}$, $R_{38}$ and $R_{39}$ are each hydrogen.

Illustrative examples of compounds of Formula (III) and Formula (IV) are set forth below and include, without limitation:

6-chloro-8-{4-[4-(1H-indole-4-yl)-piperazin-1-yl]-piperidin-1-yl}-quinoline;

8-{4-[4-(1H-indole-4-yl)-piperazin-1-yl]-piperidin-1-yl}-quinoline;

8-{4-[4-(2,3-dihydro-benzo[1,4]dioxin-5-yl)-piperazin-1-yl]-piperidin-1-yl}-quinoline;

8-[4-(4-benzofuran-3yl-piperazin-1-yl)-piperidin-1-yl]-6-chloro-quinoline;

5-fluoro-8-{4-[4-(5-fluoro-benzofuran-3-yl)-piperazin-1-yl]-piperidin-1-yl}-quinoline;

1-(1-benzo[b]thiophen-3-yl-piperidin-4-yl)-4-(2-methoxy-phenyl)-piperazine; or

3-{4-[4-(2-methoxyphenyl)-piperazin-1-yl]-1-piperidinyl}-1,2-benzisoxazole;

and pharmaceutically acceptable salts thereof.

The compounds and pharmaceutically acceptable salts of compounds of the present invention can contain an asymmetric carbon atom and some of the compounds or pharmaceutically acceptable salts of compounds of the invention can contain one or more asymmetric centers, and can thus give rise to optical isomers and diastereomers. While depicted without respect to stereochemistry in the compounds and pharmaceutically acceptable salts of compounds of the present invention, the present invention includes such optical isomers and diastereomers, as well as racemic and resolved, enantiomerically pure R and S stereoisomers, and also other mixtures of the R and S stereoisomers and pharmaceutically acceptable salts thereof. Where a stereoisomer is preferred, it can in some embodiments be provided substantially free of its corresponding opposite enantiomer.

In addition, the compounds and pharmaceutically acceptable salts of compounds of the present invention can exist as polymorphs. Such polymorphs can be transient or isolatable as a stable product.

Prodrugs of the compounds or pharmaceutically acceptable salts of compounds are also within the scope of the present invention.

Methods for Making the Compounds of the Invention

The compounds and pharmaceutically acceptable salts of compounds of the present invention can be prepared using a variety of methods starting from commercially available compounds, known compounds, or compounds prepared by known methods. General synthetic routes to many of the compounds of the invention are included in the following schemes. The methods for making some intermediates of the invention are described in WO2004/024731 and U.S. Pat. No. 4,465,482, both of which are hereby incorporated by reference. It is understood by those skilled in the art that protection and deprotection steps not shown in the Schemes may be required for these syntheses, and that the order of steps may be changed to accommodate functionality in the target molecule.

Scheme 1 illustrates the coupling of piperazine-piperidine compounds of Formulas (I), (II), (III), and (IV) through reductive amination, wherein $R_a$, $R_b$, $R_7$, $R_8$, $R_9$, $R_{10}$, $R_{11}$, $R_{12}$, $R_{13}$, $R_{14}$, $R_{15}$, $R_{16}$, and $R_{99}$ are as defined above, and $R_{99}$ can also be a substituted or unsubstituted quinoline. A compound of Formula (X) is reacted with a compound of Formula (XIV) under conditions effective to bring about reductive amination at the piperidine carbonyl, thereby providing the piperazine-piperidine compound of Formulas (I), (II), (III), and (IV). Reagents that can effect this coupling include, but are not limited to, sodium cyanoborohydride and sodium triacetoxyborohydride. Suitable solvents for performing the reaction include, but are not limited to, dichloroethane and methanol and acids such as acetic acid and hydrochloride may optionally be added to the reaction. Reaction temperatures can vary, depend on the nature of the reactants, but usually span the range from 0° C. to the boiling point of the solvent.

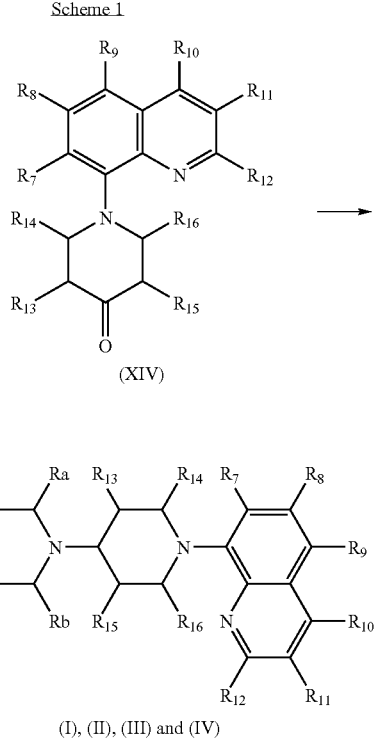

Scheme 1

Scheme 1a illustrates the coupling of piperazine-piperidine compounds of Formula (I'), through reductive amination, wherein $R_a$, $R_b$, $R_7$, $R_8$, $R_9$, $R_{10}$, $R_{11}$, $R_{12}$, $R_{13}$, $R_{14}$, $R_{15}$, $R_{16}$, and $R_{99}$ are as defined above, and $R_{99}$ can also be a substituted or unsubstituted quinoline. A compound of Formula (X) is reacted with a compound of Formula (XIVb) under conditions effective to bring about reductive amination at the piperidine carbonyl, such as those described in Scheme 1, thereby providing the piperazine-piperidine compound of Formulas (I').

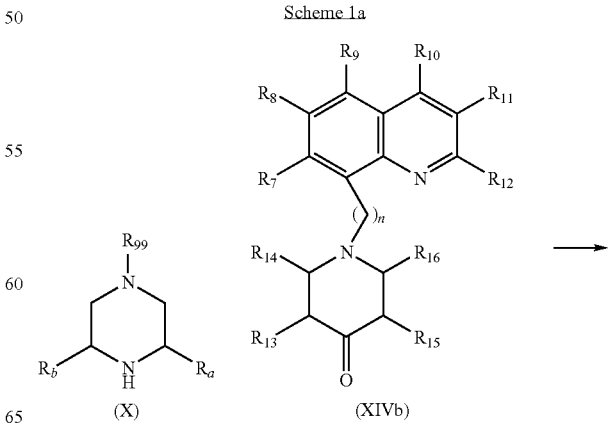

Scheme 1a

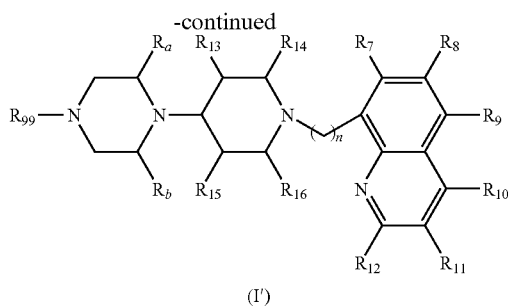

(I')

Scheme 1a' illustrates another method for making compounds of Formula (I'), wherein $R_a$, $R_b$, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ are as defined above, and $R_{99}$ is an optionally substituted quinoline (n is also as defined above). A compound of Formula (Xa) is reacted under conditions effective to provide the compound of Formula (XXXI). The compound of Formula (XXXI) is reacted under conditions effective to provide the removal of the phenyl-methyl group, thereby providing the compound of Formula (XXXI). The compound of Formula (XXXII) is reacted with an alkyl-substituted quinoline of Formula (XXXII) having a good leaving group (W) under conditions effective to produce a compound of Formula (I'). Suitable leaving groups are known to those of skill in the art and include, without limitation, halogen, —OTs, —OMs or —OTr.

Scheme 1a'

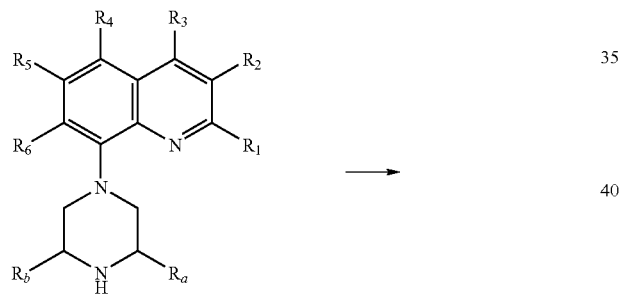

(Xa)

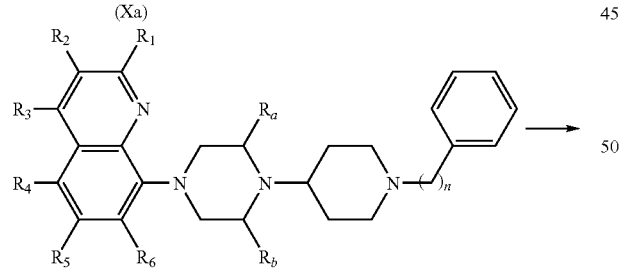

(XXXI)

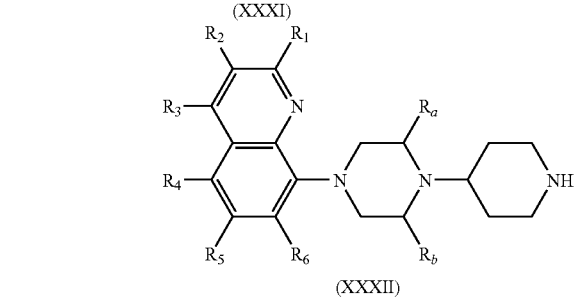

(XXXII)

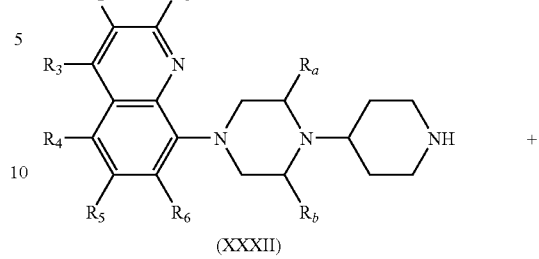

(XXXII)

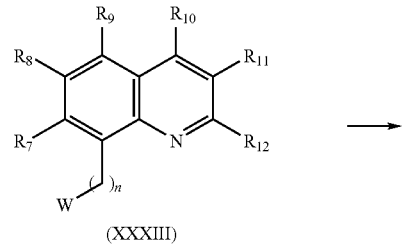

(XXXIII)

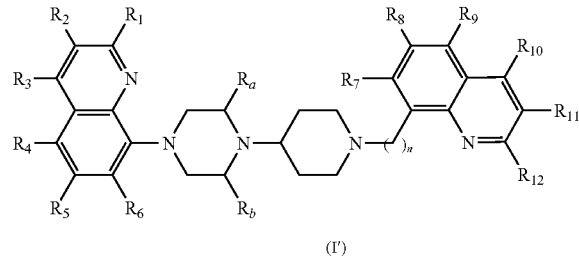

(I')

Scheme 1b illustrates the coupling of piperazine-piperidine compounds of Formula (I"), through reductive amination, wherein $R_a$, $R_b$, $R_7$, $R_{7'}$, $R_8$, $R_9$, $R_{10}$, $R_{11}$, $R_{12}$, $R_{13}$, $R_{14}$, $R_{15}$, $R_{16}$, $R_{99}$ are as defined above except for the R group through which the piperidine is connected; and n is as defined above; and $R_{99}$ can also be a substituted or unsubstituted quinoline. A compound of Formula (X) is reacted with a compound of Formula (XIVc) under conditions effective to bring about reductive amination at the piperidine carbonyl, such as those described in Scheme 1, thereby providing the piperazine-piperidine compound of Formula (I").

Scheme 1b

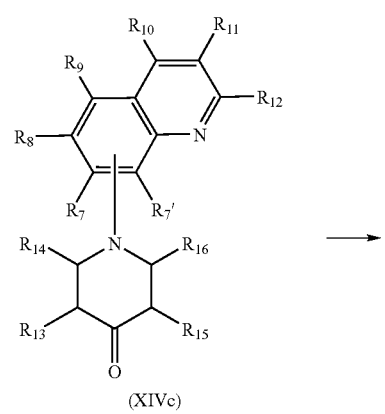

(X)  (XIVc)

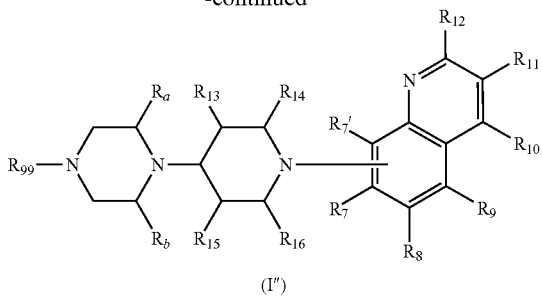

(I″)

Scheme 2 illustrates the production of compounds of Formula (I). As shown in Scheme 2, a compound of Formula (Xa) and a compound of Formula (XIV) can be reacted under conditions effective to produce the di-quinoline substituted piperazine-piperidine compound of Formula (I), such as those described in Scheme 1.

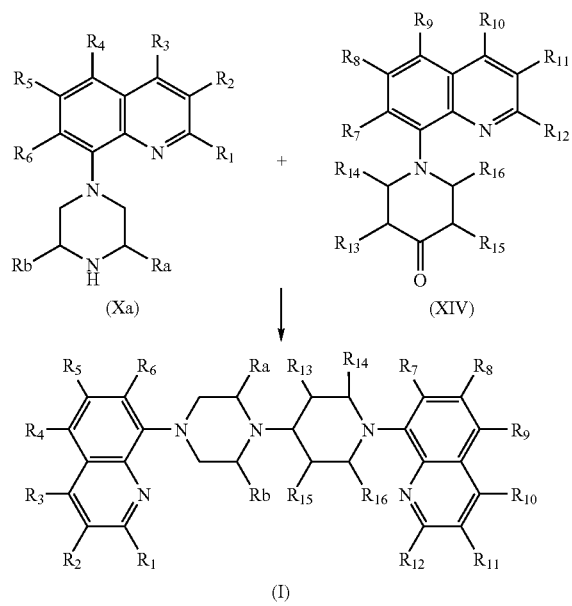

Scheme 3 illustrates the production of compounds of Formula (Xb) and Formula (XV) in which $R_1$, $R_2$, $R_3$, $R_{10}$, $R_{11}$, $R_{12}$, $R_{13}$, $R_{14}$, $R_{15}$, and $R_{16}$ are each hydrogen and $R_a$, $R_b$, $R_4$, $R_5$, $R_6$, $R_7$, $R_8$ and $R_9$ are as defined above. An optionally substituted aniline compound of Formula (VII) is reacted with an appropriate reagent under conditions effective to produce the quinoline compound of Formula (VIII). Numerous reagents and conditions affect this transformation. Many of these can be found in a review by G. Jones (Synthesis of the Quinoline Ring System, in *Heterocyclic Compounds: Volume 32 (Quinolines)*, Interscience, New York, N.Y., 1977, pp. 93-318). One such reagent is glycerol, as originally described by Skraup (Monatsh. (1880), 1,316). $R_1$, $R_2$, $R_3$, $R_4$, $R_5$ and $R_6$ of (VII) and (VIII) are as above for (I) and W is a good leaving group, for example halogen, p-toluenesulfonyl (—OTs), methanesulfonyl (—OMs) or trifluoromethanesulfonyl (—OTr). The compound of Formula (VIII) is then reacted with a protected piperazine derivative under conditions effective to provide a protected piperazino-quinoline of Formula (IX), where $X_1$ is a protecting group. Protecting groups are well known to those of skill in the art and include, without limitation, tert-butoxycarbonyl. Conditions that can effect this reaction include, but are not limited to, reacting the two components in the presence of a palladium complex such as those described by Buchwald et al., *J. Am. Chem. Soc.* 118:7215 (1996) and Hartwig et al., *J. Am. Chem. Soc.* 118:7217 (1996). The protected piperazino-quinoline of Formula (IX) is then reacted under conditions to promote the removal of the protecting group (e.g., aqueous acid or mixtures of a water miscible organic solvent and aqueous acid), providing the substituted piperazino-quinoline compound of Formula (Xb). Separately, compounds of Formula (XIV) are produced by beginning with an optionally substituted aniline compound of Formula (XI) and reacting it as described above with an appropriate reagent under conditions effective to produce the quinoline compound of Formula (XII). $R_7$, $R_8$, $R_9$, $R_{10}$, $R_{11}$, and $R_{12}$ of (XI) and (XII) are as above for Formula (I) and W is a suitable leaving group such as halogen, —OTs, —OMs or —OTr. The quinoline compound of Formula (XII) is then reacted with a piperidin-4-one derivative under conditions effective to provide the compound of Formula (XIII) (e.g., a palladium-catalyzed coupling such as that described above). The carbonyl group of the piperidin-4-one derivative is protected with a protecting group ($X_2$). Suitable protecting groups are well known to those of skill in the art and include, without limitation, 1,3-dioxolane. The compound of Formula (XIII) is then reacted under conditions to promote the removal of the protecting group (e.g., aqueous acid or a mixture of a water miscible organic solvent and aqueous acid), providing the piperidin-4-one compound of Formula (XIVa). The piperidin-4-one compound of Formula (XIVa) is then reacted with the piperazino-quinoline compound of Formula (Xb) as described above in Schemes 1 and 2 to produce the di-quinoline piperazine-piperidine compound of Formula (XV).

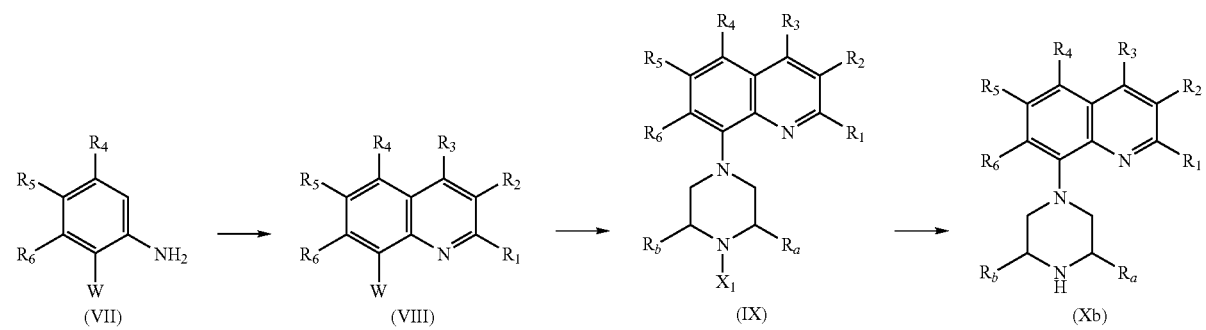

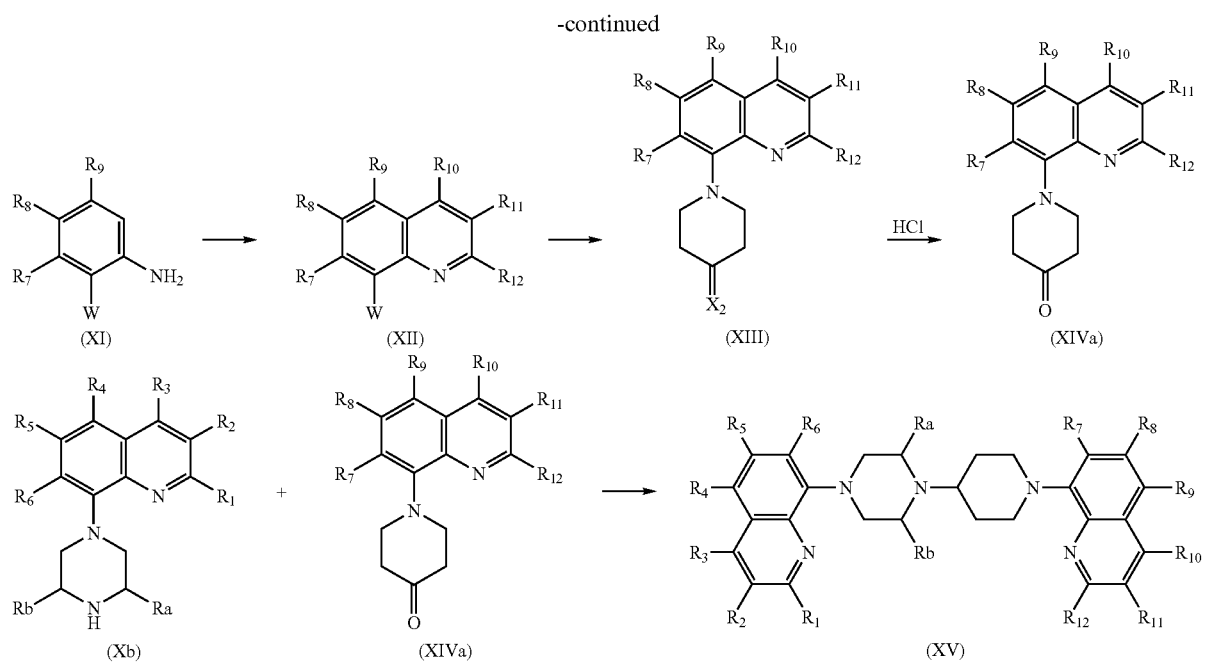

Alternative syntheses for the quinoline compounds of Formulae (VIII) and (XII) are provided in Scheme 3a. The aniline compounds of Formulae (VII) and (XI) are reacted with an appropriate reagent under conditions effective to product the quinoline compounds of Formulae (XXXIV) and (XXXV) where W is a leaving group. Reagents and conditions suitable for affecting this transformation are known to those of skill in the art and include, for example, methods described in G. Jones, supra. One exemplary reagent is glycerol, as described above. The compounds of Formulae (XXXIV) and (XXXV) are then reacted with appropriate reagents to yield the desired intermediate compounds of Formulae (VIII) and (XI).

In some embodiments, compounds of Formula (I) and Formula (XV) are further reacted to form a salt of the compounds of Formula (I) and Formula (XV) through an acid addition process. In one nonlimiting example, one or more equivalents of an acid (e.g., hydrochloride, succinic, or adipic acids) are reacted with the free base of a compound of Formula (I) and Formula (XV) to form an acid addition salt. Exemplary salts include, without limitation, mono-, di-, tri- and tetra-acid salts.

In some embodiments, the acid addition step is modified to allow for isolation of the salts of the compounds of Formula (I) and Formula (XV) without the use of potentially environmentally hazardous materials. In one embodiment, compounds of Formula (I) and Formula (XV) are reacted in the presence of non-chlorinated solvents. In one embodiment, the non-chlorinated solvent is toluene.

In some embodiments, the acid addition reaction is performed under conditions that result in relatively low amounts of residual solvent found in the final product. In some embodiments, the amount of each individual residual solvent is present in an amount that is less than about 0.25 w % of the resulting salt form of the compound of Formula (I) or Formula (XV). In one embodiment, the amount of each residual solvent is less than about 0.2 w % of the resulting salt form of the compound of Formula (III) or the compound of Formula (XV). In still other embodiments, the amount of each solvent is less than about 0.15 w % of the resulting salt form of the compound of Formula (I) or the compound of ormula (XV). In further embodiments, the amount of each solvent is less than about 0.1 w % of the resulting salt form of the compound of Formula (I) or the compound of Formula (XV). In yet more embodiments, the amount of each solvent is less than about 0.05 w % of the resulting salt form of the compound of Formula (1) or the compound of Formula (XV). In still more embodiments, the amount of each solvent is less than about 0.025 w % of the resulting salt form of the compound of Formula (I) or the compound of Formula (XV). In additional embodiments, the amount of each solvent is less than about 0.02 w % of the resulting salt form of the compound of Formula (I) or the compound of Formula (XV). In another embodiment, the amount of each solvent is less than about 0.01 w % of the resulting salt form of the compound of Formula (I) or the compound of Formula (XV). In one embodiment, the presence of chlorinated solvents is decreased significantly from the final isolated salt form of the compound of Formula (1) or the compound of Formula (XV). In one embodiment, there are no detectable chlorinated solvents is the final isolated salt form of the compound of Formula (I) or the compound of Formula (XV). In one embodiment, the amount of chlorinated solvent present in the final isolated salt form of the compound of Formula (1) or the compound of Formula (XV) is less than about 0.1%. In one embodiment, the amount of chlorinated solvent present in the final isolated salt form of the compound of Formula (I) and the compound of Formula (XV) is less than about 0.05%. In one embodiment, the amount of chlorinated solvent present in the final isolated salt form of the compound of Formula (I) and the compound of Formula (XV) is less than about 0.01%. In one embodiment, the amount of chlorinated solvent present in the final isolated salt form of the compound of Formula (1) and the compound of Formula (XV) is less than about 0.001%.

In some embodiments, the acid addition reaction occurs in the presence of organic solvents including, but not limited to, tetrahydrofuran (THF), acetone, dichloromethane, and dichloroethane. In one embodiment, the organic solvents are THF and acetone. In one embodiment, a compound of Formula (I) or a compound of Formula (XV) is mixed with a first organic solvent and then added to a solution that includes a second organic solvent and an acid. In one embodiment, the first organic solvent is THF or acetone. In one embodiment, the second organic solvent is THF or acetone. In one embodiment, the first organic solvent is THF and the second organic solvent is acetone. In one embodiment, a compound of Formula (I) or a compound of Formula (XV) is mixed with THF prior to addition to a solution of acetone and an acid. In one embodiment, the acid is an organic acid. In one embodiment, the acid is a dicarboxylic acid. In one embodiment, the organic acid is succinic acid.

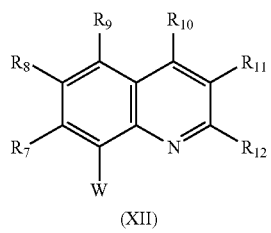

Scheme 4 illustrates the production of a compound of Formula (In) in which $R_{99}$ is an indole compound and $R_7$, $R_8$, $R_9$, $R_{10}$, $R_{11}$, $R_{12}$, $R_{28}$, $R_{29}$ and $R_{30}$ are defined as above for Formula (III). A piperidin-4-one compound of Formula (XIVa) is produced as described above in Scheme 3. A dinitro-toluene compound of Formula (XVI) is reacted with N,N-dimethylformamide dimethyl acetal and pyrrolidine under conditions effective to bring about cyclization, thereby providing an indol-4-ylamine compound of Formula (XVII). The compound of Formula (XVII) is then reacted with a bis(2-chloroethyl)-benzylamine under conditions effective to produce the compound of Formula (XVIII). The compound of Formula (XVIII) is then reacted under conditions effective to remove the benzyl protecting group to produce a 4-piperazin-1-yl-indole of Formula (XIX). The piperazin-1-yl-indole compound of Formula (XIX) is then reacted with the piperidin-4-one compound of Formula (XIVa) as described above in Scheme 1 to produce the piperazine-piperidine compound of Formula (XX), which is a compound of Formula (III).

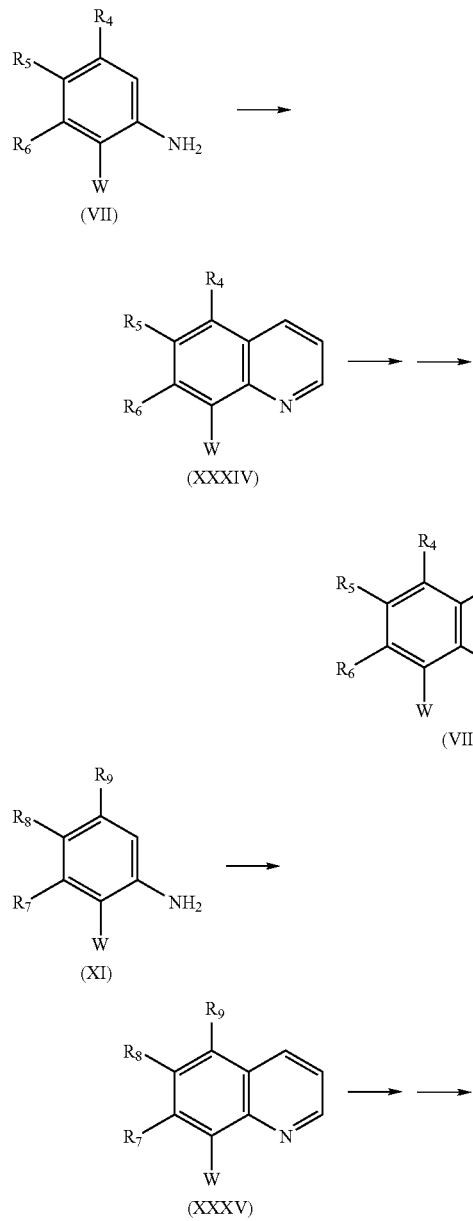

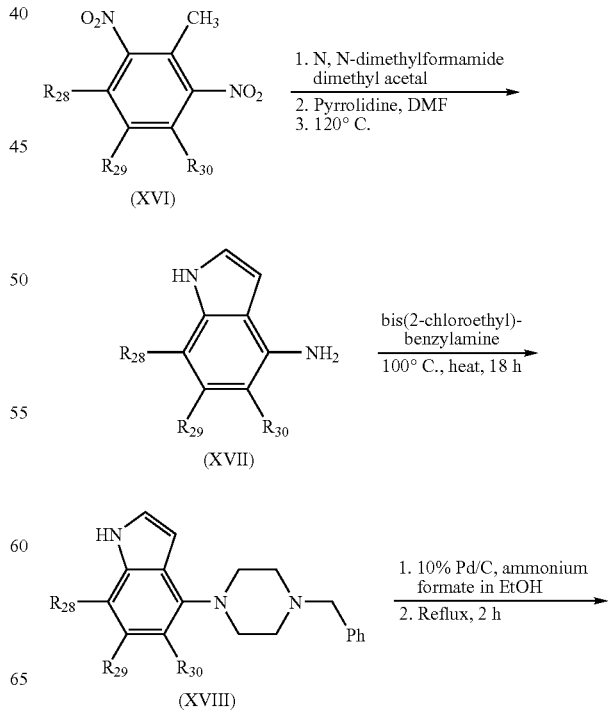

-continued

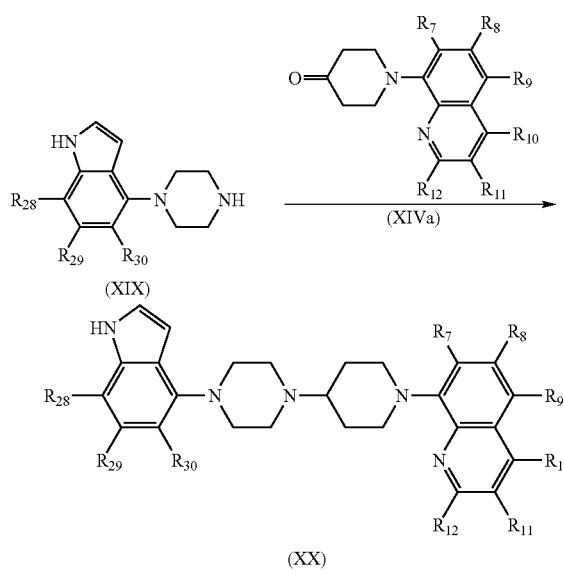

Scheme 5 illustrates the production of compounds of Formula (III) in which $R_{99}$ is a benzo[1,4]dioxane compound and $R_a$, $R_b$, $R_7$, $R_8$, $R_9$, $R_{10}$, $R_{11}$, $R_{12}$, $R_{24}$, $R_{26}$ and $R_{27}$ are defined as above for Formula (III). A piperidin-4-one compound of Formula (XIVa) is produced as described above in Scheme 3. A benzo[1,4]dioxane-piperazine compound having the Formula (XXIII) is produced by reacting a piperidine with a benzo[1,4]dioxane substituted with a good leaving group, for example a halogen —OTs, —OMs or —OTr, under conditions effective to produce a compound of Formula (XXIII). The compound of Formula (XXIII) is reacted with the piperidin-4-one compound of Formula (XIVa) as described above in Scheme 1 to produce the benzo[1,4]dioxane piperazine-piperidine quinoline compound of Formula (XXIV).

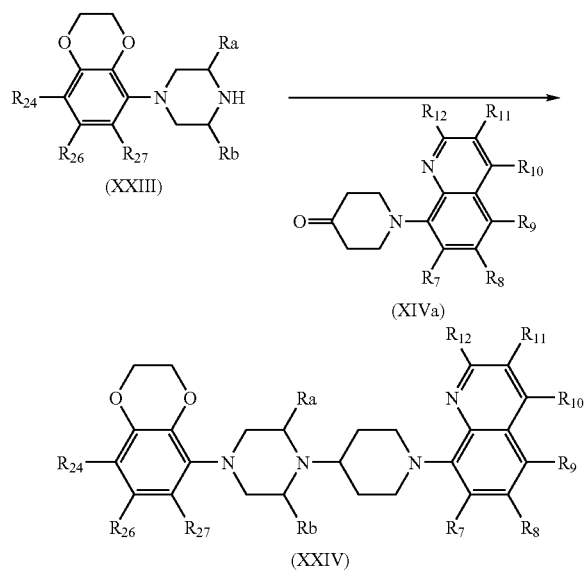

Scheme 5a illustrates an alternative production of a benzo[1,4]dioxane-piperazine compound having the Formula (XXIII) in which $R_a$, $R_b$, $R_{24}$, $R_{26}$, and $R_{27}$ are defined as above for Formula (III). A nitro-benzodioxane of Formula (XXI) is reacted under conditions effective to produce a compound of Formula (XXII). The compound of Formula (XXII) is reacted with a bis(2-chloroethyl)amine under conditions effective to produce a compound of Formula (XXIII).

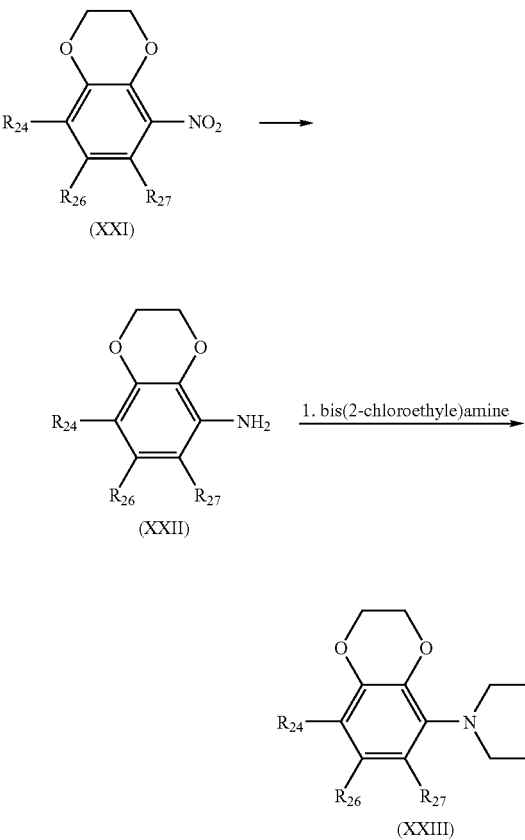

Scheme 6 illustrates the production of a compound or pharmaceutically acceptable salt of a compound of Formula (III) in which $R_{99}$ is a benzofuran compound and $R_a$, $R_b$, $R_7$, $R_8$, $R_9$, $R_{10}$, $R_{11}$, $R_{12}$, $R_{20}$, $R_{21}$, $R_{22}$ and $R_{23}$ are defined as above for Formula (III). A piperidin-4-one compound of Formula (XIVa) is produced as described above in Scheme 3. The benzofuranone of Formula (XXXI) is reacted with a protected piperazine under conditions effective to produce benzofuran-N-protected piperazine compound of Formula (XXXII). Suitable protecting groups ($X_1$) are well known to those of skill in the art and include, without limitation, ethoxycarbonyl. Deprotection of the N-protecting group (such as by hydrolysis) of the compound of Formula (XXXII) gives a compound of formula (V). The benzofuran-piperazine of Formula (V) is then reacted with the piperidin-4-one compound of Formula (XIV) as described above in Scheme 1 to produce the piperazine-piperidine compound of Formula (XXV).

Scheme 6

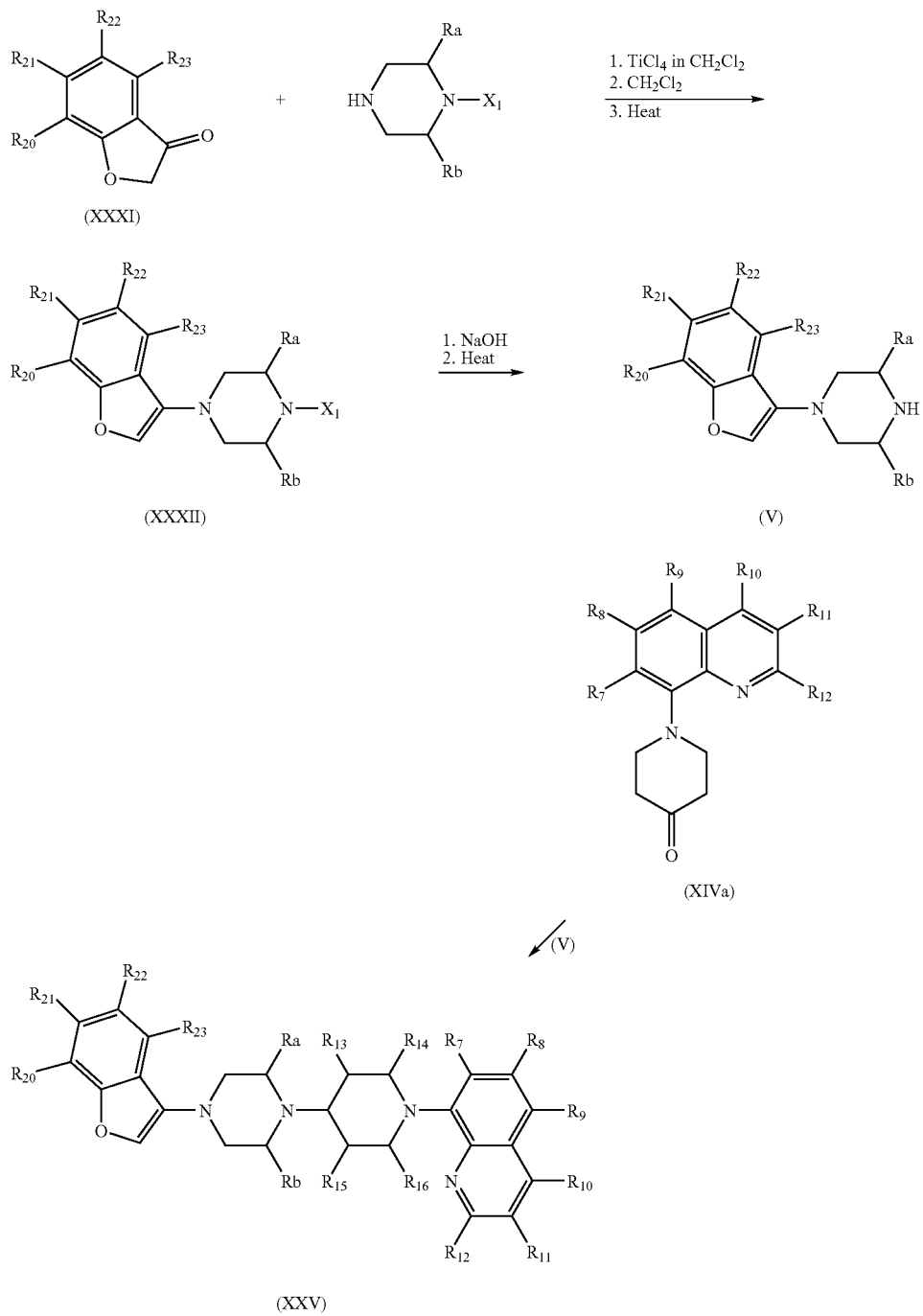

Scheme 7 illustrates the production of a compound or pharmaceutically acceptable salt of a compound of Formula (IV) in which $R_a$, $R_b$, $R_{13}$, $R_{14}$, $R_{15}$, $R_{16}$, $R_{31}$, $R_{32}$, $R_{33}$, $R_{34}$, $R_{35}$, $R_{36}$, $R_{37}$, $R_{38}$ and $R_{39}$ are defined as above for Formula (IV). As shown in Scheme 7, an optionally substituted phenyl-piperazine compound of Formula (XXVI) is reacted with an optionally substituted protected-piperazine under conditions effective to provide the compound of Formula (XXVII), wherein $X_1$ is a protecting group. Suitable protecting groups are well known to those of skill in the art and include, without limitation, tert-butoxycarbonyl. The compound of Formula (XXVII) is reacted under conditions effective to remove the protecting group, providing a phenyl-piperazine-piperidine compound of Formula (XXVIII). The phenyl-piperazine-piperidine compound of Formula (XXVII) is reacted with a bicyclic aryl compound of Formula (XXIX) possessing a suitable leaving group (W) under conditions effective to provide the compound of Formula (IV).

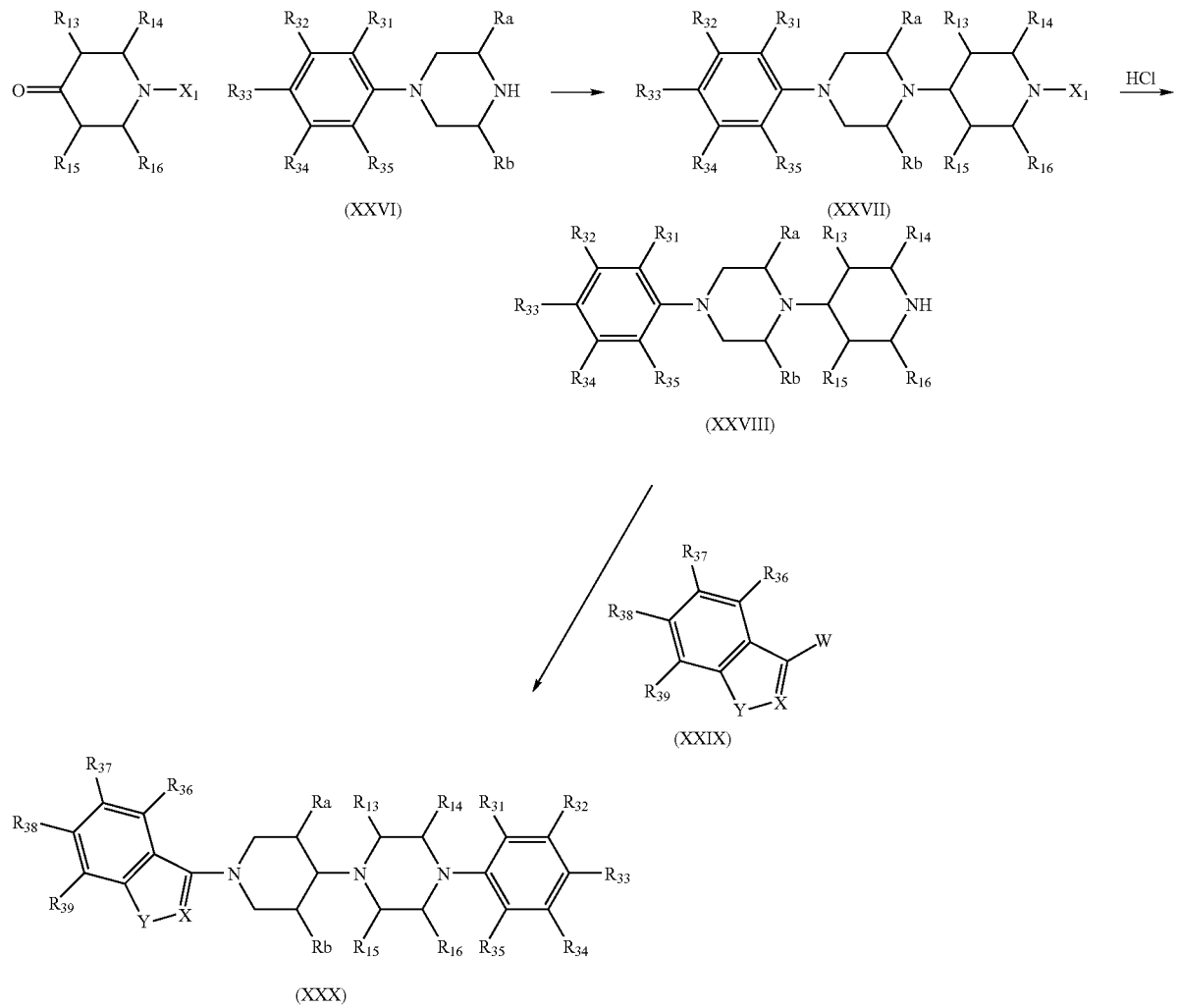

Schemes 1-7 illustrate the synthetic methodology used to prepare particular compounds of the present invention.

One of skill in the art will recognize that Schemes 1-7 can be adapted to produce the other compounds according to the present invention and that other methods may be used to produce the compounds of the present invention.

Therapeutic Administration

When administered to an animal, the compounds or pharmaceutically acceptable salts of the compounds can be administered neat or as a component of a composition that comprises a physiologically acceptable carrier or vehicle. A pharmaceutical composition of the invention can be prepared using a method comprising admixing the compound or a pharmaceutically acceptable salt of the compound and a physiologically acceptable carrier, excipient, or diluent. Admixing can be accomplished using methods well known for admixing a compound or a pharmaceutically acceptable salt of the compound and a physiologically acceptable carrier, excipient, or diluent.

The present pharmaceutical compositions, comprising compounds or pharmaceutically acceptable salts of the compounds of the invention, can be administered orally. The compound of the invention can also be administered by any other convenient route, for example, by infusion or bolus injection, by absorption through epithelial or mucocutaneous linings (e.g., oral, rectal, vaginal, and intestinal mucosa, etc.) and can be administered together with another therapeutic agent. Administration can be systemic or local. Various known delivery systems, including encapsulation in liposomes, microparticles, microcapsules, and capsules, can be used.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. In some instances, administration will result of release of the compound or a pharmaceutically acceptable salt of the compound into the bloodstream. The mode of administration is left to the discretion of the practitioner.

In one embodiment, the compound of the invention is administered orally.

In another embodiment, the compound of the invention is administered intravenously.

In another embodiment, it may be desirable to administer the compound of the invention locally. This can be achieved, for example, by local infusion during surgery, topical application, e.g., in conjunction with a wound dressing after surgery, by injection, by means of a catheter, by means of a suppository or edema, or by means of an implant, said implant being of a porous, non-porous, or gelatinous material, including membranes, such as sialastic membranes, or fibers.

In certain embodiments, it can be desirable to introduce the compound of the invention into the central nervous system, circulatory system or gastrointestinal tract by any suitable route, including intraventricular, intrathecal injection, paraspinal injection, epidural injection, enema, and by injection adjacent to the peripheral nerve. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compound or a pharmaceutically acceptable salt of the compound can be formulated as a suppository, with traditional binders and excipients such as triglycerides.

In another embodiment, the compound of the invention can be delivered in a vesicle, in particular a liposome (see Langer, *Science* 249:1527-1533 (1990) and Treat et al., *Liposomes in the Therapy of Infectious Disease and Cancer* 317-327 and 353-365 (1989)).

In yet another embodiment, the compound of the invention can be delivered in a controlled-release system or sustained-release system (see, e.g., Goodson, in *Medical Applications of Controlled Release*, vol. 2, pp. 115-138 (1984)). Other controlled or sustained-release systems discussed in the review by Langer, *Science* 249:1527-1533 (1990) can be used. In one embodiment, a pump can be used (Langer, *Science* 249:1527-1533 (1990); Sefton, *CRC Crit. Ref. Biomed. Eng.* 14:201 (1987); Buchwald et al., *Surgery* 88:507 (1980); and Saudek et al., *N. Engl. J. Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 2:61 (1983); Levy et al., *Science* 228:190 (1935); During et al., *Ann. Neural.* 25:351 (1989); and Howard et al., *J. Neurosurg.* 71:105 (1989)).

The present compositions can optionally comprise a suitable amount of a physiologically acceptable excipient.

Such physiologically acceptable excipients can be liquids, such as water and oils, including those of petroleum, animal, vegetable, or synthetic origin, such as peanut oil, soybean oil, mineral oil, sesame oil and the like. The physiologically acceptable excipients can be saline, gum acacia, gelatin, starch paste, talc, keratin, colloidal silica, urea and the like. In addition, auxiliary, stabilizing, thickening, lubricating, and coloring agents can be used. In one embodiment the physiologically acceptable excipients are sterile when administered to an animal. The physiologically acceptable excipient should be stable under the conditions of manufacture and storage and should be preserved against the contaminating action of microorganisms. Water is a particularly useful excipient when the compound or a pharmaceutically acceptable salt of the compound is administered intravenously. Saline solutions and aqueous dextrose and glycerol solutions can also be employed as liquid excipients, particularly for injectable solutions. Suitable physiologically acceptable excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

Liquid carriers may be used in preparing solutions, suspensions, emulsions, syrups, and elixirs. The compound or pharmaceutically acceptable salt of the compound of this invention can be dissolved or suspended in a pharmaceutically acceptable liquid carrier such as water, an organic solvent, a mixture of both, or pharmaceutically acceptable oils or fat. The liquid carrier can contain other suitable pharmaceutical additives including solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particularly containing additives as above, e.g., cellulose derivatives, including sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule. Other examples of suitable physiologically acceptable excipients are described in *Remington's Pharmaceutical Sciences* 1447-1676 (Alfonso R. Gennaro, ed., 19th ed. 1995).

In one embodiment, the compound or a pharmaceutically acceptable salt of the compound is formulated in accordance with routine procedures as a composition adapted for oral administration to humans. Compositions for oral delivery can be in the form of tablets, lozenges, buccal forms, troches, aqueous or oily suspensions or solutions, granules, powders, emulsions, capsules, syrups, or elixirs for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. In powders, the carrier can be a finely divided solid, which is an admixture with the finely divided compound or pharmaceutically acceptable salt of the compound. In tablets, the compound or pharmaceutically acceptable salt of the compound is mixed with a carrier having the necessary compression properties in suitable proportions and compacted in the shape and size desired. The powders and tablets can contain up to about 99% of the compound or pharmaceutically acceptable salt of the compound.

Capsules may contain mixtures of the compounds or pharmaceutically acceptable salts of the compounds with inert fillers and/or diluents such as pharmaceutically acceptable starches (e.g., corn, potato, or tapioca starch), sugars, artificial sweetening agents, powdered celluloses (such as crystalline and microcrystalline celluloses), flours, gelatins, gums, etc.

Tablet formulations can be made by conventional compression, wet granulation, or dry granulation methods and utilize pharmaceutically acceptable diluents, binding agents, lubricants, disintegrants, surface modifying agents (including surfactants), suspending or stabilizing agents (including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins.) Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine.

Moreover, when in a tablet or pill form, the compositions can be coated to delay disintegration and absorption in the gastrointestinal tract, thereby providing a sustained action over an extended period of time. Selectively permeable membranes surrounding an osmotically active driving compound or a pharmaceutically acceptable salt of the compound are also suitable for orally administered compositions. In these latter platforms, fluid from the environment surrounding the capsule can be imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the compound or a pharmaceutically acceptable salt of the compound can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen pain at the site of the injection. Generally, the ingredients are supplied either separately or mixed together in unit dosage form, for example, as a dry lyophilized powder or water-free concentrate in a hermetically sealed container such as an ampule or sachette indicating the quantity of active agent. Where the compound or a pharmaceutically acceptable salt of the compound is to be administered by infusion, it can be dispensed, for example, with an infusion bottle containing sterile pharmaceutical grade water or saline. Where the compound or a pharmaceutically acceptable salt of the compound is administered by injection, an ampule of sterile water for injection or saline can be provided so that the ingredients can be mixed prior to administration.

In another embodiment, the compound or pharmaceutically acceptable salt of the compound can be administered transdermally through the use of a transdermal patch. Transdermal administrations include administrations across the surface of the body and the inner linings of the bodily passages including epithelial and mucosal tissues. Such administrations can be carried out using the present compounds or pharmaceutically acceptable salts of the compounds, in lotions, creams, foams, patches, suspensions, solutions, and suppositories (e.g., rectal or vaginal).

Transdermal administration can be accomplished through the use of a transdermal patch containing the compound or pharmaceutically acceptable salt of the compound and a carrier that is inert to the compound or pharmaceutically acceptable salt of the compound, is non-toxic to the skin, and allows delivery of the agent for systemic absorption into the blood stream via the skin. The carrier may take any number of forms such as creams or ointments, pastes, gels, or occlusive devices. The creams or ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the compound or pharmaceutically acceptable salt of the compound into the blood stream, such as a semi-permeable membrane covering a reservoir containing the compound or pharmaceutically acceptable salt of the compound with or without a carrier, or a matrix containing the active ingredient.

The compounds or pharmaceutically acceptable salts of the compounds of the invention may be administered rectally or vaginally in the form of a conventional suppository. Suppository formulations may be made from traditional materials, including cocoa butter, with or without the addition of waxes to alter the suppository's melting point, and glycerin. Water-soluble suppository bases, such as polyethylene glycols of various molecular weights, may also be used.

The compound or a pharmaceutically acceptable salt of the compound can be administered by controlled-release or sustained-release means or by delivery devices that are known to those of ordinary skill in the art. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

In one embodiment a controlled- or sustained-release composition comprises a minimal amount of the compound or a pharmaceutically acceptable salt of the compound to treat or prevent a $5-HT_{1A}$-related disorder in a minimal amount of time. Advantages of controlled- or sustained-release compositions include extended activity of the drug, reduced dosage frequency, and increased compliance by the animal being treated. In addition, controlled- or sustained-release compositions can favorably affect the time of onset of action or other characteristics, such as blood levels of the compound or a pharmaceutically acceptable salt of the compound, and can thus reduce the occurrence of adverse side effects.

Controlled- or sustained-release compositions can initially release an amount of the compound or a pharmaceutically acceptable salt of the compound that promptly produces the desired therapeutic or prophylactic effect, and gradually and continually release other amounts of the compound or a pharmaceutically acceptable salt of the compound to maintain this level of therapeutic or prophylactic effect over an extended period of time. To maintain a constant level of the compound or a pharmaceutically acceptable salt of the compound in the body, the compound or a pharmaceutically acceptable salt of the compound can be released from the dosage form at a rate that will replace the amount of the compound or a pharmaceutically acceptable salt of the compound being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

In certain embodiments, the present invention is directed to prodrugs of the compounds or pharmaceutically acceptable salts of compounds of the present invention. Various forms of prodrugs are known in the art, for example as discussed in Bundgaard (ed.), *Design of Prodrugs*, Elsevier (1985); Widder et al. (ed.), *Methods in Enzymology*, vol. 4, Academic Press (1985); Kgrogsgaard-Larsen et al. (ed.); "*Design and Application of Prodrugs*", *Textbook of Drug Design and Development*, Chapter 5, 113-191 (1991); Bundgaard et al., *Journal of Drug Delivery Reviews*, 8:1-38 (1992); Bundgaard et al., *J. Pharmaceutical Sciences*, 77:285 et seq. (1988); and Higuchi and Stella (eds.), *Prodrugs as Novel Drug Delivery Systems*, American Chemical Society (1975).

The amount of the compound or a pharmaceutically acceptable salt of the compound delivered is an amount that is effective for treating or preventing a $5\text{-}HT_{1A}$-related disorder. In addition, in vitro or in vivo assays can optionally be employed to help identify optimal dosage ranges. The precise dose to be employed can also depend on the route of administration, the condition, the seriousness of the condition being treated, as well as various physical factors related to the individual being treated, and can be decided according to the judgment of a health-care practitioner. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy will be determined according to the judgment of a health-care practitioner. The effective dosage amounts described herein refer to total amounts administered; that is, if more than one compound or a pharmaceutically acceptable salt of the compound is administered, the effective dosage amounts correspond to the total amount administered.

The amount of the compound or a pharmaceutically acceptable salt of the compound that is effective for treating or preventing a $5\text{-}HT_{1A}$-related disorder will typically range from about 0.001 mg/kg to about 600 mg/kg of body weight per day, in one embodiment, from about 1 mg/kg to about 600 mg/kg body weight per day, in another embodiment, from about 10 mg/kg to about 400 mg/kg body weight per day, in another embodiment, from about 10 mg/kg to about 200 mg/kg of body weight per day, in another embodiment, from about 10 mg/kg to about 100 mg/kg of body weight per day, in another embodiment, from about 1 mg/kg to about 10 mg/kg body weight per day, in another embodiment, from about 0.001 mg/kg to about 100 mg/kg of body weight per day, in another embodiment, from about 0.001 mg/kg to about 10 mg/kg of body weight per day, and in another embodiment, from about 0.001 mg/kg to about 1 mg/kg of body weight per day.

In one embodiment, the pharmaceutical composition is in unit dosage form, e.g., as a tablet, capsule, powder, solution, suspension, emulsion, granule, or suppository. In such form, the composition is sub-divided in unit dose containing appropriate quantities of the active ingredient; the unit dosage form can be packaged compositions, for example, packeted powders, vials, ampoules, prefilled syringes or sachets containing liquids. The unit dosage form can be, for example, a capsule or tablet itself, or it can be the appropriate number of any such compositions in package form. Such unit dosage form may contain from about 0.01 mg/kg to about 250 mg/kg, and may be given in a single dose or in two or more divided doses. Variations in the dosage will necessarily occur depending upon the species, weight and condition of the patient being treated and the patient's individual response to the medicament.

In one embodiment, the unit dosage form is about 0.01 to about 1000 mg. In another embodiment, the unit dosage form is about 0.01 to about 500 mg; in another embodiment, the unit dosage form is about 0.01 to about 250 mg; in another embodiment, the unit dosage form is about 0.01 to about 100 mg; in another embodiment, the unit dosage form is about 0.01 to about 50 mg; in another embodiment, the unit dosage form is about 0.01 to about 25 mg; in another embodiment, the unit dosage form is about 0.01 to about 10 mg; in another embodiment, the unit dosage form is about 0.01 to about 5 mg; and in another embodiment, the unit dosage form is about 0.01 to about 10 mg;

The compound or a pharmaceutically acceptable salt of the compound can be assayed in vitro or in vivo for the desired therapeutic or prophylactic activity prior to use in humans. Animal model systems can be used to demonstrate safety and efficacy.

The present methods for treating or preventing a $5\text{-}HT_{1A}$-related disorder can further comprise administering another therapeutic agent to the animal being administered the compound or a pharmaceutically acceptable salt of the compound. In one embodiment the other therapeutic agent is administered in an effective amount.

Effective amounts of the other therapeutic agents are well known to those skilled in the art. However, it is well within the skilled artisan's purview to determine the other therapeutic agent's optimal effective amount range. The compound or a pharmaceutically acceptable salt of the compound and the other therapeutic agent can act additively or, in one embodiment, synergistically. In one embodiment of the invention, where another therapeutic agent is administered to an animal, the effective amount of the compound or a pharmaceutically acceptable salt of the compound is less than its effective amount would be where the other therapeutic agent is not administered. In this case, without being bound by theory, it is believed that the compound or a pharmaceutically acceptable salt of the compound and the other therapeutic agent act synergistically. In some cases, the patient in need of treatment is being treated with one or more other therapeutic agents. In some cases, the patient in need of treatment is being treated with at least two other therapeutic agents.

In one embodiment, the other therapeutic agent is selected from the group consisting of one or more anti-depressant agents, anti-anxiety agents, anti-psychotic agents, or cognitive enhancers. Examples of classes of antidepressants that can be used in combination with the active compounds of this invention include norepinephrine reuptake inhibitors, selective serotonin reuptake inhibitors (SSRIs), NK-1 receptor antagonists, monoamine oxidase inhibitors (MAOs), reversible inhibitors of monoamine oxidase (RIMAs), serotonin and noradrenaline reuptake inhibitors (SNRIs), corticotropin releasing factor (CRF) antagonists, α-adrenoreceptor antagonists, and atypical antidepressants. Suitable norepinephrine reuptake inhibitors include tertiary amine tricyclics and secondary amine tricyclics. Suitable tertiary amine tricyclics and secondary amine tricyclics include amitriptyline, clomipramine, doxepin, imipramine, trimipramine, dothiepin, butriptyline, iprindole, lofepramine, nortriptyline, protriptyline, amoxapine, desipramine and maprotiline. Suitable selective serotonin reuptake inhibitors include fluoxetine, citolopram, escitalopram, fluvoxamine, paroxetine and sertraline. Examples of monoamine oxidase inhibitors include isocarboxazid, phenelzine, and tranylcypromine. Suitable reversible inhibitors of monoamine oxidase include moclobemide. Suitable serotonin and noradrenaline reuptake inhibitors of use in the present invention include venlafaxine, nefazodone, milnacipran, and duloxetine. Suitable CRF antagonists include those compounds described in International Patent Publication Nos. WO 94/13643, WO 94/13644, WO 94/13661, WO 94/13676 and WO 94/13677. Suitable atypical anti-depressants include bupropion, lithium, nefazodone, trazodone and viloxazine. Suitable NK-1 receptor antagonists include those referred to in International Patent Publication WO 01/77100.

Anti-anxiety agents that can be used in combination with the active compounds of this invention include without limitation benzodiazepines and serotonin 1A (5-$HT_{1A}$) agonists or antagonists, especially 5-$HT_{1A}$ partial agonists, and corticotropin releasing factor (CRF) antagonists. Exemplary suitable benzodiazepines include alprazolam, chlordiazepoxide, clonazepam, chlorazepate, diazepam, halazepam, lorazepam, oxazepam, and prazepam. Exemplary suitable 5-$HT_{1A}$ receptor agonists or antagonists include buspirone, flesinoxan, gepirone and ipsapirone.

Anti-psychotic agents that are used in combination with the active compounds of this invention include without limitation aliphatic phethiazine, a piperazine phenothiazine, a butyrophenone, a substituted benzantide, and a thioxanthine. Additional examples of such drugs include without limitation haloperidol, olanzapine, clozapine, risperidone, pimozide, aripiprazol, and ziprasidone. In some cases, the drug is an anticonvulsant, e.g., phenobarbital, phenyloin, primidone, or carbamazepine.

Cognitive enhancers that are co-administered with the 5-$HT_{1A}$ antagonist compounds of this invention include, without limitation, drugs that modulate neurotransmitter levels (e.g., acetylcholinesterase or cholinesterase inhibitors, cholinergic receptor agonists or serotonin receptor antagonists), drugs that modulate the level of soluble Aβ, amyloid fibril formation, or amyloid plaque burden (e.g., γ-secretase inhibitors, β-secretase inhibitors, antibody therapies, and degradative enzymes), and drugs that protect neuronal integrity (e.g., antioxidants, kinase inhibitors, caspase inhibitors, and hormones). Other representative candidate drugs that are co-administered with the compounds of the invention include cholinesterase inhibitors, (e.g., tacrine (COGNEX®), donepezil (ARICEPT®), rivastigmine (EXELON®) galantamine (REMINYL®), metrifonate, physostigmine, and Huperzine A), N-methyl-D-aspartate (NMDA) antagonists and agonists (e.g., dextromethorphan, memantine, dizocilpine maleate (MK-801), xenon, remacemide, eliprodil, amantadine, D-cycloserine, felbamate, ifenprodil, CP-101606 (Pfizer), Delucemine, and compounds described in U.S. Pat. Nos. 6,821, 985 and 6,635,270), ampakines (e.g., cyclothiazide, aniracetam, CX-516 (Ampalex®), CX-717, CX-516, CX-614, and CX-691 (Cortex Pharmaceuticals, Inc. Irvine, Calif.), 7-chloro-3-methyl-3-4-dihydro-2H-1,2,4-benzothiadiazine S,S-dioxide (see Zivkovic et al., 1995, *J. Pharmacol. Exp. Therap.*, 272:300-309; Thompson et al., 1995, *Proc. Natl. Acad. Sci. USA*, 92:7667-7671), 3-bicyclo[2,2,1]hept-5-en-2-yl-6-chloro-3,4-dihydro-2H-1,2,4-benzothiadiazine-7-sulfonamide-1,1-dioxide (Yamada, et al., 1993, *J. Neurosc.* 13:3904-3915); 7-fluoro-3-methyl-5-ethyl-1,2,4-benzothiadiazine-S,S-dioxide; and compounds described in U.S. Pat. No. 6,620,808 and International Patent Application Nos. WO 94/02475, WO 96/38414, WO 97/36907, WO 99/51240, and WO 99/42456), benzodiazepine (BZD)/GABA receptor complex modulators (e.g., progabide, gengabine, zaleplon, and compounds described in U.S. Pat. Nos. 5,538,956, 5,260, 331, and 5,422,355); serotonin antagonists (e.g., 5-HT receptor modulators, including other 5-$HT_{1A}$ antagonist compounds and 5-$HT_6$ antagonists (including without limitation compounds described in U.S. Pat. Nos. 6,727,236, 6,825,212, 6,995,176, and 7,041,695)); nicotinics (e.g., niacin); muscarinics (e.g., xanomeline, CDD-0102, cevimeline, talsaclidine, oxybutin, tolterodine, propiverine, tropsium chloride and darifenacin); monoamine oxidase type B (MAO B) inhibitors (e.g., rasagiline, selegiline, deprenyl, lazabemide, safinamide, clorgyline, pargyline, N-(2-aminoethyl)-4-chlorobenzamide hydrochloride, and N-(2-aminoethyl)-5(3-fluorophenyl)-4-thiazolecarboxamide hydrochloride); phosphodiesterase (PDE) inhibitors (e.g., PDE IV inhibitors, roflumilast, arofylline, cilomilast, rolipram, RO-20-1724, theophylline, denbufylline, ARIFLO, CDP-840 (a tri-aryl ethane) CP80633 (a pyrimidone), RP 73401 (Rhone-Poulenc Rorer), denbufylline (SmithKline Beecham), arofylline (Almirall), CP-77,059 (Pfizer), pyrid[2,3d]pyridazin-5-ones (Syntex), EP-685479 (Bayer), T-440 (Tanabe Seiyaku), and SDZ-ISQ-844 (Novartis)); G proteins; channel modulators; immunotherapeutics (e.g., compounds described in U.S. Patent Application Publication No. US 2005/0197356 and US 2005/0197379); anti-amyloid or amyloid lowering agents (e.g., bapineuzumab and compounds described in U.S. Pat. No. 6,878,742 or U.S. Patent Application Publication Nos. US 2005/0282825 or US 2005/0282826); statins and peroxisome proliferators activated receptor (PPARS) modulators (e.g., gemfibrozil (LOPID®), fenofibrate (TRICOR®), rosiglitazone maleate (AVANDIA®), pioglitazone (Actos™), rosiglitazone (Avandia™), clofibrate and bezafibrate); cysteinyl protease inhibitors; an inhibitor of receptor for advanced glycation endproduct (RAGE) (e.g., aminoguanidine, pyridoxaminem carnosine, phenazinediamine, OPB-9195, and tenilsetam); direct or indirect neurotropic agents (e.g., Cerebrolysin®, piracetam, oxiracetam, AIT-082 (Emilieu, 2000, *Arch. Neurol.* 57:454)); beta-secretase (BACE) inhibitors, α-secretase, immunophilins, caspase-3 inhibitors, Src kinase inhibitors, tissue plasminogen activator (TPA) activators, AMPA (alpha-amino-3-hydroxy-5-methyl-4-isoxazolepropionic acid) modulators, M4 agonists, JNK3 inhibitors, LXR agonists, H3 antagonists, and angiotensin IV antagonists. Other cognition enhancers include, without limitation, acetyl-1-carnitine, citicholine, huperzine, DMAE (dimethylaminoethanol), Bacopa monneiri extract, Sage extract, L-alpha glyceryl phosphoryl choline, Ginko biloba and Ginko biloba extract, Vinpocetine, DHA, nootropics including Phenyltropin, Pikatropin (from Creative Compounds, LLC, Scott City, Mo.), besipirdine, linopirdine, sibopirdine, estrogen and estrogenic compounds, idebenone, T-588 (Toyama Chemical, Japan), and FK960 (Fujisawa Pharmaceutical Co. Ltd.). Compounds described in U.S. Pat. Nos. 5,219,857, 4,904,658, 4,624,954 and 4,665,183 are also useful as cognitive enhancers as described herein. Cognitive enhancers that act through one or more of the above mechanisms are also within the scope of this invention.

In one embodiment, the compound or a pharmaceutically acceptable salt of the compound of the invention and cognitive enhancer act additively or, in one embodiment, synergistically. In one embodiment, where a cognitive enhancer and a compound or a pharmaceutically acceptable salt of the compound of the invention are co-administered to an animal, the effective amount of the compound or pharmaceutically acceptable salt of the compound of the invention is less than its effective amount would be where the cognitive enhancer agent is not administered. In one embodiment, where a cognitive enhancer and a compound or a pharmaceutically acceptable salt of the compound of the invention are co-administered to an animal, the effective amount of the cognitive enhancer is less than its effective amount would be where the compound or pharmaceutically acceptable salt of the invention is not administered. In one embodiment, a cognitive enhancer and a compound or a pharmaceutically acceptable salt of the compound of the invention are co-administered to an animal in doses that are less than their effective amounts would be where they were no co-administered. In these cases, without being bound by theory, it is believed that the compound or a pharmaceutically acceptable salt of the compound and the cognitive enhancer act synergistically.

In one embodiment, the other therapeutic agent is an agent useful for treating Alzheimer's disease or conditions associate with Alzheimer's disease, such as dementia. Exemplary agents useful for treating Alzheimer's disease include, without limitation, donepezil, rivastigmine, galantamine, memantine, and tacrine.

In one embodiment, the compound or a pharmaceutically acceptable salt of the compound is administered concurrently with another therapeutic agent.

In one embodiment, a composition comprising an effective amount of the compound or a pharmaceutically acceptable salt of the compound and an effective amount of another therapeutic agent within the same composition can be administered.

In another embodiment, a composition comprising an effective amount of the compound or a pharmaceutically acceptable salt of the compound and a separate composition comprising an effective amount of another therapeutic agent can be concurrently administered. In another embodiment, an effective amount of the compound or a pharmaceutically acceptable salt of the compound is administered prior to or subsequent to administration of an effective amount of another therapeutic agent. In this embodiment, the compound or a pharmaceutically acceptable salt of the compound is administered while the other therapeutic agent exerts its therapeutic effect, or the other therapeutic agent is administered while the compound or a pharmaceutically acceptable salt of the compound exerts its preventative or therapeutic effect for treating or preventing a $5\text{-}HT_{1A}$-related disorder.

Thus, in one embodiment, the invention provides a composition comprising an effective amount of the compound or a pharmaceutically acceptable salt of the compound of the present invention and a pharmaceutically acceptable carrier. In another embodiment, the composition further comprises a second therapeutic agent.

In another embodiment, the composition further comprises a therapeutic agent selected from the group consisting of one or more other antidepressants, anti-anxiety agents, anti-psychotic agents or cognitive enhancers. Antidepressants, anti-anxiety agents, anti-psychotic agents and cognitive enhancers suitable for use in the composition include the antidepressants, anti-anxiety agents, anti-psychotic agents and cognitive enhancers provided above.

In another embodiment, the pharmaceutically acceptable carrier is suitable for oral administration and the composition comprises an oral dosage form.

Therapeutic or Prophylactic Uses

In one embodiment, the compounds or pharmaceutically acceptable salts of the compounds of the present invention are useful as $5\text{-}HT_{1A}$ receptor antagonists. In another embodiment, the compounds or pharmaceutically acceptable salts of the compounds of the present invention are useful as $5\text{-}HT_{1A}$ receptor agonists. Compounds that are $5\text{-}HT_{1A}$ antagonists and/or agonists can readily be identified by those skilled in the art using numerous art-recognized methods, including standard pharmacological test procedures such as those described herein. Accordingly, the compounds and pharmaceutically acceptable salts of the compounds of the present invention are useful for treating a mammal with a $5\text{-}HT_{1A}$-related disorder. One non-limiting example of a disorder that $5\text{-}HT_{1A}$ receptor antagonists are useful for treating is cognition-related disorder, while a non-limiting example of a disorder that $5\text{-}HT_{1A}$ receptor agonists are useful for treating is anxiety-related disorder. In some embodiments, the compounds and pharmaceutical salts of the invention are useful for improving cognitive function or cognitive deficits. Examples of improvements in cognitive function include, without limitation, memory improvement and retention of learned information. Accordingly, the compounds and pharmaceutical salts of the invention are useful for slowing the loss of memory and cognition and for maintaining independent function for patients afflicted with a cognition-related disorder. Thus, in one embodiment, the compounds and pharmaceutically acceptable salts of the compounds of the present invention that act as $5\text{-}HT_{1A}$ receptor antagonists are useful for treating a mammal with a cognition-related disorder. In one embodiment, the compounds and pharmaceutically acceptable salts of the compounds of the present invention that act as $5\text{-}HT_{1A}$ receptor antagonists are useful for improving the cognitive function of a mammal. Similarly, in one embodiment, the compounds and pharmaceutically acceptable salts of the compounds of the present invention that act as $5\text{-}HT_{1A}$ receptor agonists are useful for treating a mammal with an anxiety-related disorder.

In one embodiment, the invention provides a method for treating a $5\text{-}HT_{1A}$-related disorder, comprising administering to a mammal in need thereof a compound or a pharmaceutically acceptable salt of the compound of Formula (I), Formula (I'), Formula (I"), Formula (I"a), Formula (II), Formula (III) or Formula (IV) in an amount effective to treat a $5\text{-}HT_{1A}$-related disorder. In one embodiment, the invention provides a method for treating a cognition-related disorder, comprising administering to a mammal in need thereof a compound or a pharmaceutically acceptable salt of the compound of Formula (I), Formula (I'), Formula (I"), Formula (I"a), Formula (II), Formula (III) or Formula (IV) in an amount effective to treat a $5\text{-}HT_{1A}$-related disorder. In one embodiment, the invention provides a method for treating an anxiety-related disorder, comprising administering to a mammal in need thereof a compound or a pharmaceutically acceptable salt of the compound of Formula (I), Formula (I'), Formula (I"), Formula (I"a), Formula (II), Formula (III) or Formula (IV) in an amount effective to treat a $5\text{-}HT_{1A}$-related disorder.

In one embodiment, the invention provides a method for treating Alzheimer's disease, comprising administering to a mammal in need thereof a compound or a pharmaceutically acceptable salt of a compound of Formula (I), Formula (I'), Formula (I"), Formula (Ia"), Formula (II), Formula (III), or Formula (IV) in an amount effective to treat Alzheimer's disease. In one embodiment, the method for treating Alzheimer's disease includes administering a second therapeutic agent. In some embodiments, the second therapeutic agent is an anti-depressant agent, an anti-anxiety agent, an anti-psychotic agent, or a cognitive enhancer.

In one embodiment, the invention provides a method for treating mild cognitive impairment (MCI), comprising administering to a mammal in need thereof a compound or a pharmaceutically acceptable salt of a compound of Formula (I), Formula (I'), Formula (I"), Formula (Ia"), Formula (II), Formula (III), or Formula (IV) in an amount effective to treat mild cognitive impairment (MCI). In one embodiment, the method for treating MCI includes administering a second therapeutic agent. In some embodiments, the second therapeutic agent is an anti-depressant agent, an anti-anxiety agent, an anti-psychotic agent, or a cognitive enhancer.

In one embodiment, the invention provides a method for treating depression, comprising administering to a mammal in need thereof a compound or a pharmaceutically acceptable salt of a compound of Formula (I), Formula (I'), Formula (I"), Formula (Ia"), Formula (II), Formula (III), or Formula (IV) in an amount effective to treat depression. In one embodiment, the method for treating depression includes administering a second therapeutic agent. In some embodiments, the second therapeutic agent is an anti-depressant agent, an anti-anxiety agent, an anti-psychotic agent, or a cognitive enhancer.

In some embodiments, the invention provides a pharmaceutical composition for treating a $5\text{-HT}_{1A}$-related disorder, the composition including a compound or pharmaceutically acceptable salt of a compound of Formula (I), Formula (I'), Formula (I"), Formula (I"a), Formula (II), Formula (III), or Formula (IV). In some embodiments, the invention provides a pharmaceutical composition for treating a cognition-related disorder, the composition including a compound or pharmaceutically acceptable salt of a compound of Formula (I), Formula (I'), Formula (I"), Formula (I"a), Formula (II), Formula (III), or Formula (IV). In some embodiments, the invention provides a pharmaceutical composition for treating an anxiety-related disorder, the composition including a compound or pharmaceutically acceptable salt of a compound of Formula (I), Formula (I'), Formula (I"), Formula (I"a), Formula (II), Formula (III), or Formula (IV).

In one embodiment, the invention provides a pharmaceutical composition for treating Alzheimer's disease, the composition including a compound or a pharmaceutically acceptable salt of a compound of Formula (I), Formula (I'), Formula (I"), Formula (Ia"), Formula (II), Formula (III), or Formula (IV).

In one embodiment, the invention provides a pharmaceutical composition for treating mild cognitive impairment (MCI), the composition including a compound or a pharmaceutically acceptable salt of a compound of Formula (I), Formula (I'), Formula (I"), Formula (Ia"), Formula (II), Formula (III), or Formula (IV).

In one embodiment, the invention provides a pharmaceutical composition for treating depression, the composition including a compound or a pharmaceutically acceptable salt of a compound of Formula (I), Formula (I'), Formula (I"), Formula (Ia"), Formula (II), Formula (III), or Formula (IV).

In one embodiment, the compounds or pharmaceutically acceptable salts of the compounds of the present invention are useful for treating sexual dysfunction, e.g., sexual dysfunction associated with drug treatment such as drug treatment with an antidepressant, an antipsychotic, or an anticonvulsant. Accordingly, in one embodiment, the invention provides a method for treating sexual dysfunction associated with drug treatment in a patient in need thereof. The method includes administering to the patient an effective amount of one or more of the compounds disclosed herein. In some embodiments, the drug treatment is antidepressant drug treatment, antipsychotic drug treatment, or anticonvulsant drug treatment. The compound can be a compound or pharmaceutically acceptable salt of a compound of Formula (I), Formula (I'), Formula (I"), Formula (I"a), Formula (II), Formula (III), or Formula (IV).

In certain embodiments, the drug associated with sexual dysfunction is a selective serotonin reuptake inhibitor (SSRI) (for example, fluoxetine, citalopram, escitalopram oxalate, fluvoxamine maleate, paroxetine, or sertraline), a tricyclic antidepressant (for example, desipramine, amitriptyline, amoxipine, clomipramine, doxepin, imipramine, nortriptyline, protriptyline, trimipramine, dothiepin, butriptyline, iprindole, or lofepramine), an aminoketone class compound (for example, bupropion). In some embodiments, the drug is a monoamine oxidase inhibitor (MAOI) (for example, phenelzine, isocarboxazid, or tranylcypromine), a serotonin and norepinepherine reuptake inhibitor (SNRI) (for example, venlafaxine, nefazodone, milnacipran, duloxetine), a norepinephrine reuptake inhibitor ($NR_1$) (for example, reboxetine), a partial $5\text{-HT}_{1A}$ agonist (for example, buspirone), a $5\text{-HT}_{2A}$ receptor antagonist (for example, nefazodone), a typical antipsychotic drug, or an atypical antipsychotic drug. Examples of such antipsychotic drugs include aliphatic phethiazine, a piperazine phenothiazine, a butyrophenone, a substituted benzamide, and a thioxanthine. Additional examples of such drugs include haloperidol, olanzapine, clozapine, risperidone, pimozide, aripiprazol, and ziprasidone. In some cases, the drug is an anticonvulsant, e.g., phenobarbital, phenyloin, primidone, or carbamazepine. In some cases, the patient in need of treatment for sexual dysfunction is being treated with at least two drugs that are antidepressant drugs, antipsychotic drugs, anticonvulsant drugs, or a combination thereof.

In some embodiments of the invention, the sexual dysfunction comprises a deficiency in penile erection.

The invention also provides a method of improving sexual function in a patient in need thereof. The method includes administering to the patient a pharmaceutically effective amount of one or more of the compounds disclosed herein. The compound can be a compound or pharmaceutically acceptable salt of a compound of Formula (I), Formula (I'), Formula (I"), Formula (I"a), Formula (II), Formula (III), or Formula (IV).

In another embodiment, the invention provides a pharmaceutical composition for treating sexual dysfunction associated with drug treatment, the composition including a compound or pharmaceutically acceptable salt of a compound of Formula (I), Formula (I'), Formula (I"), Formula (I"a), Formula (II), Formula (III), or Formula (IV). In some embodiments, the drug is an antidepressant, an antipsychotic, or an anticonvulsant. In other embodiments, the compound or pharmaceutically acceptable salt of the compound is effective for ameliorating sexual dysfunction in an animal model of sexual dysfunction associated with drug treatment, for example, in an animal model of sexual dysfunction that is an antidepressant drug-induced model of sexual dysfunction.

The compounds and pharmaceutically acceptable salts of the compounds of Formula (I), Formula (I'), Formula (I"), Formula (I"a), Formula (II), Formula (III) or Formula (IV) are also useful in the manufacture of medicaments for treating a $5\text{-HT}_{1A}$-related disorder in a mammal. Similarly, the compounds and pharmaceutically acceptable salts of the compounds of Formula (I), Formula (I'), Formula (I"), Formula (I″a), Formula (II), Formula (III) or Formula (IV) are also useful in the manufacture of medicaments for treating a cognition-related disorder in a mammal. Also, the compounds and pharmaceutically acceptable salts of the compounds of Formula (I), Formula (I'), Formula (I″), Formula (I″a), Formula (II), Formula (III) or Formula (IV) are also useful in the manufacture of medicaments for treating an anxiety-related disorder in a mammal.

EXAMPLES

Preparation of Piperazine-Piperidine Compounds

A) Preparation of 6-Methoxy-8-{4-[1-(8-quinolinyl)-4-piperidinyl]-1-piperazinyl}quinoline and Intermediates

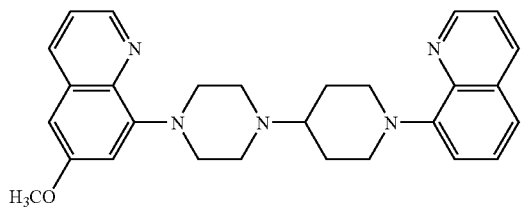

1) 8-Chloro-6-hydroxyquinoline

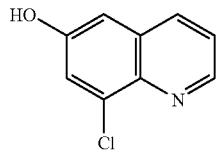

In a 500 ml 3-necked flask equipped with a mechanical stirrer, a reflux condenser, were added in order ferrous sulfate (2.0 g), 4-amino-3-chlorophenol hydrochloride (6.4 g, commercially available), nitrobenzene (2.9 mL) and a solution of boric acid (3.0 g) in glycerol (16 g). Then concentrated sulfuric acid (9 mL) was added drop by drop with cooling. The ice bath was removed and replaced by an oil bath and the mixture was heated cautiously to 120° C. for 2 hours, then at 150° C. and kept stirring under this temperature for 20 hours. After cooling, the reaction was poured on crushed ice and the resulting solution was neutralized with K2CO3. The product separated as a light brown solid that was filtered off, washed with water and hexanes and dried in a vacuum oven (35° C.) overnight giving 7 g (77%) of the desired product. MS (ES) m/z (relative intensity): 180 (M⁺+–H, 100).

2) 8-Chloro-6-methoxyquinoline

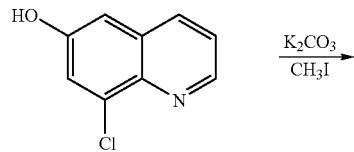

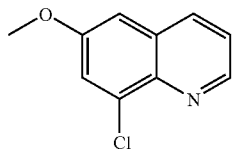

To a solution of 3.3 g of 8-chloro-6-hydroxyquinoline (Step 1, 3.3 g) in dimethylformamide was added $K_2CO_3$ (3.8 g), followed by iodomethane (5.2 g). The mixture was stirred at room temperature overnight. Water was then added and the aqueous mixture was extracted with $CH_2Cl_2$. The combined organic layers were dried over anhydrous $MgSO_4$, filtered and concentrated on a rotary evaporator. The crude product was purified by flash chromatography on silica gel using 100% $CH_2Cl_2$, to give 2.2 g of the desired product as a beige solid; MP=74-75° C.; MS (ES) m/z (relative intensity): 194 (M+H)⁺ (100).

3) 6-Methoxy-8-[1-(tert-butoxycarbonyl)-4-piperazino]quinoline

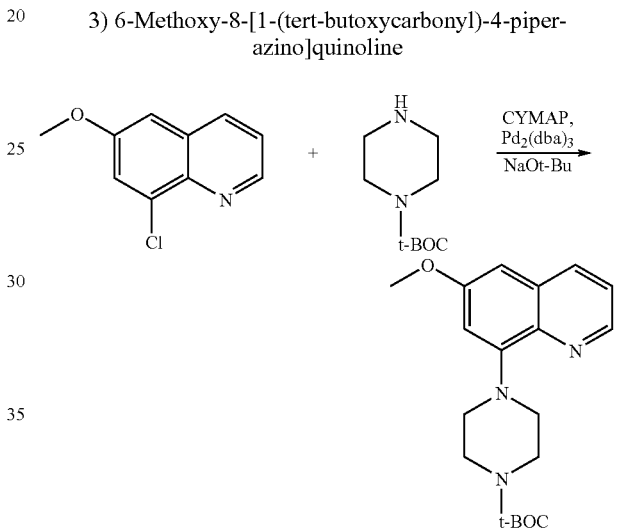

To a mixture of 8-chloro-6-methoxyquinoline (Step 2, 2.7 g) in anhydrous tetrahydrofuran, was added tris(dibenzylideneacetone)dipalladium(0) ($Pd_2(dba)_3$, 0.064 g), sodium tert-butoxide (1.9 g), 2-dicyclohexylphosphino-2'-(N,N-dimethylamino)biphenyl (CYMAP, 0.08 g) and tert-butoxycarbonylpiperazine (3.4 g). The mixture was refluxed for 5 hours under a nitrogen atmosphere. The reaction was then cooled to room temperature, diluted with ether, filtered through celite and concentrated on a rotary evaporator. The crude material was purified by flash chromatography using 100% $CH_2Cl_2$ to give 4.0 g of the desired product as a beige solid; mp=92-93° C.; MS (ES) m/z (relative intensity): 344 (M⁺+H) (100).

4) 6-Methoxy-8-piperazinoquinoline

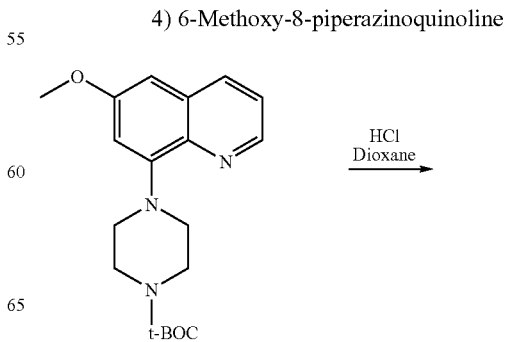

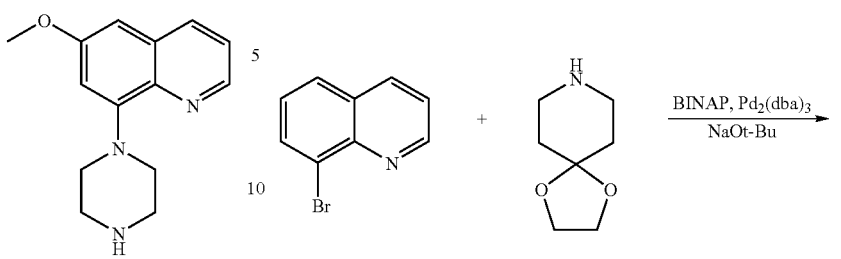

To a solution of 6-methoxy-8-[1-(tert-butoxycarbonyl)-4-piperazino]quinoline (Step 3, 4.0 g) in 20 mL of Dioxane was added 10 mL of 4 N HCl/Dioxane. The mixture was stirred at room temperature overnight. The resulting precipitate was collected by vacuum filtration, dissolved in water, neutralized with aqueous sodium hydroxide and extracted with CH$_2$Cl$_2$. The combined organic layers were dried over anhydrous Na$_2$SO$_4$, filtered and concentrated on a rotary evaporator to give 2.8 g of the desired product as a beige solid; MP=105-107° C.; MS (ES) m/z (relative intensity): 244 (M+H)$^+$ (100).

5) 8-(1,4-Dioxa-8-azaspairo[4,5]dec-8-yl)quinoline

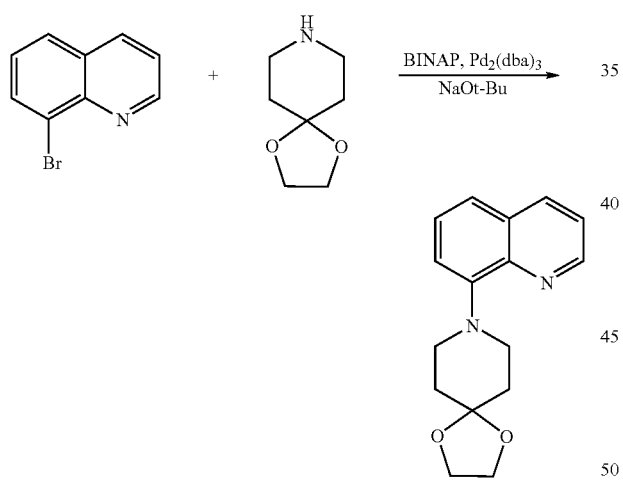

To a solution of 8-bromoquinoline (commercially available, 4.0 g) in 20 mL of anhydrous tetrahydrofuran, was added tris(dibenzylideneacetone)dipalladium(0) (Pd$_2$(dba)$_3$, 0.2 g), sodium tert-butoxide (2.6 g), 2,2'-bis(diphenylphosphino)-1,1'-binapthyl (BINAP, 0.1 g), tetrakis-(triphenylphosphine)palladium(0) (0.1 g) and 1,4-dioxo-8-azaspiro-4,5-decane (3,3 g). The mixture was refluxed for 3 hours under a nitrogen atmosphere. The reaction mixture was then cooled to room temperature, diluted with ether, filtered through celite and concentrated on a rotary evaporator. The crude material was then purified by flash chromatography on silica gel using hexane/ethyl acetate to give 3.0 g of the desired product as a brown oil; MS (ES) m/z (relative intensity): 271 (M+H)$^+$ (100).

6) 1-quinolin-8-yl-piperidin-4-one

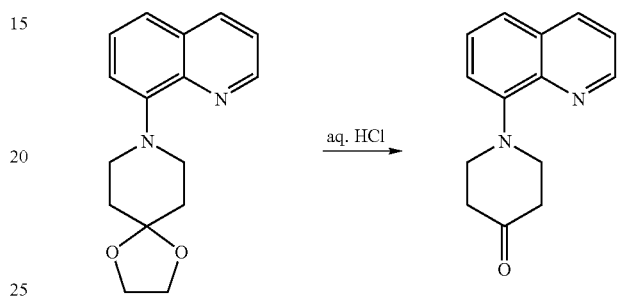

To a solution of (4.0 g) 8-(1,4-Dioxa-8-azaspairo[4,5]dec-8-yl)quinoline (Step 4, 4.0 g) in 10 mL of tetrahydrofuran was added 10 mL of 2N HCl. The reaction was stirred at room temperature overnight. The mixture was then diluted with water, made basic with aqueous sodium hydroxide and extracted with CH$_2$Cl. The combined organic layers were dried over anhydrous and the product is extracted with CH$_2$Cl$_2$, dried over Na$_2$SO$_4$, filtered and concentrated on a rotary evaporator and to give 3.2 g of the desired product as a sticky yellow oil; MS (ES) m/z (relative intensity): 227 (M+H)$^+$ (100).

7) 6-Methoxy-8-{4-[1-(8-quinolinyl)-4-piperidinyl]-1-piperazinyl}quinoline

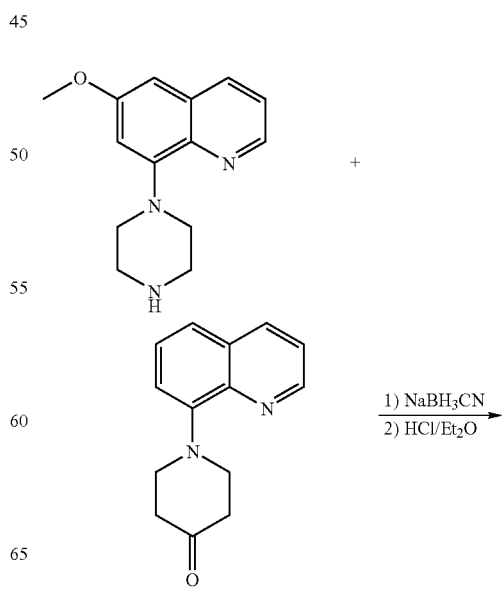

-continued

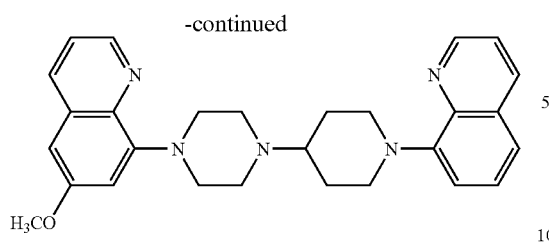

To a solution of 0.247 g of 6-methoxy-8-piperazino-quinoline (Step 4) in 10 mL of dichloroethane, was added 0.226 g of 1-quinolin-8-yl-piperidin-4-one (Step 6) followed by 0.274 g of sodium triacetoxyborohydride and 0.1 mL acetic acid. The reaction was stirred at room temperature overnight. It was quenched with 1N NaOH, and the product was extracted with $CH_2Cl_2$. The organic phase was washed with water and dried over magnesium sulfate. The product crystallized and filtered to give 0.200 g of the desired product. Mp.194-197° C.; MS (ES) m/z (relative intensity): 454 ($M^+$+$-$H, 100).

B) Preparation of 6-fluoro-8-{4-[1-(8-quinolinyl)-4-piperidinyl]-1-piperazinyl}quinoline and Intermediates

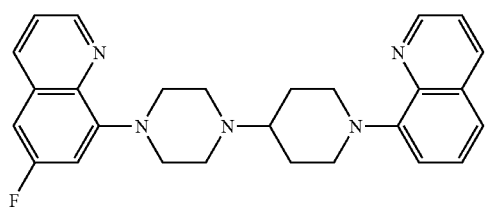

1) 6-Fluoro-8 bromoquinoline

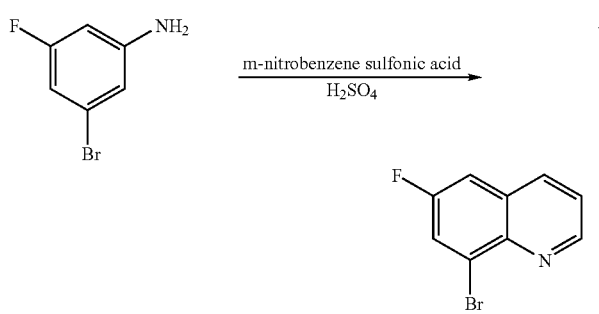

To a mixture of 2-bromo-4-fluoroaniline (commercially available, 7.0 g), glycerol (7.0 g) and m-nitrobenzene sulfonic acid sodium salt (13.0 g) was added 20 ml of 70% sulfuric acid dropwise. The reaction temperature was raised to 150° C. for 4 hr. The mixture then was cooled to room temperature, poured on ice water and filtered through celite. The filtrate was neutralized with NaOH and the resulting precipitate was collected by vacuum filtration to yield 3.47 g of the title compound as a light yellow solid; MP=75-78° C.; MS (ES) m/z (relative intensity): 227 $(M+H)^+$ (100).

2) 6-Fluoro-8-[1-(tert-butoxycarbonyl)-4-piperazino]quinoline

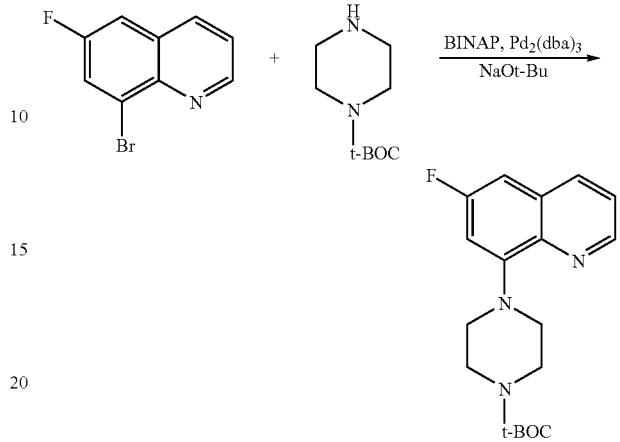

To a mixture of 6-fluoro-8-bromoquinoline (Step 1, 2.2 g) in anhydrous tetrahydrofuran, was added tris(dibenzylideneacetone)dipalladium(0) ($Pd_2(dba)_3$, 0.045 g) sodium tert-butoxide (1.3 g), 2,2'-bis(diphenylphosphino)-1,1'-binapthyl (BINAP, 0.044 g), 0.052 g tetrakis(triphenylphosphine)-palladium (0) (0.052 g) and tert-butoxycarbonyl-piperazine (2.2 g). The mixture was refluxed for 3 hours under a nitrogen atmosphere. The reaction was then cooled to room temperature, diluted with ether, filtered through celite and concentrated on a rotary evaporator. The crude material was purified by flash chromatography using 100% $CH_2Cl_2$ to give 3.0 g of the desired product as a brown oil; MS (ES) m/z (relative intensity): 332 $(M+H)^+$ (100).

3) 6-fluoro-8-piperazinoquinoline

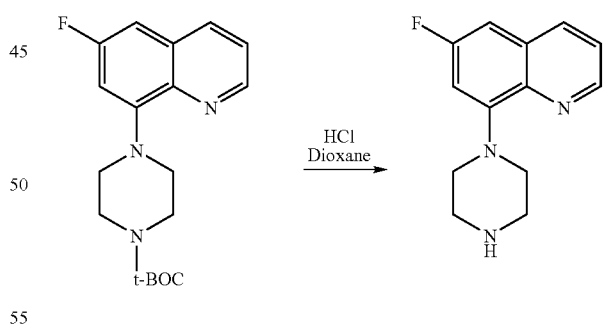

To a solution of 6-fluoro-8-[1-(tert-butoxycarbonyl)-4-piperazino]quinoline (Step 2, 3.0 g) in 10 mL Dioxane was added 10 mL of 4 N HCl/Dioxane. The mixture was stirred at room temperature overnight. The resulting precipitate was collected by vacuum filtration, dissolved in water, neutralized with aqueous sodium hydroxide and extracted with $CH_2Cl_2$ The combined organic layers were dried over anhydrous $Na_2SO_4$, filtered and concentrated on a rotary evaporator to give 1.9 g of the desired product as an off-white solid. Mp. 101-103° C.; MS (ES) m/z (relative intensity): 233 $(M+H)^+$ (100).

4) 6-fluoro-8-{4-[1-(8-quinolinyl)-4-piperidinyl]-1-piperazinyl}quinoline

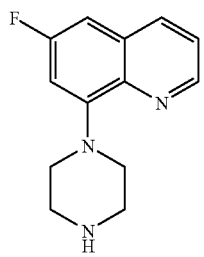

+

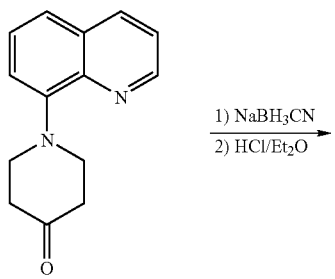

1) NaBH₃CN
2) HCl/Et₂O

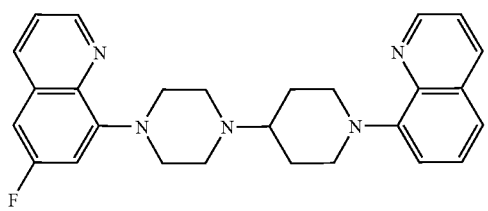

To a solution of 0.247 g of 6-fluoro-8-piperazino-quinoline (Step 3) in 10 mL of dichloroethane, was added 0.226 g of 1-quinolin-8-yl-piperidin-4-one (Example A, Step 6, above) followed by 0.274 g of sodium triacetoxyborohydride and 0.1 mL acetic acid. The reaction was stirred at room temperature overnight. It was quenched with 1N NaOH, and the product was extracted with CH₂Cl₂. The organic phase was washed with water and dried over magnesium sulfate. The product crystallized and filtered to give 0.200 g of the desired product. Mp: 211° C.; MS (ES) m/z (relative intensity): 442 (M⁺+−H, 100).

C) Preparation of 5-fluoro-8-{4-[4-(8-quinolinyl)-1-piperazinyl]-1-piperidinyl}-quinoline and Intermediates

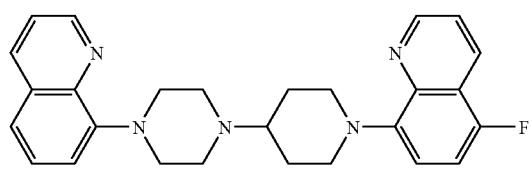

1) 5-Fluoro-8 chloroquinoline

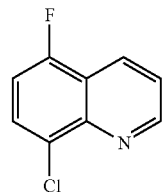

To a mixture of (5.0 g) 2-chloro-5-fluoroaniline (commercially available, 6.0 g), glycerol (6.0 g) and m-nitrobenzene sulfonic acid sodium salt (11.0 g), was added 20 ml of 70% sulfuric acid dropwise. The reaction temperature was raised to 140° C. for 2 hr. The mixture was then cooled, poured on ice water and filtered through celite. The filtrate was neutralized with NaOH and extracted with CH₂Cl₂. The combined organic layers were dried over anhydrous MgSO₄ and concentrated on a rotary evaporator. The crude product was purified by flash chromatography on silica gel using 100% CH₂Cl₂ to give 3.7 g of the desired product of a yellow solid; MP=74-76° C.; MS (ES) m/z (relative intensity): 182 (M+H)⁺ (100).

2) 8-(1,4-Dioxa-8-azaspiro[4,5]dec-5-yl)-5-fluoroquinoline

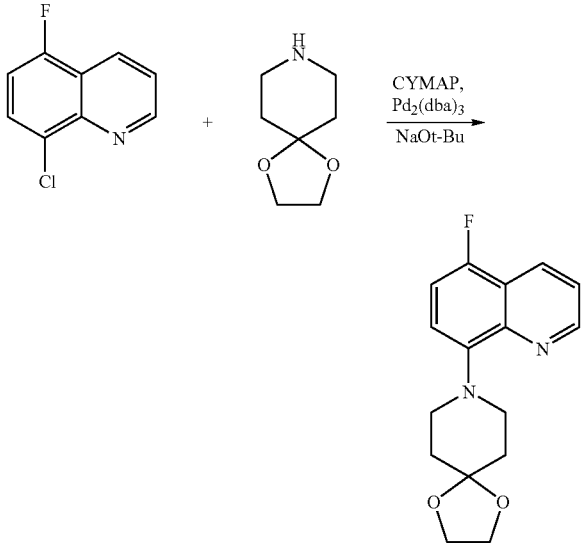

To a solution of 5-fluoro-8-chloroquinoline (Step 1, 1.12 g) in 20 mL of anhydrous tetrahydrofuran, was added 0.085 g of tris(dibenzylideneacetone)dipalladium(0) (Pd₂(dba)₃, 0.085 g), sodium tert-butoxide (0.83 g), 2-dicyclohexylphosphino-2'-(N,N-dimethylamino)-biphenyl (CYMAP, 0.036 g), and 1,4-dioxo-8-azaspiro-4,5-decane (1.05 g). The mixture was refluxed for 6 hours under a nitrogen atmosphere. The reaction mixture was then cooled to room temperature, diluted with ether, filtered through celite and concentrated on a rotary evaporator. The crude material was then purified by flash chromatography on silica gel using hexane/ethyl acetate to give 0.700 g of the desired product as a brown oil; MS (ES) m/z (relative intensity): 289 (M+H)+ (100).

3) 1-(5-Fluoroquinolin-8-yl)piperidin-4-one

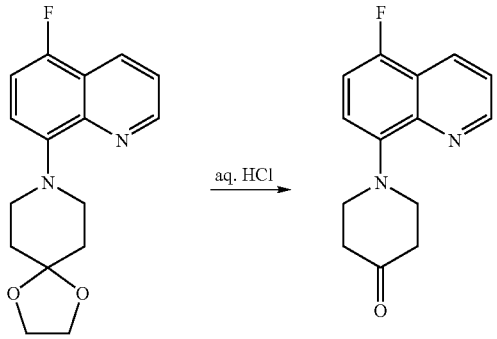

A solution of 8-(1,4-dioxa-8-azaspiro[4,5]dec-5-yl)-5-fluoroquinoline (Step 2, 2.1 g)) in 10 mL of 1:1 tetrahydrofuran/2N aqueous HCl was stirred at room temperature overnight. The reaction mixture was diluted with water, made basic with 1N aqueous NaOH and extracted with $CH_2Cl_2$. The combined organic layers were dried over anhydrous $MgSO_4$, filtered and concentrated on a rotary evaporator to give 1.68 g of the desired product as a yellow solid, which was pure enough to use in subsequent reactions; MS m/z=245 [M+H]+.

4) 5-fluoro-8-{4-[4-(8-quinolinyl)-1-piperazinyl]-1-piperidinyl}-quinoline

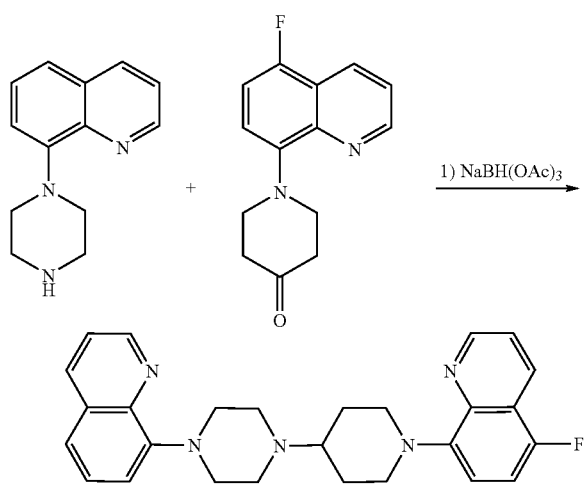

To a solution of 0.120 g of 1-(5-fluoro-quinolin-8-yl)-piperidin-4-one (Step 3, 0.22 g) and 8-piperazin-1-ylquinoline (Oruz, et al., *J. Med. Chem.* 45:4128 (2002), 0.19 g) was added of 0.19 g sodium triacetoxyborohydride and 0.1 mL acetic acid. The reaction was stirred at room temperature overnight. It was quenched with 1N NaOH, and the product was extracted with $CH_2Cl_2$. The organic phase was washed with water and dried over magnesium sulfate. The product was filtered through 75 ml of silica gel using 100% Ethyl acetate, to give 0.30 g of the desired product. Mp: 224° C.; MS (ES) m/z (relative intensity): 442 (M++–H, 100).

D) Preparation of 8-{4-[4-(1H-indole-4-yl)-1-piperazinyl]-1-piperidinyl}quinoline

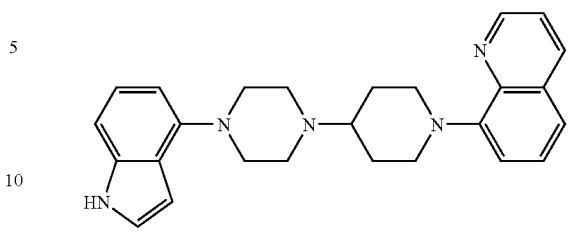

To a solution of 0.270 g of 1-quinolin-8-yl-piperidin-4-one (Example A, Step 6, above) and 0.240 g of 4-piperazino-indole (commercially available) in 15 mL $CH_2Cl_2$ was added 0.327 g of sodium triacetoxyborohydride and 0.2 mL acetic acid. The reaction was stirred at room temperature overnight. It was quenched with 1N NaOH, and the product was extracted with $CH_2Cl_2$. The organic phase was washed with water, dried over magnesium sulfate and evaporated. The product crystallized to give 0.200 g of the desired product. Mp: 256° C.; MS (ES) m/z (relative intensity): 412 (M++–H, 100).

E) Preparation of 8-{4-[4-(2,3-dihydro-1,4-benzo[1,4]dioxane-5-yl)-1-piperazinyl]-1-piperidinyl}quinoline

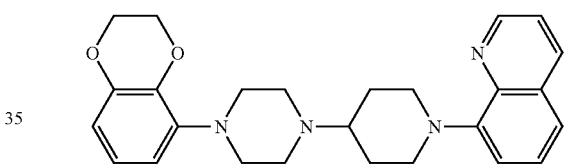

To a solution of 1-quinolin-8-yl-piperidin-4-one (Example A, Step 6, above, 0.220 g) in 10 mL of dichloroethane, was added 0.226 g of 8-piperazino-1,3-benzdioxane (Childers et al., *J. Med. Chem.* 48:3467 (2005), 0.226 g) followed by 0.274 g of sodium triacetoxyborohydride and 0.1 mL acetic acid. The reaction was stirred at room temperature overnight. It was quenched with 1N NaOH, and the product was extracted with $CH_2Cl_2$. The organic phase was washed with water, dried over magnesium sulfate and evaporated. The product crystallized to give 0.140 g of the desired product. Mp: 226° C.; MS (ES) m/z (relative intensity): 431 (M++–H, 100).

F) Preparation of 5-fluoro-8-{4-[4-(5-fluoro-1-benzofuran-3-yl)-1-piperazinyl]-1-piperidinyl}quinoline

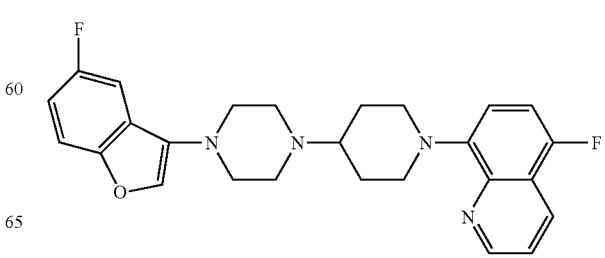

1) 4-(5-fluorobenzofuran-3-yl)-piperazine-1-carboxylic acid ethyl ester

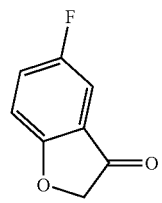 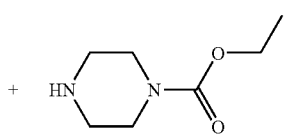

To a stirred solution of TiCl₄ (1M solution in CH₂Cl₂, 7 ml) and 5-fluoro-benzofuran -3-one (Cagniant, et al., *Comptus Rendus des Seances Acad. de Sci., Ser. C,* 282:993 (1976), 3.0 g) (3.0 g, 19.7 mmol) in methylene chloride (200 ml) at −10° C., ethyl-1-piperizine carboxylate (commercially available) (3.9 g, 35 mmol) was slowly added. After the addition, the reaction mixture was warmed to room temperature and slowly refluxed for 24 hours. After cooling to room temperature, the reaction was quenched with 2 N aqueous HCl. The organic layer was separated and the aqueous layer was extracted with chloroform. The combined organic layers were washed well with water and dried over anhydrous MgSO₄, then filtered and concentrated resulting in a brown oil. Yield: 3.5 g, (60%); MS (ESI) m/z 293 [M+−H]⁺.

2) 4-(5-fluorobenzofuran-3-yl)-piperazine

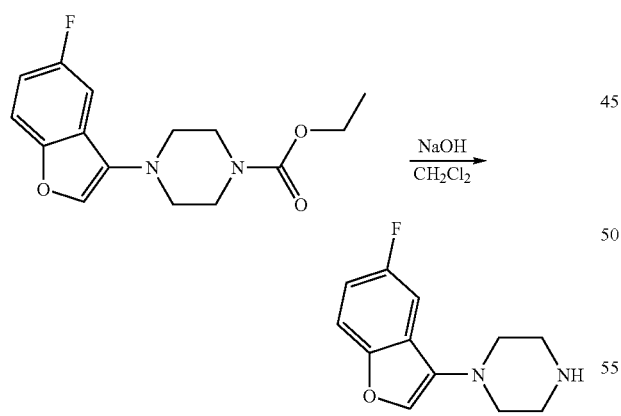

4-(5-fluorobenzofuran-3-yl)-piperazine-1-carboxylic acid ethyl ester (Step 1, 3 g) was dissolved in 95% ethanol and 3N aqueous sodium hydroxide (25 mL) was added. The reaction mixture was stirred at reflux for 24 hours. The mixture was then cooled to room temperature, concentrated on a rotary evaporator to remove the ethanol and extracted with chloroform. The combined organic layers were washed with brine, dried over anhydrous MgSO₄, filtered and concentrated on a rotary evaporator. The desired product (0.8 g) was obtained as a brown oil and was used without further purification; MS (ES) m/z (relative intensity): 221 (M+H)⁺ (100).

3) 5-fluoro-8-{4-[4-(5-fluoro-1-benzofuran-3-yl)-1-piperazinyl]-1-piperidinyl}quinoline

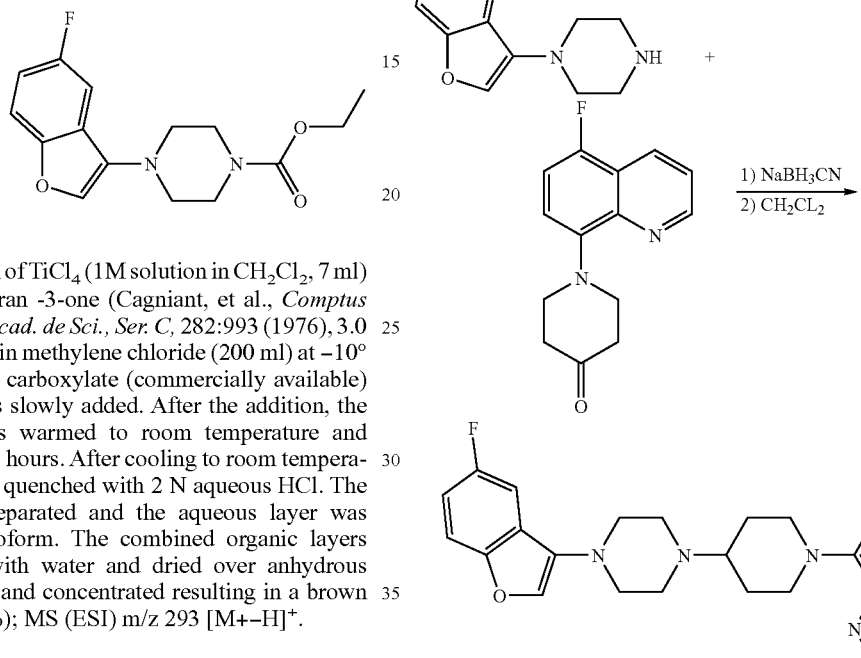

To a solution of 0.200 g of 1-(5-fluoro-quinolin-8-yl)-piperidin-4-one (Example C, Step 3, 0.20 g) and 5-fluoro-3-piperazino benzofuran (Step 2, 0.20 g) in CH₂Cl₂ (10 mL) was added sodium triacetoxyborohydride (0.224 g) and 0.02 mL acetic acid. The reaction was stirred at room temperature overnight. It was quenched with 1N NaOH, and the product was extracted with CH₂Cl₂. The organic phase was washed with water and dried over magnesium sulfate. The product was filtered through 100 ML of silica gel using 50% Ethyl acetate/Hexanes then 100% Ethyl acetate to give 0.100 g of the desired product. Mp: 187-189° C.; MS (ES) m/z (relative intensity): 449 (M⁺+−H, 100).

G) Preparation of 1-[1-(1-benzothien-3-yl)-4-piperidinyl]-4-(2-methoxyphenyl)piperazine
[Table 1, #18]

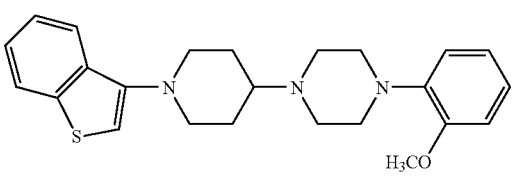

1) 4-(1-Benzylpiperidin-4-yl)-1-(2-methoxyphenyl) piperazine

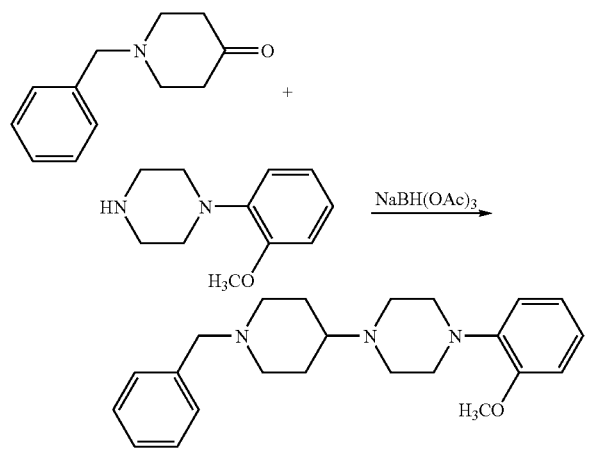

Sodium triacetoxyborohydride (21.2 g) was added portionwise to a stirred solution of 1-(2-methoxyphenyl)piperazine (commercially available, 19.23 g) and 1-benzyl-4-piperidone (commercially available, 18.93 g) in $CH_2Cl_2$ (300 mL) at room temperature, followed by glacial acetic acid (6 mL). The resulting mixture was stirred at room temperature for 24 hours. The reaction was made basic by careful addition of saturated aqueous $NaHCO_3$. The organic layer was separated, washed with brine, dried over anhydrous $MgSO_4$, filtered and concentrated on a rotary evaporator to give the desired product (20.65 g) as an off-white solid which was used without further purification. The compound was characterized as the dihydrochloride salt, which was formed by dissolving the free base in ethanol and treating it with an excess of 1 N $HCl/Et_2O$ to give a white solid, which was collected by vacuum filtration, washed with $Et_2O$ and dried in vacuo; MP. 238-242° C.; MS (ES) m/z (relative intensity) 366 (M+H)+ (100).

2) 4-(4-(2-Methoxyphenyl)piperazin-1-yl)piperidine

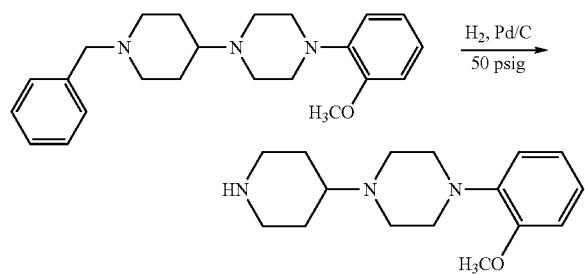

A solution of 4-(1-benzylpiperidine-4-yl)-1-(2-methoxyphenyl)piperazine (Step 1, 20.0 g) in ethanol (120 mL) containing acetic acid (12 mL) was hydrogenated over 10% palladium on carbon (1 g) at 50 psig on a Parr apparatus for 12 hours. The catalyst was removed by filtration through Celite and the mixture was concentrated to dryness on a rotary evaporator. The residue was partitioned between chloroform and saturated aqueous $NaHCO_3$. The combined organic layers were dried over anhydrous $MgSO_4$, filtered and concentrated on a rotary evaporator to provide the desired product (14.4 g) as a yellow oil which was used without further purification. The compound was characterized as the dihydrochloride salt, which was formed by dissolving the oil in ethanol and treating it with an excess of 1N $HCl/Et_2O$ to give an off-white precipitate, which was collected by vacuum filtration, washed with Et2O and dried in vacuo; MP. 274-288° C.; MS (ES) m/z (relative intensity): 276 (M+H)+ (100).

3) 1-[1-(1-benzothien-3-yl)-4-piperidinyl]-4-(2-methoxyphenyl)piperazine

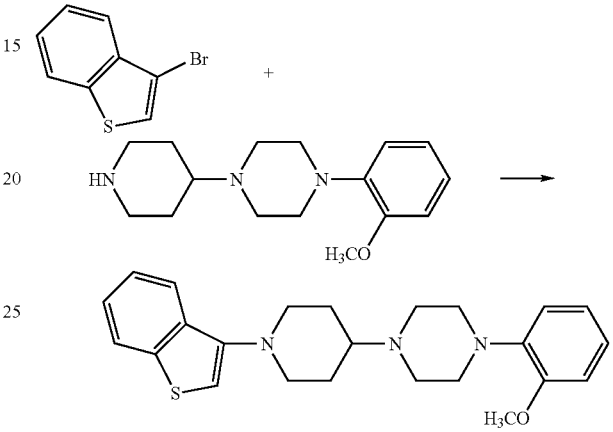

A solution of 3-bromo-benzothiophene (commercially available, 0.232 g) and 4-(4-(2-methoxyphenyl)piperazin-1-yl)piperidine (Step 2, 0.30 g) in tetrahydrofuran was added sodium tert-butoxide (0.15 g), tris-(dibenzylideneacetone)dipalladium(0) $(Pd_2(dba)_3, 0.10$ g) and 2-dicyclohexylphosphino-2'-(N,N-dimethylamino)-biphenyl (CYMAP, 0.01 g). The reaction was heated at reflux for 24 hours. It was then cooled and filtered through celite. The filtrate was evaporated and purified by flash chromatography on silica gel using ethyl acetate/hexanes to give 0.10 g of the desired product. MP: 156-158° C.; MS (ES) m/z (relative intensity): 408 (M+H)+ (100).

H) Preparation of 3-{4-[4-(2-methoxyphenyl)-1-piperazinyl]-1-piperidinyl}-1,2-benzisoxazole

1) 1,2-benzoxazole-3-trifluoromethylsulfonate

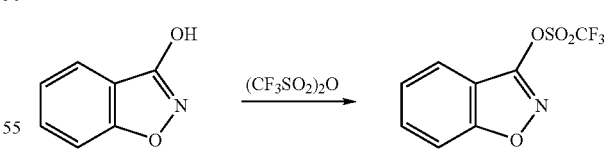

To a cold solution (−15° C.) of benzo-[D]-isoxazole-3-ol (2.0 g) in $CH_2Cl_2$ (20 mL) and triethylamine (4.5 g), was added a solution of trifluoromethanesulfonic anhydride (5.0 g) in $CH_2Cl_2$ (10 mL) dropwise with. The reaction was stirred at 0° C. for one hour and then poured into ice water. The mixture was extracted with $CH_2Cl_2$. The organic phase was dried over anhydrous $MgSO_4$, filtered and concentrated on a rotary evaporator to give 3.0 g of the desired product as a brown oil, which was used immediately without characterization or further purification.

2) 3-{4-[4-(2-methoxyphenyl)-1-piperazinyl]-1-piperidinyl}-1,2-benzisoxazole

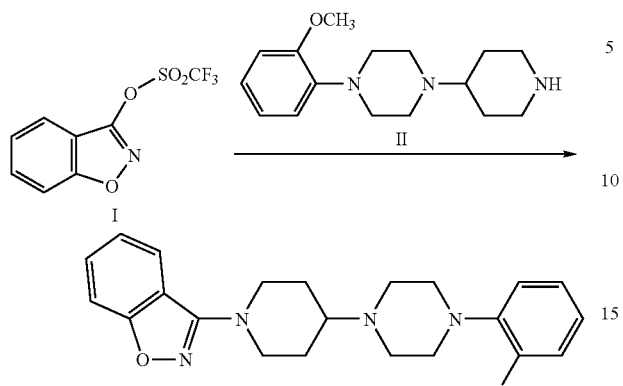

1,2-benz-isoxazole-3-trifluoromethyl sulfonate I (Step 1, 0.50 g) and 4-(4-(2-methoxyphenyl)piperazin-1-yl)piperidine (Example G, Step 2, above, 0.514 g) were added to a cold suspension of $CsCO_3$ (0.92 g) in acetonitrile (6 mL) under vigorous stirring. The reaction mixture was stirred at room temperature for 48 hours. The mixture was then filtered and concentrated on a rotary evaporator. The residue was dissolved in water extracted with $CH_2Cl_2$, dried over anhydrous MgSO4, filtered and concentrated on a rotary evaporator. The desired product was purified by flash chromatography on silica gel using ethyl acetate/hexane to give 0.34 g as an off-white solid; MP 71-73° C.; MS (ES) m/z (relative intensity): 393 $(M+H)^+$ (100).

I) Preparation of 6-Chloro-8-{4-[4-(1H-indole-4-yl)-1-piperazinyl]-1-piperidinyl}quinoline

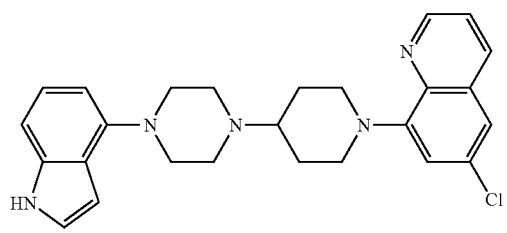

1) 1-(6-Chloro-8-quinolinyl)-4-piperidinone

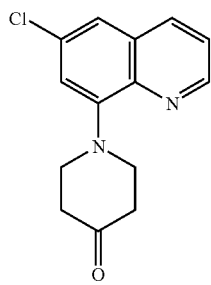

This compound was prepared from the known 8-bromo-6-chloroquinoline (Lachowicz et al., *Rocz. Chem.*, 40:1848 (1966)) using a synthetic sequence and reagents identical to those described for the synthesis of 1-quinolin-8-yl-piperidin-4-one (Step 5, Example A, above). The compound was obtained as an off-white solid; MP: 223-225° C.; MS (ES) m/z (relative intensity): 261 $(M+H)^+$ (100).

2) 6-Chloro-8-{4-[4-(1H-indole-4-yl)-1-piperazinyl]-1-piperidinyl}quinoline

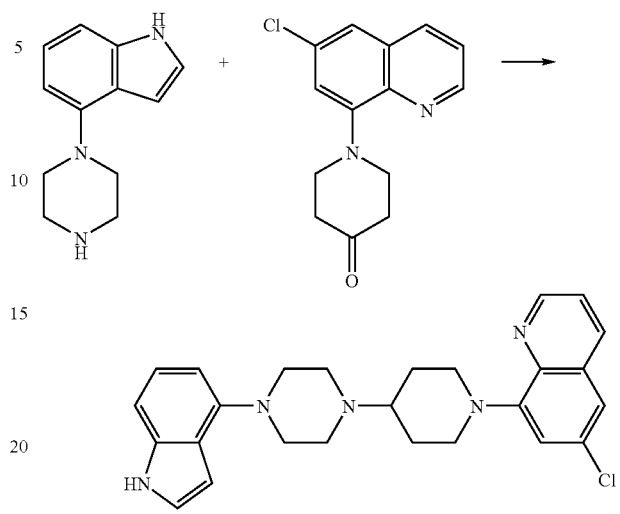

To a solution of 1-(6-chloro-quinolin-8-yl)-piperidin-4-one (Step 1, 0.13 g) and of 4-piperazino-indole (commercially available, 0.100 g) in 15 mL $CH_2Cl_2$ in 10 mL of dichloroethane, was added 0.137 g of sodium triacetoxyborohydride and 0.1 mL acetic acid. The reaction was stirred at room temperature overnight. It was quenched with 1N NaOH, and the product was extracted with $CH_2Cl_2$. The organic phase was washed with water and dried over magnesium sulfate. The product was filtered through 100 ml of silica gel using 100% Ethyl acetate, to give 0.070 g of the desired product. Mp: 224° C.; MS (ES) m/z (relative intensity): 447 $(M^++H, 100)$.

J) Preparation of 8-{4-[1-(7-Fluoroquinolin-8-yl)piperidin-4-yl]piperazin-1-yl}-6-methoxyquinoline (Table 1, # 24)

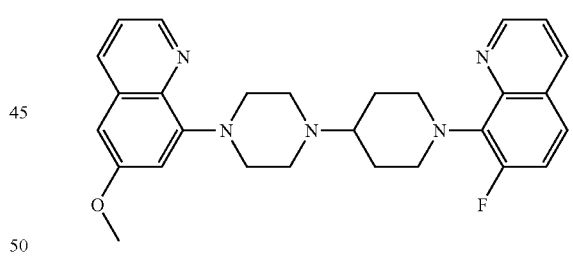

1) 7,8-Difluoroquinoline (intermediate)

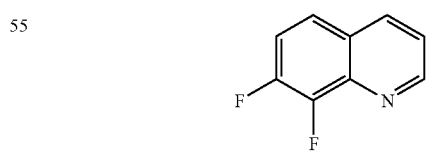

To a mixture of 2,3-difluoroaniline (commercially available, 3.57 g), glycerol (5.55 g) and m-nitrobenzene sulfonic acid sodium salt (10.12 g) was added dropwise 70% $H_2SO_4$ (20 mL). The reaction was heated at 135° C. for 3.5 hours and then cooled to room temperature. It was poured over ice, made basic with 50% aqueous NaOH and extracted with Et$_2$O. The combined organic layers were washed with brine, dried over anhydrous MgSO$_4$ and concentrated on a rotary evaporator to give 4.13 g of the desired product as a light brown solid; MS (ES) m/z (relative intensity); 166 (M+H)$^+$ (100).

2) 8-(1.4-Dioxa-8-azaspiro{4.5]dec-8-yl)-7-fluoro-quinoline and 7-(1.4-Dioxa-8-azaspiro[4.5]dec-8-yl)-8-fluoroquinoline (Intermediates)

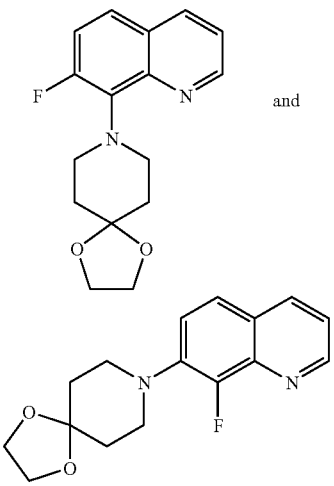

A mixture of 7,8-difluoroquinoline (Step 1, 0.50 g) and dioxa-8-azaspiro-4.5-decane (5 mL) was heated at 120° C. for 48 hours. The reaction was cooled to room temperature, poured into water and extracted with Et$_2$O. The combined organic layers were dried over anhydrous Na$_2$SO$_4$, filtered and concentrated on a rotary evaporator. The crude residue was purified by flash chromatography on silica gel. Eluting with 30% ethyl acetate in hexane provided 0.39 g of 8-(1.4-dioxa-8-azaspiro[4.5]dec-8-yl)-7-fluoroquinoline as yellow oil; MS (ES) m/z (relative intensity): 289 (M+H)$^+$ (100).

The eluent was then switched to 50% ethyl acetate in hexane, which provided 0.23 g of the regioisomeric 7-(1.4-dioxa-8-azaspirol[4.5]dec-8-yl)-8-fluoroquinoline as a white solid; MS (ES) m/z (relative intensity): 289 (M+H)$^+$ (100).

3) 1-(7-Fluoroquinolin-8-yl)piperidin-4-one (Intermediate)

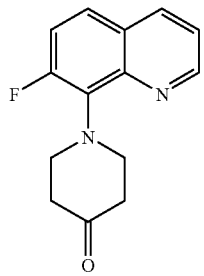

To a solution of 8-(1.4-dioxa-8-azaspiro[4.5]dec-8-yl)-7-fluoroquinoline (Step 2, 1.73 g) in tetrahydrofuran (50 mL) was added aq. 2N aqueous HCl (10 mL). The resulting mixture was stirred at 50° C. for 3 hours. The reaction mixture was then cooled to room temperature, poured into 2.5 N aqueous NaOH and extracted with ethyl acetate. The combined organic layers were dried over anhydrous MgSO$_4$, filtered and concentrated on a rotary evaporator. The crude product was purified by flash chromatography on silica gel using hexane/ethyl acetate to give 1.17 g of the desired product as a yellow oil; MS (ES) m/z (relative intensity): 245 (M+H)$^+$ (100).

4) 8-{4-[1-(7-Fluoroquinolin-8-yl)piperidin-4-yl] piperazin-1-yl}-6-methoxyquinoline (Final product)

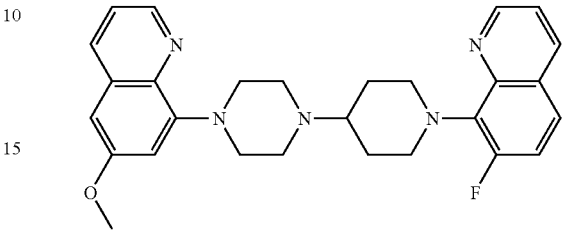

To a solution of 1-(7-fluoroquinolin-8-yl)piperidin-4-one (Step 3, 0.26 g) and 6-methoxy-8-(1-piperazinyl)quinoline (Example A, Step 4; 0.26 g) in anhydrous methanol (10 mL) was added sodium cyanoborohydride (0.11 g). The resulting mixture was stirred at room temperature under nitrogen for 18 hours. An additional aliquot of sodium cyanoborohydride (0.11 g) was added and stirring at room temperature was continued for another 24 hours. The resulting reaction mixture was poured into brine and extracted with ethyl acetate. The combined organic layers were dried over anhydrous Na$_2$SO$_4$, filtered and concentrated on a rotary evaporator. The crude product was purified by flash chromatography on silica gel using hexane/acetone to give the desired product, which was converted to its trihydrochloride salt in CH$_2$Cl$_2$ using 1M HCl/Et$_2$O to provide 0.12 g of a yellow solid; MS (ES) m/z (relative intensity): 472 (M+H)$^+$ (100).

K) 6-Fluoro-8-{4-[T-(8-fluoroquinolin-7-yl)piperidin-4-yl]piperazin-1-yl}quinoline (Table 1, #25)

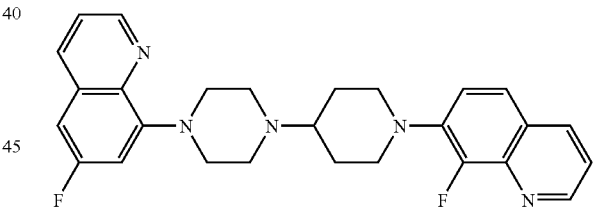

1) 1-(8-Fluoroquinolin-7-yl)piperidin-4-one (Intermediate)

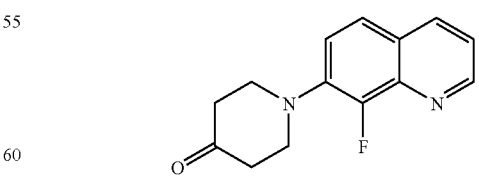

To a solution of 7-(1.4-dioxa-8-azaspiro[4.5]dec-8-yl)-8-fluoroquinoline (Example J, Step 2; 1.30 g) in tetrahydrofuran (60 mL) was added aq. 2N aqueous HCl (10 mL). The resulting mixture was stirred at room temperature for 18 hours and then heated at 60° C. for 5 hours. The reaction mixture was cooled to room temperature, poured into 1N aqueous NaOH and extracted with ethyl acetate. The combined organic layers were dried over anhydrous MgSO4, filtered and concentrated on a rotary evaporator. The crude product was purified by flash chromatography using hexane/acetone to give 0.89 g of the desired product as a yellow solid; MS (ES) m/z (relative intensity): 245 (M+H)+ (100).

2) 6-Fluoro-8-{4-[1-(8-fluoroquinolin-7-yl)piperidin-4-yl]piperazin-1-yl}quinoline (Final product)

To a solution of 1-(8-fluoroquinolin-7-yl)piperidin-4-one (Step 1, 0.25 g) and 6-fluoro-8-(1-piperazinyl)quinoline (Example B, Step 3; 0.25 g) in anhydrous methanol (10 mL) was added sodium cyanoborohydride (0.11 g). The resulting mixture was stirred at room temperature for 18 hours. An additional aliquot of sodium cyanoborohydride (0.10 g) was added and stirring at room temperature was continued for another 24 hours. The reaction mixture was poured into brine and extracted with ethyl acetate. The combined organic layers were dried over anhydrous Na2SO4, filtered and concentrated on a rotary evaporator. The crude product was isolated by flash chromatography on silica gel using hexane/acetone to give the desired product as a off-white solid, which was converted to its trihydrochloride salt in CH2Cl2/Et2O diethyl ether using 1M HCl/Et2O to provide 0.11 g as a yellow solid; MS (ES) m/z (relative intensity): 460 (M+H)+ (100).

L) 8-{4-[4-(6-Methoxyquinolin-8-yl)piperazin-1-yl) piperidin-1-yl}-3-(trifluoromethyl)quinoline (Table 1, #22)

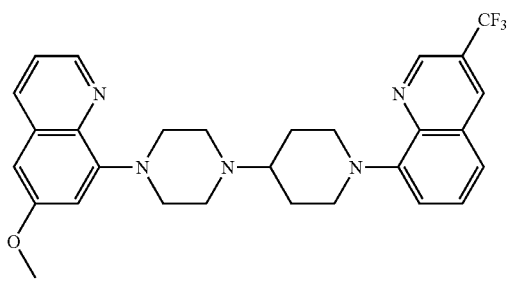

1) 8-Bromo-3-iodoquinoline (intermediate)

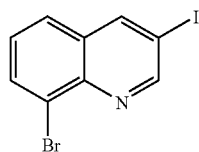

To a solution of 8-bromoquinoline (commercially available, 1.0 g) in glacial acetic acid (6 mL) was added portionwise, N-iodosuccinimide (1.08 g). The resulting mixture was stirred at 70° C. for 18 hours. The reaction was cooled to room temperature and concentrated on a rotary evaporator. The residue was taken up in CH2Cl2 and washed with saturated aqueous NaHCO3 and brine. The organic layer was dried over anhydrous Na2SO4, filtered and concentrated on a rotary evaporator. The crude product was purified by flash chromatography on silica using hexane/ethyl acetate to give 0.74 g of the desired product as a white solid; MS (ES) m/z (relative intensity): 334 (M+H)+ (100).

2) 8-Bromo-3-(trifluoromethyl)quinoline (intermediate)

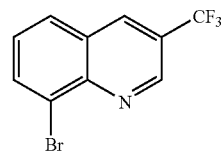

A mixture of cuprous iodide (0.25 g) and potassium fluoride (0.077 g) was placed under a high vacuum and heated until the solid assumed a sight green color. The cooled solid mass was suspended in anhydrous N-methylpyrrolidinone (5 mL) and then treated with 8-bromo-3-iodoquinoline (Step 1, 0.40 g), followed by trifluoromethyl-trimethylsilane (0.17 g). The resulting mixture was stirred at 50° C. for 18 hours. The mixture was then cooled to room temperature and poured into 15% aqueous NH4OH and then extracted with Et2O. The organic layer was washed with water and brine, dried over anhydrous Na2SO4, filtered and concentrated on a rotary evaporator. The crude product was purified by flash chromatography on silica gel using hexane/ethyl acetate to give 0.24 g of the desired product as a brown oil; MS (ES) m/z (relative intensity); 277 (M+H)+ (100).

3) 8-(1,4-Dioxa-8-azaspiro[4.5]dec-8-yl)-3-(trifluoromethyl)quinoline (intermediate)

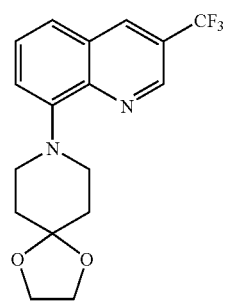

To a solution of mixture 8-bromo-3-(trifluoromethyl) quinoline (Step 2, 0.22 g) in anhydrous tetrahydrofuran was added tris(dibenzylideneacetone)dipalladium(0) (Pd2(dba)3, 0.03 g), sodium tert-butoxide (0.085 g), 2,2'-bis(diphenylphosphino)-1,1'-binapthyl (BINAP, 0.02 g), tetrakis-(triphenylphosphine)palladium(0) (0.037) g) and 1.4-dioxo-8-azaspiro-4.5-decane (0.14 g). The resulting mixture was stirred at 70° C. for 18 hours under a nitrogen atmosphere. The reaction was then cooled to room temperature, diluted with CH2Cl2, filtered through celite and concentrated on a rotary evaporator. The crude product was purified by flash chromatography on silica gel using hexane/ethyl acetate to give 0.21 g of the desired product as a beige solid; MS (ES) m/z (relative intensity); 399 (M+H)+ (100).

4) 1-[3-(Trifluoromethyl)quinolin-8-yl]piperidin-4-one (intermediate)

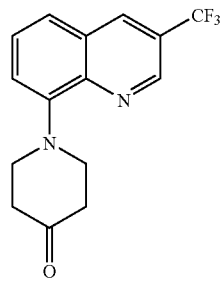

A solution of 8-(1.4-dioxa-8-azaspiro[4.5]dec-8-yl)-3-(trifluoromethyl)quinoline (Step 3, 0.19 g) in tetrahydrofuran (3 mL) was treated with 2N aqueous HCl (1 mL) and then stirred at 40° C. for 18 hours. The mixture was cooled to room temperature and concentrated on a rotary evaporator. The residue was taken up in $CH_2Cl_2$, washed with water and brine, dried over anhydrous $Na_2SO_4$, filtered and concentrated on a rotary evaporator to give 0.11 g of the desired product as a yellow oil; MS (ES) m/z (relative intensity); 295 $(M+H)^+$ (100).

5) 8-{4-[4-(6-Methoxyquinolin-8-yl)piperazin-1-yl]piperidin-1-yl}-3-(trifluoromethyl)quinoline A mixture of 6-methoxy-8-piperazinoquinoline (Example A, Step 4; 0.0825 g) and 1-[3-(trifluoromethyl)quinolin-8-yl]piperidin-4-one (0.1 g) in methanol (5 mL) was treated with sodium cyanoborohydride (Step 4, 0.032 g). The resulting mixture was stirred at room temperature for 18 hours and then concentrated on a rotary evaporator. The residue was taken up in $CH_2C_2$, washed with water and brine, dried over anhydrous $Na_2SO_4$, filtered and concentrated on a rotary evaporator. The crude product was purified by flash chromatography on silica gel using hexane/ethyl acetate to give the desired product, which was converted to its dihydrochloride salt in using 1N $HCl/Et_2O$ to yield 0.035 g as a yellow solid; MS (ES) m/z (relative intensity): 522 $(M+H)^+$ (100).

M) 6-Methoxy-8-{4-[1-(quinolin-8-ylmethyl)piperidin-4-yl]piperazin-1-yl}quinoline (Table 1, #23)

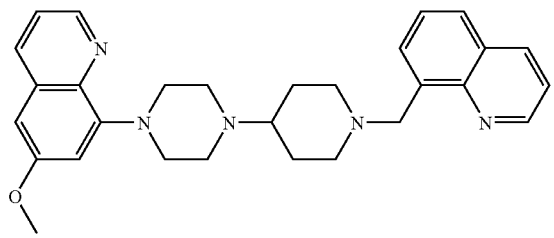

1) 8-[4-(1-Benzylpiperidin-4-yl)piperazin-1-yl]-6-methoxyquinoline (intermediate)

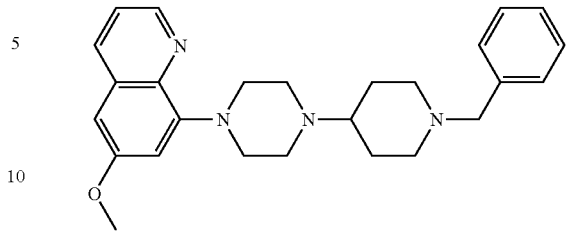

To a stirred mixture of 6-methoxy-8-piperazinoquinoline (Example A, Step 4, 0.24 g) and 4-benzyl-1-piperidinone (0.20 mL) in methanol (12 mL) was added glacial acetic acid (0.06 g), followed by sodium cyanoborohydride (0.123 g). The resulting mixture was stirred at room temperature for 18 hours. The reaction was then concentrated on a rotary evaporator and re-dissolved in $CH_2Cl_2$. The solution was washed with water and brine and then dried over anhydrous $Na_2SO_4$, filtered and concentrated on a rotary evaporator. The crude product was purified by flash chromatography on silica gel using hexane/ethyl acetate to give 0.23 g of the desired product as an off-white solid; MS (ES) m/z (relative intensity); 417 $(M+H)^+$ (100).

2) 6-Methoxy-8-(4-piperidin-4-ylpiperazin-1-yl)quinoline (intermediate)

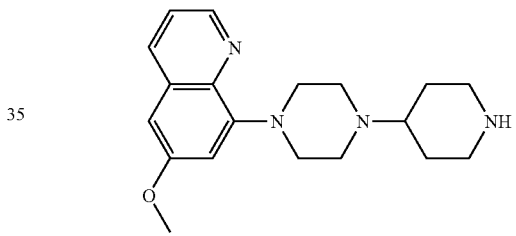

A solution of 8-[4-(1-benzylpiperidin-4-yl)piperazin-1-yl]-6-methoxyquinoline (Step 1, 0.22 g) and vinylchloroformate (0.067 mL) in anhydrous $CH_2Cl_2$ (5 mL) was stirred at reflux for 1 hour. The reaction was cooled to room temperature and then concentrated on a rotary evaporator. The residue was taken up in dioxane (5 mL), treated with concentrated HCl (0.35 mL) and stirred at room temperature for 1 hour. The resulting reaction was concentrated on a rotary evaporator, taken up in ethanol (1 mL) and stirred at 50° C. for 30 minutes. The reaction was again concentrated on a rotary evaporator and partitioned between $CH_2Cl_2$ and 1N aqueous NaOH. The organic layer was washed with water and then brine and was then dried over anhydrous $Na_2SO_4$, filtered and concentrated on a rotary evaporator. The crude product was purified by flash chromatography on silica gel using ethyl acetate/methanol/conc, $NH_4OH$ to give 0.14 g of the desired product as a yellow oil; MS (ES) m/z (relative intensity); 326 $(M+H)^+$ (100).

3) 6-Methoxy-8-{4-[1-(quinolin-8-ylmethyl)piperidin-4-yl]piperazin-1-yl}quinoline (final product)

To a mixture of 6-methoxy-8-(4-piperidin-4-ylpiperazin-1-yl)quinoline (Step 2, 0.06 g) and 8-(bromo)methylquinoline (commercially available, 0.055 g) in anhydrous dimethylsulfoxide (5 mL) was added anhydrous $K_2CO_3$ (0.051 g).

The resulting mixture was stirred at 70° C. for 18 hours. The reaction mixture was cooled to room temperature and partitioned between ethyl acetate and water. The organic layer was washed with water and brine and was then dried over anhydrous Na$_2$SO$_4$, filtered and concentrated on a rotary evaporator to give the desired product, which was converted to its dihydrochloride salt in CH$_2$Cl$_2$ using 1N HCl/Et$_2$O to give 0.31 g of a light yellow solid; MS (ES) m/z (relative intensity); 468 (M+H)$^+$ (100).

N) Preparation of 8-{4-[1-(8-quinolinyl)-4-piperidinyl]-1-piperazinyl}quinoline (Table 1, #3)

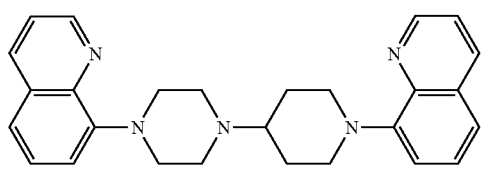

Using the synthetic methods described in previous examples, 8-(piperazin-1-yl)quinoline (Oruz et al., *J. Med. Chem.* 45:4128 (2002)) and 1-quinolin-8-yl-piperidin-4-one (Example A, Step 5, above) were reacted with sodium triacetoxyborohydride to give the desired product as a light yellow solid; MP. 194-196° C.; MS (ES) m/z (relative intensity) 424 (M+H)$^+$ (100).

O) Preparation of 6-chloro-8-{4-[4-(6-chloro-8-quinolinyl)-1-piperazinyl]-1-piperidinyl}quinoline (Table 1, #4)

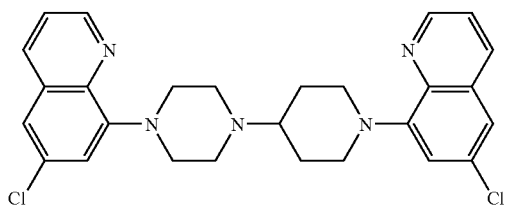

1) 6-Chloro-8-aminoquinoline

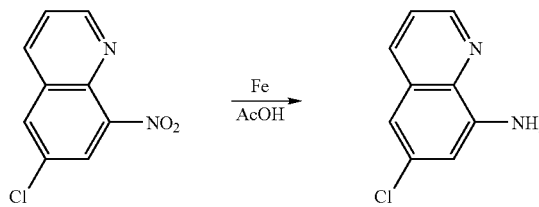

To a hot suspension of 6-chloro-8-nitroquinoline (Mosher, et al., *Org. Syn.* 27:48 (1947), 0.8 g) in a mixture of ethanol/glacial acetic acid/water (2:2:1, 25 mL) was added iron powder (0.5 g) portionwise. The resulting mixture was stirred at reflux for 1.5 hours. The reaction was the cooled to room temperature, filtered through celite and made basic by addition of solid Na$_2$CO$_3$. The aqueous mixture was extracted with Et$_2$O. The combined organic layers were dried over anhydrous MgSO$_4$, filtered and concentrated on a rotary evaporator to give the desired product (0.5 g) as a yellow solid; MP. 70-73° C.; MS (ES) m/z (relative intensity) 179 (M+H)$^+$ (100).

2) 6-Chloro-8-piperazin-1-yl-quinoline

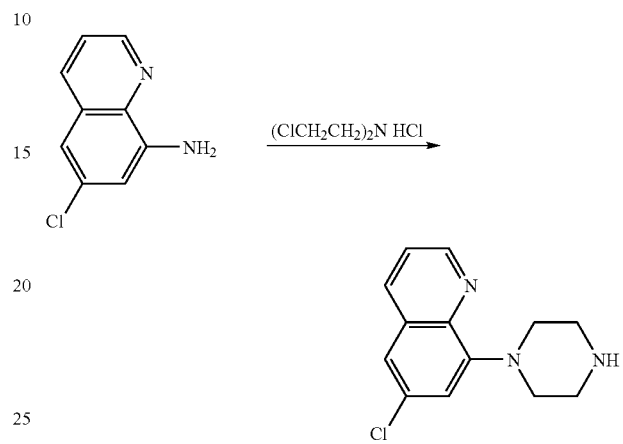

8-amino-6-chloroquinoline (Step 1, 0.49 g) and bis(chloroethyl)amine hydrochloride (0.49 g) were dissolved in chlorobenzene (13 mL) and heated with vigorous stirring at 135° C. for 5 days. The reaction was cooled to room temperature, diluted with water and extracted with Et$_2$O. The aqueous phase was made basic by addition of solid Na$_2$CO3 and then extracted with Et$_2$O. The combined organic layers were dried over anhydrous Na$_2$SO$_4$, filtered and concentrated on a rotary evaporator to give the desired compound (0.20 g) as a yellow semi-solid; MS (ES) m/z (relative intensity) 248 (M+H)$^+$ (100).

3) Preparation of 6-chloro-8-{4-[4-(6-chloro-8-quinolinyl)-1-piperazinyl]-1-piperidinyl}quinoline

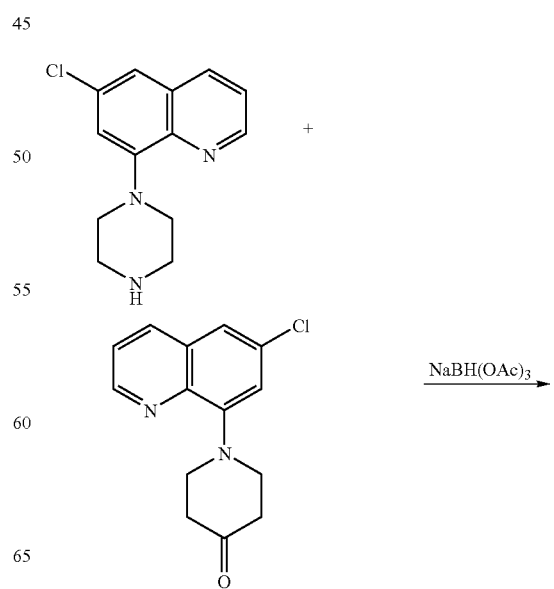

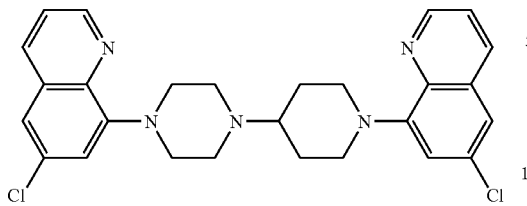

Using the synthetic methods described in previous examples, 6-chloro-8-(piperazin-1-yl)quinoline (Step 2) and 1-quinolin-8-yl-piperidin-4-one (Example 1, Step 1, above) were reacted with sodium triacetoxyborohydride to give the desired product as an off-white solid; MP. 269-271° C.; MS (ES) m/z (relative intensity) 493 (M+H)+ (100).

P) Preparation of 8-{4-[1-(6-chloro-8-quinolinyl)-4-piperidinyl]-1-piperazinyl}-6-fluoroquinoline (Table 1, #5)

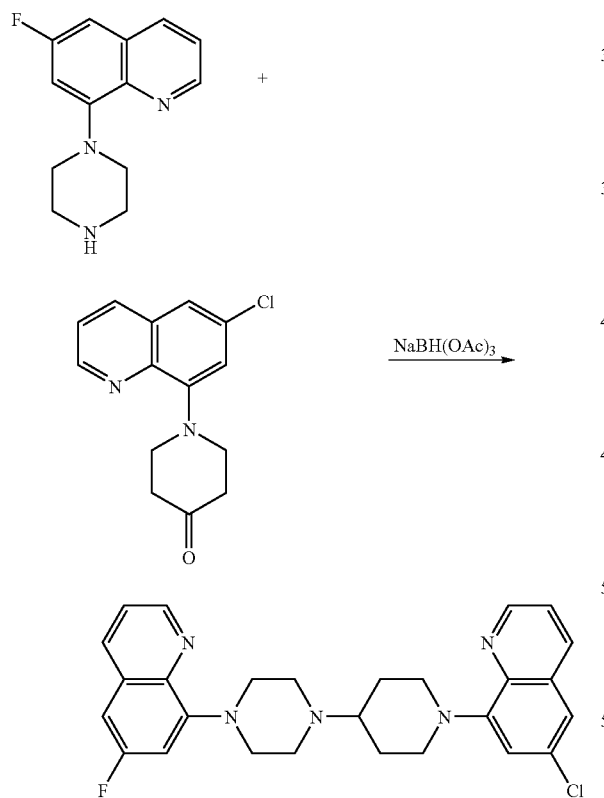

Using the synthetic methods described in previous examples, 6-fluoro-8-(piperazin-1-yl)quinoline (Example B, Step 3, above) and 1-quinolin-8-yl-piperidin-4-one (Example I, Step 1, above) were reacted with sodium triacetoxyborohydride to give the desired product as a white solid; MP. 256-258° C.; MS (ES) m/z (relative intensity) 477 (M+H)+ (100).

R) Preparation of 5-chloro-8-{4-[1-(8-quinolinyl)-4-piperidinyl]-1-piperazinyl}quinoline (Table 1, #8)

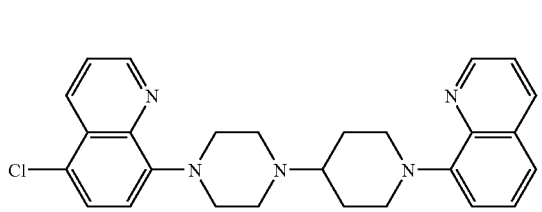

1) 5-Chloro-8-(trifluoromethylsulfonyloxy)quinoline

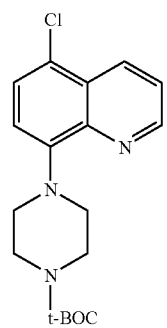

To a suspension of 5-chloro, 8-hydroxy-quinoline (commercially available, 8.95 g) in 100 ml CH$_2$Cl$_2$, TEA is added (20 ml). The mixture becomes homogeneous and is then cooled to −15° C. The suspension dissolved, then cooled to −15° C. A solution of 21.1 g of triflic anhydride in 50 ml of CH$_2$Cl$_2$, is added drop by drop with cooling. After complete addition, the reaction was stirred at −15° C. for hour; The reaction was diluted with CH$_2$Cl$_2$, washed with a solution of NaHCO$_3$, then with water dried and the solvent was removed to give 15.0 g of product. MP: 80-83° C. MS (ES) m/z (relative intensity): 312 (M$^+$+−H, 100

2) 5-Chloro-8-[(4-tert-butoxycarbonyl)-piperazin-1-yl]quinoline

To a mixture of 5-chloro-8-(trifluoromethylsulfonyloxy) quinoline (Step 1, 4.0 g) in tetrahydrofuran (30 mL), was added 5.9 g of cesium carbonate (5.9 g), 2,2'-bis(diphenylphosphino)-1,1'-binapthyl (BINAP, 0.36 g), palladium acetate (0.12 g) and tert-butoxycarbonylpiperazine (2.8 g). The mixture was refluxed for 5 hours. The reaction mixture was then cooled to room temperature, diluted with Et$_2$O, filtered through celite and concentrated on a rotary evaporator. The crude material was purified by flash chromatography on silica gel using CH₂Cl₂ to give 2.4 g of the desired product as an off-white solid; MP. 127° C. MS (ES) m/z (relative intensity): 348 (M+H)⁺ (100).

3) 5-Chloro-8-piperazinoquinoline

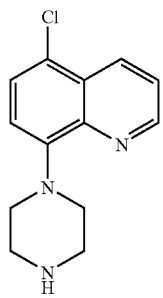

To a solution of 5-chloro-8-[(4-tert-butoxycarbonyl)-piperazin-1-yl]quinoline (Step 2, 2.2 g) in dioxane (10 mL), was added 4 N HCl/dioxane (5 mL). The mixture was stirred at room temperature overnight. The formed precipitate was collected by vacuum filtration, dissolved in water, made basic with solid NaHCO₃ and extracted with CH₂Cl₂. The combined organic layers were dried over anhydrous Na₂SO₄, filtered and concentrated on a rotary evaporator to give 1.0 g of the desired product as a brown semi-solid; MS (ES) m/z (relative intensity): 248 (M+H)⁺ (100).

4) 5-Chloro-8-{4-[1-(8-quinolinyl)-4-piperidinyl]-1-piperazinyl}quinoline

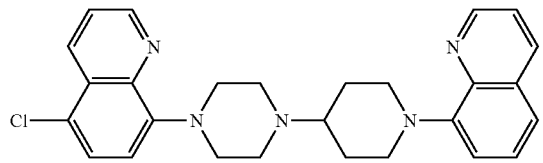

Using the synthetic methods described in previous examples, 5-chloro-8-(piperazin-1-yl)quinoline (Step 3) and 1-quinolin-8-yl-piperidin-4-one (Example A, Step 5, above) were reacted with sodium triacetoxyborohydride to give the desired product as a beige solid; MP. 201-203° C.; MS (ES) m/z (relative intensity) 459 (M+H)⁺ (100).

S) Preparation of 2-methyl-8-{4-[1-(8-quinolinyl)-4-piperidinyl]-1-piperazinyl}quinoline (Table 1, #10)

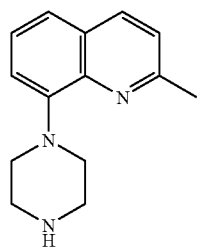

+

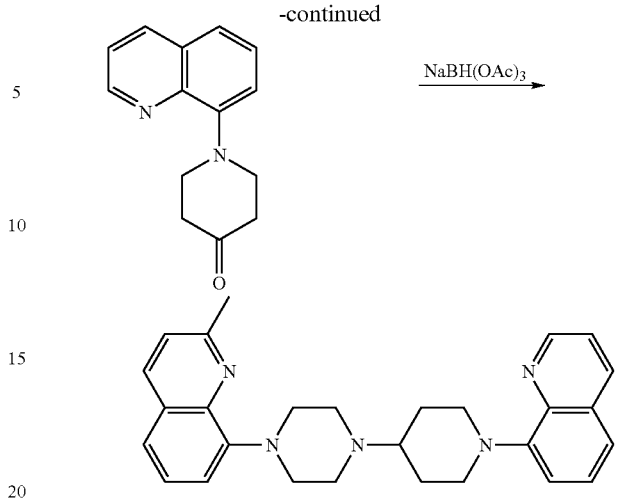

Using the synthetic methods described in previous examples, 2-methyl-8-(piperazin-1-yl)quinoline (Oruz, et al., *J. Med. Chem.* 45:4128 (2002)) and 1-quinolin-8-yl-piperidin-4-one (Example A, Step 5, above) were reacted with sodium triacetoxyborohydride to give the desired product as a light brown semi-solid; MS (ES) m/z (relative intensity) 438 (M+H)⁺ (100).

T) Preparation of 6-chloro-8-{4-[1-(8-quinolinyl)-4-piperidinyl]-1-piperazinyl}quinoline (Table 1, #11)

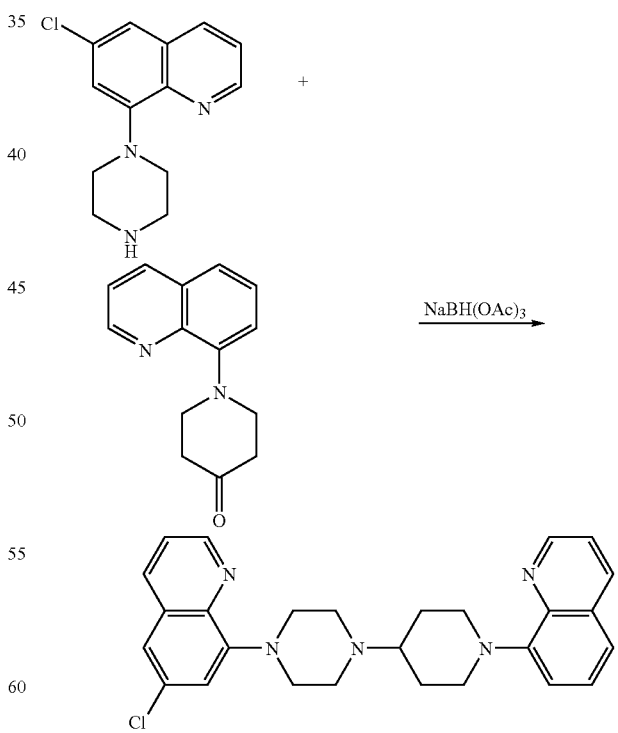

Using the synthetic methods described in previous examples, 6-chloro-8-(piperazin-1-yl)quinoline (Example O, step 2, above) and 1-quinolin-8-yl-piperidin-4-one (Example A, Step 5, above) were reacted with sodium triacetoxyborohydride to give the desired product as a white solid; MP. 209-211° C.; MS (ES) m/z (relative intensity) 459 (M+H)+ (100).

U) Preparation of 8-{4-[1-(8-quinolinyl)-4-piperidinyl]-1-piperazinyl}-5-(trifluoromethyl)quinoline (Table 1, #12)

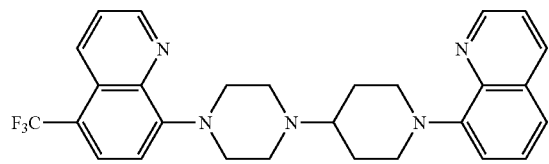

1) 8-Bromo-5-(trifluorommethyl)quinoline

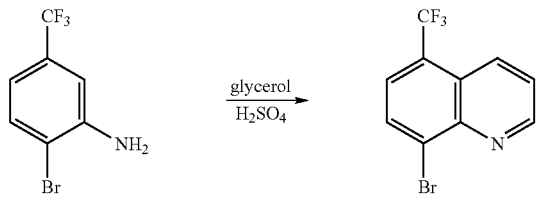

To a mixture of 2-bromo-4-(trifluoromethyl)aniline (commercially available, 5.0 g), glycerol (3.8 g) and m-nitrobenzene sulfonic acid sodium salt 7.0 g) was added 18 ml of 70% sulfuric acid dropwise. The reaction temperature was raised to 150° C. for 4 hours. The mixture then was cooled to room temperature, poured on ice water and filtered through celite. The filtrate was neutralized with NaOH and the resulting precipitate was collected by vacuum filtration to yield 3.00 g of the title compound as a brown solid that was used without further purification; MS (ES) m/z (relative intensity): 277 (M+H)+ (100).

2) Tert-butyl 4-[5-(trifluoromethyl)-8-quinolinyl]-1-piperazinecarboxylate

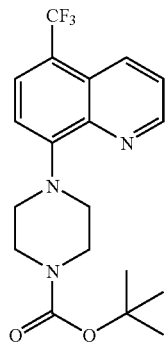

To a mixture of 5-bromo-8-trifluoromethylsulfonyloxy)quinoline (Step 1, 2.83 g) in anhydrous tetrahydrofuran (38 mL), was added tris(dibenzylideneacetone)dipalladium(0) (Pd₂(dba)₃, 0.04 g) sodium tert-butoxide (5.1 g), 2,2'-bis(diphenylphosphino)-1,1'-binapthyl (BINAP, 0.04 g), tetrakis(triphenylphosphine)-palladium (0) (0.04 g) and tert-butoxycarbonyl-piperazine (2.33 g). The mixture was refluxed for 3 hours under a nitrogen atmosphere. The reaction was then cooled to room temperature, diluted with ether, filtered through celite and concentrated on a rotary evaporator. The crude material was purified by flash chromatography on slilca gel using 100% CH₂Cl₂ to give 0.85 g of the desired product as an off-white solid; MP. 105-107° C.; MS (ES) m/z (relative intensity): 332 (M+H)+ (100).

3) 8-(1-piperazinyl)-5-(trifluoromethyl)quinoline

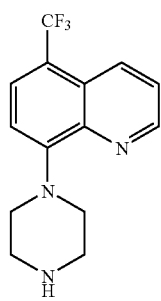

To a solution of tert-butyl 4-[5-(trifluoromethyl)-8-quinolinyl]-1-piperazine-carboxylate (Step 2, 0.85 g) in 5 mL dioxane was added 5 mL of 4 N HCl/dioxane. The mixture was stirred at room temperature overnight. The reaction was concentrated on a rotary evaporator, dissolved in water, neutralized with aqueous sodium hydroxide and extracted with CH₂Cl₂ The combined organic layers were dried over anhydrous Na₂SO₄, filtered and concentrated on a rotary evaporator to give 0.65 g of the desired product as an off-white solid; MP. 155-157° C.; MS (ES) m/z (relative intensity): 282 (M+H)+ (100).

4) 8-{4-[1-(8-quinolinyl)-4-piperidinyl]-1-piperazinyl}-5-(trifluoromethyl)-quinoline

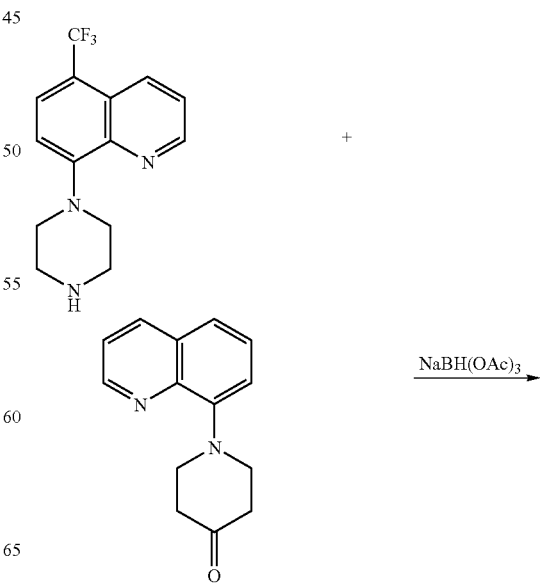

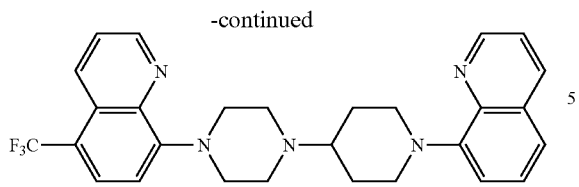

Using the synthetic methods described in previous examples, 5-(trifluoromethyl)-8-(piperazin-1-yl)quinoline (Step 3) and 1-quinolin-8-yl-piperidin-4-one (Example A, Step 5, above) were reacted with sodium triacetoxyborohydride to give the desired product as a white solid; MP. 202-204° C.; MS (ES) m/z (relative intensity) 492 (M+H)+ (100).

V) 5-Methoxy-8-{4-[1-(8-quinolinyl)-4-piperidinyl]-1-piperazinyl}-quinoline (Table 1, #14)

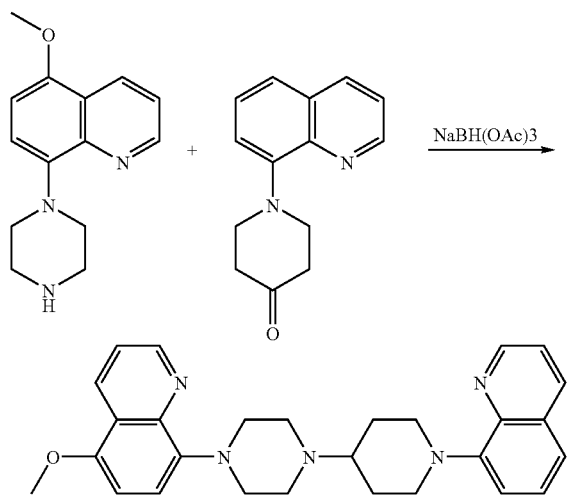

Using the synthetic methods described in previous examples, 5-methoxy-8-(piperazin-1-yl)quinoline (prepared from 2-chloro-5-methoxyaniline using the methodology described for the preparation of Example N, Step 3, above) and 1-quinolin-8-yl-piperidin-4-one (Example A, Step 5, above) were reacted with sodium triacetoxyborohydride to give the desired product as a beige solid; MP. 218-220° C.; MS (ES) m/z (relative intensity) 454 (M+H)+ (100).

X) Preparation of 5-fluoro-8-{4-[4-(8-quinolinyl)-1-piperazinyl]-1-piperidinyl}quinoline (Table 1, #15)

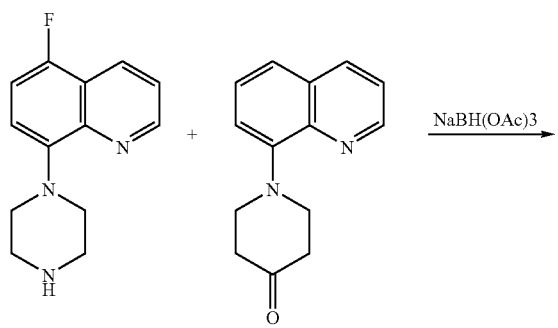

Using the synthetic methods described in previous examples, 5-fluoro 8-(piperazin-1-yl)quinoline (Prepared from commercially available 5-fluoro-8-hydroxyquinoline using the methodology described for Example R, step 3, above) and 1-quinolin-8-yl-piperidin-4-one (Example A, Step 5, above) were reacted with sodium triacetoxyborohydride to give the desired product as a yellow solid; MP. 222-224° C.; MS (ES) m/z (relative intensity) 442 (M+H)+ (100).

Y) 8-{4-[4-(1-Benzofuran-3-yl)-1-piperazinyl]-1-piperidinyl}-6-chloroquinoline (Table 1, #16)

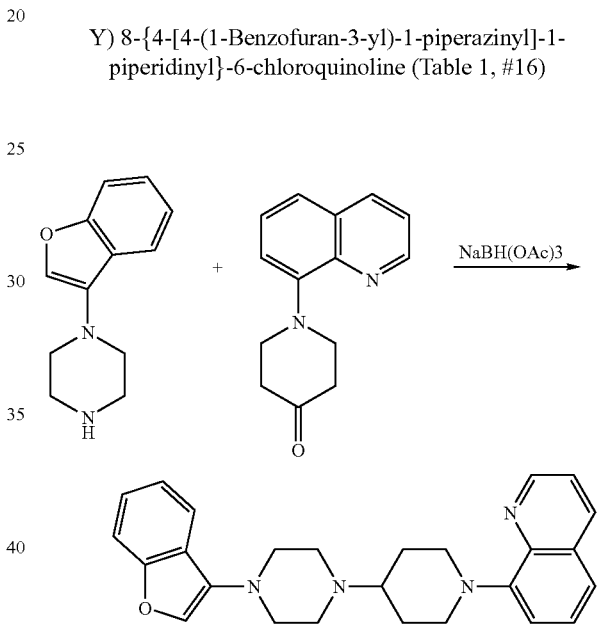

Using the synthetic methods described in previous examples, 1-(1-benzofuran-3-yl)piperazine (Prepared from commercially available benzofuran-3-one using the methodology described for Example F, step 2, above) and 1-quinolin-8-yl-piperidin-4-one (Example A, Step 5, above) were reacted with sodium triacetoxyborohydride to give the desired product as a yellow solid; MP. 86-88° C.; MS (ES) m/z (relative intensity) 447 (M+H)+ (100).

Z) Preparation of 5-fluoro-4-methoxy-8-(4-(4-(6-methoxyquinolin-8-yl)piperazin-1-yl)piperidin-1-yl)-2-(trifluoromethyl)quinoline and Intermediates

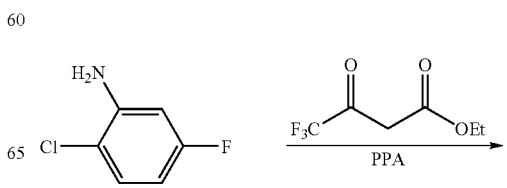

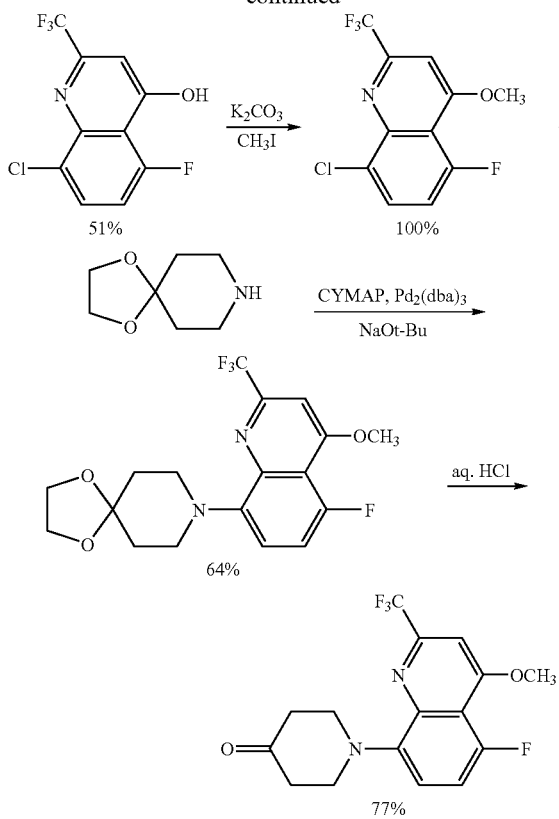

1) 8-Chloro-5-fluoro-2-(trifluoromethyl)quinolin-4-ol

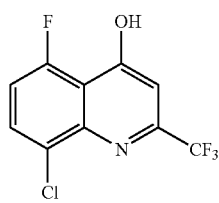

A solution of ethyl 4,4,4-trifluoroacetoacetate (commercially available, 4 mL, 27.3 mmol, 1.05 eq.) in polyphosphoric acid (22 mL) was heated to 100° C. 2-chloro-5-fluoroaniline (3.78 g, 26.0 mmol, 1 eq.) was added slowly to the stirred hot solution. The resulting reaction mixture was further heated to 150° C. and then stirred at that temperature overnight (approximately 18 hours). The reaction was cooled to room temperature and water was added carefully. The resulting light brown precipitate was collected by vacuum filtration, washed with water and dissolved in ethyl acetate. The ethyl acetate solution was washed with brine, dried over anhydrous MgSO₄ and concentrated on a rotary evaporator. The crude product was purified by flash chromatography on silica gel using hexane/ethyl acetate to give 3.54 g (51% yield) of the desired product as an off-white solid; MP=141-142; MS (ES) m/z (relative intensity): 266 (M+H)⁺ (100).

2) 8-Chloro-5-fluoro-4-methoxy-2-(trifluoromethyl)quinoline

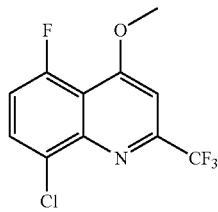

To a solution of 8-Chloro-5-fluoro-2-(trifluoromethyl)quinolin-4-ol (Step 1, 3.54 g, 13.3 mmol, 1 eq.) in acetone (75 mL) was added anhydrous K₂CO₃ (3.88 g, 28.0 mmol, 2.1 eq.), followed by iodomethane (1.8 mL, 28.9 mmol, 2.17 eq.). The resulting mixture was stirred at reflux for 1.5 hours. An additional aliquot of iodomethane (1.8 mL, 28.9 mmol, 2.17 eq.) was added and reflux was continued for an additional 1 hour. The reaction was cooled to room temperature, poured onto ice and extracted with ethyl acetate. The combined organic layers were dried over anhydrous MgSO₄, filtered and concentrated on a rotary evaporator to give 3.72 g (100% yield) of the desired product as a yellow solid, which was used in subsequent reactions without further purification. An analytical sample was prepared by recrystallization from hexane/ethyl acetate; MP=198-200° C.; MS (ES) m/z (relative intensity): 280 (M+H)⁺ (100).

3) 8-(1,4-Dioxa-8-azaspiro[4,5]dec-8-yl)-5-fluoro-4-methoxy-2-(trifluoromethyl)-quinoline To a solution of 8-chloro-5-fluoro-4-methoxy-2-(trifluoromethyl)quinoline (Step 2, 1.24 g, 4.45 mmol, 1 eq.) in anhydrous tetrahydrofuran (44 mL) was added tris(dibenzylideneacetone)-dipalladium(0) (Pd₂(dba)₃, 0.125 g, 0.14 mmol, 0.03 eq.), sodium tert-butoxide (0.69 g, 7.18 mmol, 1.61 eq.), 2-dicyclohexyl-phosphino-2'-(N,N-dimethylamino)biphenyl (CYMAP, 0.054 g, 0.14 mmol, 0.03 eq.), and 1,4-dioxo-8-azaspiro-4,5-decane (0.8 mL, 6.24 mmol, 1.4 eq.). The resulting mixture was stirred at 70° C. overnight (approximately 18 hours) under a nitrogen atmosphere. The reaction was then cooled to room temperature, diluted with ether, filtered through a plug of silica gel and concentrated on a rotary evaporator. The crude product was purified by flash chromatography on silica gel using hexane/ethyl acetate to give 1.09 g (64% yield) of the desired product as a beige solid; MP=101-103° C.; MS (ES) m/z (relative intensity): 387 (M+H)⁺ (100).

4) 1-[5-Fluoro-4-methoxy-2-(trifluoromethyl)quinolin-8-yl]piperidin-4-one

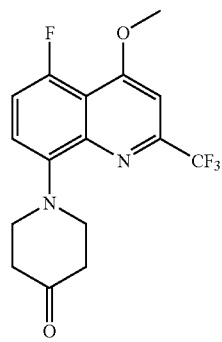

To a solution of 8-(1,4-dioxa-8-azaspiro[4,5]dec-8-yl)-5-fluoro-4-methoxy-2-(trifluoro-methyl)quinoline (Step 3, 0.6 g, 1.56 mmol, 1 eq.) in tetrahydrofuran (20 mL) was added 2N aqueous HCl (6 mL). The resulting mixture was stirred at 70° C. for 5 hours. The reaction was cooled to room temperature, poured into 1N aqueous sodium hydroxide and extracted with ethyl acetate. The combined organic layers were dried over anhydrous Na$_2$SO$_4$, and concentrated on a rotary evaporator. The crude product was purified by flash chromatography on silica gel using hexane/ethyl acetate to give 0.41 g of the desired product as a light yellow solid; MP=171-173 C; MS (ES) m/z (relative intensity): 343 (M+H)$^+$ (100).

5) 5-fluoro-4-methoxy-8-(4-(4-(6-methoxyquinolin-8-yl)piperazin-1-yl)piperidin-1-yl)-2-(trifluoromethyl)quinoline trihydrochloride

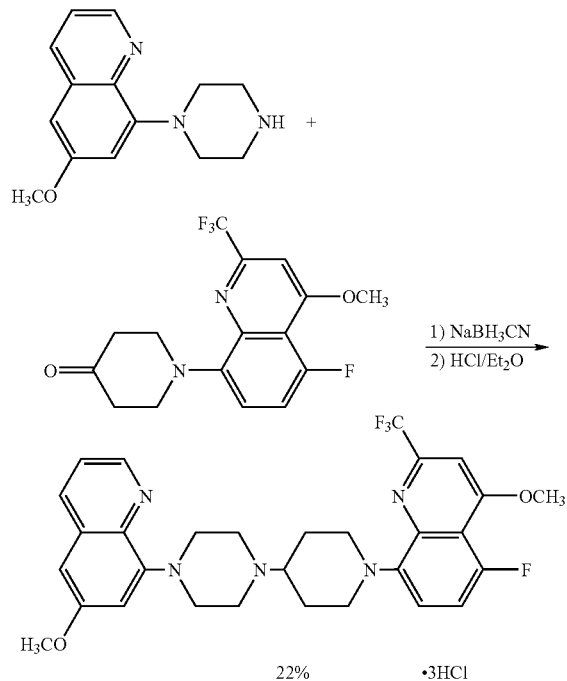

To a solution of 1-[5-fluoro-4-methoxy-2-(trifluoromethyl)quinolin-8-yl]piperidin-4-one (Step 4, 0.31 g, 0.9 mmol, 1 eq.) and 6-methoxy-8-(1-piperazinyl)quinoline (Example A, Step 4, 0.30 g, 1.23 mmol, 1.37 eq.) in anhydrous methanol (20 mL) was added sodium cyanoborohydride (0.103 g, 1.64 mmol, 1.82 eq.). The resulting mixture was stirred overnight at room temperature under nitrogen (app. 18 hr). An additional aliquot of sodium cyanoborohydride (0.10 g, 1.59 mmol, 1.76 eq.) was added and stirring at room temperature was continued overnight. The resulting reaction mixture was poured into brine and extracted with ethyl acetate. The organic layer was dried over anhydrous sodium sulfate and concentrated on a rotary evaporator to a yellow oil. The desired product was isolated by chromatography on a 40 g silica column (1000 mL 20% acetone in hexane followed by 500 mL 30% acetone in hexane) as a yellow solid (0.113 g, 22% yield). The free base was converted to its trihydrochloride sesquihydrate salt by dissolving it in dichloromethane (3 mL), adding diethyl ether (9 mL), cooling in an ice bath and adding 1M HCl/Et2O (1 mL). The resulting yellow solid was collected by vacuum filtration, washed with ether and dried in vacuo to give 0.152 g. MS (ES) m/z (relative intensity): 570 (M+H)$^+$ (100).

AA) Preparation of 5-fluoro-8-(4-(4-(6-methoxyquinolin-8-yl)piperazin-1-yl)piperidin-1-yl)quinoline trihydrochloride dihydrate

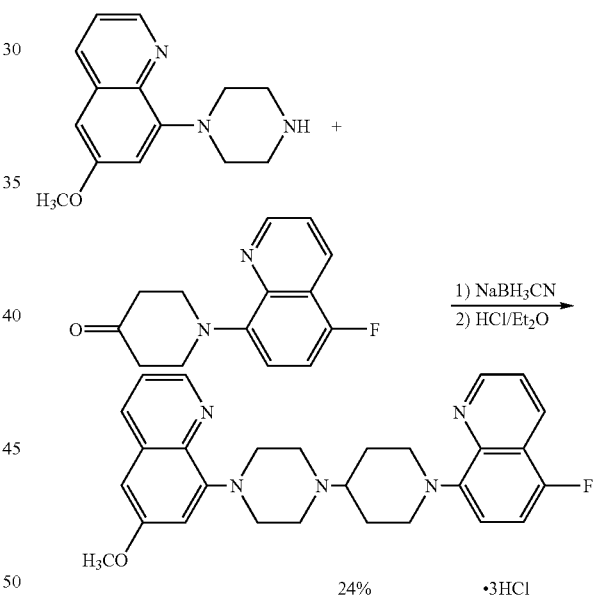

0.25 g (0.001 mol) of 1-(5-fluoro-quinolin-8-yl)-piperidin-4-one (Example C, Step 3) and 0.25 g (0.001 mol) of 6-methoxy-8-piperazin-1-yl-quinoline (Example A, Step 4) were stirred in 20 mL of anhydrous methanol. 1.1 eq, (0.07 gm) of sodium cyanoborohydride was added and the reaction was stirred at room temperature for eighteen hours. The reaction mixture was concentrated on a rotary evaporator and the residue was taken up in ethyl acetate and washed with water. The organic layer was dried over anhydrous sodium sulfate, filtered and concentrated on a rotary evaporator. The desired product was obtained by flash chromatography on silica gel column using ethyl acetate and converted to the trihydrochloride salt using methanolic HCl to yield 0.15 gm (24%) of the title compound as a yellow solid. Mp: 200-202° C.; MS (ES) m/z (relative intensity): 472 (M+H)+ (100).

BB) Preparation of 5-Fluoro-8-(4-(4-(6-methoxyquinolin-8-yl)piperazin-1-yl)piperidin-1-yl)-quinoline and Intermediates

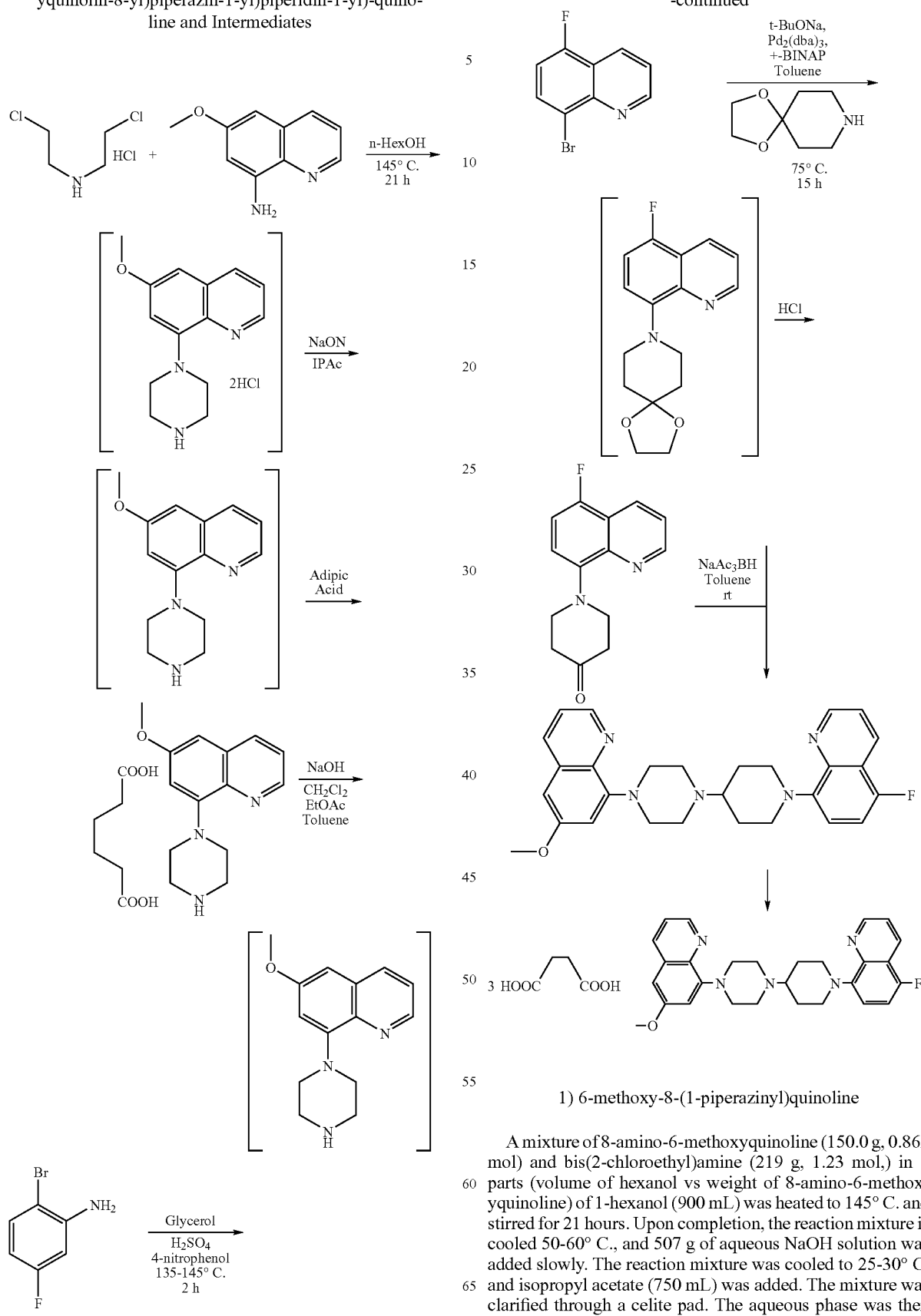

1) 6-methoxy-8-(1-piperazinyl)quinoline

A mixture of 8-amino-6-methoxyquinoline (150.0 g, 0.862 mol) and bis(2-chloroethyl)amine (219 g, 1.23 mol,) in 6 parts (volume of hexanol vs weight of 8-amino-6-methoxyquinoline) of 1-hexanol (900 mL) was heated to 145° C. and stirred for 21 hours. Upon completion, the reaction mixture is cooled 50-60° C., and 507 g of aqueous NaOH solution was added slowly. The reaction mixture was cooled to 25-30° C. and isopropyl acetate (750 mL) was added. The mixture was clarified through a celite pad. The aqueous phase was then split off. The organic solution was treated with a slurry of adipic acid (126 g, 0.862 mol) in isopropyl acetate (250 ml). The resulting mixture was stirred for 16 hours to form 6-methoxy-8-(1-piperazinyl)quinoline adipate salt. The adipate salt was filtered and washed with isopropyl acetate (2×150 ml) and dried by nitrogen flow to give adipate of 6-Methoxy-8-piperazin-1-yl-quinoline (186 g, 55% yield) with ~97% HPLC area, 88% strength purity in 51% yield.

The salt can be recrystallized from a mixture of methanol and isopropyl acetate if further purification is required. To purify the adipate salt, 580 g of the crude adipate salt and 2.8 liter of methanol were mixed and heated to 65° C. and a dark solution was obtained. To this solution was charged slowly 1.1 liter of isopropyl acetate over 40 min at about 63° C. The mixture was stirred at about 63° C. for about 1 h and cooled to 0-5° C. After stirring at 0-5° C. for 2 hours, the mixture was filtered and washed with 300 ml of isopropyl acetate and dried with airflow. Yield, 395 g, 68.1% recovery yield.

To liberate 6-methoxy-8-(1-piperazinyl)quinoline from its adipate salt, 100 g (0.257 mol) of the adipate salt was added into a 2-L reactor followed by the addition of 500 ml of dichloromethane. To this mixture was added 100 g of water followed by the slow (in about 15 min) addition of 41 g of 50% sodium hydroxide solution to maintain the pH in the 13-14 range, adding sodium hydroxide solution as necessary if the pH is below 10. The organic bottom layer was separated and filtered through a pad of activated basic aluminum oxide (100 g, 6.5 cm diameter×3 cm depth). The pad was washed with 100 ml of isopropyl acetate twice. The dichloromethane was replaced by toluene by distillation under vacuum (450 to 500 mm Hg) while 3×150 ml of toluene was added into the reactor until the final volume was about 135 ml. Some white solid precipitated after distillation, the solid was removed by filtration, the filter cake was washed with 50 ml of toluene. Final volume, 185 ml, purity 97.56%, solution strength 27.4%)

2) 8-bromo-5-fluoroquinoline

To a 2-L reactor equipped with a mechanic agitator, a condenser, a thermocouple, a baffle, and nitrogen inlet were charged 228 g of water, 200 g of 2-bromo-5-fluoroaniline and 80 g of 4-nitrophenol. To this mixture was charged 96% sulfuric acid in 10-30 min at 20-120° C. The mixture was heated to 135-140° C. and 194 g of glycerol was charged into the reactor over two hours at 135-145° C. The mixture was held at 135-145° C. for 1 hour after the addition. The reaction mixture was cooled to below 20-50° C. and slowly transferred to a 5-L reactor containing 1100 g of water and 1210 g of toluene. The 2-L reactor was washed with 300 g of water and the wash was combined into the 5-L reactor. The pH of the contents in the 5-L reactor was adjusted to pH 8-10 by adding approximately 1233 g (1370 mL) ammonium hydroxide (28-30% $NH_3$) at 20-40° C. The mixture was stirred at room temperature for 15 min and the solid by-product was filtered off while the filtrate was retained. The filter cake was washed with 400 ml of toluene and the all the filtrate was combined and charged a 3-L reactor. About 500 ml of 8.5% KOH solution was charged into the 3-L reactor and stirred for 10 min and bottom aqueous layer was spit off. A second portion of 500 ml of 8.5% KOH solution was added and the mixture was stirred for 15 min and the bottom aqueous layer was split off. Water 500 ml was added and stirred for 15 min before the bottom aqueous layer was split off. The organic layer was heated to distill off about 100-200 ml of toluene to azeotropically remove water. A clear solution will be obtained. Typical yield 178 g real 8-bromo-5-fluoroquinoline, ~75%.

Alternatively, 8-bromo-5-fluoroquinoline was prepared by adding a warm mixture containing 2-bromo-5-fluoroaniline (100 g, 1.0 eq), 4-nitrophenol (40 g, 0.54 eq), and glycerol (97 g, 2.0 eq) over 1.5 hours to sulfuric acid (267 ml) and water (114 mL) at 140-150° C. The initial mixture showed 37.8% 4-nitrophenol by relative HPLC area %. Samples showed 4.7% 4-nitrophenol immediately after adding 50% of mixed starting materials and 5.0% immediately after adding all of the materials. The yield upon workup was 87.5%, with total impurities 0.29%. Addition of less (0.46 eq, 34 g) 4-nitrophenol also successfully produced the intermediate of interest at acceptable yield.

3) 1-(5-fluoroquinolin-8-yl)piperidin-4-one

To a 5-L jacketed cylindrical reactor equipped with an impeller-style agitator, condenser, thermocouple, and vacuum/nitrogen inlet was charged 2-L, 15% toluene solution of 8-bromo-5-fluoroquinoline, 209 g of 1,4-Dioxa-8-azaspiro [4.5]decane. Meanwhile in a 500-mL Erlenmeyer flask, a suspension of 16.5 g (26.5 mmol)±-[1,1'-binaphthalene]-2,2'-diylbis[diphenyl-Phosphine, and 6.08 g (6.64 mmol) tris[µ-[(1,2-η:4,5-η)-(1E,4E)-1,5-diphenyl -1,4-pentadien-3-one]] dipalladium in 260 g of toluene was prepared. This freshly made suspension was charged into the 5-L reactor followed by a rinse of 170 g of toluene. 166 g sodium tert-butoxide was then charged into the reactor followed by a rinse with 430 g of toluene. The reactor was degassed by vacuum to less than 125 mmHg and then filled with nitrogen to atmosphere three times. The mixture was then heated to 50-60° C. and stirred for 1 h and then heat to 65-75° and stirred at this temperature for about 10 hours. The mixture was cooled to 40-50° C. and then quenched with 800 g of water. The lower aqueous layer was split off and the volume of the organic layer was reduced to about 1.5 L by vacuum distillation. To this residual was charged 2.28 kg of 20% sulfuric acid at 25-30° C. The mixture was stirred for an hour and was clarified by filtration and a bi-phase filtrate was obtained. The aqueous phase was split and retained. Toluene 870 g was added to the aqueous solution and the mixture was neutralized by slowly adding 770 g 50% sodium hydroxide solution. The lower aqueous layer was split off and extracted with 600 g of toluene. The organic layers were combined and the volume of the reaction was reduced to about 1 L by vacuum distillation. The residue was cooled to room temperature and 480 g of toluene was charged. The mixture was heated to 45-55° C. to form a clear solution, which was filtered through a celite/charcoal pad to remove palladium. The filtrate was concentrated by vacuum distillation to about 0.7 L and diluted with 620 g heptane, cooled to −15 to −5° C. to form a slurry. The solid was collected by filtration. The product was dried by air flow at room temperature. Typical yield is about 70%.

4) 5-fluoro-8-{4-[4-(6-methoxyquinolin-8-yl)piperazin-1-yl]piperidin-1-yl}quinoline Toluene (118 g), sodium triacetoxyborohydride (44.5 g) were mixed at 0° C. to room temperature. To this mixture was charged a premixed toluene solution of 6-methoxy-8-(1-piperazinyl)quinoline (Step 1, 160 g, 27.4 wt % in toluene) and 1-(5-fluoroquinolin-8-yl)piperidin-4-one (Step 3, 41 g). The resulting mixture was stirred for 2 to 3 hours at about 30° C. KOH solution (443 g 9% in water) was charged to quench the residual sodium triacetoxyborohydride. Heptane (118 g) was added to further precipitate the product. The product was then filtered and washed with ethanol (2×100 ml).Yield 68 g, 86%. This crude product (67 g) was dissolved in 586 g dichloromethane and passed through a charcoal/celite pad to remove palladium. The dichloromethane was distilled off while 400 g of ethanol was slowly added at the same time. The resulting slurry was filtered and washed with ethanol twice (65 g+100 g). The product was dried in oven at 55° C. overnight. Purification recovery yield 59.9 g, 89.4%.

CC) 6-methoxy-8-(1-piperazinyl)quinoline

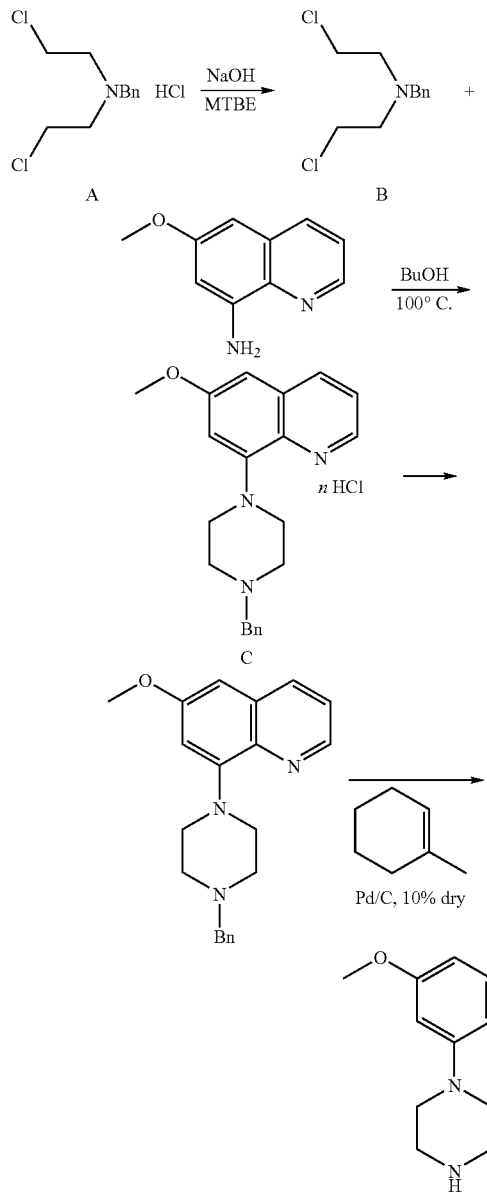

6-methoxy-8-(1-piperazinyl)quinoline (Example P, Step 1) is also prepared as shown in the reaction scheme above. To a 2 L reactor equipped with a mechanic stirrer, an addition funnel, a thermocouple, nitrogen inlet and a bottom outlet was added 442 g of water, 134.5 g (0.5 mol) compound A and 177 g methyl tert-butyl ether. To this mixture was slowly added 125 ml 5 N sodium hydroxide in 20 min. The mixture was stirred for 10 min and the aqueous layer was split off. The organic layer was washed with 20% aq sodium chloride solution twice (2×200 g). The methyl tert-butyl ether was distilled off and the product was obtained as an oil, crude yield: 117 g~100% yield (still containing trace amount solvent).

To a 1-L reactor a mechanic stirrer, a thermocouple, and nitrogen inlet was charged with 380 g of butanol, 42 g of 8-amino-6-methyoxyquinoline, and 97 g of compound B (nor-mustard free amine). The mixture was heated to 100° C. for 18 hours before cooled to 0-5° C. The solid was formed upon cooling and was filled with nitrogen protection (solid is hygroscopic). The filter cake was washed with 100 g cold butanol and 2×200 g of MTBE. The solid was dissolved in 160 g of water to obtain an orange solution. This orange solution was slowly charged into a 2-L reactor containing a potassium hydroxide solution prepared with 537 g water and 60 g 45% KOH. The product was precipitated upon addition into the base. The slurry was stirred for 1 h and then filtered. The filter cake was washed with 100 g water, 100 g MeOH and 100 g methyl tert-butyl ether. The product was dried under vacuum at 50° C. Weight=48.2 g, 60%

To a 100 ml flask equipped with a stirrer, a thermocouple, a condenser and nitrogen inlet was charged ethanol (2B) 27 g, compound C (2 g), methylcyclohexene (10 g) and 0.6 g of dry 10% palladium on carbon. The mixture was heated to reflux for 30 h and cooled to ambient temperature. The palladium on carbon was filtered off, the solvent was removed by rotavap, and the resulting compound isolated (weight 1.7 g (>100%, the product contained small amount of solvent)).

DD) 1-(5-fluoroquinolin-8-yl)piperidin-4-one

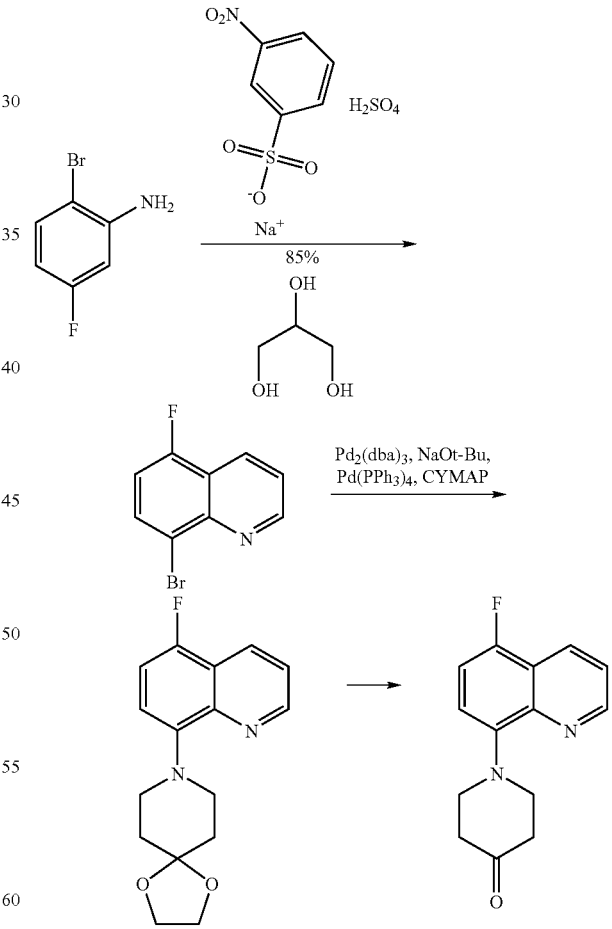

1-(5-fluoroquinolin-8-yl)piperidin-4-one (Example P, Step 3) is also prepared as shown in the reaction scheme above. To a 500 ml flask equipped with a stirrer, a thermocouple, a condenser and nitrogen inlet were charged 50 g 2-bromo-5-fluoroaniline and 60 g glycerol. The mixture was heated to 60° C. and 55 g nitrobenzene sulfonic acid was charged in portion. The mixture was then heated to 100-110° C., started charge 200 ml 70% sulfuric acid. After sulfuric acid addition, the mixture was heat to 130° C. and stirred for 3 hours before cooled to room temperature. Water (300 g) was added and a grayish by product was filtered off. The filtrate was slowly added into a 2-L reactor containing a mix of 420 g 50% NaOH, 420 g of water, 352 g methyl tert-butyl ether. After filtering off small amount solid, the aqueous layer was split off and the organic layer was washed with 10% NaOH (2×100 ml), 20% NaCl (2×200 ml), the solvent was removed, weight 56 g, 89.8%.

To a 2-L reactor with a stirrer, a thermocouple, a condenser and nitrogen inlet were charged 8-bromo-5fluoroquinoline (50 g), tetrahydrofuran (795 g), Pd2(dba)₃ (3.78 g), Cymap (1.6 g), and 1,4-Dioxa-8-azaspiro[4.5]decane (47.3 g). the mixture was heated to reflux (66° C.) and the reaction was complete. The reaction mixture was quenched into a 5 L reactor containing 1000 g of water and 640 g of MTBE. The bottom aqueous layer was split off and the organic layer was washed with 5% NaOH (1120 g) and 20% NaCl (2×100 g). The solvent was evaporated, weight 87 g vs 79.4 g by theory.

The remaining steps are as described above in Example P, Step 3.

DD) Preparation of 6-methoxy-8-[4-(1-(5-fluoro)-quinolin-8-yl-piperidin-4-yl)-piperazin-1-yl]-quinoline trisuccinate salt (Polymorph Form A)

6-Methoxy-8-[4-(1-(5-fluoro)-quinolin-8-yl-piperidin-4-yl)-piperazin-1-yl]-quinoline (1.5089 g) was slurried in 100 mL of dichloromethane (99.8% HPLC) to obtain a clear light yellow solution of free base. Succinic acid (99%; 258.6 mg) was dissolved in 17 mL of acetone (99% HPLC). Then 15.275 mL of the succinic acid solution was added to 20 mL of the free base solution slowly. No immediate precipitation was observed. The resulting solution was allowed to evaporate to dryness at room temperature. The solid was analyzed by powder X-ray diffraction and found to be crystalline having Form A.

EE) Preparation of 5-Fluoro-4-methoxy-8-(4-(4-(6-methoxy-quinolin-8-yl)-piperazin-1-yl)-piperidin-1-yl)-2-trifluoromethyl-quinoline disuccinate salt

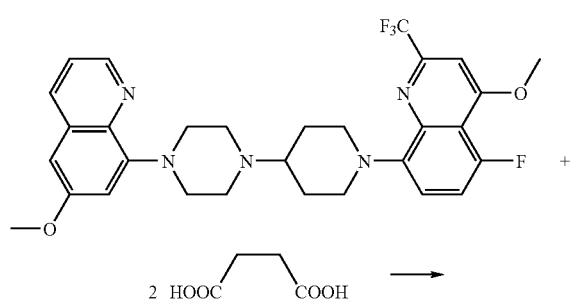

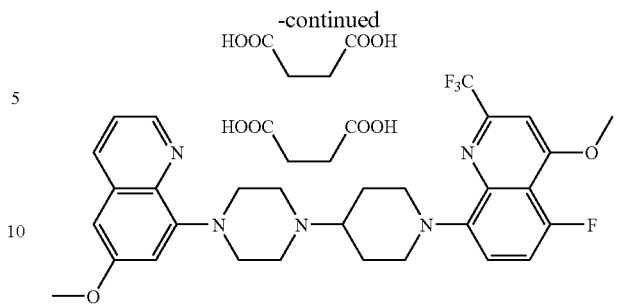

The free base of 5-fluoro-4-methoxy-8-(4-(4-(6-methoxy-quinolin-8-yl)-piperazin 1-yl)-piperidin-1-yl)-2-trifluoromethyl-quinoline was prepared as described in Example Z. This compound was further isolated by conversion to a disuccinic acid. To a 12-L reactor equipped with heating mantle, thermocouple and nitrogen inlet were charged 124 g of succinic acid and 2470 g of acetone. The mixture was heated to 50° C. and a colorless solution was formed. Meanwhile, in a 3-L flask were charged 240 g of 5-fluoro-4-methoxy-8-(4-(4-(6-methoxy-quinolin -8-yl)-piperazin-1-yl)-piperidin-1-yl)-2-trifluoromethyl-quinoline and 2250 g of tetrahydrofuran (THF). 5-Fluoro-4-methoxy-8-(4-(4-(6-methoxy-quinolin-8-yl)-piperazin-1-yl)-piperidin-1-yl)-2-trifluoromethyl-quinoline in THF mixture was heated to 50° C. and a yellow solution was achieved. This yellow solution was slowly (over the course of about 3 hours) charged into the 12-L reactor while maintaining both solutions at a temperature of about 50° C. The resulting slurry was stirred over night at room temperature, and then cooled to 5-10° C. After stirring at 5-10° C. for 2 hours, the slurry was filtered and the product was washed with acetone 3×600 ml. The product was dried with airflow at room temperature for 3 hours.

The weight of the resulting product was 311 g, or about 91.6% yield. NMR analysis indicated that the compound was the disuccinate salt form of 5-fluoro-4-methoxy-8-(4-(4-(6-methoxy-quinolin-8-yl)-piperazin-1-yl)-piperidin-1-yl)-2-trifluoromethyl-quinoline. In addition, residual solvents were found at concentrations of 0.047% for acetone, 0.027% for THF, and 0.14% for water.

BIOLOGICAL ASSAYS AND PROCEDURES

Novel Object Recognition Model

Male Long-Evans hooded rats (~200 g at the time of testing) were individually housed with ad libitum access to food and water. Novel object recognition (NOR) training and testing was performed in a circular field (diameter ~70 cm, 30 cm high) constructed out of plastic and containing soiled bedding (without feces). The field was surrounded by black curtains to mask extra-field cues and was located in a dimly lit room (~10 lux at the level of the area) in the presence of white noise (~65 dB). Animal performance was tracked by video and monitored by an experimenter located outside of the testing room. Objects, constructed with Duplo® (Lego), could be affixed to the floor in one of four locations spaced evenly around the field approximately 10 cm from the field's edge. To avoid possible olfactory cues, multiple copies of the objects were used throughout the study and were cleaned with a 30% ethanol solution between animals.

The visual recognition task was divided into 3 sessions—habituation, a sample trial and a choice trial. During habituation the animals were placed into the field containing 2 identical yellow cubes (~10 cm×10 cm×10 cm) and were allowed to explore the field for ten minutes. Following habituation, rats were returned to their home cage. One day after habituation, animals were dosed with a test compound and following the pretreatment interval the sample trial was initiated. During the sample trial, rats were allowed to explore the field, now containing two identical stimuli (complex, multicolored, Duplo objects; ~10 cm×10 cm×10 cm) located at opposing compass points, for 5 minutes. The amount of time investigating the objects was recorded for the entire trial. Investigation was defined as orientation toward the object with the nose of the rat within <2 cm of the object. Following the sample trial rats were returned to their home cages for the 48 hour inter-trial interval and then tested in the choice trial for recognition memory. The choice trial consisted of a 5 minute exploration of the field containing both a familiar, previously explored, object and a novel object with an investigator again recording contact time. The location of the objects, counterbalanced across treatment groups, remained constant for each animal during the habituation, sample and choice trials.

The effect of treatment on object exploration during trial one was examined using a one-way ANOVA on total contact time followed by Fisher's LSD group mean pair-wise comparisons. The amount of time exploring the novel and familiar objects across treatment groups was analyzed using a repeated measures ANOVA followed by Fisher's LSD post-hoc comparisons. Significantly more time spent exploring the novel object than the familiar one represents intact recognition memory for that treatment group. Control and untreated animals show no significant differences between familiar and novel object exploration following the 48 hour delay indicating no memory for the sample trial (significant differences are evident with shorter delays).

Treatments: Animals were treated with a compound of the invention 60 minutes prior to the sample trials. Each candidate compound was dissolved in the appropriate vehicle and administered orally at 1 ml/kg.

Representative compounds of the invention were tested according to the protocol described. In these experiments, a positive effect of a compound on recognition memory is demonstrated by animals spending significantly more time exploring the novel object than the familiar one. It was found that the tested compounds had a positive effect on recognition memory. Doses of the representative compounds of the invention that were identified as having a positive effect in this assay were dosed at 0.3-10 mg/kg p.o., with 10 mg/kg p.o. being the highest dose tested. These data demonstrate that selected compounds of the invention are useful for improving recognition memory, and that the protocol is suitable for identifying compounds that have a positive effect on recognition memory.

Synergy of Test Compounds with Acetylcholinesterase Inhibitors

Acetylcholinesterase inhibitors are currently used to treat mild cognitive deficits resulting from Alzheimer's disease. However, the use of acetylcholinesterase inhibitors is hindered by the side effects often seen with this class of therapeutic agent, and have limited efficacy. Representative compounds of the invention were shown to have a synergistic effect on the cognitive enhancing properties of a representative acetylcholinesterase inhibitor, Aricept®, lowering the dose of both agents required to obtain efficacy in the Novel Object Recognition Model.

Novel Object Recognition Model: The Novel Object Recognition Model was employed as described above. Sub-threshold doses (doses that did not provide a positive effect on recognition memory) of Aricept® and representative compounds of this invention were administered to test animals and their effects on recognition memory were recorded as described above.

Treatments: Animals were treated with a compound of the invention 60 minutes prior to the sample trials. Each candidate compound was dissolved in an appropriate vehicle and administered orally. The same animals were then treated with Aricept® 30 minutes prior to the sample trials. Aricept® was dissolved in an appropriate vehicle and administered intraperitoneally.

Animals were separately administered sub-threshold doses of Aricept® (0.5 mg/kg i.p.) or a representative compound of the invention (0.1 mg/kg p.o.). When administered separately, the contact times for the animals in the familiar and novel environments were not statistically different ($P<0.05$). Co-administration of Aricept® and the each of candidate compounds at the same doses used in the separate administration test for each agent resulted in a statistically significant decrease in the contact time for the familiar environment compared to the novel environment ($P<0.05$). The decrease in contact time averaged more than 10 seconds. These data suggest co-administration of a representative compound of the invention and a cognitive enhancer resulted in a positive effect of recognition memory, as demonstrated by the animals spending significantly more time exploring the novel object than the familiar one. These data demonstrate that this test is effective in identifying a synergistic effect between representative compounds and cognitive enhancers to enhance cognition.

Treatment of Sexual Dysfunction

An animal model was used to demonstrate the utility of treating or preventing sexual dysfunction, e.g., sexual dysfunction associated with SSRI treatment, with compounds of this invention. The animal model is based on the finding that sexually experienced rats that are administered an SSRI, a drug used to treat certain conditions such as depression, display a reduction in the number of non-contact penile erections. SSRI treatment is associated with sexual dysfunction in human subjects. In general, the animal model exposes sexually experienced male rats (Sprague-Dawley rats) to female rats in estrous in a novel testing arena that is not the regular housing environment. The number of non-contact penile erections is assayed over a specified test period, e.g., 30 minutes (Sukoff, Rizzo, et al., 2006, Society for Neurosci. Abstr. 559.4; U.S. Application Ser. No. 60/682,3379, filed May 19, 2005). In the experiments described herein, animals were generally treated either with 0.9% saline (vehicle) or a drug (i.e., a compound of the invention) in the vehicle.

The ability of fluoxetine, an SSRI associated with sexual dysfunction in humans, to cause sexual dysfunction in the animal model was tested by examining a 10 mg/kg dose of fluoxetine or vehicle alone (0.9% saline), each administered intraperitoneally, once daily for 14 days, on the number of non-contact penile erections over a 30 minute trial period. Fluoxetine produced a decrease in sexual function under these experimental conditions compared to treatment with vehicle alone. These data demonstrate that sexual dysfunction is induced in the animal model using SSRIs, thereby providing support for the validity of using the animal model.

To examine the time course of the effects of a drug that causes sexual dysfunction, rats that were handled and tested as described above were treated acutely: rats were treated with vehicle for 6 days, and on the test day (day 7) instead of vehicle, the animals received a single dose of fluoxetine in vehicle (i.p.). For a subchronic (7 day) study, fluoxetine was administered each day for 7 days and the animals were evaluated on test day 7. For the chronic 14 day study, fluoxetine was administered each day for 14 days and the animals were tested on day 14. Each fluoxetine dose was 10 mg/kg in vehicle and was delivered i.p. on each of the test days as described above. The testing session for each section of the study was begun immediately following compound administration and the behavior observed for 30 minutes immediately following the drug administration.

It was found that both a sub-chronic and chronic administration of fluoxetine were associated with a significant increase in sexual dysfunction, further demonstrating the utility of the animal model for sexual dysfunction testing.

To test the ability of the compounds of this invention to ameliorate the effects of sexual dysfunction, sexually experienced rats were administered fluoxetine using a subchronic (7 day) or chronic (14 day) schedule and then tested for sexual function as described above. A single acute dose of a test compound given intraperitoneally after 7 or 14 days of fluoxetine ameliorated sexual dysfunction as demonstrated by the compound's ability to significantly reverse the fluoxetine-induced decrease in non-contact penile erections. Doses of selected test compounds of the invention that were effective in this model were 0.1-1 mg/kg i.p., with 1 mg/kg i.p. being the highest dose tested.

To further test the ability of compounds described herein to ameliorate the effects of sexual dysfunction, sexually experienced rats were co-administered fluoxetine (10 mg/kg i.p.) and selected compounds of the invention once daily for 14 days and then tested for sexual function as described above. Chronic dosing of the selected compounds of this invention ameliorated the sexual dysfunction induced by chronic dosing of fluoxetine, as demonstrated by the compound's ability to significantly reverse the fluoxetine-induced decrease in non-contact penile erections. Doses of the selected test compounds that were effective in this model were 0.3-1 mg/kg i.p., with 1 mg/kg i.p. being the highest dose tested.

These data demonstrate this test is successful in identifying compounds that can be used to treat sexual dysfunction associated with treatment with antidepressants (e.g., SSRI's). Moreover, these data demonstrate the test is useful for identifying compounds that are efficacious for treating sexual dysfunction, e.g., that is associated with antidepressant treatment, whether the treatment with the test compound is initiated at the same time as antidepressant treatment (e.g., SSRI treatment) or when the treatment with the test compound is provided after initiation of treatment with the antidepressant. Further, these data demonstrate that the candidate compounds tested ameliorated sexual dysfunction associated with treatment with antidepressants (e.g., SSRI'S) and suggest the candidate compounds are efficacious for treating sexual dysfunction.

Enhancement of SSRI Activity

SSRIs are currently used to treat depression in humans. They are thought to exert their antidepressant effect by increasing serotonin levels in the brain. One liability of SSRIs is a delay between initiation of drug treatment and onset of antidepressant action, which can be 2-4 weeks. This delay in onset of action is thought to be associated with an acute stimulation of pre-synaptic 5-$HT_{1A}$ autoreceptors induced by the elevated levels in serotonin (which result from inhibition of serotonin re-uptake). These autoreceptors are responsible for controlling serotonin release, responding to elevated serotonin levels by inhibiting neurotransmitter release. The 2-4 week delay is thought to be the time required for these autoreceptors to become desensitized. A 5-$HT_{1A}$ antagonist that acts to block the pre-synaptic autoreceptor would be expected to inhibit the contribution of these autoreceptors to acute serotonin levels. The result should be an acute, sustained increase in serotonin levels and a reduction in the onset of SSRI drug action.

The ability of the compounds of this invention to reduce time for onset of action of the representative SSRI fluoxetine was assessed using in vivo microdialysis. Using 2-3% halothane anesthesia (Fluothane; Zeneca, Cheshire, UK), male Sprague-Dawley rats (280-350 g; Charles River, Wilmington, Mass.) were secured in a stereotaxic frame with ear and incisor bars (David Kopf, Tujunga, Calif.) while a microdialysis guide cannula (CMA/12, CMA Microdialysis, Sweden) was directed above the dorsal lateral frontal cortex (A/P+ 3.2 mm, M/L–3.5 mm, D/L–1.3 mm). Coordinates were taken with a flat skull using the rat brain atlas of Paxinos and Watson (1986). The guide cannula was secured to the skull with two stainless-steel screws (Small Parts, Roanoke, Va.) and dental acrylic (Plastics One, Roanoke, Va.). Following a 24 h post-operative recovery, animals were individually housed in Plexiglas cages (45 $cm^2$) where they had free access to water and standard rat chow.

For in vivo neurochemical experiments, a microdialysis probe (CMA/12; active membrane length 2 mm; OD 0.5 mm; 20 kD cut-off) was pre-washed with artificial CSF (aCSF; 125 mM NaCl, 3 mM KCl, 0.75 mM $MgSO_4$ and 1.2 mM $CaCl_2$, pH 7.4) according to the manufacturers specifications. On the morning of the study, probes were inserted, via the guide cannula, into the frontal cortex and perfused with aCSF at 1 μl/min. Following a 3 hour stabilization period, three control samples (20 μl) were collected to establish a steady baseline. Immediately following the last baseline sample, animals were treated with the compound of the invention (10 mg/kg p.o. in 2% Tween™, 0.5% methyl cellulose, using a dose volume of 1 ml/kg). Thirty minutes later rats were dosed with vehicle or fluoxetine (30 mg/kg s.c.). Subsequent microdialysis samples were collected for 3 h post-injection and analyzed for 5-HT content by high performance liquid chromatography (HPLC). The HPLC conditions have been described previously (Beyer et al, *J Psychopharmacol.* 16(4): 297-304 (2002)). All neurochemical data were acquired using the Atlas software package (Thermo Labsystems, Beverly, Mass.) and compared to an external standard curve. The fmol concentrations of all neurotransmitters during the baseline samples were averaged and this value denoted as 100%. Subsequent sample values were expressed as a percent change from this preinjection baseline value (or % change from baseline). Neurochemical data, excluding preinjection values, were analyzed by a two-way analysis of variance (ANOVA) with repeated measures (time). Post-hoc analyses were made using the Bonferroni/Dunns adjustment for multiple comparisons.

Acute treatment with fluoxetine did not increase serotonin levels in the frontal cortex of text animals. However, co-administration of representative compounds of the invention caused a significant increase in fronatal cortex serotonin levels. Representative compounds of this invention had no effect on frontal cortex serotonin levels when administered. Doses of representative compounds of this invention that were effective in enhancing the effect of acute fluoxetine treatment were 3-10 mg/kg p.o., with 10 mg/kg p.o. being the highest dose tested. These data demonstrate this test is effective in identifying compounds of the invention that are able to shorten the time to onset of action for SSRIs.

Cell line

The PCR cloning of the human 5-HT$_{1A}$ receptor subtype from a human genomic library has been described previously (Chanda et al., *Mol. Pharmacol.*, 43:516 (1993)). A stable Chinese hamster ovary cell line expressing the human 5-HT$_{1A}$ receptor subtype (5-HT$_{1A}$.CHO cells) was employed throughout this study. Cells were maintained in DMEM supplemented with 10% fetal calf serum, non-essential amino acids and penicillin/streptomycin.

Radioligand Binding

Radioligand binding assays were performed as described in Dunlop, J. et al., *J. Pharmacol. and Toxicol. Methods* 40: 47-55 (1998), which is incorporated by reference. Cells were grown to 95-100% confluency as a monolayer before membranes were harvested for binding studies. Cells were gently scraped from the culture plates, transferred to centrifuge tubes, and washed twice by centrifugation (2000 rpm for 10 min., 4° C.) in buffer (50 mM Tris; pH 7.5). The resulting pellets were aliquoted and placed at −80° C. On the day of assay, the cells were thawed on ice, and resuspended in buffer. Studies were conducted using [$^3$H]8-OH-DPAT as the radioligand. The binding assay was performed in 96 well microtiter plates in a final total volume of 250 µL of buffer. Competition experiments were performed by using seven different concentrations of unlabelled drug and a final ligand concentration of 1.5 nM. Non-specific binding was determined in the presence of 10 µM 5HT. Saturation analysis was conducted by using [$^3$H]8-OH-DPAT at concentrations ranging from 0.3-30 nM. Following a 30 minute incubation at room temperature, the reaction was terminated by the addition of ice cold buffer and rapid filtration using a M-96 Brandel Cell Harvester (Gaithersburg, Md.) through a GF/B filter presoaked for 30 minutes in 0.5% polyethyleneimine. Table 1 provides Ki values for the tested compounds.

cAMP Measurements

Measurements were performed as described in Dunlop, J. et al., supra. Assays were performed by incubating the cells with DMEM containing 25 mM HEPES, 5 mM theophylline and 10 µM pargyline for a period of 20 minutes at 37° C. Functional activity was assessed by treating the cells with forskolin (1 uM final concentration) followed immediately by test compound (6 different concentrations) for an additional 10 minutes at 37° C. In separate experiments, 6 concentrations of antagonist were preincubated for 20 min prior to the addition of 10 nM 8-OH-DPAT and forskolin. The reaction was terminated by removal of the media and addition of 0.5 ml ice cold assay buffer. Plates were stored at −20° C. prior to assessment of cAMP formation by a cAMP SPA assay (Amersham).

Compounds of the invention were tested according to the protocol described. The data demonstrate the protocol is effective for identifying compounds that have 5-HT$_{1A}$ agonist activity and 5-HT$_{1A}$ antagonist activity. 5-HT$_{1A}$ agonist activity is demonstrated by inhibiting the forskolin-induced increase in cAMP levels and the results reported as EC$_{50}$ values (Table 1, "Agonist Activity EC50"). Compounds having 5-HT$_{1A}$ antagonist activity show no effect on forskolin-induced increases in cAMP levels on their own, but block the 8-OH-DPAT-induced inhibition of forskolin-stimulated increases in cAMP levels. Results are required as IC$_{50}$ values (Table 1, "Antagonist Activity IC50")

TABLE 1

5HT$_{1A}$ Affinity

G$_1$—N(piperazine)N—(piperidine)N—G$_2$

| | G$_1$ | G$_2$ | 5-HT1A Affinity Ki | Antagonist Activity IC50 | Agonist Activity EC50 |
|---|---|---|---|---|---|
| A | 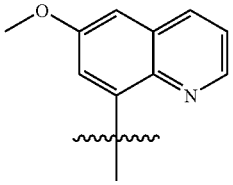 | 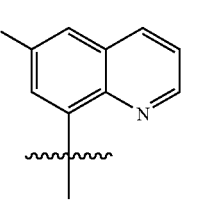 | 0.40 nM | 3.86 nM | |
| B | (6-fluoro-8-quinolinyl, methoxy variant) | (8-quinolinyl) | 0.46 nM | 25.0 nM | |

TABLE 1-continued
5HT$_{1A}$ Affinity
G$_1$—N‿N—N‿N—G$_2$
| | G$_1$ | G$_2$ | 5-HT1A Affinity Ki | Antagonist Activity IC50 | Agonist Activity EC50 |
|---|---|---|---|---|---|
| C | 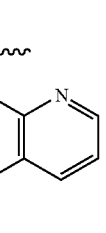 | 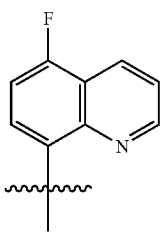 | 0.24 nM | | 6.85 nM |
| D | 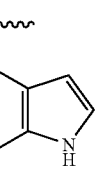 | 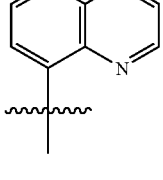 | 0.59 nM | 24.0 nM | |
| E | 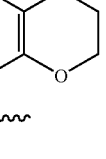 | 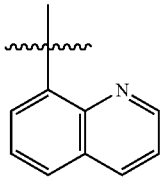 | 0.38 nM | | 2.40 nM |
| F | 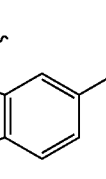 | 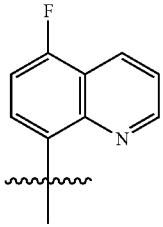 | 1.69 nM | 10.8 nM | |
| G | 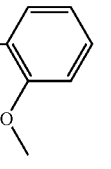 | 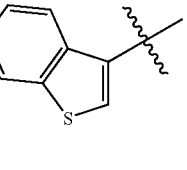 | 26.67 nM | | 22.03 nM |
| H | 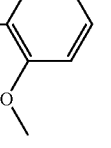 | 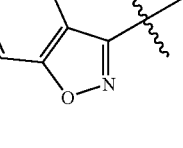 | 1.45 nM | | 2.53 nM |

TABLE 1-continued

5HT$_{1A}$ Affinity

G$_1$—N(piperazine)N—(piperidine)N—G$_2$

| | G$_1$ | G$_2$ | 5-HT1A Affinity Ki | Antagonist Activity IC50 | Agonist Activity EC50 |
|---|---|---|---|---|---|
| I | 4-indolyl | 6-chloroquinolin-8-yl | 40.81 nM | NA | NA |
| J | 6-methoxyquinolin-8-yl | 7-fluoroquinolin-8-yl | 0.61 nM | 9.95 nM | |
| K | 6-fluoroquinolin-8-yl | 8-fluoroquinolin-7-yl | 0.27 nM | | 0.83 nM |
| L | 6-methoxyquinolin-8-yl | 3-trifluoromethylquinolin-8-yl | 1.2 nM | | 29.5 nM |
| M | 6-methoxyquinolin-8-yl | (quinolin-8-yl)methyl | 75.7 nM | 176 nM | |
| N | 6-methoxyquinolin-8-yl | 5-fluoro-4-methoxy-2-trifluoromethylquinolin-8-yl | 2.02 nM | | 9.2 nM |

TABLE 1-continued

5HT$_{1A}$ Affinity $G_1-N\overset{\frown}{\underset{\smile}{N}}-\overset{\frown}{\underset{\smile}{\phantom{N}}}-N-G_2$

| | G$_1$ | G$_2$ | 5-HT1A Affinity Ki | Antagonist Activity IC50 | Agonist Activity EC50 |
|---|---|---|---|---|---|
| P | 6-methoxy-quinolin-8-yl (methyl) | 5-fluoro-quinolin-8-yl | 0.40 mM | 3.7 nM | |
| 3 | quinolin-8-yl | quinolin-8-yl | 0.40 nM | | 10.0 nM |
| 4 | 6-chloro-quinolin-8-yl (methyl) | 6-chloro-quinolin-8-yl | 500 nM | NA | |
| 5 | 6-fluoro-quinolin-8-yl | 6-chloro-quinolin-8-yl | 106 nM | NA | |
| 8 | 5-chloro-quinolin-8-yl | quinolin-8-yl | 0.31 nM | | 20.0 nM |
| 10 | 2-methyl-quinolin-8-yl | quinolin-8-yl | 0.83 nM | | 3.28 nM |

TABLE 1-continued

5HT$_{1A}$ Affinity

G$_1$—N⟨ ⟩N—⟨ ⟩N—G$_2$

| | G$_1$ | G$_2$ | 5-HT1A Affinity Ki | Antagonist Activity IC50 | Agonist Activity EC50 |
|---|---|---|---|---|---|
| 11 | 6-Cl-quinolin-8-yl | quinolin-8-ylmethyl | 0.48 nM | | 3.84 nM |
| 12 | 5-CF$_3$-quinolin-8-yl | quinolin-8-ylmethyl | 3.04 nM | | 35.5 nM |
| 14 | 5-methoxy-quinolin-8-yl | quinolin-8-yl | 1.45 nM | | 64.5 nM |
| 15 | 5-F-quinolin-8-yl | quinolin-8-ylmethyl | 0.15 nM | | 23.5 nM |
| 16 | benzofuran-3-yl | 6-Cl-quinolin-8-ylmethyl | 147.55 nM | | 1076 nM |

What is claimed is:

1. A compound of Formula (I'):

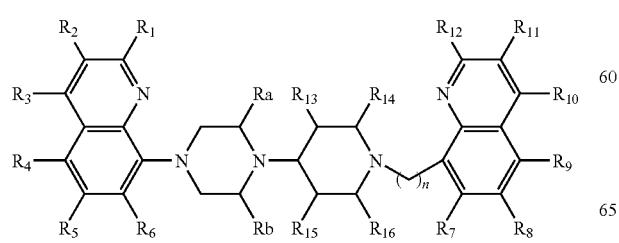

and pharmaceutically acceptable salts and hydrates thereof, wherein

R$_1$, R$_2$, R$_3$, R$_4$, R$_5$, R$_6$, R$_7$, R$_8$, R$_9$, R$_{10}$, R$_{11}$, R$_{12}$, R$_{13}$, R$_{14}$, R$_{15}$, and R$_{16}$, are each independently —H, (C$_1$-C$_6$)-alkyl, (C$_1$-C$_6$)-haloalkyl, (C$_2$-C$_6$)-alkenyl, or (C$_2$-C$_6$)-alkynyl, halogen, —CF$_3$, —NO$_2$, —CN, —OR$_{25}$, —OSO$_2$R$_{25}$, —SR$_{25}$, —SO$_2$R$_{25}$, —SO$_2$N(R$_{25}$)$_2$, —N(R$_{25}$)$_2$, —COR$_{25}$, —CO$_2$R$_{25}$, —NR$_{25}$CO$_2$R$_{25}$, —NR$_{25}$COR$_{25}$, —NR$_{25}$CON(R$_{25}$)$_2$, or —CON(R$_{25}$)$_2$;

R$_a$ and R$_b$ are each independently —H or —CH$_3$;

$R_{25}$ is —H; or linear or branched $(C_1\text{-}C_6)$-alkyl, $(C_1\text{-}C_6)$-haloalkyl, $(C_2\text{-}C_6)$-alkenyl, or $(C_2\text{-}C_6)$-alkynyl; and n is 0, 1 or 2.

2. The compound or pharmaceutically acceptable salt of the compound of claim 1, wherein $R_5$ is —H, $(C_1\text{-}C_6)$-alkyl, —$OR_{25}$, halogen, or —$CF_3$.

3. The compound or pharmaceutically acceptable salt of the compound of claim 1, wherein $R_9$ is —H, $(C_1\text{-}C_6)$-alkyl, —$OR_{25}$, halogen, —$CF_3$, —$NO_2$, or —CN.

4. The compound or pharmaceutically acceptable salt of the compound of claim 1, wherein $R_{10}$ is —H, $(C_1\text{-}C_6)$-alkyl, —$OR_{25}$, halogen, —$CF_3$, —$NO_2$, or —CN.

5. The compound or pharmaceutically acceptable salt of the compound of claim 1, wherein $R_{12}$ is —H, $(C_1\text{-}C_6)$-alkyl, —$OR_{25}$, halogen, —$CF_3$, —$NO_2$, or —CN.

6. The compound or pharmaceutically acceptable salt of the compound of claim 1, wherein $R_5$ is —H, $(C_1\text{-}C_6)$-alkyl, —$OR_{25}$, halogen, or —$CF_3$; and $R_9$ is —H, $(C_1\text{-}C_6)$-alkyl, —$OR_{25}$, halogen, —$CF_3$, —$NO_2$, or —CN.

7. The compound or pharmaceutically acceptable salt of the compound of claim 1, wherein $R_9$ is —H, $(C_1\text{-}C_6)$-alkyl, —$OR_{25}$, halogen, —$CF_3$, —$NO_2$, or —CN; one of $R_1$, $R_2$, $R_3$, $R_4$, $R_5$, and $R_6$ is —H, $(C_1\text{-}C_6)$-alkyl, —$OR_{25}$, halogen, or —$CF_3$; $R_a$ and $R_b$ are each independently —H or —$CH_3$; and $R_7$, $R_8$, $R_9$, $R_{10}$, $R_{11}$, $R_{12}$, $R_{13}$, $R_{14}$, $R_{15}$, $R_{16}$, and the five remaining substituents of $R_1$, $R_2$, $R_3$, $R_4$, $R_5$, and $R_6$ are each hydrogen.

8. The compound or pharmaceutically acceptable salt of the compound of claim 1, wherein $R_5$ is —H, $(C_1\text{-}C_6)$-alkyl, —$OR_{25}$, halogen, or —$CF_3$ and one of $R_7$, $R_8$, $R_9$, $R_{10}$, $R_{11}$, and $R_{12}$ is —H, $(C_1\text{-}C_6)$-alkyl, —$OR_{25}$, halogen, —$CF_3$, —$NO_2$, or —CN.

9. The compound or pharmaceutically acceptable salt of the compound of claim 1, wherein $R_1$ is —H, —$CF_3$ $(C_1\text{-}C_6)$-alkyl; $R_4$ and $R_5$ are each independently —H, halogen, —$OR_{25}$, or —$CF_3$; $R_7$, $R_8$, $R_9$, $R_{10}$, $R_{11}$, and $R_{12}$ are each independently —H, halogen, -alkyl, —$OR_{25}$, —$CF_3$, or —$NO_2$; $R_{16}$ is —H or —$CH_3$.

10. The compound or pharmaceutically acceptable salt of the compound of claim 1, wherein any one of $R_1$, $R_2$, $R_3$, $R_4$, $R_5$, and $R_6$ is —H, $(C_1\text{-}C_6)$-alkyl, —$OR_{25}$, halogen, or —$CF_3$; and any one of $R_7$, $R_8$, $R_9$, $R_{10}$, $R_{11}$, and $R_{12}$ is —H, $(C_1\text{-}C_6)$-alkyl, —$OR_{25}$, halogen, —$CF_3$, —$NO_2$, or —CN.

11. The compound or pharmaceutically acceptable salt of the compound of claim 1, wherein any one of $R_1$, $R_2$, $R_3$, $R_4$, $R_5$, and $R_6$ is —H, $(C_1\text{-}C_6)$-alkyl, —$OR_{25}$, halogen, or —$CF_3$; and any two of $R_7$, $R_8$, $R_9$, $R_{10}$, $R_{11}$, and $R_{12}$ are each independently —H, $(C_1\text{-}C_6)$-alkyl, —$OR_{25}$, halogen, —$CF_3$, —$NO_2$, or —CN.

12. The compound or pharmaceutically acceptable salt of the compound of claim 1, wherein any one of $R_1$, $R_2$, $R_3$, $R_4$, $R_5$, and $R_6$ is —H, $(C_1\text{-}C_6)$-alkyl, —$OR_{25}$, halogen, or —$CF_3$; and any three of $R_7$, $R_8$, $R_9$, $R_{10}$, $R_{11}$, and $R_{12}$ are each independently is —H, $(C_1\text{-}C_6)$-alkyl, —$OR_{25}$, halogen, —$CF_3$, —$NO_2$, or —CN.

13. The compound or pharmaceutically acceptable salt of the compound of claim 1, wherein $R_{25}$ is $(C_1\text{-}C_6)$-alkyl.

14. The compound or pharmaceutically acceptable salt of the compound of claim 1, wherein n is 1.

15. A compound of Formula (I″):

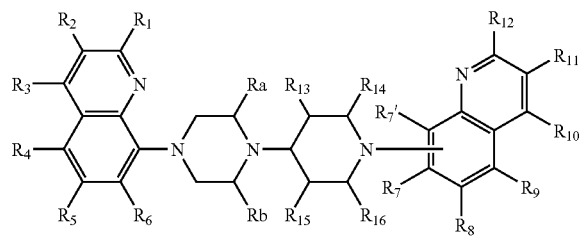

I″ and pharmaceutically acceptable salts thereof,
wherein $R_1$, $R_2$, $R_3$, $R_4$, $R_5$, $R_6$, $R_7$, $R_{7'}$, $R_8$, $R_9$, $R_{10}$, $R_{11}$, $R_{12}$, $R_{13}$, $R_{14}$, $R_{15}$, and $R_{16}$, are each independently —H, $(C_1\text{-}C_6)$-alkyl, $(C_1\text{-}C_6)$-haloalkyl, $(C_2\text{-}C_6)$-alkenyl, $(C_2\text{-}C_6)$-alkynyl, halogen, —$CF_3$, —$NO_2$, —CN, —$OR_{25}$, —$OSO_2R_{25}$, —$SR_{25}$, —$SO_2R_{25}$, —$SO_2N(R_{25})_2$, —$N(R_{25})_2$, —$COR_{25}$, —$CO_2R_{25}$, —$NR_{25}CO_2R_{25}$, —$NR_{25}COR_{25}$, —$NR_{25}CON(R_{25})_2$, or —$CON(R_{25})_2$ except for the R group through which the piperidine is connected;

$R_a$ and $R_b$ are each independently —H or —$CH_3$;

$R_{25}$ is —H; or linear or branched $(C_1\text{-}C_6)$-alkyl, $(C_1\text{-}C_6)$-haloalkyl, $(C_2\text{-}C_6)$-alkenyl, or $(C_2\text{-}C_6)$-alkynyl; and where the piperidine group can be attached to the non-hetero atom containing ring of the quinoline through positions $R_7$, $R_{7'}$, $R_8$, or $R_9$.

16. The compound or pharmaceutically acceptable salt of the compound of claim 15, wherein any one of $R_1$, $R_2$, $R_3$, $R_4$, $R_5$, and $R_6$ is —H, $(C_1\text{-}C_6)$-alkyl, —$OR_{25}$, halogen, or —$CF_3$; and any one of $R_7$, $R_{7'}$, $R_8$, $R_9$, $R_{10}$, $R_{11}$, and $R_{12}$ is —H, $(C_1\text{-}C_6)$-alkyl, —$OR_{25}$, halogen, —$CF_3$, —$NO_2$, or —CN, except for the R group through which the piperidine is connected.

17. The compound or pharmaceutically acceptable salt of the compound of claim 15, wherein $R_5$ is —H, $(C_1\text{-}C_6)$-alkyl, —$OR_{25}$, halogen, or —$CF_3$; and any one of $R_7$, $R_{7'}$, $R_8$, $R_9$, $R_{10}$, $R_{11}$, and $R_{12}$ is —H, $(C_1\text{-}C_6)$-alkyl, —$OR_{25}$, halogen, —$CF_3$, —$NO_2$, or —CN, except for the R group through which the piperidine is connected.

18. The compound or pharmaceutically acceptable salt of the compound of claim 15, wherein $R_5$ is —H, $(C_1\text{-}C_6)$-alkyl, —$OR_{25}$, halogen, or —$CF_3$; and any two of $R_7$, $R_{7'}$, $R_8$, $R_9$, $R_{10}$, $R_{11}$, and $R_{12}$ are each independently —H, $(C_1\text{-}C_6)$-alkyl, —$OR_{25}$, halogen, —$CF_3$, —$NO_2$, or —CN, except for the R group through which the piperidine is connected.

19. The compound or pharmaceutically acceptable salt of the compound of claim 15, wherein $R_5$ is —H, $(C_1\text{-}C_6)$-alkyl, —$OR_{25}$, halogen, or —$CF_3$; and any three of $R_7$, $R_{7'}$, $R_8$, $R_9$, $R_{10}$, $R_{11}$, and $R_{12}$ are each independently —H, $(C_1\text{-}C_6)$-alkyl, —$OR_{25}$, halogen, —$CF_3$, —$NO_2$, or —CN, except for the R group through which the piperidine is connected.

20. The compound or pharmaceutically acceptable salt of the compound of claim 15, wherein $R_5$ is —H, $(C_1\text{-}C_6)$-alkyl, —$OR_{25}$, halogen, or —$CF_3$; and $R_{7'}$ is —H, $(C_1\text{-}C_6)$-alkyl, —$OR_{25}$, halogen, —$CF_3$, —$NO_2$ or —CN, and $R_1$, $R_2$, $R_3$ $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_a$, and $R_b$ are each hydrogen except for the R group through which the piperidine is connected.

21. The compound or pharmaceutically acceptable salt of the compound of claim 20, wherein the piperidine is connected through $R_7$.

22. The compound or pharmaceutically acceptable salt of the compound of claim 15, wherein $R_{25}$ $(C_1$-$C_6)$-alkyl.

23. The compound or pharmaceutically acceptable salt of the compound of claim 15, wherein the piperidine is connected through $R_7$.

24. The compound or pharmaceutically acceptable salt of the compound of claim 15, wherein the piperidine is connected through $R_7$.

25. The compound or pharmaceutically acceptable salt of the compound of claim 15, wherein the piperidine is connected through $R_8$.

26. The compound or pharmaceutically acceptable salt of the compound of claim 15, wherein the piperidine is connected through $R_9$.

27. A compound of Formula (I″a):

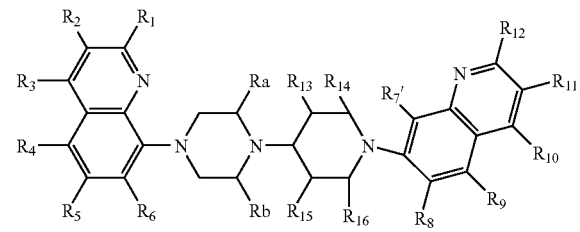

(I″a)

and pharmaceutically acceptable salts thereof,
wherein $R_1$, $R_2$, $R_3$, $R_4$, $R_5$, $R_6$, $R_{7'}$, $R_8$, $R_9$, $R_{10}$, $R_{11}$, $R_{12}$, $R_{13}$, $R_{14}$, $R_{15}$, and $R_{16}$, are each independently —H, $(C_1$-$C_6)$-alkyl, $(C_1$-$C_6)$-haloalkyl, $(C_2$-$C_6)$-alkenyl, $(C_2$-$C_6)$-alkynyl, halogen, —$CF_3$, —$NO_2$, —CN, —$OR_{25}$, —$OSO_2R_{25}$, —$SR_{25}$, —$SO_2R_{25}$, —$SO_2N(R_{25})_2$, —$N(R_{25})_2$, —$COR_{25}$, —$CO_2R_{25}$, —$NR_{25}CO_2R_{25}$, —$NR_{25}COR_{25}$, —$NR_{25}CON(R_{25})_2$, or —$CON(R_{25})_2$;
$R_a$ and $R_b$ are each independently —H or —$CH_3$; and
$R_{25}$ is —H; or linear or branched $(C_1$-$C_6)$-alkyl, $(C_1$-$C_6)$-haloalkyl, $(C_2$-$C_6)$-alkenyl, or $(C_2$-$C_6)$-alkynyl.

28. The compound or pharmaceutically acceptable salt of the compound of claim 27, wherein $R_5$, is —H, $(C_1$-$C_6)$-alkyl, —$OR_{25}$, halogen, or —$CF_3$.

29. The compound or pharmaceutically acceptable salt of the compound of claim 27, wherein any one $R_1$, $R_2$, $R_3$, $R_4$, $R_5$, and $R_6$ is —H, $(C_1$-$C_6)$-alkyl, —$OR_{25}$, halogen, or —$CF_3$; and any one of $R_{7'}$, $R_8$, $R_9$, $R_{10}$, $R_{11}$, and $R_{12}$ is —H, $(C_1$-$C_6)$-alkyl, —$OR_{25}$, halogen, —$CF_3$, —$NO_2$, or —CN.

30. The compound or pharmaceutically acceptable salt of the compound of claim 27, wherein $R_4$ is —H, $(C_1$-$C_6)$-alkyl, —$OR_{25}$, halogen, or —$CF_3$ and any one of $R_{13}$, $R_{14}$, $R_{15}$, and $R_{16}$ is —H, $(C_1$-$C_6)$-alkyl, —$OR_{25}$, or halogen; and any two of $R_{7'}$, $R_8$, $R_9$, $R_{10}$, $R_{11}$, and $R_{12}$ is —H, $(C_1$-$C_6)$-alkyl, —$OR_{25}$, halogen, —$CF_3$, —$NO_2$, or —CN; and wherein the any two $R_{7'}$, $R_8$, $R_9$, $R_{10}$, $R_{11}$, and $R_{12}$ can be either on the same ring of the quinoline or on different rings.

31. The compound or pharmaceutically acceptable salt of the compound of claim 27, wherein $R_5$ is —H, $(C_1$-$C_6)$-alkyl, —$OR_{25}$, halogen, or —$CF_3$ and any one of $R_{13}$, $R_{14}$, $R_{15}$, and $R_{16}$ is —H, $(C_1$-$C_6)$-alkyl, —$OR_{25}$, halogen; and any two of $R_{7'}$, $R_8$, $R_9$, $R_{10}$, $R_{11}$, and $R_{12}$ are each independently —H, $(C_1$-$C_6)$-alkyl, —$OR_{25}$, halogen, —$CF_3$, —$NO_2$, or —CN; and wherein the any two of $R_{7'}$, $R_8$, $R_9$, $R_{10}$, $R_{11}$, and $R_{12}$ can be either on the same ring of the quinoline or on different rings.

32. The compound or pharmaceutically acceptable salt of the compound of claim 29, wherein $R_5$ is —H, $(C_1$-$C_6)$-alkyl, —$OR_{25}$, halogen, or —$CF_3$ and $R_{7'}$ is —H, $(C_1$-$C_6)$-alkyl, —$OR_{25}$, halogen, —$CF_3$, —$NO_2$, or —CN; and $R_1$, $R_2$, $R_3$, $R_4$, $R_5$, $R_6$, $R_8$, $R_9$, $R_{10}$, $R_{11}$, $R_{12}$, $R_{13}$, $R_{14}$, $R_{15}$, $R_{16}$, $R_a$, and $R_b$ are each hydrogen.

33. The compound or pharmaceutically acceptable salt of the compound of claim 29, wherein $R_{25}$ is $(C_1$-$C_6)$-alkyl.

34. A compound of Formula (II):

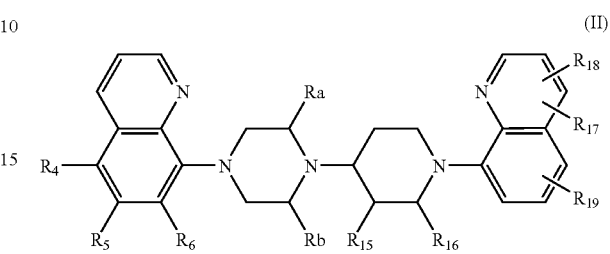

(II)

or a pharmaceutically acceptable salt thereof,
wherein
$R_4$, $R_5$, $R_{15}$, $R_{16}$, $R_{17}$, $R_{18}$ and $R_{19}$ are each independently —H, $(C_1$-$C_6)$-alkyl, $(C_1$-$C_6)$-haloalkyl, $(C_2$-$C_6)$-alkenyl, $(C_2$-$C_6)$-alkynyl, halogen, —$CF_3$, —$NO_2$, —CN, —$OR_{25}$, —$OSO_2R_{25}$, —$SR_{25}$, —$SO_2R_{25}$, —$SO_2N(R_{25})_2$, —$N(R_{25})_2$, —$COR_{25}$, —$CO_2R_{25}$, —$NR_{25}CO_2R_{25}$, —$NR_{25}COR_{25}$, —$NR_{25}CON(R_{25})_2$, or —$CON(R_{25})_2$;
$R_a$ and $R_b$ are each independently —H or —$CH_3$;
$R_{25}$ is —H; or linear or branched $(C_1$-$C_6)$-alkyl, $(C_1$-$C_6)$-haloalkyl, $(C_2$-$C_6)$-alkenyl, or $(C_2$-$C_6$-alkynyl); and
$R_4$ and $R_5$ cannot both be hydrogen.

35. The compound or pharmaceutically acceptable salt of the compound of claim 34, wherein $R_4$ and $R_5$ are each independently —H, —$OR_{25}$, halogen, or $(C_1$-$C_6)$-alkyl; $R_{15}$ and $R_{16}$ are each independently —H or —$CH_3$; and $R_{17}$, $R_{18}$, and $R_{19}$ are each independently —H, —$OR_{25}$, halogen, $(C_1$-$C_6)$-alkyl, —$CF_3$, —$NO_2$, or —CN.

36. The compound or pharmaceutically acceptable salt of the compound of claim 34, wherein $R_4$ and $R_5$ are each independently —H, —$OCH_3$, F, or —$CH_3$; $R_{15}$ and $R_{16}$ are each independently —H or —$CH_3$; and $R_{17}$, $R_{18}$, and $R_{19}$ are each independently —H, F, —$CH_3$, —$CF_3$, —$NO_2$, —CN or Br.

37. The compound or pharmaceutically acceptable salt of the compound of claim 34, wherein $R_4$ and $R_5$ are each independently —H, or —$OR_{25}$; and $R_{17}$, $R_{18}$, and $R_{19}$ are each independently —H, —$OR_{25}$, halogen, $(C_1$-$C_6)$-alkyl, or —$CF_3$.

38. The compound or pharmaceutically acceptable salt of the compound of claim 34, wherein $R_4$ and $R_5$ are each independently —H, —$OR_{25}$; $R_{17}$, $R_{18}$, and $R_{19}$ are each independently —H, —$OR_{25}$, halogen, $(C_1$-$C_6)$-alkyl, or —$CF_3$; and the remaining R groups are hydrogen.

39. The compound or pharmaceutically acceptable salt of the compound of claim 34, wherein $R_{19}$ is in the para position relative to the nitrogen of the piperidine.

40. The compound or pharmaceutically acceptable salt of the compound of claim 34, wherein $R_{17}$ and $R_{18}$ are located at positions 2 and 4 of the quinoline ring.

41. The compound or pharmaceutically acceptable salt of the compound of claim 34, wherein $R_5$ is $(C_1$-$C_6)$-alkyl, —$OR_{25}$, halogen, or —$CF_3$ and one of $R_{17}$, $R_{18}$, and $R_{19}$ is $(C_1$-$C_6)$-alkyl, —$OR_{25}$, halogen, or —$CF_3$.

42. The compound or pharmaceutically acceptable salt of the compound of claim 34, wherein $R_5$ is —H, $(C_1$-$C_6)$-alkyl, —OR$_{25}$, halogen, or —CF$_3$ and two of R$_{17}$, R$_{18}$, and R$_{19}$ are each independently —H, (C$_1$-C$_6$)-alkyl, —OR$_{25}$, halogen, or —CF$_3$.

43. The compound or pharmaceutically acceptable salt of the compound of claim 34, wherein R$_5$ is —H, (C$_1$-C$_6$)-alkyl, —OR$_{25}$, halogen, or —CF$_3$ and R$_{17}$, R$_{18}$, and R$_{19}$ are each independently —H, (C$_1$-C$_6$)-alkyl, —OR$_{25}$, halogen, or —CF$_3$.

44. The compound or pharmaceutically acceptable salt of the compound of claim 34, wherein R$_5$ is —H, (C$_1$-C$_6$)-alkyl, —OR$_{25}$, halogen, or —CF$_3$ and one of R$_{17}$, R$_{18}$, and R$_{19}$ is —H, (C$_1$-C$_6$)-alkyl, —OR$_{25}$, halogen, or —CF$_3$; and R$_4$, R$_{15}$, R$_{16}$, R$_a$, R$_b$ and the two remaining substituents from R$_{17}$, R$_{18}$, and R$_{19}$ are each hydrogen.

45. The compound or pharmaceutically acceptable salt of the compound of claim 1 wherein the compound is
   6-methoxy-8-[4-(1-quinolin-8-yl-piperidin-4-yl)-piperazin-1-yl]-quinoline;
   6-fluoro-8-[4-(1-quinolin-8-yl-piperidin-4-yl)-piperazin-1-yl]-quinoline;
   5-fluoro-8-[4-(1-quinolin-8-yl-piperidin-4-yl)-piperazin-1-yl]-quinoline;
   7-fluoro-8-(4-(4-(6-methoxyquinolin-8-yl)piperazin-1-yl)piperidin-1-yl)quinoline;
   6-fluoro-8-{4-[1-(8-fluoroquinolin-7-yl)piperidin-4-yl]piperazin-1-yl}quinoline;
   3-trifluoromethyl-8-(4-(4-(6-methoxyquinolin-8-yl)piperazin-1-yl)piperidin-1-yl)quinoline;
   6-methoxy-8-(4-(1-(quinolin-8-ylmethyl)piperidin-4-yl)piperazin-1-yl)quinoline;
   5-fluoro-4-methoxy-8-(4-(4-(6-methoxyquinolin-8-yl)piperazin-1-yl)piperidin-1-yl)-2-(trifluoromethyl)quinoline;
   5-fluoro-8-(4-(4-(6-methoxyquinolin-8-yl)piperazin-1-yl)piperidin-1-yl)quinoline;
   8-[4-(1-quinolin-8-yl-piperidin-4-yl)-piperazin-1-yl]-quinoline;
   6-chloro-8-[4-(4-(6-chloro)-quinolin-8-yl-piperidin-1-yl)-piperazin-1-yl]-quinoline;
   6-fluoro-8-[4-(4-(6-chloro)-quinolin-8-yl-piperidin-1-yl)-piperazin-1-yl]-quinoline;
   5-chloro-8-[4-(1-quinolin-8-yl-piperidin-4-yl)-piperazin-1-yl]-quinoline;
   2-methyl-8-[4-(1-quinolin-8-yl-piperidin-4-yl)-piperazin-1-yl]-quinoline;
   6-chloro-8-[4-(1-quinolin-8-yl-piperidin-4-yl)-piperazin-1-yl]-quinoline;
   8-[4-(1-quinolin-8-yl-piperidin-4-yl)-piperazin-1-yl]-5-trifluoromethyl-quinoline;
   5-methoxy-8-[4-(1-quinolin-8-yl-piperidin-4-yl)-piperazin-1-yl]-quinoline;
   5-fluoro-8-[4-(4-quinolin-8-yl-piperazin-1-yl)-piperidin-1-yl]-quinoline;
   6-methoxy-8-[4-(2-methylquinolin-8-yl-piperidin-4-yl)-piperazin-1-yl]-quinoline;
   6-fluoro-8-(4-(1-(2-methylquinolin-8-yl)piperidin-4-yl)piperazin-1-yl)quinoline;
   6-methoxy-8-[4-(3-methylquinolin-8-yl-piperidin-4-yl)-piperazin-1-yl]-quinoline;
   6-methoxy-8-(4-(1-(4-methylquinolin-8-yl)piperidin-4-yl)piperazin-1-yl)quinoline;
   6-methoxy-8-(4-(1-(2,4-dimethylquinolin-8-yl)piperidin-4-yl)piperazin-1-yl)quinoline;
   6-methoxy-8-(4-(1-(2,4-dimethyl-5-fluoroquinolin-8-yl)piperidin-4-yl)piperazin-1-yl)quinoline;
   6-methoxy-8-(4-(1-(2-(trifluoromethyl)quinolin-8-yl)piperidin-4-yl)piperazin-1-yl)quinoline;
   6-fluoro-8-(4-(1-(5-fluoroquinolin-8-yl)piperidin-4-yl)piperazin-1-yl)quinoline;
   6-methoxy-8-(4-(1-(6-bromoquinolin-8-yl)piperidin-4-yl)piperazin-1-yl)quinoline;
   6-methoxy-8-(4-(1-(6-fluoroquinolin-8-yl)piperidin-4-yl)piperazin-1-yl)quinoline;
   6-fluoro-8-(4-(1-(7-fluoroquinolin-8-yl)piperidin-4-yl)piperazin-1-yl)quinoline;
   6-methoxy-8-{4-[1-(8-fluoroquinolin-7-yl)piperidin-4-yl]piperazin-1-yl}quinoline;
   6-methoxy-8-{4-[1-(2-trifluoromethyl-4-methoxyquinolin-7-yl)piperidin-4-yl]piperazin -1-yl}quinoline;
   6-methoxy-8-(4-(1-(2-trifluoromethyl-4-methoxyquinolin-8-yl)piperidin-4-yl)piperazin -1-yl)quinoline;
   5-fluoro-8-(4-(4-(6-methoxyquinolin-8-yl)piperazin-1-yl)piperidin-1-yl) -2-trifluoromethylquinoline;
   5-fluoro-8-(4-(4-(6-methoxyquinolin-8-yl)piperazin-1-yl)piperidin-1-yl) -3-trifluoromethylquinoline;
   5-fluoro-8-(4-(4-(6-methoxyquinolin-8-yl)piperazin-1-yl)piperidin-1-yl) -4-trifluoromethylquinoline;
   2,5-difluoro-8-(4-(4-(6-methoxyquinolin-8-yl)piperazin-1-yl)piperidin-1-yl)quinoline;
   3,5-difluoro-8-(4-(4-(6-methoxyquinolin-8-yl)piperazin-1-yl)piperidin-1-yl)quinoline; or
   4,5-difluoro-8-(4-(4-(6-methoxyquinolin-8-yl)piperazin-1-yl)piperidin-1-yl)quinoline.

46. A pharmaceutical formulation comprising an effective amount of the compound or a pharmaceutically acceptable salt of the compound of claim 1 and a pharmaceutically acceptable carrier.

47. The pharmaceutical formulation of claim 46, further comprising a second therapeutic agent.

48. The pharmaceutical formulation of claim 47, wherein the second therapeutic agent is a selective serotonin reuptake inhibitor or a cholinesterase inhibitor.

49. A pharmaceutical formulation comprising an effective amount of the compound or a pharmaceutically acceptable salt of the compound of claim 15 and a pharmaceutically acceptable carrier.

50. The pharmaceutical formulation of claim 49, further comprising a second therapeutic agent.

51. The pharmaceutical formulation of claim 50, wherein the second therapeutic agent is a selective serotonin reuptake inhibitor or a cholinesterase inhibitor.

52. A pharmaceutical formulation comprising an effective amount of the compound or a pharmaceutically acceptable salt of the compound of claim 27 and a pharmaceutically acceptable carrier.

53. The pharmaceutical formulation of claim 52, further comprising a second Therapeutic agent.

54. The pharmaceutical formulation of claim 53, wherein the second therapeutic agent is a selective serotonin reuptake inhibitor or a cholinesterase inhibitor.

55. A pharmaceutical formulation comprising an effective amount of the compound or a pharmaceutically acceptable salt of the compound of claim 34 and a pharmaceutically acceptable carrier.

56. The pharmaceutical formulation of claim 55, further comprising a second therapeutic agent.

57. The pharmaceutical formulation of claim 56, wherein the second therapeutic agent is a selective serotonin reuptake inhibitor or a cholinesterase inhibitor.

58. A method of synthesizing a compound comprising:
   a) reacting an optionally substituted aniline compound of Formula (VII):

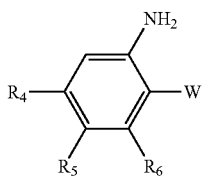

(VII)

wherein:
W is a leaving group;
$R_4$, $R_5$, and $R_6$ are each independently —H, $(C_1$-$C_6)$-alkyl, $(C_1$-$C_6)$-haloalkyl, $(C_2$-$C_6)$-alkenyl, $(C_2$-$C_6)$-alkynyl, halogen, —$CF_3$, —$NO_2$, —CN, —$OR_{25}$, —$SR_{25}$, —$SO_2R_{25}$, —$SO_2N(R_{25})_2$, —$N(R_{25})_2$, —$COR_{25}$, —$CO_2R_{25}$, —$NR_{25}CO_2R_{25}$, —$NR_{25}COR_{25}$, —$NR_{25}CON(R_{25})_2$, or —$CON(R_{25})_2$;
$R_{25}$ is —H; or linear or branched $(C_1$-$C_6)$-alkyl, $(C_1$-$C_6)$-haloalkyl, $(C_2$-$C_6)$-alkenyl, or $(C_2$-$C_6)$-alkynyl;
under conditions effective to produce an optionally substituted quinoline of Formula (VIII):

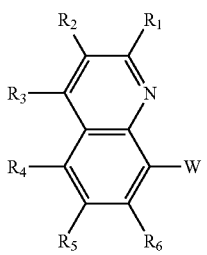

(VIII)

wherein:
$R_1$, $R_2$, and $R_3$ are each independently —H, $(C_1$-$C_6)$-alkyl, $(C_1$-$C_6)$-haloalkyl, $(C_2$-$C_6)$-alkenyl, $(C_2$-$C_6)$-alkynyl, halogen, —$CF_3$, —$NO_2$, —CN, —$OR_{25}$, —$SR_{25}$, —$SO_2R_{25}$, —$SO_2N(R_{25})_2$, —$N(R_{25})_2$, —$COR_{25}$, —$CO_2R_{25}$, —$NR_{25}CO_2R_{25}$, —$NR_{25}COR_{25}$, —$NR_{25}CON(R_{25})_2$, or —$CON(R_{25})_2$;
b) reacting the quinoline of Formula (VIII) with a protected piperazine derivative under conditions effective to provide a protected piperazino-quinoline of Formula (IX):

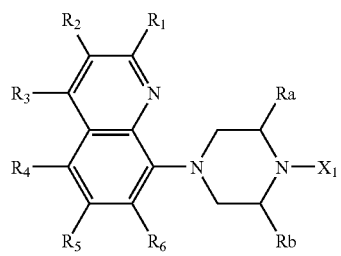

(IX)

wherein:
$R_a$ and $R_b$ are each independently —H or —$CH_3$ and
$X_1$ is a protecting group c) reacting the protected piperazino-quinoline of Formula (IX) under conditions effective to provide a substituted piperazino-quinoline compound of Formula (Xb):

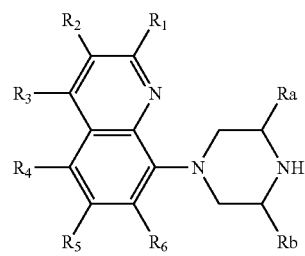

(Xb)

d) reacting a second optionally substituted aniline compound of Formula (XI):

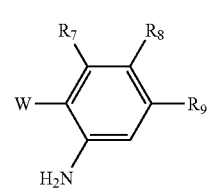

(XI)

wherein
$R_7$, $R_8$, and $R_9$, are each independently —H, $(C_1$-$C_6)$-alkyl, $(C_1$-$C_6)$-haloalkyl, $(C_2$-$C_6)$-alkenyl, $(C_2$-$C_6)$-alkynyl, halogen, —$CF_3$, —$NO_2$, —CN, —$OR_{25}$, —$SR_{25}$, —$SO_2R_{25}$, —$SO_2N(R_{25})_2$, —$N(R_{25})_2$, —$COR_{25}$, —$CO_2R_{25}$, —$NR_{25}CO_2R_{25}$, —$NR_{25}COR_{25}$, —$NR_{25}CON(R_{25})_2$, or —$CON(R_{25})_2$;
$R_{25}$ is —H; or linear or branched $(C_1$-$C_6)$-alkyl, $(C_1$-$C_6)$-haloalkyl, $(C_2$-$C_6)$-alkenyl, or $(C_2$-$C_6$-alkynyl; and
W is a leaving group
under conditions effective to produce a second optionally substituted quinoline of Formula (XII):

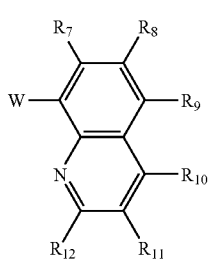

(XII)

wherein $R_{10}$, $R_{11}$, and $R_{12}$, are each independently —H, $(C_1$-$C_6)$-alkyl, $(C_1$-$C_6)$-haloalkyl, $(C_2$-$C_6)$-alkenyl, $(C_2$-$C_6)$alkynyl, halogen, —$CF_3$, —$NO_2$, —CN, —$OR_{25}$, —$SR_{25}$, —$SO_2R_{25}$, —$SO_2N(R_{25})_2$, —$N(R_{25})_2$, —$COR_{25}$, —$CO_2R_{25}$, —$NR_{25}CO_2R_{25}$, —$NR_{25}COR_{25}$, —$NR_{25}CON(R_{25})_2$, or —$CON(R_{25})_2$;
$R_{25}$ is —H; or linear or branched $(C_1$-$C_6)$-alkyl, $(C_1$-$C_6)$-haloalkyl, $(C_2$-$C_6)$-alkenyl, or $(C_2$-$C_6)$-alkynyl; and W is a leaving group e) reacting the quinoline of Formula (XII) with a protected piperidin-4-one derivative, under conditions effective to provide a compound of Formula (XIII):

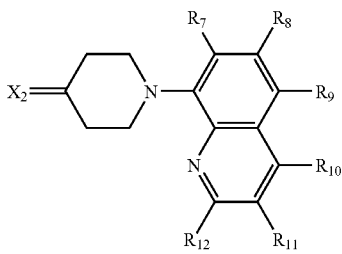

(XIII)

wherein $X_2$ is a protecting group;

f) reacting the compound of Formula (XIII) under conditions effective to provide a piperidin-4-one compound of (XIVa):

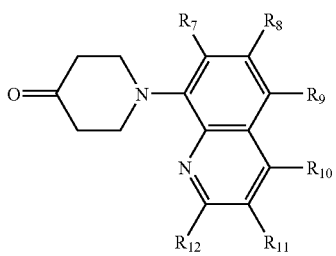

(XIVa)

g) reacting the substituted piperazine compound of Formula (Xb) with the substituted piperidin-4-one compound of Formula (XIVa) under conditions effective to provide a piperazine-piperidine compound having the Formula (XV):

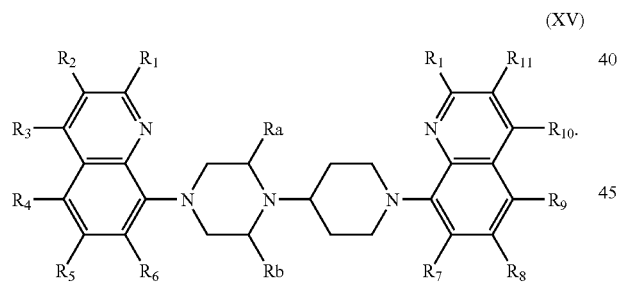

(XV)

59. A compound of Formula (XV):

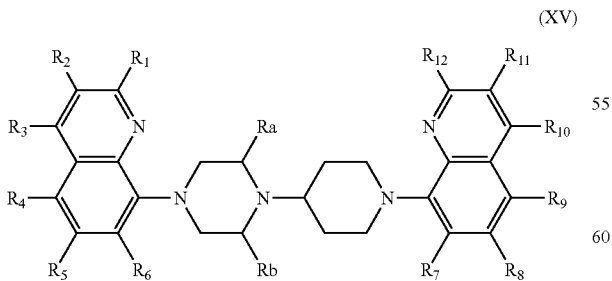

(XV)

wherein $R_1$, $R_2$, $R_3$, $R_4$, $R_5$, $R_6$, $R_7$, $R_8$, $R_9$, $R_{10}$, $R_{11}$ and $R_{12}$ are each independently —H, $(C_1-C_6)$-alkyl, $(C_1-C_6)$-haloalkyl, $(C_2-C_6)$-alkenyl, or $(C_2-C_6)$alkynyl, halogen, —$CF_3$, —$NO_2$, —CN, —$OR_{25}$, —$OSO_2R_{25}$, —$SR_{25}$, —$SO_2R_{25}$, —$SO_2N(R_{25})_2$, —$N(R_{25})_2$, —$COR_{25}$, —$CO_2R_{25}$, —$NR_{25}CO_2R_{25}$, —$NR_{25}COR_{25}$, —$NR_{25}CON(R_{25})_2$, or —$CON(R_{25})_2$;

$R_a$ and $R_b$ are each independently —H or —$CH_3$; and $R_{25}$ is —H; or linear or branched $(C_1-C_6)$-alkyl, $(C_1-C_6)$-haloalkyl, $(C_2-C_6)$-alkenyl, or $(C_2-C_6)$-alkynyl;

prepared by the method comprising:

a) reacting an optionally substituted aniline compound of Formula (VII):

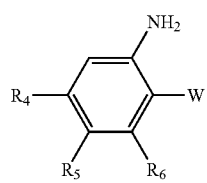

(VII)

wherein W is a leaving group;

under conditions effective to produce an optionally substituted quinoline of Formula (VIII):

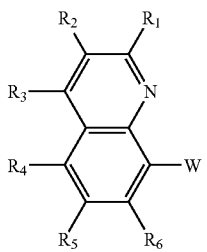

(VIII)

b) reacting the leaving group of the quinoline of Formula (VIII) with a protected piperazine derivative under conditions effective to provide a protected piperazino-quinoline of Formula (XI):

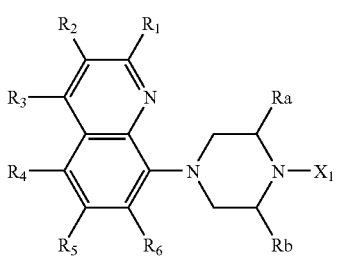

(IX)

wherein $X_1$ is a protecting group.

c) reacting the protected piperazino-quinoline of Formula (IX) under conditions effective to provide a substituted piperazine compound of Formula (Xb):

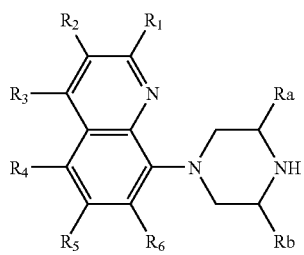
(Xb)

d) reacting a second optionally substituted aniline compound of Formula (XI):

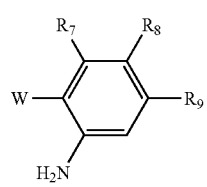
(XI)

wherein W is a leaving group;
under conditions effective to produce a second optionally substituted quinoline of Formula (XII):

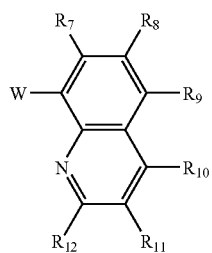
(XII)

e) reacting the leaving group of the second quinoline of Formula (XII) with a protected piperidin-4-one derivative under conditions effective to provide the compound (XIII):

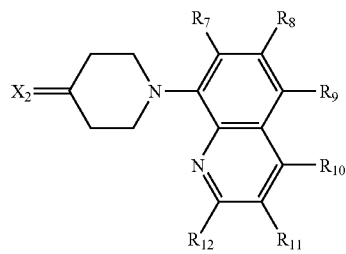
(XIII)

wherein $X_2$ is a protecting group.
f) reacting the compound of Formula (XIII) under conditions effective to provide the compound of (XIVa):

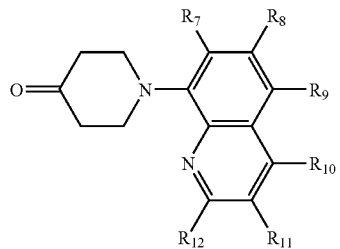
(XIVa)

g) reacting the substituted piperazine compound of Formula (X) with the substituted piperidin-4-one compound of Formula (XIV) under conditions effective to provide a piperazine-piperidine compound having the Formula (XV):

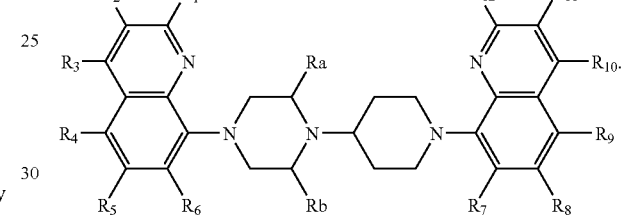
(XV)

60. A compound of Formula (I):

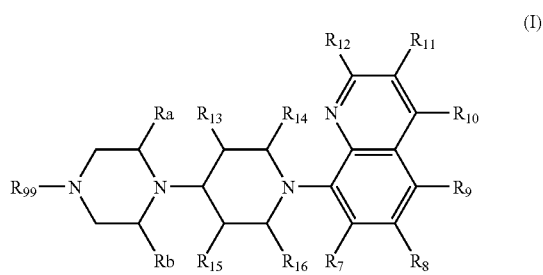
(I)

or a pharmaceutically acceptable salt thereof,
wherein
$R_{99}$ is

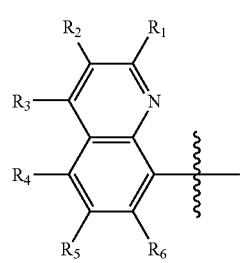

$R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$, are each independently —H, ($C_1$-$C_6$)-alkyl, ($C_1$-$C_6$)-haloalkyl, ($C_2$-$C_6$)-alkenyl, ($C_2$-$C_6$)-alkynyl, halogen, —$CF_3$, —$NO_2$, —CN, —$OR_{25}$, —$OSO_2R_{25}$, —$SR_{25}$, —$SO_2R_{25}$, —$SO_2N(R_{25})_2$, —$N(R_{25})_2$, —$COR_{25}$, —$CO_2R_{25}$, —$NR_{25}CO_2R_{25}$, —$NR_{25}COR_{25}$, —$NR_{25}CON(R_{25})_2$, or —$CON(R_{25})_2$;

$R_a$ and $R_b$ are each independently —H or —$CH_3$; and $R_{25}$ is —H; or linear or branched ($C_1$-$C_6$)-alkyl, ($C_1$-$C_6$)-haloalkyl, ($C_2$-$C_6$)-alkenyl, or ($C_2$-$C_6$)-alkynyl;

prepared by the method comprising:

reacting a substituted piperazine compound of Formula (X):

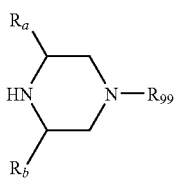
(X)

with a substituted piperidin-4-one compound of Formula (XIV):

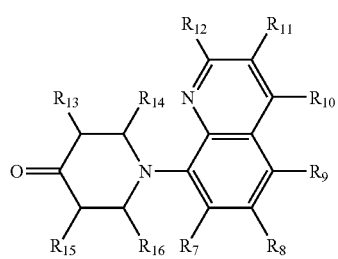
(XIV)

under conditions effective to bring about reductive amination at the piperidine carbonyl, thereby providing an piperazine-piperidine compound having the Formula (I):

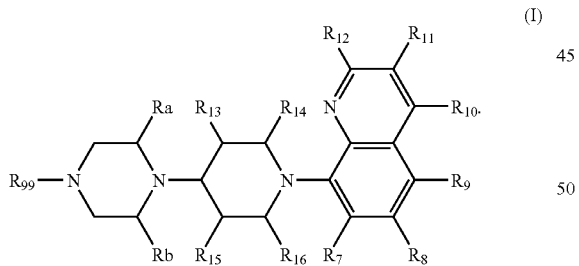
(I)

61. A compound of Formula (I'):

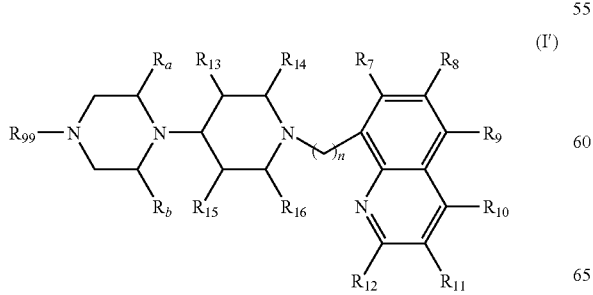
(I')

or a pharmaceutically acceptable salt thereof, wherein $R_{99}$ is

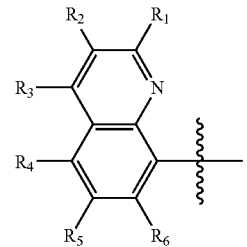

$R_1$, $R_2$, $R_3$, $R_4$, $R_5$, $R_6$, $R_7$, $R_8$, $R_9$, $R_1$, $R_{11}$, $R_{12}$, $R_{13}$, $R_{14}$, $R_{15}$, and $R_{16}$, are each independently —H, ($C_1$-$C_6$)-alkyl, ($C_1$-$C_6$)-haloalkyl, ($C_2$-$C_6$)-alkenyl, ($C_2$-$C_6$)-alkynyl, halogen, —$CF_3$, —$NO_2$, —CN, —$OR_{25}$, —$OSO_2R_{25}$, —$SR_{25}$, —$SO_2R_{25}$, —$SO_2N(R_{25})_2$, —$N(R_{25})_2$, —$COR_{25}$, —$CO_2R_{25}$, —$NR_{25}CO_2R_{25}$, —$NR_{25}CON(R_{25})_2$, or —$CON(R_{25})_2$;

$R_a$ and $R_b$ are each independently —H or —$CH_3$;

$R_{25}$ is —H; or linear or branched ($C_1$-$C_6$)-alkyl, ($C_1$-$C_6$)-haloalkyl, ($C_2$-$C_6$)-alkenyl, or ($C_2$-$C_6$)-alkynyl; and n is 1 or 2;

prepared by the method comprising:

reacting a substituted piperazine compound of Formula (X):

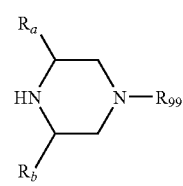
(X)

with a substituted piperidin-4-one compound of Formula (XIVb):

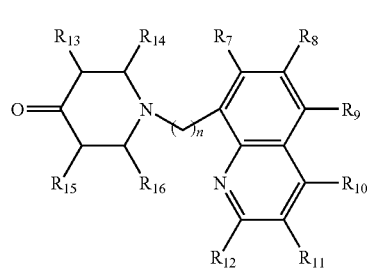
(XIVb)

under conditions effective to bring about reductive amination at the piperidine carbonyl, thereby providing a piperazine-piperidine compound having the Formula (I'):

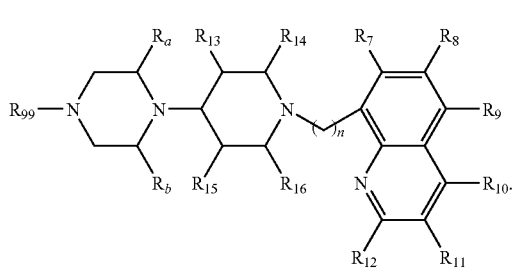

(I')

62. A compound of Formula (I''):

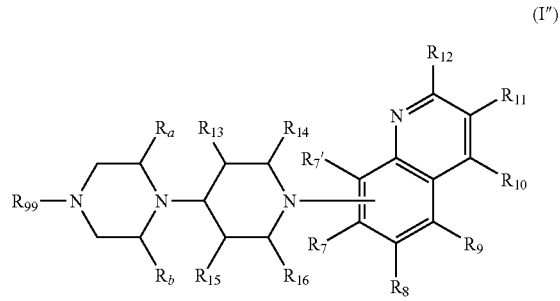

(I'')

or a pharmaceutically acceptable salt thereof, wherein $R_{99}$ is

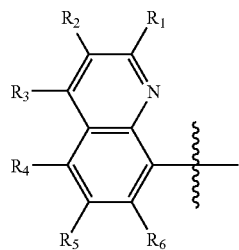

$R_1, R_2, R_3, R_4, R_5, R_6, R_7, R_{7'}, R_8, R_9, R_{10}, R_{11}, R_{12}, R_{13}, R_{14}, R_{15},$ and $R_{16}$ are each independently —H, $(C_1$-$C_6)$-alkyl, $(C_1$-$C_6)$-haloalkyl, $(C_2$-$C_6)$-alkenyl, $(C_2$-$C_6)$-alkynyl, halogen, —$CF_3$, —$NO_2$, —CN, —$OR_{25}$, —$OSO_2R_{25}$, —$SR_{25}$, —$SO_2R_{25}$, —$SO_2N(R_{25})_2$, —$N(R_{25})_2$, —$COR_{25}$, —$CO_2R_{25}$, —$NR_{25}CO_2R_{25}$, —$NR_{25}COR_{25}$, —$NR_{25}CON(R_{25})_2$, or —$CON(R_{25})_2$ except for the R group through which the piperidine is connected;

$R_a$ and $R_b$ are each independently —H or —$CH_3$;

$R_{25}$ is —H; or linear or branched $(C_1$-$C_6)$-alkyl, $(C_1$-$C_6)$-haloalkyl, $(C_2$-$C_6)$-alkenyl, or $(C_2$-$C_6)$-alkynyl; and where the piperidine group can be attached to the non-hetero atom containing ring of the piperidine through positions $R_7, R_{7'}, R_8,$ or $R_9$;

prepared by the method comprising:

reacting a substituted piperazine compound of Formula (X):

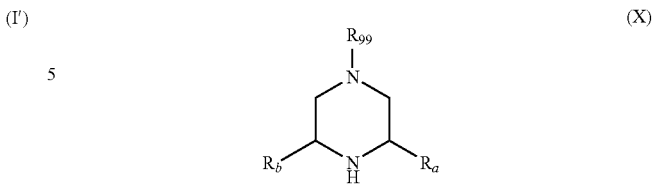

(X)

with a compound of formula (XIVc):

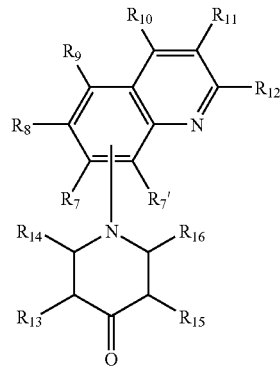

(XIVc)

under conditions effective to bring about reductive amination at the piperidine carbonyl, thereby providing a piperazine-piperidine compound having the Formula (I''):

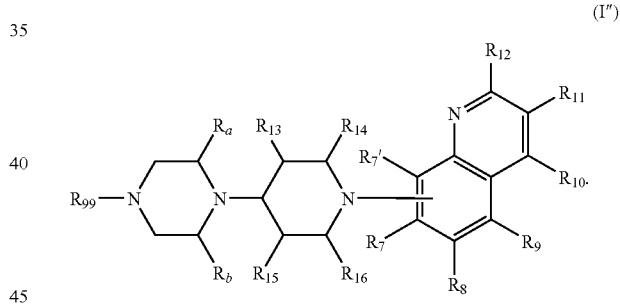

(I'')

63. The pharmaceutical composition of claim 55, wherein $R_4$ and $R_5$ are each independently —H, —$OCH_3$, F, or —$CH_3$; $R_{15}$ and $R_{16}$ are each independently —H or —$CH_3$; and $R_{17}, R_{18},$ and $R_{19}$ are each independently —H, F, —$CH_3$, —$CF_3$, —$NO_2$, —CN or Br.

64. The pharmaceutical composition of claim 55, wherein $R_4$ and $R_5$ are each independently —H or —$OR_{25}$; $R_{17}, R_{18},$ and $R_{19}$ are each independently —H, —$OR_{25}$, halogen, $(C_1$-$C_6)$-alkyl, or —$CF_3$; and $R_{15}, R_{16}, R_a,$ and $R_b$ are hydrogen.

65. The compound or pharmaceutically acceptable salt of the compound of claim 1, wherein n is 0.

66. The compound or pharmaceutically acceptable salt of the compound of claim 1 wherein the compound is 5-fluoro-8-(4-(4-(6-methoxyquinolin-8-yl) piperazin-1-yl)piperidin-1-yl)quinoline.

67. A pharmaceutical composition comprising a compound or a pharmaceutically acceptable salt of a compound wherein the compound is 5-fluoro-8-(4-(4-(6-methoxyquinolin-8-yl)piperazin-1-yl)piperidin-1-yl)quinoline.

\* \* \* \* \*